(12) United States Patent
Ding et al.

(10) Patent No.: US 12,103,915 B2
(45) Date of Patent: Oct. 1, 2024

(54) TEAD INHIBITORS AND METHODS OF USES THEREOF

(71) Applicant: Insilico Medicine IP Limited, Hong Kong (HK)

(72) Inventors: Xiao Ding, Shanghai (CN); Jinxin Liu, Shanghai (CN); Feng Ren, Shanghai (CN); Jianfei Wan, Shanghai (CN); Wei Zhu, Shanghai (CN)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 0 days.

(21) Appl. No.: 18/529,689

(22) Filed: Dec. 5, 2023

(65) Prior Publication Data

US 2024/0166608 A1    May 23, 2024

Related U.S. Application Data

(63) Continuation of application No. PCT/CN2023/122446, filed on Sep. 28, 2023.

(30) Foreign Application Priority Data

| Sep. 29, 2022 | (WO) | PCT/CN2022/122654 |
| Feb. 24, 2023 | (WO) | PCT/CN2023/078150 |
| Aug. 11, 2023 | (WO) | PCT/CN2023/112540 |

(51) Int. Cl.
| *C07D 231/56* | (2006.01) |
| *A61P 35/00* | (2006.01) |
| *C07D 209/44* | (2006.01) |
| *C07D 215/14* | (2006.01) |
| *C07D 401/04* | (2006.01) |
| *C07D 403/08* | (2006.01) |
| *C07D 471/04* | (2006.01) |
| *C07D 487/04* | (2006.01) |

(52) U.S. Cl.
CPC .......... *C07D 231/56* (2013.01); *A61P 35/00* (2018.01); *C07D 209/44* (2013.01); *C07D 215/14* (2013.01); *C07D 401/04* (2013.01); *C07D 403/08* (2013.01); *C07D 471/04* (2013.01); *C07D 487/04* (2013.01)

(58) Field of Classification Search
None
See application file for complete search history.

(56) References Cited

U.S. PATENT DOCUMENTS

| 11,420,935 | B2 | 8/2022 | Konradi et al. |
| 11,458,149 | B1 | 10/2022 | Castro |
| 2022/0184037 | A1 | 6/2022 | Hoque et al. |
| 2022/0281819 | A1 | 9/2022 | Zbieg et al. |
| 2022/0298102 | A1 | 9/2022 | Konradi et al. |
| 2023/0098872 | A1 | 3/2023 | Rennie et al. |
| 2023/0115350 | A1 | 4/2023 | Rennie et al. |
| 2023/0399314 | A1 | 12/2023 | Zhang et al. |

FOREIGN PATENT DOCUMENTS

| WO | WO-2011045344 A1 | 4/2011 |
| WO | WO-2012038743 A1 | 3/2012 |
| WO | WO-2014012050 A2 | 1/2014 |
| WO | WO-2015022283 A1 | 2/2015 |
| WO | WO-2016198401 A1 | 12/2016 |
| WO | WO-2017045751 A1 | 3/2017 |
| WO | WO-2017053706 A1 | 3/2017 |
| WO | WO-2017058716 A1 | 4/2017 |
| WO | WO-2017064277 A1 | 4/2017 |
| WO | WO-2018102419 A1 | 6/2018 |
| WO | WO-2018185266 A1 | 10/2018 |
| WO | WO-2018204532 A1 | 11/2018 |
| WO | WO-2019040380 A1 | 2/2019 |
| WO | WO-2019113236 A1 | 6/2019 |
| WO | WO-2019222431 A1 | 11/2019 |
| WO | WO-2019232216 A1 | 12/2019 |
| WO | WO-2020051099 A1 | 3/2020 |
| WO | WO-2020070181 A1 | 4/2020 |
| WO | WO-2020081572 A1 | 4/2020 |
| WO | WO-2020087063 A1 | 4/2020 |
| WO | WO-2020097389 A1 | 5/2020 |
| WO | WO-2020135513 A1 | 7/2020 |
| WO | WO-2020190774 A1 | 9/2020 |
| WO | WO-2020214734 A1 | 10/2020 |
| WO | WO-2020243415 A2 | 12/2020 |
| WO | WO-2020243423 A1 | 12/2020 |
| WO | WO-2021018869 A1 | 2/2021 |
| WO | WO-2021097110 A1 | 5/2021 |
| WO | WO-2021102204 A1 | 5/2021 |
| WO | WO-2021108483 A1 | 6/2021 |
| WO | WO-2021133896 A1 | 7/2021 |
| WO | WO-2021178339 A1 | 9/2021 |
| WO | WO-2021186324 A1 | 9/2021 |
| WO | WO-2021204823 A1 | 10/2021 |
| WO | WO-2021222522 A1 | 11/2021 |
| WO | WO-2021224291 A1 | 11/2021 |
| WO | WO-2021247634 A1 | 12/2021 |
| WO | WO-2022006548 A1 | 1/2022 |
| WO | WO-2022018072 A1 | 1/2022 |
| WO | WO-2022020716 A1 | 1/2022 |

(Continued)

OTHER PUBLICATIONS

Cancer.Net. Immunotherapy 2.0: The 2017 Clinical Cancer Advance of the Year. Retrieved from the Internet on Feb. 21, 2024, https://www.cancer.net/blog/2017-02/immunotherapy-20-2017-clinical-cancer-advance-year. (Year: 2017).*

(Continued)

*Primary Examiner* — Amy C Bonaparte
*Assistant Examiner* — Lauren Wells
(74) *Attorney, Agent, or Firm* — WILSON SONSINI GOODRICH & ROSATI

(57) ABSTRACT

The disclosure provides for compounds and methods for modulating or inhibiting TEAD. Further provided herein are pharmaceutical compositions comprising the TEAD inhibitors and methods of treatment using the TEAD inhibitors or the pharmaceutical compositions.

26 Claims, No Drawings

(56) References Cited

FOREIGN PATENT DOCUMENTS

| | | |
|---|---|---|
| WO | WO-2022023460 A1 | 2/2022 |
| WO | WO-2022037568 A1 | 2/2022 |
| WO | WO-2022072741 A1 | 4/2022 |
| WO | WO-2022087008 A1 | 4/2022 |
| WO | WO-2022120353 A1 | 6/2022 |
| WO | WO-2022120354 A1 | 6/2022 |
| WO | WO-2022120355 A1 | 6/2022 |
| WO | WO-2022150768 A1 | 7/2022 |
| WO | WO-2022159986 A1 | 7/2022 |
| WO | WO-2022164835 A1 | 8/2022 |
| WO | WO-2022177869 A1 | 8/2022 |
| WO | WO-2022204452 A1 | 9/2022 |
| WO | WO-2022219246 A1 | 10/2022 |
| WO | WO-2022232088 A1 | 11/2022 |
| WO | WO-2022233442 A1 | 11/2022 |
| WO | WO-2022240966 A1 | 11/2022 |
| WO | WO-2022246459 A1 | 11/2022 |
| WO | WO-2022250466 A1 | 12/2022 |
| WO | WO-2022272036 A1 | 12/2022 |
| WO | WO-2023009785 A1 | 2/2023 |
| WO | WO-2023031781 A1 | 3/2023 |
| WO | WO-2023031798 A1 | 3/2023 |
| WO | WO-2023031799 A1 | 3/2023 |
| WO | WO-2023031801 A1 | 3/2023 |
| WO | WO-2023049199 A1 | 3/2023 |
| WO | WO-2023049808 A2 | 3/2023 |
| WO | WO-2023057371 A1 | 4/2023 |
| WO | WO-2023060227 A1 | 4/2023 |
| WO | WO-2023072974 A1 | 5/2023 |
| WO | WO-2023078813 A1 | 5/2023 |
| WO | WO-2023097194 A2 | 6/2023 |
| WO | WO-2023097195 A1 | 6/2023 |
| WO | WO-2023114984 A1 | 6/2023 |
| WO | WO-2023122780 A2 | 6/2023 |
| WO | WO-2023122781 A2 | 6/2023 |
| WO | WO-2023122782 A2 | 6/2023 |
| WO | WO-2023122783 A2 | 6/2023 |
| WO | WO-2023122784 A2 | 6/2023 |
| WO | WO-2023146511 A1 | 8/2023 |
| WO | WO-2023146512 A1 | 8/2023 |
| WO | WO-2023146513 A1 | 8/2023 |
| WO | WO-2023147063 A2 | 8/2023 |
| WO | WO-2023150619 A2 | 8/2023 |
| WO | WO-2023151560 A1 | 8/2023 |
| WO | WO-2023154811 A2 | 8/2023 |
| WO | WO-2023164596 A1 | 8/2023 |
| WO | WO-2023180385 A1 | 9/2023 |
| WO | WO-2023183437 A1 | 9/2023 |
| WO | WO-2023183768 A2 | 9/2023 |

OTHER PUBLICATIONS

Tang et al. Small Molecule Inhibitors of TEAD Auto-palmitoylation Selectively Inhibit Proliferation and Tumor Growth of NF2-deficient Mesothelioma. Mol Can Ther 20(6):986-998 (2021).

PCT/CN2023/122446 International Search Report and Written Opinion dated Dec. 28, 2023.

* cited by examiner

TEAD INHIBITORS AND METHODS OF USES THEREOF

CROSS-REFERENCE

This patent application is a continuation of International Application No. PCT/CN2023/122446, filed Sep. 28, 2023, which claims the benefit of International Application No. PCT/CN2022/122654, filed Sep. 29, 2022; International Application No. PCT/CN2023/078150, filed Feb. 24, 2023; and International Application No. PCT/CN2023/112540, filed Aug. 11, 2023; which are incorporated herein by reference in their entirety.

BACKGROUND

The Hippo pathway is a signaling pathway that regulates cell proliferation and cell death and determines organ size. The pathway is believed to play a role as a tumor suppressor in mammals, and disorders of the pathway are often detected in human cancers. The pathway is involved in and/or may regulate the self-renewal and differentiation of stem cells and progenitor cells. In addition, the Hippo pathway may be involved in wound healing and tissue regeneration. Furthermore, it is believed that as the Hippo pathway cross-talks with other signaling pathways such as Wnt, Notch, Hedgehog, and MAPK/ERK, it may influence a wide variety of biological events, and that its dysfunction could be involved in many human diseases in addition to cancer.

The Hippo signaling pathway is conserved from drosophila to mammals. The core of the pathway consists of a cascade of kinases (Hippo-MST1-2 being upstream of Lats 1-2 and NDRI-2) leading to the phosphorylation of two transcriptional co-activators, YAP (Yes-Associated Protein) and TAZ.

Because the Hippo signaling pathway is a regulator of animal development, organ size control and stem cell regulation, it has been implicated in cancer development. In vitro, the overexpression of YAP or TAZ in mammary epithelial cells induces cell transformation, through interaction of both proteins with the TEAD family of transcription factors. Increased YAP/TAZ transcriptional activity induces oncogenic properties such as epithelial-mesenchymal transition and was also shown to confer stem cells properties to breast cancer cells. In vivo, in mouse liver, the overexpression of YAP or the genetic knockout of its upstream regulators MST1-2 triggers the development of hepatocellular carcinomas. Furthermore, when the tumor suppressor NF2 is inactivated in the mouse liver, the development of hepatocellular carcinomas can be blocked completely by the co-inactivation of YAP.

It is believed that deregulation of the Hippo tumor suppressor pathway is a major event in the development of a wide range of malignancies such as lung cancer, breast cancer, head and neck cancer, colon cancer, ovarian cancer, liver cancer, brain cancer, prostate cancer, mesotheliomas, sarcomas, and leukemia.

Two of the core components of the mammalian Hippo pathway are Lats1 and Lats2, which are nuclear Dbf2-related (NDR) family protein kinases homologous to Drosophila Warts (Wts). The Lats1/2 proteins are activated by association with the scaffold proteins Mob1A/B (Mps one binder kinase activator-like 1A and 1B), which are homologous to Drosophila Mats. Lats1/2 proteins are also activated by phosphorylation by the STE20 family protein kinases Mst1 and Mst2, which are homologous to Drosophila Hippo. Lats1/2 kinases phosphorylate the downstream effectors YAP (Yes-associated protein) and TAZ (transcriptional coactivator with PDZ-binding motif; WWTR1), which are homologous to Drosophila Yorkie. The phosphorylation of YAP and TAZ by Lats1/2 are crucial events within the Hippo signaling pathway. Lats1/2 phosphorylates YAP at multiple sites, but phosphorylation of Ser127 is critical for YAP inhibition. Phosphorylation of YAP generates a protein-binding motif for the 14-3-3 family of proteins, which upon binding of a 14-3-3 protein, leads to retention and/or sequestration of YAP in the cell cytoplasm. Likewise, Lats1/2 phosphorylates TAZ at multiple sites, but phosphorylation of Ser89 is critical for TAZ inhibition. Phosphorylation of TAZ leads to retention and/or sequestration of TAZ in the cell cytoplasm. In addition, phosphorylation of YAP and TAZ is believed to destabilize these proteins by activating phosphorylation-dependent degradation catalyzed by YAP or TAZ ubiquitination. Thus, when the Hippo pathway is "on," YAP and/or TAZ is phosphorylated, inactive, and generally sequestered in the cytoplasm; in contrast, when the Hippo pathway is "off," YAP and/or TAZ is non-phosphorylated, active, and generally found in the nucleus.

Non-phosphorylated, activated YAP is translocated into the cell nucleus where its major target transcription factors are the four proteins of the TEAD-domain-containing family (TEAD1-TEAD4, collectively "TEAD"). YAP together with TEAD (or other transcription factors such as Smad1, RUNX, ErbB4 and p73) has been shown to induce the expression of a variety of genes, including connective tissue growth factor (CTGF), Gli2, Birc5, Birc2, fibroblast growth factor 1 (FGF1), and amphiregulin (AREG). Like YAP, non-phosphorylated TAZ is translocated into the cell nucleus where it interacts with multiple DNA-binding transcription factors, such as peroxisome proliferator-activated receptor γ (PPARγ), thyroid transcription factor-1 (TTF-1), Pax3, TBX5, RUNX, TEAD1 and Smad2/3/4. Many of the genes activated by YAP/TAZ-transcription factor complexes mediate cell survival and proliferation. Therefore, under some conditions YAP and/or TAZ acts as an oncogene and the Hippo pathway acts as a tumor suppressor.

Hence, pharmacological targeting of the Hippo cascade through inhibition of TEAD would be valuable approach for the treatment of cancers that harbor functional alterations of this pathway.

SUMMARY

Disclosed herein are compounds, or a pharmaceutically acceptable salt, or stereoisomer thereof, that are TEAD inhibitors.

Disclosed herein is a compound of Formula (I), or a pharmaceutically acceptable salt, or stereoisomer thereof:

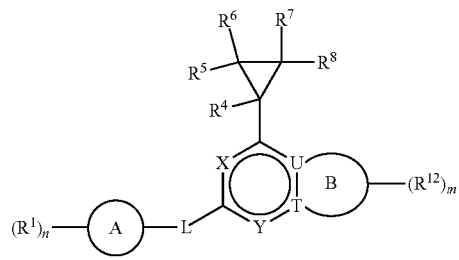

Formula (I), as described herein; provided that the compound is not

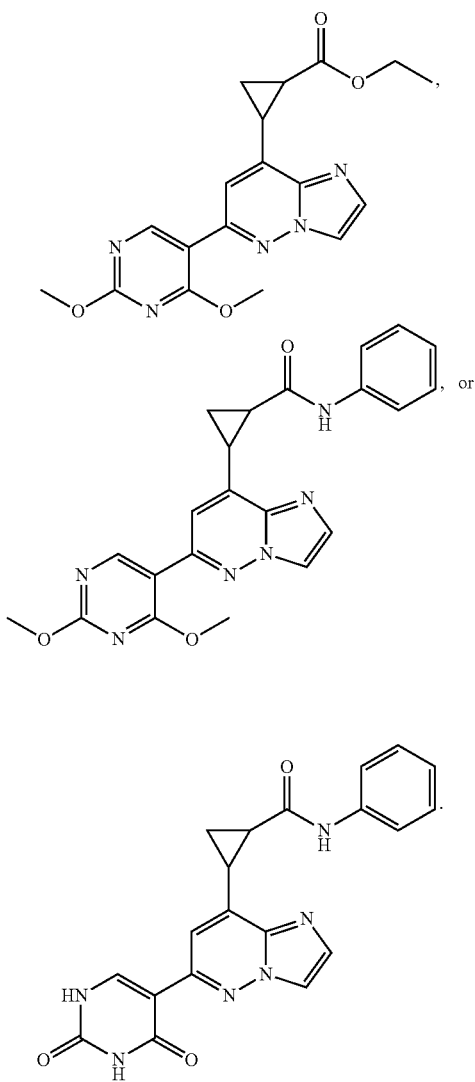

Also disclosed herein is a pharmaceutical composition comprising a compound disclosed herein, or a pharmaceutically acceptable salt, or stereoisomer thereof, and a pharmaceutically acceptable excipient.

A method of treating a cancer in a subject in need thereof, the method comprising administering an effective amount of a compound disclosed herein, or a pharmaceutically acceptable salt, or stereoisomer thereof, to the subject in need thereof.

In some embodiments of a method of treating cancer, the cancer is mesothelioma. In some embodiments of a method of treating cancer, the cancer is NF2 deficient mesothelioma.

In some embodiments of a method of treating cancer, the cancer is epithelioid hemangioendothelioma.

In some embodiments of a method of treating cancer, the cancer is a solid tumor.

In some embodiments of a method of treating cancer, the solid tumor has a NF2 mutation, a LATS1 mutation, a LATS2 mutation, or any combination thereof. In some embodiments of a method of treating cancer, the solid tumor has a NF2 mutation. In some embodiments of a method of treating cancer, the solid tumor has a LATS1 mutation. In some embodiments of a method of treating cancer, the solid tumor has a LATS2 mutation. In some embodiments of a method of treating cancer, the solid tumor has a YAP1/TAZ gene fusion.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.
"Carboxyl" refers to —COOH.
"Cyano" refers to —CN.
"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH₂, or —NO₂. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH═CH₂), 1-propenyl (—CH₂CH═CH₂), iso-propenyl [—C(CH₃)═CH₂], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH₂, or —NO₂. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH₂, or —NO₂. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH₂, or —NO₂. In some embodiments, the alkylene is optionally substituted with halogen, —CN, —OH, or —OMe. In some embodiments, the alkylene is optionally substituted with halogen.

"Alkylidenyl" is alkenyl as defined above that is attached via the terminal divalent carbon. For example, in the compound below:

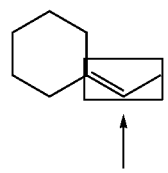

the alkylidenyl group is enclosed by the box which is indicated by the arrow.

"Alkoxy" refers to a radical of the formula —Oalkyl where alkyl is as defined above. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH₂, or —NO₂. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF₃, —OH, —OMe, —NH₂, or —NO₂. In some embodiments, the aryl is optionally substituted with halogen, methyl, ethyl, —CN, —CF₃, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom), spiro, or bridged ring systems. In some embodiments, the cycloalkyl is fully saturated. Representative cycloalkyls include, but are not limited to, cycloalkyls having from three to fifteen carbon atoms (e.g., $C_3$-$C_{15}$ fully saturated cycloalkyl or $C_3$-$C_{15}$ cycloalkenyl), from three to ten carbon atoms (e.g., $C_3$-$C_{10}$ fully saturated cycloalkyl or $C_3$-$C_{10}$ cycloalkenyl), from three to eight carbon atoms (e.g., $C_3$-$C_8$ fully saturated cycloalkyl or $C_3$-$C_8$ cycloalkenyl), from three to six carbon atoms (e.g., $C_3$-$C_6$ fully saturated cycloalkyl or $C_3$-$C_6$ cycloalkenyl), from three to five carbon atoms (e.g., $C_3$-$C_5$ fully saturated cycloalkyl or $C_3$-$C_5$ cycloalkenyl), or three to four carbon atoms (e.g., $C_3$-$C_4$ fully saturated cycloalkyl or $C_3$-$C_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (e.g., $C_2$-$C_{15}$ fully saturated heterocycloalkyl or $C_2$-$C_{15}$ heterocycloalkenyl), from two to ten carbon atoms (e.g., $C_2$-$C_{10}$ fully saturated heterocycloalkyl or $C_2$-$C_{10}$ heterocycloalkenyl), from two to eight carbon atoms (e.g., $C_2$-$C_8$ fully saturated heterocycloalkyl or $C_2$-$C_8$ heterocycloalkenyl), from two to seven carbon atoms (e.g., $C_2$-$C_7$ fully saturated heterocycloalkyl or $C_2$-$C_7$ heterocycloalkenyl), from two to six carbon atoms (e.g., $C_2$-$C_6$ fully saturated heterocycloalkyl or $C_2$-$C_6$ heterocycloalkenyl), from two to five carbon atoms (e.g., $C_2$-$C_5$ fully saturated heterocycloalkyl or $C_2$-$C_5$ heterocycloalkenyl), or two to four carbon atoms (e.g., $C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns that are sterically impractical and/or synthetically non-feasible. Thus, any substituents described should generally be understood as having a maximum molecular weight of about 1,000 daltons, and more typically, up to about 500 daltons.

The term "one or more" when referring to an optional substituent means that the subject group is optionally substituted with one, two, three, four, or more substituents. In some embodiments, the subject group is optionally substituted with one, two, three or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

An "effective amount" or "therapeutically effective amount" refers to an amount of a compound administered to a mammalian subject, either as a single dose or as part of a series of doses, which is effective to produce a desired therapeutic effect.

The terms "treat," "treating" or "treatment," as used herein, include alleviating, abating, or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition.

As used herein, a "disease or disorder associated with TEAD" or, alternatively, "a TEAD-mediated disease or disorder" means any disease or other deleterious condition in which TEAD, or a mutant thereof, is known or suspected to play a role.

Compounds

Described herein are compounds, or a pharmaceutically acceptable salt, or stereoisomer thereof useful in the treatment of a disease or disorder associated with TEAD.

Disclosed herein is a compound of Formula (I), or a pharmaceutically acceptable salt, or stereoisomer thereof:

Formula (I)

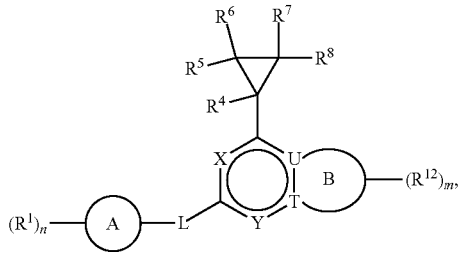

wherein:

X is —N— or —CR$^X$—;

R$^X$ is hydrogen, halogen, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

Y is —N—, —CR$^Y$—, or —C(=O)—;

R$^Y$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

Ring A is cycloalkyl, heterocycloalkyl, aryl, or heteroaryl;

each R$^1$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NRS(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R$^{1a}$;

or two R$^1$ on the same atom are taken together to form an oxo;

each R$^{1a}$ is independently halogen, —CN, —NO$_2$, —OH, —OW, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two R$^{1a}$ on the same atom are taken together to form an oxo;

n is 0, 1, 2, 3, or 4;

L is absent, —O—, —S—, —NR$^2$—, —C(R$^3$)$_2$—, —C(R$^3$)$_2$—C(R$^3$)$_2$—, —C(R$^3$)=C(R$^3$)—,

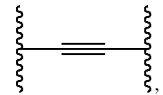

—C(R$^3$)$_2$O—, —OC(R$^3$)$_2$—, —C(R$^3$)$_2$S—, —SC(R$^3$)$_2$—, —C(R$^3$)$_2$NR$^2$—, or —NR$^2$C(R$^3$)$_2$—;

R$^2$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;

each R$^3$ is independently hydrogen, halogen, —CN, —OH, —OW, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;

or two R$^3$ on the same carbon are taken together to form an oxo;

or two R$^3$ on the same carbon are taken together to form a cycloalkyl or heterocycloalkyl; each optionally substituted with one or more R;

or two R$^3$ on different carbons are taken together to form a cycloalkyl, heterocycloalkyl, aryl, or heteroaryl; each optionally substituted with one or more R;

R$^4$, R$^5$, R$^6$, and R$^7$ are each independently hydrogen, halogen, or C$_1$-C$_6$alkyl;

R$^8$ is —C(=O)OR$^9$, —C(=O)NR$^{10}$R$^{11}$, —C(=O)R$^9$, —S(=O)$_2$NR$^{10}$R$^{11}$,

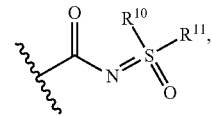

-S(=O)$_2$R$^9$, —S(=O)R$^9$, —P(=O)(OR$^{10}$)(OR$^{11}$), or —B(OR$^{10}$)(OR$^{11}$);

R$^9$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R$^{9a}$;

each R$^{9a}$ is independently halogen, —CN, —NO$_2$, —OH, —OW, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NRS(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two R$^{9a}$ on the same atom are taken together to form an oxo;

R$^{10}$ and R$^{11}$ are each independently hydrogen, —CN, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R$^{10a}$;

or R$^{10}$ and R$^{11}$ are taken together with the atom to which they are attached to form a heterocycloalkyl optionally substituted with one or more R$^{10b}$;

each R$^{10a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two R$^{10a}$ on the same atom are taken together to form an oxo;

each R$^{10b}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two R$^{10b}$ on the same atom are taken together to form an oxo;

U is —C— or —N—;

T is —C— or —N—;

provided that U and T are not both —N—; and provided that U and T are both —C— when Ring B is a phenyl or 6-membered heteroaryl;

Ring B is a phenyl, 5- or 6-membered heteroaryl, 5- or 6-membered heterocycloalkyl, or C$_5$-C$_7$ cycloalkyl;

each R$^{12}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NRS(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two R$^{12}$ on the same atom are taken together to form an oxo;

or two R$^{12}$ on the same carbon are taken together to form a cycloalkyl or heterocycloalkyl; each optionally substituted with one or more R;

or two R$^{12}$ on different atoms are taken together to form a cycloalkyl, heterocycloalkyl, aryl, or heteroaryl; each optionally substituted with one or more R;

m is 0, 1, 2, 3, 4, 5, or 6;

or one R$^{12}$ and R$^Y$ are taken together to form a cycloalkyl, heterocycloalkyl, aryl, or heteroaryl; each optionally substituted with one or more R;

each R$^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

each R$^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

R$^c$ and R$^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —SF$_5$, —SH, —S(=O)C$_1$-C$_3$alkyl, —S(=O)$_2$C$_1$-C$_3$alkyl, —S(=O)$_2$NH$_2$, —S(=O)$_2$NHC$_1$-C$_3$alkyl, —S(=O)$_2$N(C$_1$-C$_3$alkyl)$_2$, —S(=O)(=NC$_1$-C$_3$alkyl)(C$_1$-C$_3$alkyl), —NH$_2$, —NHC$_1$-C$_3$alkyl, —N(C$_1$-C$_3$alkyl)$_2$, —N=S(=O)(C$_1$-C$_3$alkyl)$_2$, —C(=O)C$_1$-C$_3$alkyl, —C(=O)OH, —C(=O)OC$_1$-C$_3$alkyl, —C(=O)NH$_2$, —C(=O)NHC$_1$-C$_3$alkyl, —C(=O)N(C$_1$-C$_3$alkyl)$_2$, —P(=O)(C$_1$-C$_3$alkyl)$_2$, C$_1$-C$_3$alkyl, C$_1$-C$_3$alkoxy, C$_1$-C$_3$haloalkyl, C$_1$-C$_3$haloalkoxy, C$_1$-C$_3$hydroxyalkyl, C$_1$-C$_3$aminoalkyl, C$_1$-C$_3$heteroalkyl, or C$_3$-C$_6$cycloalkyl;

or two R on the same atom form an oxo.

In some embodiments of a compound of Formula (I), the compound is not

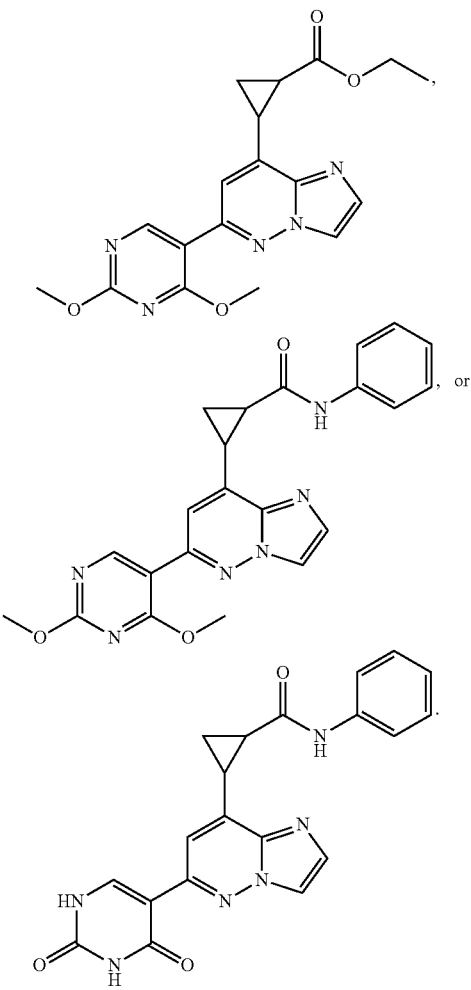

In some embodiments of a compound of Formula (I), the compound is of Formula (Ia):

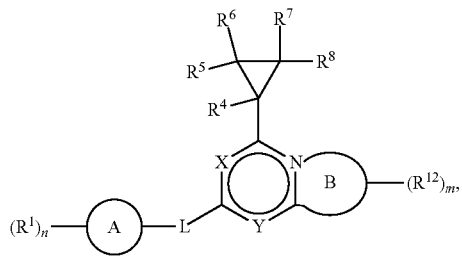

Formula (Ia)

wherein Ring B is a 5-membered heteroaryl or 5-membered heterocycloalkyl.

In some embodiments of a compound of Formula (I), the compound is of Formula (Ib):

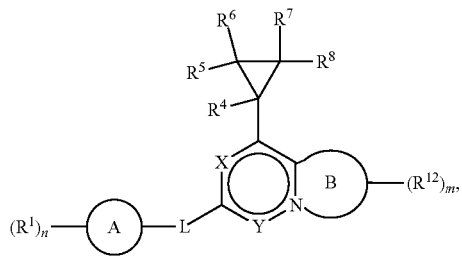

Formula (Ib)

wherein Ring B is a 5-membered heteroaryl or 5-membered heterocycloalkyl.

In some embodiments of a compound of Formula (I), the compound is of Formula (Ic):

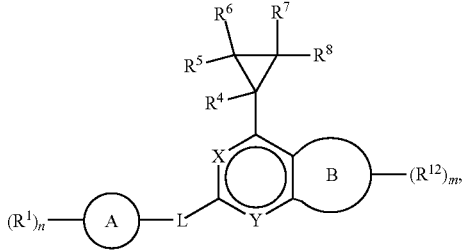

Formula (Ic)

wherein Ring B is a phenyl, 5- or 6-membered heteroaryl or 5-membered heterocycloalkyl.

In some embodiments of a compound of Formula (I) or (Ia)-(Ic),

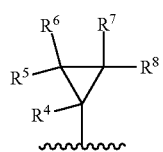

is

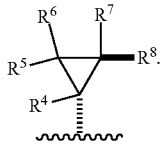

In some embodiments of a compound of Formula (I) or (Ia)-(Ic),

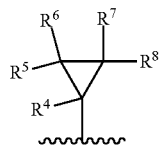

is

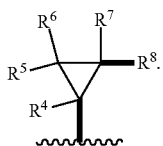

In some embodiments of a compound of Formula (I) or (Ia)-(Ic),

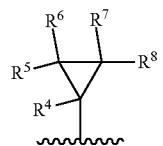

is

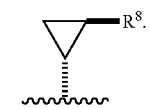

In some embodiments of a compound of Formula (I) or (Ia)-(Ic), X is —N—. In some embodiments of a compound of Formula (I) or (Ia)-(Ic), X is —$CR^X$—.

In some embodiments of a compound of Formula (I) or (Ia)-(Ic), $R^X$ is hydrogen, halogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ia)-(Ic), $R^X$ is hydrogen, halogen, $C_1$-$C_6$alkyl, or $C_1$-$C_6$haloalkyl. In some embodiments of a compound of Formula (I) or (Ia)-(Ic), $R^X$ is hydrogen, halogen, or $C_1$-$C_6$alkyl. In some embodiments of a compound of Formula (I) or (Ia)-(Ic), $R^X$ is hydrogen or halogen. In some embodiments of a compound of Formula (I) or (Ia)-(Ic), $R^X$ is hydrogen.

In some embodiments of a compound of Formula (I) or (Ia)-(Ic), Y is —N— or —$CR^Y$—. In some embodiments of a compound of Formula (I) or (Ia)-(Ic), Y is —N—. In some embodiments of a compound of Formula (I) or (Ia)-(Ic), Y is —$CR^Y$—.

In some embodiments of a compound of Formula (I) or (Ia)-(Ic), $R^Y$ is hydrogen, halogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ia)-(Ic), $R^Y$ is hydrogen, halogen, $C_1$-$C_6$alkyl, or $C_1$-$C_6$haloalkyl. In some embodiments of a compound of Formula (I) or (Ia)-(Ic), $R^Y$ is hydrogen, halogen, or $C_1$-$C_6$alkyl. In some embodiments of a compound of Formula (I) or (Ia)-(Ic), $R^Y$ is hydrogen or halogen. In some embodiments of a compound of Formula (I) or (Ia)-(Ic), $R^Y$ is hydrogen.

In some embodiments of a compound of Formula (I) or (Ia)-(Ic), X is —$CR^X$— and Y is —$CR^Y$—. In some embodiments, X is —CH— and Y is —CH—.

In some embodiments of a compound of Formula (I) or (Ia)-(Ic), L is absent, —O—, —S—, —$NR^2$—, —$C(R^3)_2$—, —$C(R^3)_2$—$C(R^3)_2$—, —$C(R^3)$=$C(R^3)$—, —$C(R^3)_2$O—, —$OC(R^3)_2$—, —$C(R^3)_2$S—, —$SC(R^3)_2$—, —$C(R^3)_2NR^2$—, or —$NR^2C(R^3)_2$—.

In some embodiments of a compound of Formula (I) or (Ia)-(Ic), L is absent, —O—, —$C(R^3)_2$—, or —$C(R^3)_2$O—. In some embodiments of a compound of Formula (I) or (Ia)-(Ic), L is absent, —O—, or —$C(R^3)_2$—. In some embodiments of a compound of Formula (I) or (Ia)-(Ic), L is absent or —O—. In some embodiments of a compound of Formula (I) or (Ia)-(Ic), L is —O— or —$C(R^3)_2$O—. In some embodiments of a compound of Formula (I) or (Ia)-(Ic), L is absent. In some embodiments of a compound of Formula (I) or (Ia)-(Ic), L is —O—. In some embodiments of a compound of Formula (I) or (Ia)-(Ic), L is —$C(R^3)_2$—.

In some embodiments of a compound of Formula (I) or (Ia)-(Ic), $R^2$ is hydrogen, $C_1$-$C_6$alkyl, or $C_1$-$C_6$haloalkyl. In some embodiments of a compound of Formula (I) or (Ia)-(Ic), $R^2$ is hydrogen or $C_1$-$C_6$alkyl. In some embodiments of a compound of Formula (I) or (Ia)-(Ic), $R^2$ is hydrogen.

In some embodiments of a compound of Formula (I) or (Ia)-(Ic), each $R^3$ is independently hydrogen, $C_1$-$C_6$alkyl, or $C_1$-$C_6$haloalkyl. In some embodiments of a compound of Formula (I) or (Ia)-(Ic), each $R^3$ is independently hydrogen or $C_1$-$C_6$alkyl. In some embodiments of a compound of Formula (I) or (Ia)-(Ic), each $R^3$ is hydrogen.

In some embodiments of a compound of Formula (I) or (Ia)-(Ic), Ring A is cycloalkyl or heterocycloalkyl. In some embodiments of a compound of Formula (I) or (Ia)-(Ic), Ring A is cycloalkyl. In some embodiments of a compound of Formula (I) or (Ia)-(Ic), Ring A is fully saturated cycloalkyl. In some embodiments of a compound of Formula (I) or (Ia)-(Ic), Ring A is fully saturated $C_5$-$C_6$ mono-cycloalkyl, fully saturated $C_7$-$C_{10}$ spiro-cycloalkyl, or fully saturated $C_7$-$C_{10}$ bridged-cycloalkyl. In some embodiments of a compound of Formula (I) or (Ia)-(Ic), Ring A is partially saturated cycloalkyl. In some embodiments of a compound of Formula (I) or (Ia)-(Ic), Ring A is partially saturated $C_5$-$C_6$ cycloalkyl. In some embodiments of a compound of Formula (I) or (Ia)-(Ic), Ring A is heterocycloalkyl. In some embodiments of a compound of Formula (I) or (Ia)-(Ic), Ring A is mono-heterocycloalkyl, fused-heterocycloalkyl, spiro-heterocycloalkyl, or bridged-heterocycloalkyl. In some embodiments of a compound of Formula (I) or (Ia)-(Ic), Ring A is 5- or 6-membered mono-heterocycloalkyl, 7- to 10-membered spiro-heterocycloalkyl, or 7- to 10-membered bridged-heterocycloalkyl. In some embodiments of a compound of Formula (I) or (Ia)-(Ic), Ring A is aryl or heteroaryl. In some embodiments of a compound of Formula (I) or (Ia)-(Ic), Ring A is aryl. In some embodiments of a compound of Formula (I) or (Ia)-(Ic), Ring A is phenyl. In some embodiments of a compound of Formula (I) or (Ia)-

(Ic), Ring A is heteroaryl. In some embodiments of a compound of Formula (I) or (Ia)-(Ic), Ring A is 5- or 6-membered heteroaryl. In some embodiments of a compound of Formula (I) or (Ia)-(Ic), Ring A is pyridyl or pyrimidyl.

In some embodiments of a compound of Formula (I) or (Ia)-(Ic), each $R^1$ is independently halogen, —CN, —OH, —$SF_5$, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more Ria. In some embodiments of a compound of Formula (I) or (Ia)-(Ic), each $R^1$ is independently halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ia)-(Ic), each $R^1$ is independently halogen, —CN, —OH, —$OR^a$, —$NR^cR^d$, $C_1$-$C_6$alkyl, or $C_1$-$C_6$haloalkyl. In some embodiments of a compound of Formula (I) or (Ia)-(Ic), each $R^1$ is independently halogen, —OR, $C_1$-$C_6$alkyl, or $C_1$-$C_6$haloalkyl. In some embodiments of a compound of Formula (I) or (Ia)-(Ic), each $R^1$ is independently halogen, $C_1$-$C_6$alkyl, or $C_1$-$C_6$haloalkyl. In some embodiments of a compound of Formula (I) or (Ia)-(Ic), each $R^1$ is independently halogen or $C_1$-$C_6$haloalkyl. In some embodiments of a compound of Formula (I) or (Ia)-(Ic), each $R^1$ is independently $C_1$-$C_6$haloalkyl. In some embodiments of a compound of Formula (I) or (Ia)-(Ic), each $R^1$ is independently halogen. In some embodiments of a compound of Formula (I) or (Ia)-(Ic), each $R^1$ is independently —$OCF_3$, —$CF_3$, —$CHF_2$, —F, —Cl, —$SF_5$, methyl, ethyl, isopropyl, or n-propyl.

In some embodiments of a compound of Formula (I) or (Ia)-(Ic), each $R^{1a}$ is independently halogen, —CN, —OH, —OR, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two $R^{1a}$ on the same atom are taken together to form an oxo. In some embodiments of a compound of Formula (I) or (Ia)-(Ic), each $R^{1a}$ is independently halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia)-(Ic), each $R^{1a}$ is independently halogen, —CN, —OH, —$OR^a$, —$NR^cR^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia)-(Ic), each $R^{1a}$ is independently halogen, $C_1$-$C_6$alkyl, or $C_1$-$C_6$haloalkyl.

In some embodiments of a compound of Formula (I) or (Ia)-(Ic), n is 0, 1, 2, or 3. In some embodiments of a compound of Formula (I) or (Ia)-(Ic), n is 0, 1, or 2. In some embodiments of a compound of Formula (I) or (Ia)-(Ic), n is 0 or 1. In some embodiments of a compound of Formula (I) or (Ia)-(Ic), n is 1 or 2. In some embodiments of a compound of Formula (I) or (Ia)-(Ic), n is 0. In some embodiments of a compound of Formula (I) or (Ia)-(Ic), n is 1. In some embodiments of a compound of Formula (I) or (Ia)-(Ic), n is 2. In some embodiments of a compound of Formula (I) or (Ia)-(Ic), n is 3.

In some embodiments of a compound of Formula (I) or (Ia)-(Ic),

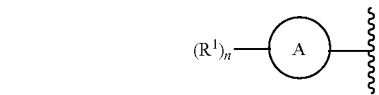

is

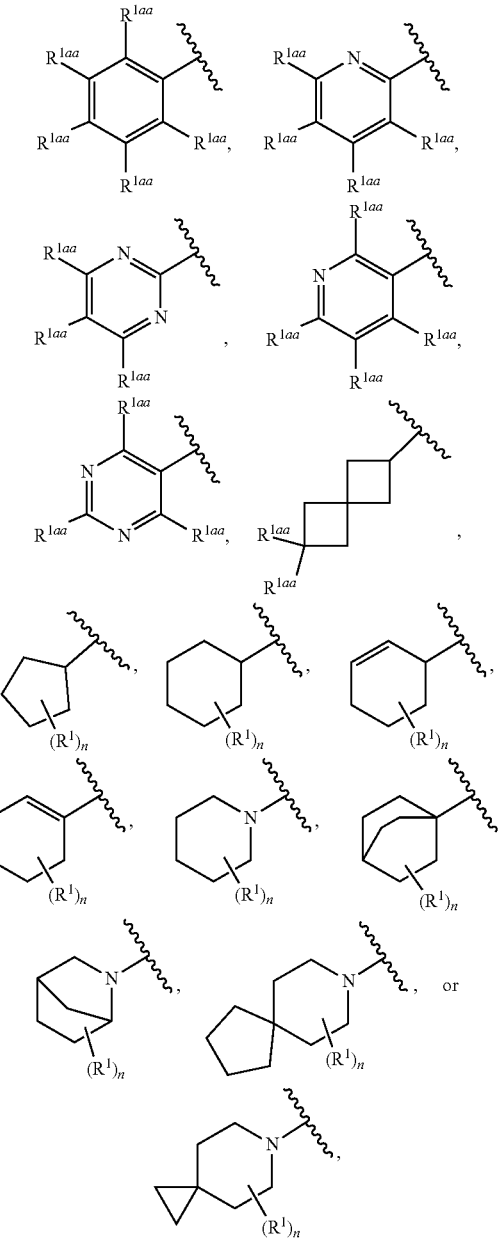

each $R^{1aa}$ is independently hydrogen or $R^1$.

In some embodiments of a compound of Formula (I) or (Ia)-(Ic),

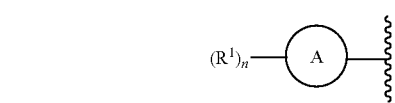
is
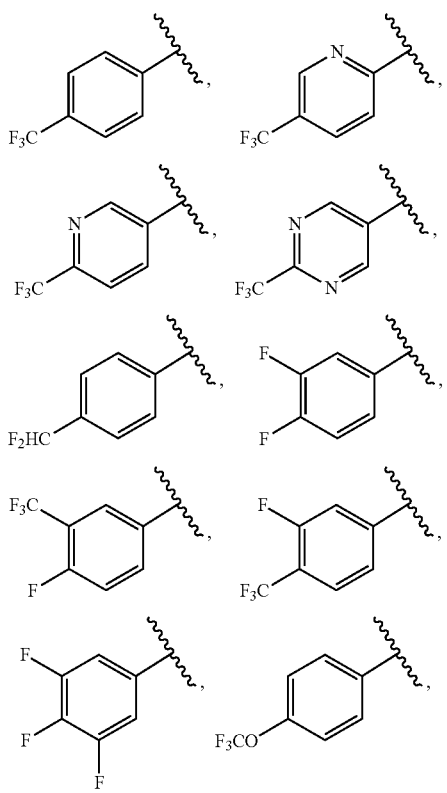
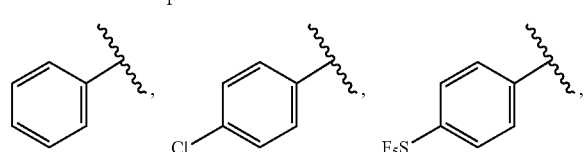
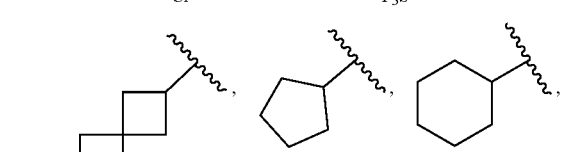
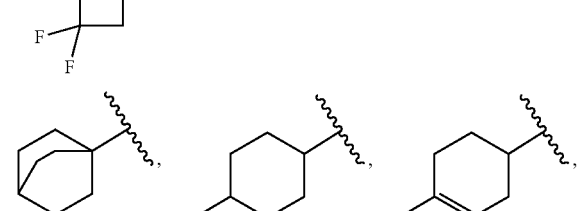
-continued
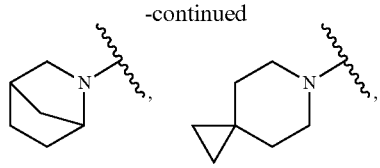
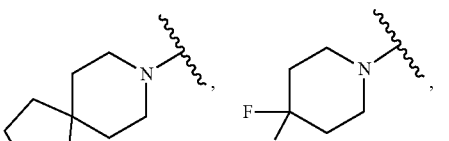
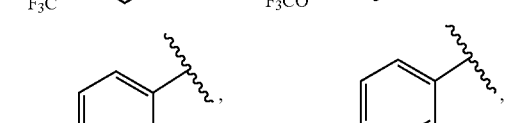
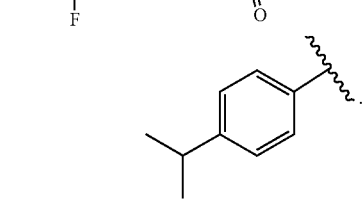
In some embodiments of a compound of Formula (I) or (Ia)-(Ic),
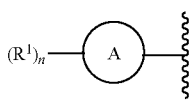
is
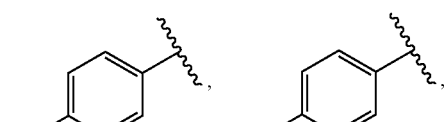
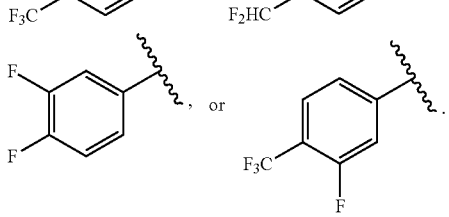
In some embodiments of a compound of Formula (I) or (Ia)-(Ic),

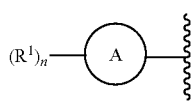

is

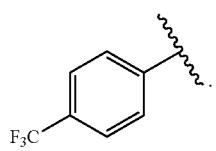

In some embodiments of a compound of Formula (I) or (Ia)-(Ic),

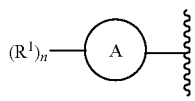

is

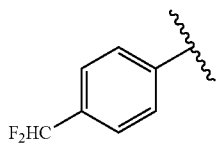

In some embodiments of a compound of Formula I or (Ia)-(Ic),

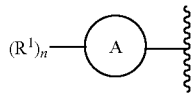

is

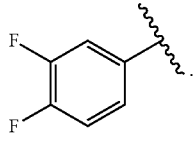

In some embodiments of a compound of Formula (I) or (Ia)-(Ic),

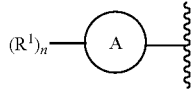

is

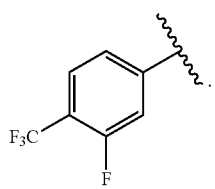

In some embodiments of a compound of Formula (I) or (Ia)-(Ic), $R^4$ is hydrogen or $C_1$-$C_6$alkyl. In some embodiments of a compound of Formula (I) or (Ia)-(Ic), $R^4$ is hydrogen.

In some embodiments of a compound of Formula (I) or (Ia)-(Ic), $R^5$ is hydrogen or $C_1$-$C_6$alkyl. In some embodiments of a compound of Formula (I) or (Ia)-(Ic), $R^5$ is hydrogen.

In some embodiments of a compound of Formula (I) or (Ia)-(Ic), $R^6$ is hydrogen or $C_1$-$C_6$alkyl. In some embodiments of a compound of Formula (I) or (Ia)-(Ic), $R^6$ is hydrogen.

In some embodiments of a compound of Formula (I) or (Ia)-(Ic), $R^7$ is hydrogen or $C_1$-$C_6$alkyl. In some embodiments of a compound of Formula (I) or (Ia)-(Ic), $R^7$ is hydrogen.

In some embodiments of a compound of Formula (I) or (Ia)-(Ic), each of $R^4$, $R^5$, $R^6$, and $R^7$ is hydrogen.

In some embodiments of a compound of Formula (I) or (Ia)-(Ic), $R^8$ is —C(=O)O$R^9$, —C(=O)N$R^{10}R^{11}$, —S(=O)$_2$N$R^{10}R^{11}$, —P(=O)(O$R^{10}$)(O$R^{11}$), or —B(O$R^{10}$)(O$R^{11}$).

In some embodiments of a compound of Formula (I) or (Ia)-(Ic), $R^8$ is —C(=O)O$R^9$, —C(=O)N$R^{10}R^{11}$, or —S(=O)$_2$N$R^{10}R^{11}$. In some embodiments of a compound of Formula (I) or (Ia)-(Ic), $R^8$ is —C(=O)O$R^9$. In some embodiments of a compound of Formula (I) or (Ia)-(Ic), $R^8$ is —C(=O)N$R^{10}R^{11}$. In some embodiments of a compound of Formula (I) or (Ia)-(Ic), $R^8$ is —S(=O)$_2$N$R^{10}R^{11}$.

In some embodiments of a compound of Formula (I) or (Ia)-(Ic), $R^9$ is hydrogen, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more $R^{9a}$. In some embodiments of a compound of Formula (I) or (Ia)-(Ic), $R^9$ is hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more $R^{9a}$. In some embodiments of a compound of Formula (I) or (Ia)-(Ic), $R^9$ is hydrogen, $C_1$-$C_6$alkyl, $C_1$-$C_6$haloalkyl, cycloalkyl, heterocycloalkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more $R^{9a}$. In some embodiments of a compound of Formula (I) or (Ia)-(Ic), $R^9$ is hydrogen, $C_1$-$C_6$alkyl, $C_1$-$C_6$haloalkyl, cycloalkyl, or heterocycloalkyl, wherein each alkyl, cycloalkyl, and heterocycloalkyl is independently optionally substituted with one or more $R^{9a}$. In some embodiments of a compound of Formula (I) or (Ia)-(Ic), $R^9$ is hydrogen, $C_1$-$C_6$alkyl, $C_1$-$C_6$haloalkyl, cycloalkyl, or heterocycloalkyl. In some embodiments of a compound of Formula (I) or (Ia)-(Ic), $R^9$ is hydrogen, $C_1$-$C_6$alkyl, or $C_1$-$C_6$haloalkyl. In some embodiments of a compound of Formula (I) or (Ia)-(Ic), $R^9$ is hydrogen or $C_1$-$C_6$alkyl. In some embodiments of a compound of Formula (I) or (Ia)-(Ic), $R^9$ is hydrogen.

In some embodiments of a compound of Formula (I) or (Ia)-(Ic), each $R^{9a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two $R^{9a}$ on the same atom are taken together to form an oxo. In some embodiments of a compound of Formula (I) or (Ia)-(Ic), each $R^{9a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia)-(Ic), each $R^{9a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia)-(Ic), each $R^{9a}$ is independently halogen, $C_1$-$C_6$alkyl, or $C_1$-$C_6$haloalkyl.

In some embodiments of a compound of Formula (I) or (Ia)-(Ic), each $R^{10a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, or heteroaryl; wherein each alkyl, alkenyl, alkynyl, cycloalkyl, heterocycloalkyl, aryl, and heteroaryl is independently optionally substituted with one or more R.

In some embodiments of a compound of Formula (I) or (Ia)-(Ic), $R^{10}$ and $R^{11}$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more $R^{10a}$.

In some embodiments of a compound of Formula (I) or (Ia)-(Ic), $R^{10}$ and $R^{11}$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more $R^{10a}$. In some embodiments of a compound of Formula (I) or (Ia)-(Ic), $R^{10}$ and $R^{11}$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_1$-$C_6$alkylene(aryl), or $C_1$-$C_6$alkylene(heteroaryl), wherein each alkyl, alkylene, aryl, and heteroaryl is independently optionally substituted with one or more $R^{10a}$. In some embodiments of a compound of Formula (I) or (Ia)-(Ic), $R^{10}$ and $R^{11}$ are each independently hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia)-(Ic), $R^{10}$ and $R^{11}$ are each independently hydrogen, $C_1$-$C_6$alkyl, $C_1$-$C_6$hydroxyalkyl, or $C_1$-$C_6$heteroalkyl. In some embodiments of a compound of Formula (I) or (Ia)-(Ic), $R^{10}$ and $R^{11}$ are each independently hydrogen or $C_1$-$C_6$alkyl. In some embodiments of a compound of Formula (I) or (Ia)-(Ic), $R^{10}$ and $R^{11}$ are each independently hydrogen or heterocycloalkyl optionally substituted with one or more $R^{10a}$.

In some embodiments of a compound of Formula (I) or (Ia)-(Ic), $R^{10}$ is hydrogen and $R^{11}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more $R^{10a}$.

In some embodiments of a compound of Formula (I) or (Ia)-(Ic), $R^{10}$ is hydrogen and $R^{11}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, heterocycloalkyl, $C_1$-$C_6$alkylene(aryl), or $C_1$-$C_6$alkylene(heteroaryl), wherein each alkyl, alkylene, aryl, and heteroaryl is independently optionally substituted with one or more $R^{10a}$.

In some embodiments of a compound of Formula (I) or (Ia)-(Ic), $R^{10}$ is hydrogen and $R^{10}$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, or heterocycloalkyl, wherein each alkyl and heterocycloalkyl is independently optionally substituted with one or more $R^{10a}$.

In some embodiments of a compound of Formula (I) or (Ia)-(Ic), $R^{10}$ is hydrogen and $R^{11}$ is $C_1$-$C_6$alkyl, $C_1$-$C_6$hydroxyalkyl, $C_1$-$C_6$heteroalkyl, or heterocycloalkyl, wherein each alkyl and heterocycloalkyl is independently optionally substituted with one or more $R^{10a}$.

In some embodiments of a compound of Formula (I) or (Ia)-(Ic), $R^{10}$ is hydrogen and $R^{11}$ is heterocycloalkyl optionally substituted with one or more $R^{10a}$.

In some embodiments of a compound of Formula (I) or (Ia)-(Ic), $R^{10}$ is hydrogen and $R^{11}$ is monocyclic heterocycloalkyl optionally substituted with one or more $R^{10a}$.

In some embodiments of a compound of Formula (I) or (Ia)-(Ic), $R^{10}$ is hydrogen and $R^{11}$ is bicyclic heterocycloalkyl optionally substituted with one or more $R^{10a}$. In some embodiments of a compound of Formula (I) or (Ia)-(Ic), $R^{10}$ is hydrogen and $R^{11}$ is fused bicyclic heterocycloalkyl optionally substituted with one or more $R^{10a}$. In some embodiments of a compound of Formula (I) or (Ia)-(Ic), $R^{10}$ is hydrogen and $R^{11}$ is bridged bicyclic heterocycloalkyl optionally substituted with one or more $R^{10a}$. In some embodiments of a compound of Formula (I) or (Ia)-(Ic), $R^{10}$ is hydrogen and $R^{11}$ is bicyclic spiroheterocycloalkyl optionally substituted with one or more $R^{10a}$.

In some embodiments of a compound of Formula (I) or (Ia)-(Ic), $R^{10}$ is hydrogen and $R^{11}$ is

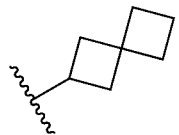 [SMILES: *C1CC2(CCC2)C1]

or

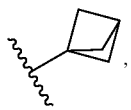, each optionally substituted with one or more $R^{10a}$.

In some embodiments of a compound of Formula (I) or (Ia)-(Ic), each $R^{10a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two $R^{10a}$ on the same atom are taken together to form an oxo. In some embodiments of a compound of Formula (I) or (Ia)-(Ic), each $R^{10a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia)-(Ic), each $R^{10a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (I) or (Ia)-(Ic), each $R^{10a}$ is independently halogen, $C_1$-$C_6$alkyl, or $C_1$-$C_6$haloalkyl. In some embodiments of a compound of Formula (I) or (Ia)-(Ic), each $R^{10a}$ is independently halogen, —CN, —OH, —OR$^a$, —NR$^c$R$^d$, $C_1$-$C_6$alkyl, or $C_1$-$C_6$haloalkyl. In some embodiments of a compound of Formula (I) or (Ia)-(Ic), each $R^{10a}$ is independently halogen, —OH, —OR$^a$, $C_1$-$C_6$alkyl, or $C_1$-$C_6$haloalkyl. In some embodiments of a compound of Formula (I) or (Ia)-(Ic), each $R^{10a}$ is independently halogen, —OH, $C_1$-$C_6$alkyl, or $C_1$-$C_6$haloalkyl. In some embodiments of a compound of Formula (I) or (Ia)-(Ic), each $R^{10a}$ is independently —OH, $C_1$-$C_6$alkyl, or $C_1$-$C_6$haloalkyl. In some embodiments of a compound of Formula (I) or (Ia)-(Ic), each $R^{10a}$ is independently —OH.

In some embodiments of a compound of Formula (I) or (Ia)-(Ic), $R^{10}$ and $R^{11}$ are taken together with the atom to which they are attached to form a heterocycloalkyl optionally substituted with one or more $R^{10b}$. In some embodiments of a compound of Formula (I) or (Ia)-(Ic), $R^{10}$ and $R^{11}$ are taken together with the atom to which they are attached to form a monocyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a 4- to 6-membered monocyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a bicyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a 5- to 12-membered bicyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a fused bicyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a 5- to 12-membered fused bicyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a bridged bicyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a 5- to 12-membered bridged bicyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a 6- to 8-membered bridged bicyclic heterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a bicyclic spiroheterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a 5- to 12-membered bicyclic spiroheterocycloalkyl optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form a heterocycloalkyl, wherein the heterocycloalkyl comprises 1-2 nitrogen and 0-1 oxygen. In some embodiments of a compound of Formula (I) or (Ia)-(Ic), $R^{10}$ and $R^{11}$ are taken together with the atom to which they are attached to form a heterocycloalkyl, wherein the heterocycloalkyl comprises 1 nitrogen.

In some embodiments of a compound of Formula (I) or (Ia)-(Ic), $R^{10}$ and $R^{11}$ are taken together with the atom to which they are attached to form

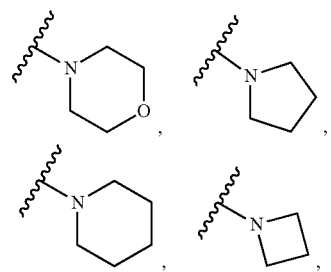

each optionally substituted with one or more (e.g., one, two, or three) $R^{10b}$.

In some embodiments of a compound of Formula (I) or (Ia)-(Ic), $R^{10}$ and $R^{11}$ are taken together with the atom to which they are attached to form

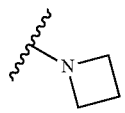

optionally substituted with one or more (e.g., one, two, or three) $R^{10b}$.

In some embodiments of a compound of Formula (I) or (Ia)-(Ic), $R^{10}$ and $R^{11}$ are taken together with the atom to which they are attached to form

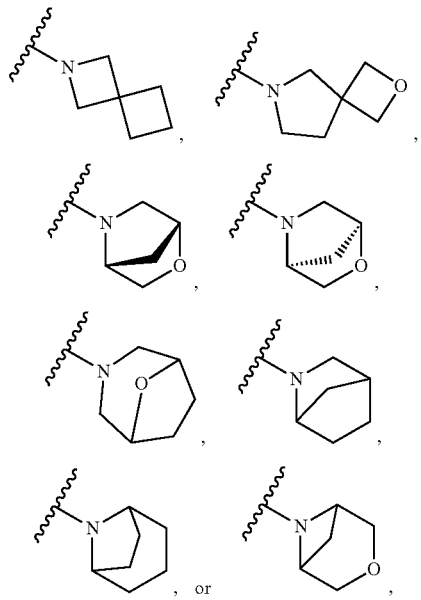

each optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form

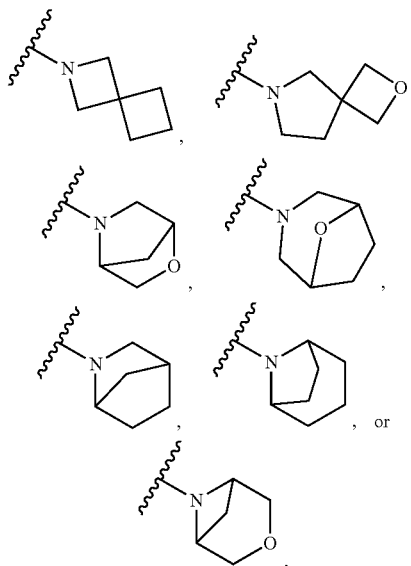

each optionally substituted with one or more (e.g., one, two, or three) $R^{10b}$. In some embodiments of a compound of Formula (I) or (Ia)-(Ic), $R^{10}$ and $R^{11}$ are taken together with the atom to which they are attached to form

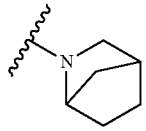

optionally substituted with one or more (e.g., one, two, or three) $R^{10b}$.

In some embodiments of a compound of Formula (I) or (Ia)-(Ic), each $R^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl; wherein each alkyl, cycloalkyl, and heterocycloalkyl is independently optionally substituted with one or more R; or two $R^{10b}$ on the same atom are taken together to form an oxo. In some embodiments of a compound of Formula (I) or (Ia)-(Ic), each $R^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (I) or (Ia)-(Ic), each $R^{10b}$ is independently halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (I) or (Ia)-(Ic), each $R^{10b}$ is independently halogen, C$_1$-C$_6$alkyl, or C$_1$-C$_6$haloalkyl. In some embodiments of a compound of Formula (I) or (Ia)-(Ic), each $R^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl. In some embodiments of a compound of Formula (I) or (Ia)-(Ic), each $R^{10b}$ is independently —CN, —OH, —OR$^a$, or —NR$^c$R$^d$. In some embodiments of a compound of Formula (I) or (Ia)-(Ic), each $R^{10b}$ is independently —CN. In some embodiments of a compound of Formula (I) or (Ia)-(Ic), each $R^{10b}$ is independently —OH.

In some embodiments of a compound of Formula (I) or (Ia)-(Ic), $R^8$ is

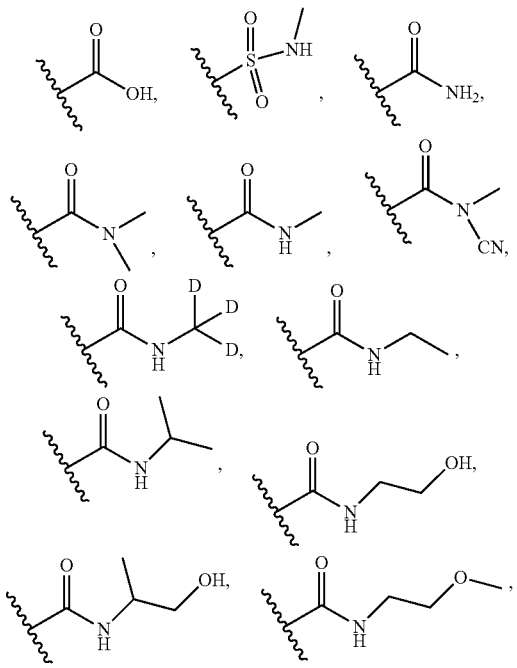

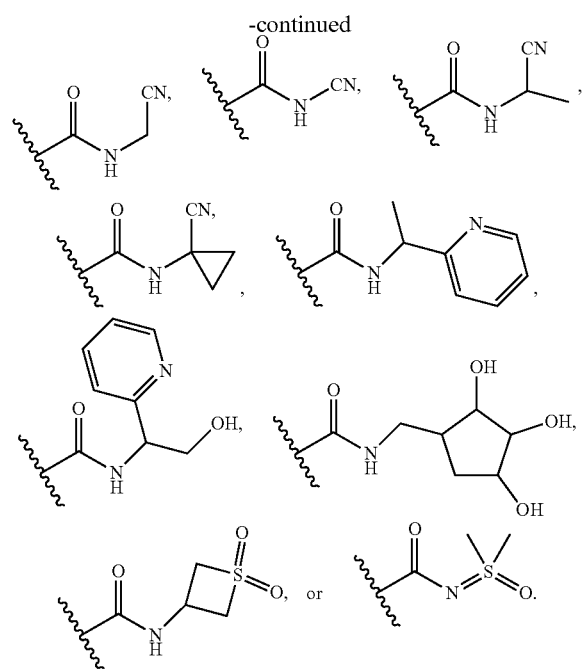
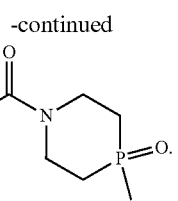
In some embodiments of a compound of Formula (I) or (Ia)-(Ic), $R^8$ is
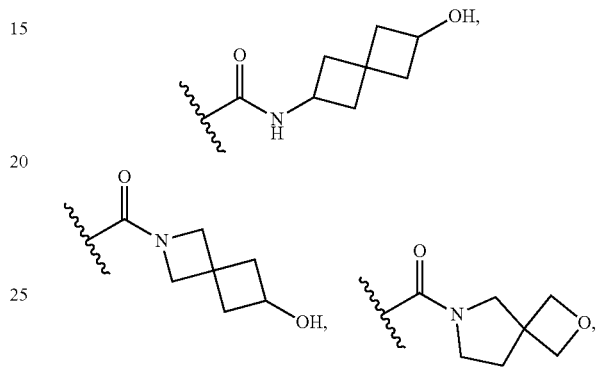
In some embodiments of a compound of Formula (I) or (Ia)-(Ic), $R^8$ is
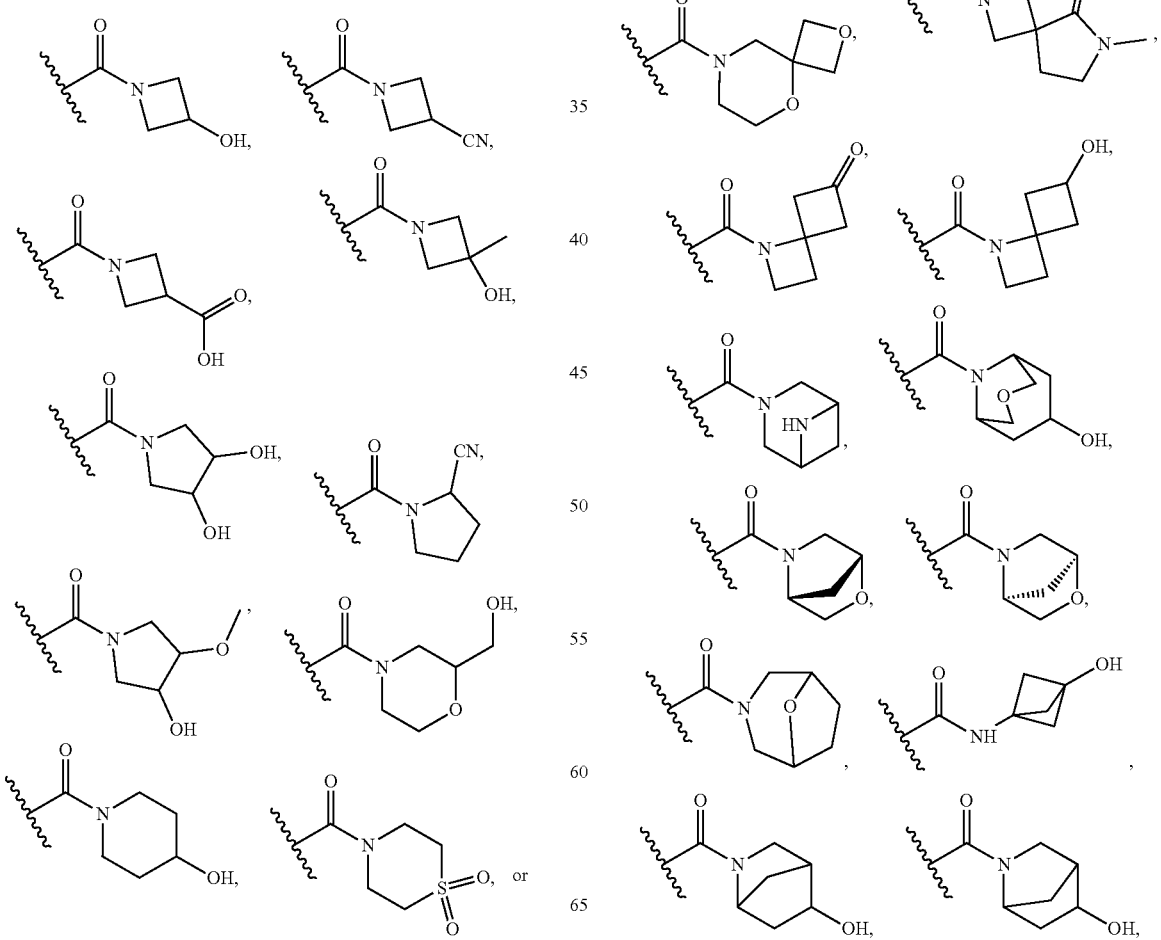

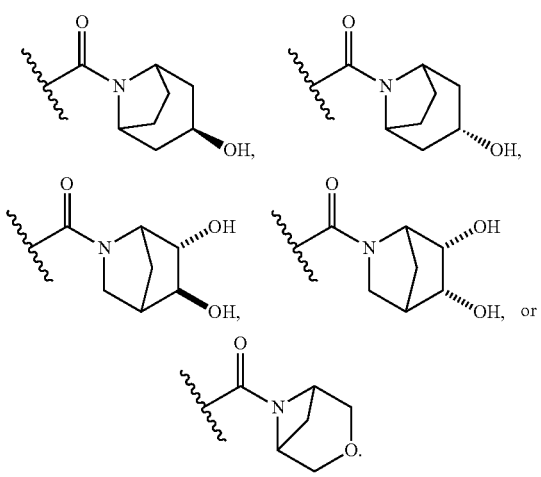

In some embodiments of a compound of Formula (I) or (Ia)-(Ic), $R^8$ is

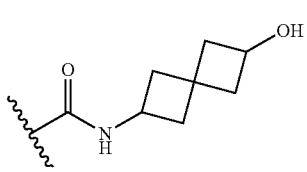 [SMILES: *C(=O)NC1CC2(CC(O)C2)C1]

or

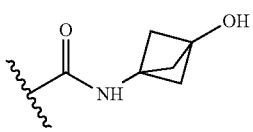

In some embodiments of a compound of Formula (I) or (Ia)-(Ic), $R^8$ is

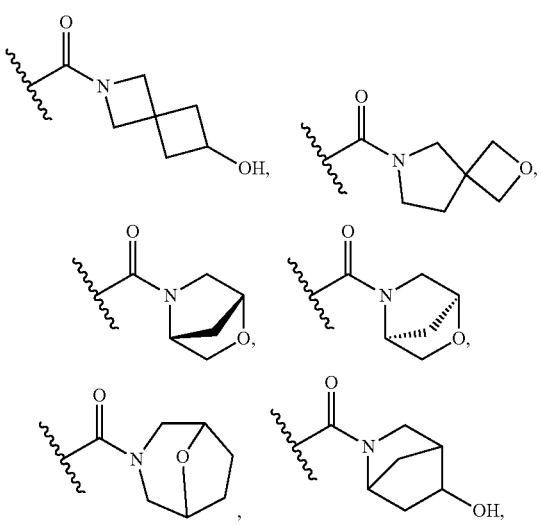

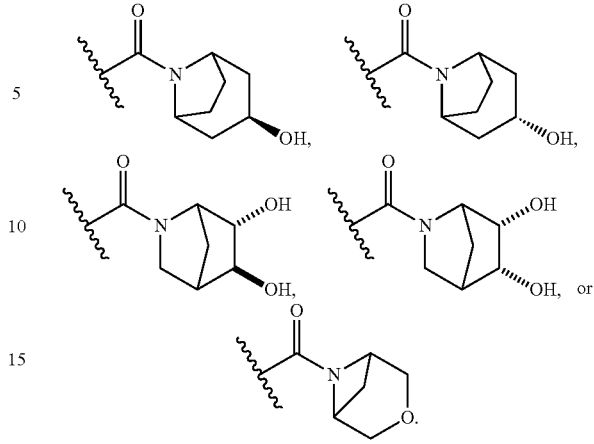

In some embodiments of a compound of Formula (I) or (Ia)-(Ic), $R^8$ is

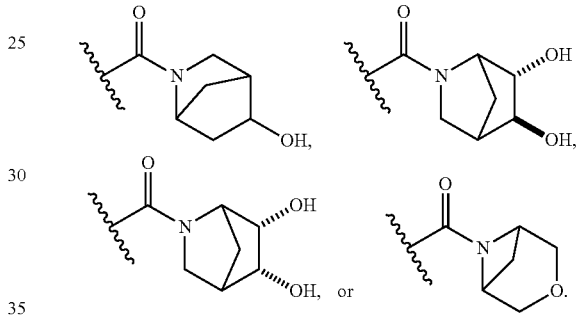

In some embodiments, Ring B is phenyl, and U and T are both —C—. In some embodiments, Ring B is 6-membered heteroaryl, and U and T are both —C—.

In some embodiments of a compound of Formula (I) or (Ia)-(Ic), Ring B is a phenyl, 5- or 6-membered heteroaryl, or 5-membered heterocycloalkyl.

In some embodiments of a compound of Formula (I) or (Ia)-(Ic), Ring B is a 5-membered heteroaryl, 6-membered heteroaryl, 5-membered heterocycloalkyl, 6-membered heterocycloalkyl, cyclopentyl, or cyclohexyl. In some embodiments of a compound of Formula (I) or (Ia)-(Ic), Ring B is a 5-membered heteroaryl or 5-membered heterocycloalkyl. In some embodiments of a compound of Formula (I) or (Ia)-(Ic), Ring B is a phenyl. In some embodiments of a compound of Formula (I) or (Ia)-(Ic), Ring B is a 5- or 6-membered heteroaryl. In some embodiments of a compound of Formula (I) or (Ia)-(Ic), Ring B is a 5-membered heteroaryl. In some embodiments of a compound of Formula (I) or (Ia)-(Ic), Ring B is pyrrolyl, furanyl, thiophenyl, imidazolyl, pyrazolyl, thiazolyl, oxazolyl, or triazolyl. In some embodiments of a compound of Formula (I) or (Ia)-(Ic), Ring B is imidazolyl, pyrazolyl, thiazolyl, or oxazolyl. In some embodiments of a compound of Formula (I) or (Ia)-(Ic), Ring B is pyrazolyl. In some embodiments of a compound of Formula (I) or (Ia)-(Ic), Ring B is a 6-membered heteroaryl. In some embodiments of a compound of Formula (I) or (Ia)-(Ic), Ring B is a pyridinyl, pyrimidinyl, or pyrazinyl. In some embodiments of a compound of Formula (I) or (Ia)-(Ic), Ring B is a pyridinyl. In some embodiments of a compound of Formula (I) or (Ia)-(Ic), Ring B is a 5-membered heterocycloalkyl.

In some embodiments of a compound of Formula (I) or (Ia)-(Ic), each $R^{12}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (I) or (Ia)-(Ic), each $R^{12}$ is independently halogen, —CN, —OH, —OR$^a$, —NR$^c$R$^d$, $C_1$-$C_6$alkyl, $C_1$-$C_6$haloalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (I) or (Ia)-(Ic), each $R^{12}$ is independently halogen, —CN, —OH, $C_1$-$C_6$alkyl, $C_1$-$C_6$haloalkyl, cycloalkyl, or heterocycloalkyl. In some embodiments of a compound of Formula (I) or (Ia)-(Ic), each $R^{12}$ is independently phenyl. In some embodiments of a compound of Formula (I) or (Ia)-(Ic), each $R^{12}$ is independently 5- or 6-membered heteroaryl. In some embodiments of a compound of Formula (I) or (Ia)-(Ic), each $R^{12}$ is independently $C_3$-$C_6$ cycloalkyl. In some embodiments of a compound of Formula (I) or (Ia)-(Ic), each $R^{12}$ is independently 5- or 6-membered heterocycloalkyl. In some embodiments of a compound of Formula (I) or (Ia)-(Ic), each $R^{12}$ is independently —CN, $C_1$-$C_6$alkyl, or $C_1$-$C_6$haloalkyl. In some embodiments of a compound of Formula (I) or (Ia)-(Ic), each $R^{12}$ is independently $C_1$-$C_6$alkyl. In some embodiments of a compound of Formula (I) or (Ia)-(Ic), each $R^{12}$ is independently —CN, methyl, —CHF$_2$, cyclopropyl, or pyridyl. In some embodiments of a compound of Formula (I) or (Ia)-(Ic), methyl is —CD$_3$.

In some embodiments of a compound of Formula (I) or (Ia)-(Ic), m is 0 or 1. In some embodiments of a compound of Formula (I) or (Ia)-(Ic), m is 1 or 2. In some embodiments of a compound of Formula (I) or (Ia)-(Ic), m is 0. In some embodiments of a compound of Formula (I) or (Ia)-(Ic), m is 1. In some embodiments of a compound of Formula (I) or (Ia)-(Ic), m is 2. In some embodiments of a compound of Formula (I) or (Ia)-(Ic), m is 3.

In some embodiments of a compound of Formula (I) or (Ia)-(Ic),

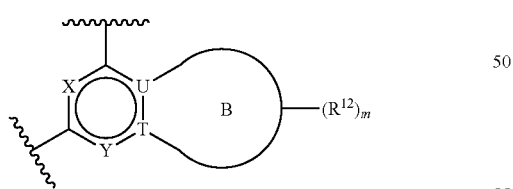

is

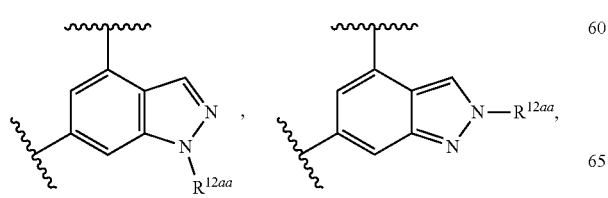

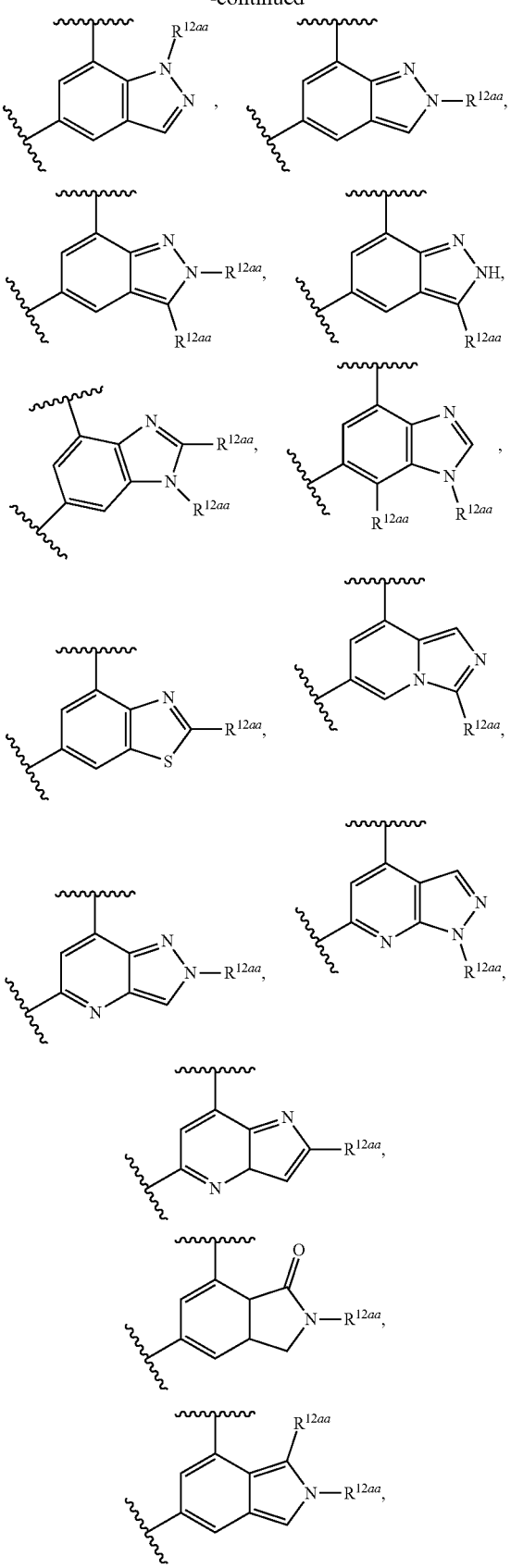

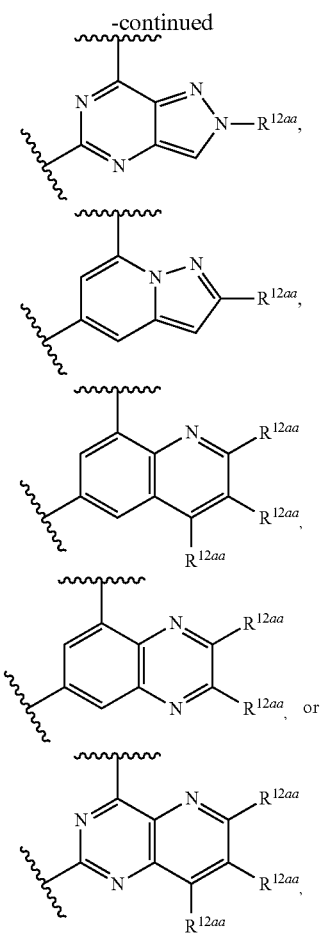
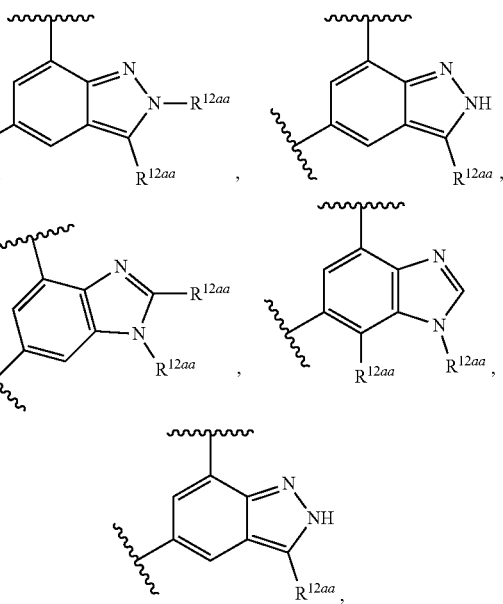
each $R^{12aa}$ is independently hydrogen or $R^{12}$. In some embodiments of a compound of Formula (I) or (Ia)-(Ic),
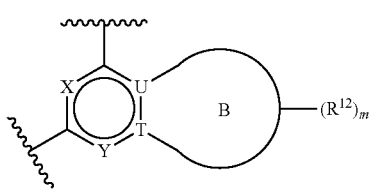
is
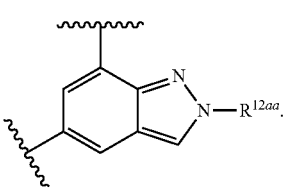
each $R^{12a}$ is independently hydrogen or $R^{12}$. In some embodiments of a compound of Formula (I) or (Ia)-(Ic),
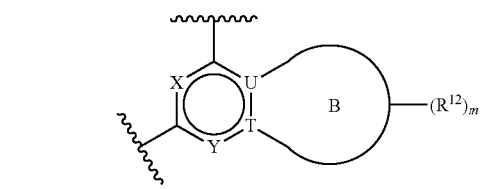
is
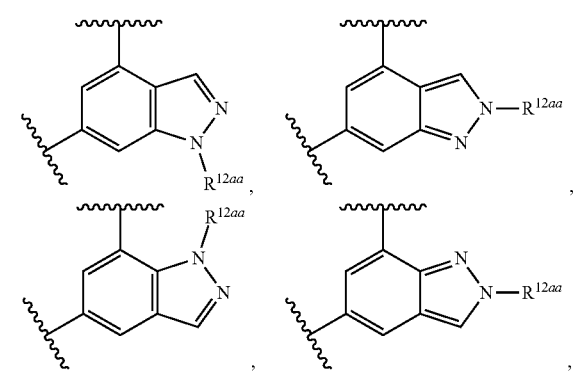
In some embodiments of a compound of Formula (I) or (Ia)-(Ic),
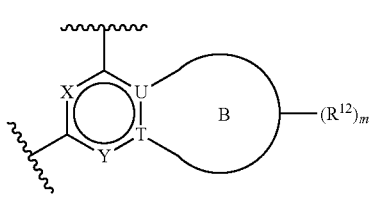

is
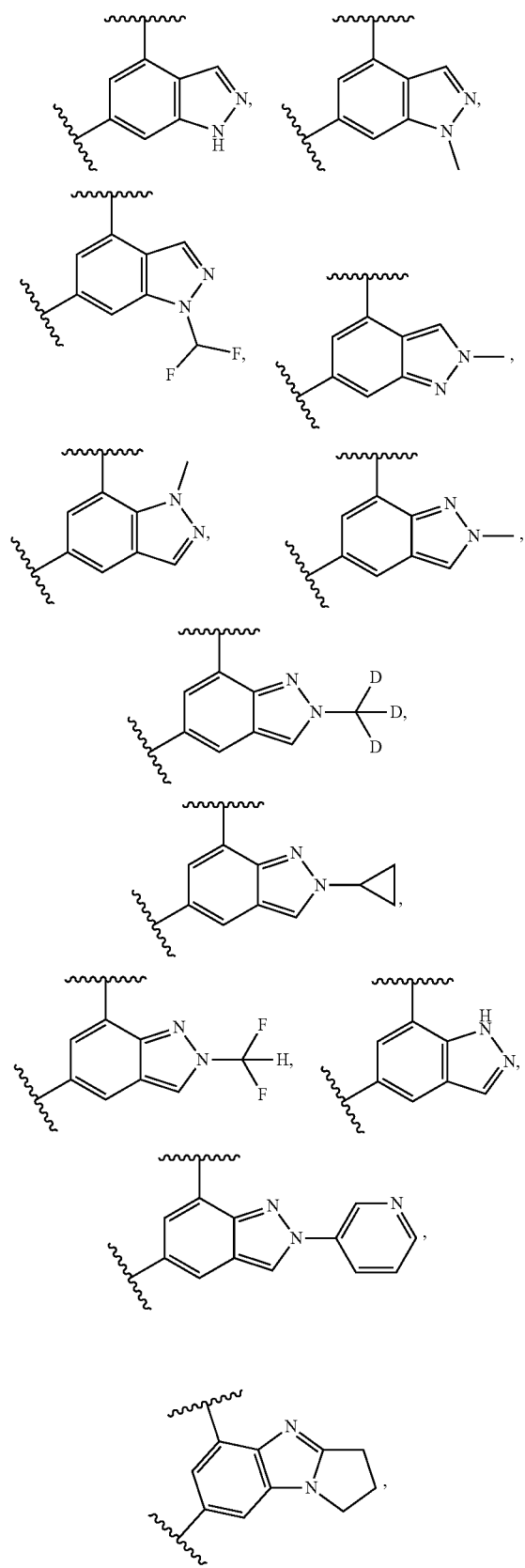
-continued
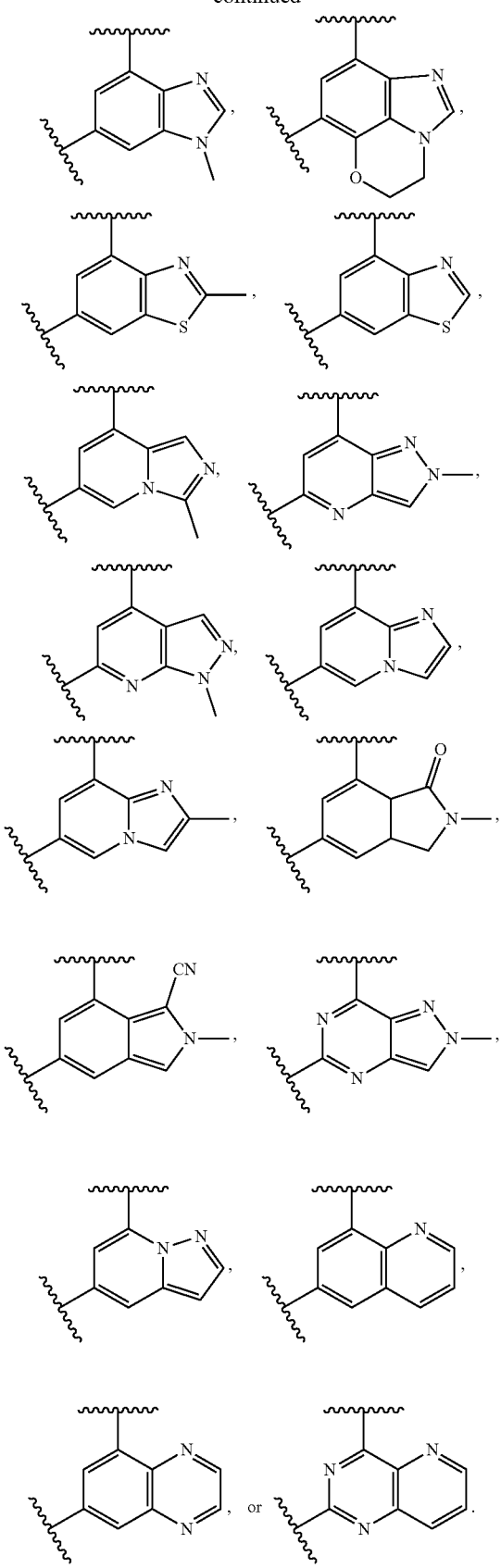

In some embodiments of a compound of Formula (I) or (Ia)-(Ic),

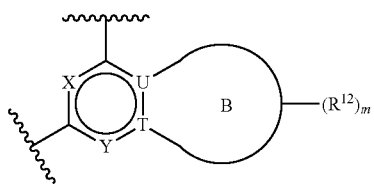

is

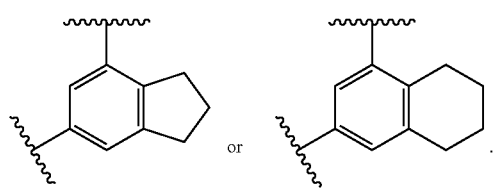 [SMILES: *c1cc(*)c2c(c1)CCC2 ; *c1cc(*)c2c(c1)CCCC2]

In some embodiments of a compound of Formula (I) or (Ia)-(Ic),

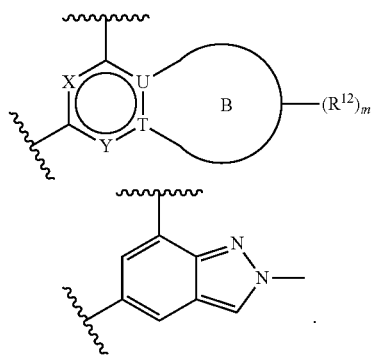

Also disclosed herein is a compound of Formula (II), or a pharmaceutically acceptable salt, or stereoisomer thereof:

Formula (II)

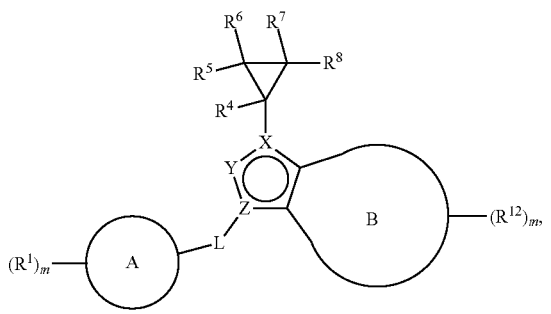

wherein:
X is —N— or —C—;
Y is —N— or —CR$^Y$—;
R is hydrogen, halogen, —CN, —OH, —OR$^a$, —NR$^c$R$^d$, methyl, C$_1$-C$_6$haloalkyl, C$_1$-C$_6$hydroxyalkyl, C$_1$-C$_6$aminoalkyl, or C$_1$-C$_6$heteroalkyl;
Z is —N— or —C—;

Ring A is cycloalkyl, heterocycloalkyl, aryl, or heteroaryl;
each R$^1$ is independently halogen, —CN, —NO$_2$, —OH, —OR$^a$, —OC(=O)R$^a$, —OC(=O)OR$^b$, —OC(=O)NR$^c$R$^d$, SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R$^{1a}$;
or two R$^1$ on the same atom are taken together to form an oxo;
each R$^{1a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
or two R$^{1a}$ on the same atom are taken together to form an oxo;
n is 0, 1, 2, 3, or 4;
L is absent, —O—, —S—, —NR$^2$—, —C(R$^3$)$_2$—, —C(R$^3$)$_2$—C(R$^3$)$_2$—, —C(R$^3$)=C(R$^3$)—,

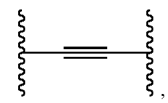

—C(R$^3$)$_2$O—, —OC(R$^3$)$_2$—, —C(R$^3$)$_2$S—, —SC(R$^3$)$_2$—, —C(R$^3$)$_2$NR$^2$—, or —NR$^2$C(R$^3$)$_2$—;
R$^2$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;
each R$^3$ is independently hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;
or two R$^3$ on the same carbon are taken together to form an oxo;

or two $R^3$ on the same carbon are taken together to form a cycloalkyl or heterocycloalkyl; each optionally substituted with one or more R;

or two $R^3$ on different carbons are taken together to form a cycloalkyl, heterocycloalkyl, aryl, or heteroaryl; each optionally substituted with one or more R;

$R^4$, $R^5$, $R^6$, and $R^7$ are each independently hydrogen, halogen, or $C_1$-$C_6$alkyl;

$R^8$ is —C(=O)$OR^9$, —C(=O)$NR^{10}R^{11}$, —S(=O)$_2NR^{10}R^{11}$, —P(=O)($OR^{10}$)($OR^{11}$), or —B($OR^{10}$)($OR^{11}$);

$R^9$ is hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more $R^{9a}$;

each $R^{9a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{9a}$ on the same atom are taken together to form an oxo;

$R^{10}$ and $R^{11}$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more $R^{10a}$;

or $R^{10}$ and $R^{11}$ are taken together with the atom to which they are attached to form a heterocycloalkyl optionally substituted with one or more $R^{10b}$;

each $R^{10a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{10a}$ on the same atom are taken together to form an oxo;

each $R^{10b}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{10b}$ on the same atom are taken together to form an oxo;

Ring B is a phenyl or 6-membered heteroaryl;

each $R^{12}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{12}$ on the same atom are taken together to form an oxo;

or two $R^{12}$ on different atoms are taken together to form a cycloalkyl, heterocycloalkyl, aryl, or heteroaryl; each optionally substituted with one or more R;

m is 0, 1, 2, 3, or 4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —SF$_5$, —SH, —S(=O)C$_1$-C$_3$alkyl, —S(=O)$_2$C$_1$-C$_3$alkyl, —S(=O)$_2$NH$_2$, —S(=O)$_2$NHC$_1$-C$_3$alkyl, —S(=O)$_2$N(C$_1$-C$_3$alkyl)$_2$, —S(=O)(=NC$_1$-C$_3$alkyl)(C$_1$-C$_3$alkyl), —NH$_2$, —NHC$_1$-C$_3$alkyl, —N(C$_1$-C$_3$alkyl)$_2$, —N=S(=O)(C$_1$-C$_3$alkyl)$_2$, —C(=O)C$_1$-C$_3$alkyl, —C(=O)OH, —C(=O)OC$_1$-C$_3$alkyl, —C(=O)NH$_2$, —C(=O)NHC$_1$-C$_3$alkyl, —C(=O)N(C$_1$-C$_3$alkyl)$_2$, —P(=O)(C$_1$-C$_3$alkyl)$_2$, C$_1$-C$_3$alkyl, C$_1$-C$_3$alkoxy, C$_1$-C$_3$haloalkyl, C$_1$-C$_3$haloalkoxy, C$_1$-C$_3$hydroxyalkyl, C$_1$-C$_3$aminoalkyl, C$_1$-C$_3$heteroalkyl, or C$_3$-C$_6$cycloalkyl;

or two R on the same atom form an oxo.

In some embodiments, the compound of Formula (II) is:

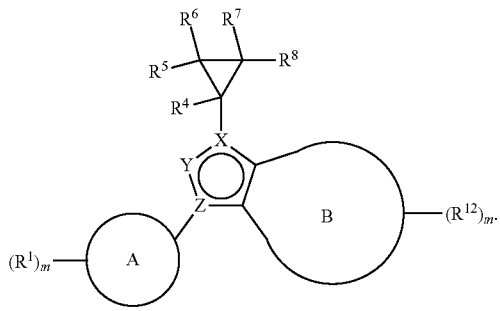

In some embodiments of a compound of Formula (II), the compound is of Formula (IIa):

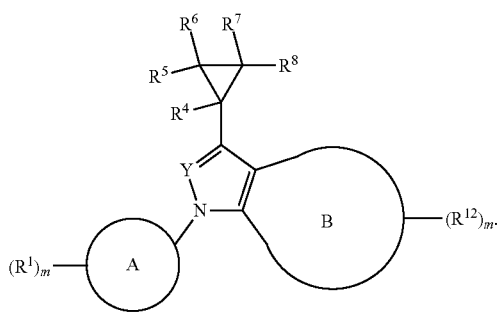

Formula (IIa)

In some embodiments of a compound of Formula (II), the compound is of Formula (IIb):

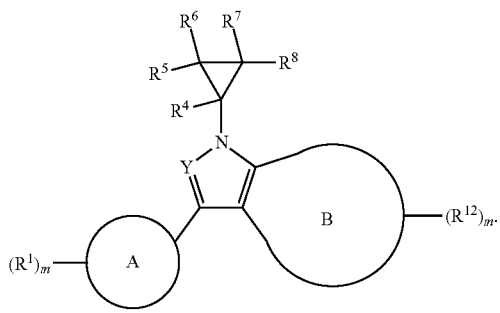

Formula (IIb)

In some embodiments of a compound of Formula (II), (IIa), or (IIb), Y is —N—. In some embodiments of a compound of Formula (II), (IIa), or (IIb), Y is —CR$^Y$—.

In some embodiments of a compound of Formula (II), (IIa), or (IIb), R$^Y$ is hydrogen, halogen, methyl, or C$_1$-C$_6$haloalkyl. In some embodiments of a compound of Formula (II), (IIa), or (IIb), R is hydrogen.

In some embodiments of a compound of Formula (II), (IIa), or (IIb), Ring A is cycloalkyl or heterocycloalkyl. In some embodiments of a compound of Formula (II), (IIa), or (IIb), Ring A is cycloalkyl. In some embodiments of a compound of Formula (II), (IIa), or (IIb), Ring A is heterocycloalkyl. In some embodiments of a compound of Formula (II), (IIa), or (IIb), Ring A is aryl or heteroaryl. In some embodiments of a compound of Formula (II), (IIa), or (IIb), Ring A is phenyl. In some embodiments of a compound of Formula (II), (IIa), or (IIb), Ring A is heteroaryl. In some embodiments of a compound of Formula (II), (IIa), or (IIb), Ring A is 5- or 6-membered heteroaryl.

In some embodiments of a compound of Formula (II), (IIa), or (IIb), each R$^1$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, cycloalkyl, heterocycloalkyl, aryl, and heteroaryl is independently optionally substituted with one or more R$^{1a}$. In some embodiments of a compound of Formula (II), (IIa), or (IIb), each R$^1$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (II), (IIa), or (IIb), each R$^1$ is independently halogen, —CN, —OH, —OR$^a$, —NR$^c$R$^d$, C$_1$-C$_6$alkyl, or C$_1$-C$_6$haloalkyl. In some embodiments of a compound of Formula (II), (IIa), or (IIb), each R$^1$ is independently halogen, —OR$^a$, C$_1$-C$_6$alkyl, or C$_1$-C$_6$haloalkyl. In some embodiments of a compound of Formula (II), (IIa), or (IIb), each R$^1$ is independently halogen, C$_1$-C$_6$alkyl, or C$_1$-C$_6$haloalkyl. In some embodiments of a compound of Formula (II), (IIa), or (IIb), each R$^1$ is independently C$_1$-C$_6$haloalkyl.

In some embodiments of a compound of Formula (II), (IIa), or (IIb), each R$^{1a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl; wherein each alkyl, cycloalkyl, and heterocycloalkyl is independently optionally substituted with one or more R; or two R$^{1a}$ on the same atom are taken together to form an oxo. In some embodiments of a compound of Formula (II), (IIa), or (IIb), each R$^{1a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (II), (IIa), or (IIb), each R$^{1a}$ is independently halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (II), (IIa), or (IIb), each R$^{1a}$ is independently halogen, C$_1$-C$_6$alkyl, or C$_1$-C$_6$haloalkyl.

In some embodiments of a compound of Formula (II), (IIa), or (IIb), n is 0, 1, 2, or 3. In some embodiments of a compound of Formula (II), (IIa), or (IIb), n is 0, 1, or 2. In some embodiments of a compound of Formula (II), (IIa), or (IIb), n is 0 or 1. In some embodiments of a compound of Formula (II), (IIa), or (IIb), n is 1 or 2. In some embodiments of a compound of Formula (II), (IIa), or (IIb), n is 0. In some embodiments of a compound of Formula (II), (IIa), or (IIb), n is 1. In some embodiments of a compound of Formula (II), (IIa), or (IIb), n is 2. In some embodiments of a compound of Formula (II), (IIa), or (IIb), n is 3.

In some embodiments of a compound of Formula (II), (IIa), or (IIb),

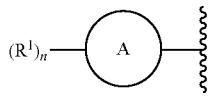

is

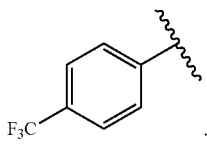

In some embodiments of a compound of Formula (II), (IIa), or (IIb), $R^4$ is hydrogen or $C_1$-$C_6$alkyl. In some embodiments of a compound of Formula (II), (IIa), or (IIb), $R^4$ is hydrogen.

In some embodiments of a compound of Formula (II), (IIa), or (IIb), $R^5$ is hydrogen or $C_1$-$C_6$alkyl. In some embodiments of a compound of Formula (II), (IIa), or (IIb), $R^5$ is hydrogen.

In some embodiments of a compound of Formula (II), (IIa), or (IIb), $R^6$ is hydrogen or $C_1$-$C_6$alkyl. In some embodiments of a compound of Formula (II), (IIa), or (IIb), $R^6$ is hydrogen.

In some embodiments of a compound of Formula (II), (IIa), or (IIb), $R^7$ is hydrogen or $C_1$-$C_6$alkyl. In some embodiments of a compound of Formula (II), (IIa), or (IIb), $R^7$ is hydrogen.

In some embodiments of a compound of Formula (II), (IIa), or (IIb), $R^8$ is —C(=O)O$R^9$, —C(=O)N$R^{10}R^{11}$, or —S(=O)$_2$N$R^{10}R^{11}$. In some embodiments of a compound of Formula (II), (IIa), or (IIb), $R^8$ is —C(=O)O$R^9$. In some embodiments of a compound of Formula (II), (IIa), or (IIb), $R^8$ is —C(=O)N$R^{10}R^{11}$. In some embodiments of a compound of Formula (II), (IIa), or (IIb), $R^8$ is —S(=O)$_2$N$R^{10}R^{11}$.

In some embodiments of a compound of Formula (II), (IIa), or (IIb), $R^9$ is hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more $R^{9a}$. In some embodiments of a compound of Formula (II), (IIa), or (IIb), $R^9$ is hydrogen, $C_1$-$C_6$alkyl, $C_1$-$C_6$haloalkyl, cycloalkyl, heterocycloalkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more $R^{9a}$. In some embodiments of a compound of Formula (II), (IIa), or (IIb), $R^9$ is hydrogen, $C_1$-$C_6$alkyl, $C_1$-$C_6$haloalkyl, cycloalkyl, or heterocycloalkyl, wherein each alkyl, cycloalkyl, and heterocycloalkyl is independently optionally substituted with one or more $R^{9a}$. In some embodiments of a compound of Formula (II), (IIa), or (IIb), $R^9$ is hydrogen, $C_1$-$C_6$alkyl, $C_1$-$C_6$haloalkyl, cycloalkyl, or heterocycloalkyl. In some embodiments of a compound of Formula (II), (IIa), or (IIb), $R^9$ is hydrogen, $C_1$-$C_6$alkyl, or $C_1$-$C_6$haloalkyl. In some embodiments of a compound of Formula (II), (IIa), or (IIb), $R^9$ is hydrogen or $C_1$-$C_6$alkyl. In some embodiments of a compound of Formula (II), (IIa), or (IIb), $R^9$ is hydrogen.

In some embodiments of a compound of Formula (II), (IIa), or (IIb), each $R^{9a}$ is independently halogen, —CN, —OH, —O$R^a$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two $R^{9a}$ on the same atom are taken together to form an oxo. In some embodiments of a compound of Formula (II), (IIa), or (IIb), each $R^{9a}$ is independently halogen, —CN, —OH, —O$R^a$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (II), (IIa), or (IIb), each $R^{9a}$ is independently halogen, —CN, —OH, —O$R^a$, —N$R^cR^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (II), (IIa), or (IIb), each $R^{9a}$ is independently halogen, $C_1$-$C_6$alkyl, or $C_1$-$C_6$haloalkyl.

In some embodiments of a compound of Formula (II), (IIa), or (IIb), $R^{10}$ and $R^{11}$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more $R^{10a}$. In some embodiments of a compound of Formula (II), (IIa), or (IIb), $R^{10}$ and $R^{11}$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_1$-$C_6$alkylene(aryl), or $C_1$-$C_6$alkylene(heteroaryl), wherein each alkyl, alkylene, aryl, and heteroaryl is independently optionally substituted with one or more $R^{10a}$. In some embodiments of a compound of Formula (II), (IIa), or (IIb), $R^{10}$ and $R^{11}$ are each independently hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (II), (IIa), or (IIb), $R^{10}$ and $R^{11}$ are each independently hydrogen, $C_1$-$C_6$alkyl, $C_1$-$C_6$hydroxyalkyl, or $C_1$-$C_6$heteroalkyl. In some embodiments of a compound of Formula (II), (IIa), or (IIb), $R^{10}$ and $R^{11}$ are each independently hydrogen or $C_1$-$C_6$alkyl.

In some embodiments of a compound of Formula (II), (IIa), or (IIb), each $R^{10a}$ is independently halogen, —CN, —OH, —O$R^a$, —N$R^cR^d$, —C(=O)$R^a$, —C(=O)O$R^b$, —C(=O)N$R^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two $R^{10a}$ on the same atom are taken together to form an oxo. In some embodiments of a compound of Formula (II), (IIa), or (IIb), each $R^{10a}$ is independently halogen, —CN, —OH, —O$R^a$, —N$R^cR^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (II), (IIa), or (IIb), each R$^{10a}$ is independently halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (II), (IIa), or (IIb), each R$^{10a}$ is independently halogen, C$_1$-C$_6$alkyl, or C$_1$-C$_6$haloalkyl.

In some embodiments of a compound of Formula (II), (IIa), or (IIb), R$^{10}$ and R$^{11}$ are taken together with the atom to which they are attached to form a heterocycloalkyl optionally substituted with one or more R$^{10b}$.

In some embodiments of a compound of Formula (II), (IIa), or (IIb), each R$^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl; wherein each alkyl, cycloalkyl, and heterocycloalkyl is independently optionally substituted with one or more R; or two R$^{10b}$ on the same atom are taken together to form an oxo. In some embodiments of a compound of Formula (II), (IIa), or (IIb), each R$^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (II), (IIa), or (IIb), each R$^{10b}$ is independently halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (II), (IIa), or (IIb), each R$^{10b}$ is independently halogen, C$_1$-C$_6$alkyl, or C$_1$-C$_6$haloalkyl. In some embodiments of a compound of Formula (II), (IIa), or (IIb), each R$^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl. In some embodiments of a compound of Formula (II), (IIa), or (IIb), each R$^{10b}$ is independently —OH, —OR$^a$, or —NR$^c$R$^d$.

In some embodiments of a compound of Formula (II), (IIa), or (IIb), Ring B is a phenyl. In some embodiments of a compound of Formula (II), (IIa), or (IIb), Ring B is a 6-membered heteroaryl. In some embodiments of a compound of Formula (II), (IIa), or (IIb), Ring B is a pyridinyl, pyrimidinyl, or pyrazinyl. In some embodiments of a compound of Formula (II), (IIa), or (IIb), Ring B is a pyridinyl. In some embodiments of a compound of Formula (II), (IIa), or (IIb), Ring B is a pyrimidinyl. In some embodiments of a compound of Formula (II), (IIa), or (IIb), Ring B is a pyrazinyl.

In some embodiments of a compound of Formula (II), (IIa), or (IIb), each R$^{12}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (II), (IIa), or (IIb), each R$^{12}$ is independently halogen, —CN, —OH, —OR$^a$, —NR$^c$R$^d$, C$_1$-C$_6$alkyl, C$_1$-C$_6$haloalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (II), (IIa), or (IIb), each R$^{12}$ is independently halogen, —CN, —OH, C$_1$-C$_6$alkyl, C$_1$-C$_6$haloalkyl, cycloalkyl, or heterocycloalkyl. In some embodiments of a compound of Formula (II), (IIa), or (IIb), each R$^{12}$ is independently —CN, C$_1$-C$_6$alkyl, or C$_1$-C$_6$haloalkyl. In some embodiments of a compound of Formula (II), (IIa), or (IIb), each R$^{12}$ is independently C$_1$-C$_6$alkyl.

In some embodiments of a compound of Formula (II), (IIa), or (IIb), m is 0 or 1. In some embodiments of a compound of Formula (II), (IIa), or (IIb), m is 1 or 2. In some embodiments of a compound of Formula (II), (IIa), or (IIb), m is 0. In some embodiments of a compound of Formula (II), (IIa), or (IIb), m is 1. In some embodiments of a compound of Formula (II), (IIa), or (IIb), m is 2. In some embodiments of a compound of Formula (II), (IIa), or (IIb), m is 3.

In some embodiments of a compound of Formula (II), (IIa), or (IIb),

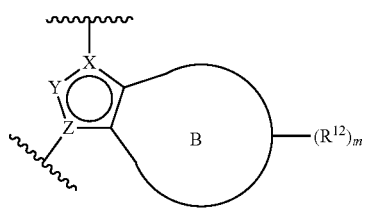

is

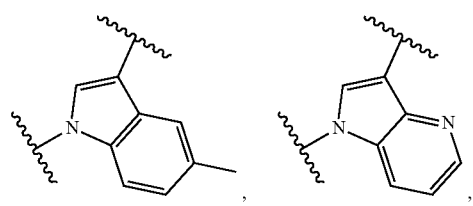

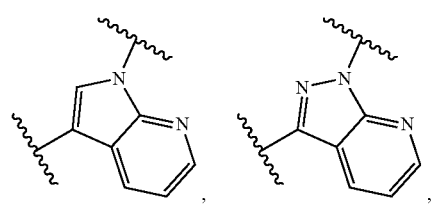

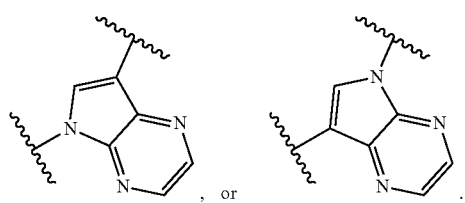

Also disclosed herein is a compound of Formula (III), or a pharmaceutically acceptable salt, or stereoisomer thereof:

Formula (III)

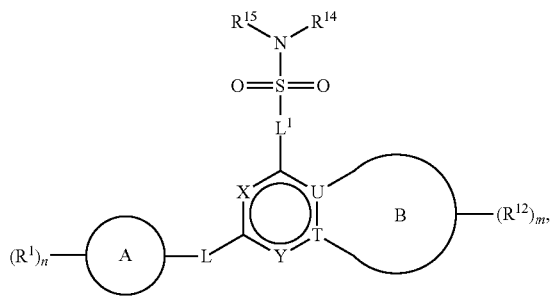

wherein:
X is —N— or —CR$^X$—;
R$^X$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
Y is —N— or —CR$^Y$—;
R$^Y$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
Ring A is cycloalkyl, heterocycloalkyl, aryl, or heteroaryl;
each R$^1$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R$^{1a}$;
or two R$^1$ on the same atom are taken together to form an oxo;
each R$^{1a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
or two R$^{1a}$ on the same atom are taken together to form an oxo;
n is 0, 1, 2, 3, or 4;
L is absent, —O—, —S—, —NR$^2$—, —C(R$^3$)$_2$—, —C(R$^3$)$_2$—C(R$^3$)$_2$—, —C(R$^3$)=C(R$^3$)—, —C(R$^3$)$_2$O—, —OC(R$^3$)$_2$—, —C(R$^3$)$_2$S—, —SC(R$^3$)$_2$—, —C(R$^3$)$_2$NR$^2$—, or —NR$^2$C(R$^3$)$_2$—;
R$^2$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;
each R$^3$ is independently hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;
or two R$^3$ on the same carbon are taken together to form an oxo;
or two R$^3$ on the same carbon are taken together to form a cycloalkyl or heterocycloalkyl; each optionally substituted with one or more R;
or two R$^3$ on different carbons are taken together to form a cycloalkyl, heterocycloalkyl, aryl, or heteroaryl; each optionally substituted with one or more R;
L$^1$ is —[C(R$^{13}$)$_2$]$_p$—;
each R$^{13}$ is independently hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;
or two R$^{13}$ on the same carbon are taken together to form an oxo;
or two R$^{13}$ on the same carbon are taken together to form a C$_2$-C$_6$ alkylidenyl optionally substituted with or more R;
or two R$^{13}$ on adjacent carbons are taken together to form a double bond;
or two R$^{13}$ on the same carbon are taken together to form a cycloalkyl or heterocycloalkyl; each optionally substituted with one or more R;
p is 2, 3, or 4;
R$^{14}$ and R$^{15}$ are independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
or R$^{14}$ and R$^{15}$ are taken together to form a heterocycloalkyl optionally substituted with one or more R;
U is —C— or —N—;
T is —C— or —N—;
provided that U and T are not both —N—;
Ring B is a 5-membered heteroaryl or 5-membered heterocycloalkyl;

each $R^{12}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{12}$ on the same atom are taken together to form an oxo;

or two $R^{12}$ on the same carbon are taken together to form a cycloalkyl or heterocycloalkyl; each optionally substituted with one or more R;

or two $R^{12}$ on different atoms are taken together to form a cycloalkyl, heterocycloalkyl, aryl, or heteroaryl; each optionally substituted with one or more R;

m is 0, 1, 2, 3, 4, 5, or 6;

or one $R^{12}$ and R are taken together to form a cycloalkyl, heterocycloalkyl, aryl, or heteroaryl; each optionally substituted with one or more R;

each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

$R^c$ and $R^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —SF$_5$, —SH, —S(=O)C$_1$-C$_3$alkyl, —S(=O)$_2$C$_1$-C$_3$alkyl, —S(=O)$_2$NH$_2$, —S(=O)$_2$NHC$_1$-C$_3$alkyl, —S(=O)$_2$N(C$_1$-C$_3$alkyl)$_2$, —S(=O)(=NC$_1$-C$_3$alkyl)(C$_1$-C$_3$alkyl), —NH$_2$, —NHC$_1$-C$_3$alkyl, —N(C$_1$-C$_3$alkyl)$_2$, —N=S(=O)(C$_1$-C$_3$alkyl)$_2$, —C(=O)C$_1$-C$_3$alkyl, —C(=O)OH, —C(=O)OC$_1$-C$_3$alkyl, —C(=O)NH$_2$, —C(=O)NHC$_1$-C$_3$alkyl, —C(=O)N(C$_1$-C$_3$alkyl)$_2$, —P(=O)(C$_1$-C$_3$alkyl)$_2$, C$_1$-C$_3$alkyl, C$_1$-C$_3$alkoxy, C$_1$-C$_3$haloalkyl, C$_1$-C$_3$haloalkoxy, C$_1$-C$_3$hydroxyalkyl, C$_1$-C$_3$aminoalkyl, C$_1$-C$_3$heteroalkyl, or C$_3$-C$_6$cycloalkyl;

or two R on the same atom form an oxo.

In some embodiments of a compound of Formula (III), the compound is of Formula (IIIa):

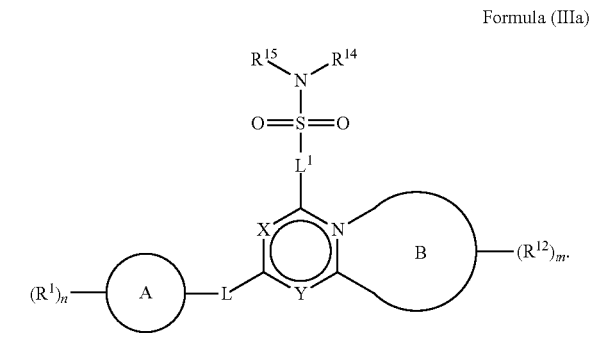

Formula (IIIa)

In some embodiments of a compound of Formula (III), the compound is of Formula (IIIb):

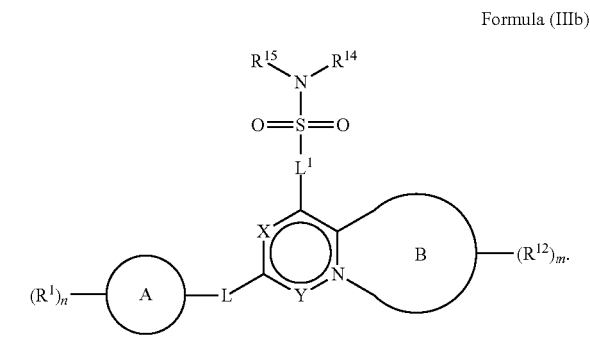

Formula (IIIb)

In some embodiments of a compound of Formula (III), (IIIa), or (IIIb), X is —N—. In some embodiments of a compound of Formula (III), (IIIa), or (IIIb), X is —CR$^X$—. In some embodiments of a compound of Formula (III), (IIIa), or (IIIb), R$^X$ is hydrogen, halogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (III), (IIIa), or (IIIb), R$^X$ is hydrogen, halogen, C$_1$-C$_6$alkyl, or C$_1$-C$_6$haloalkyl. In some embodiments of a compound of Formula (III), (IIIa), or (IIIb), R$^X$ is hydrogen, halogen, or C$_1$-C$_6$alkyl. In some embodiments of a compound of Formula (III), (IIIa), or (IIIb), R$^X$ is hydrogen or halogen. In some embodiments of a compound of Formula (III), (IIIa), or (IIIb), R$^X$ is hydrogen.

In some embodiments of a compound of Formula (III), (IIIa), or (IIIb), Y is —N—. In some embodiments of a compound of Formula (III), (IIIa), or (IIIb), Y is —CR$^Y$—. In some embodiments of a compound of Formula (III), (IIIa), or (IIIb), R$^Y$ is hydrogen, halogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (III), (IIIa), or (IIIb), R is hydrogen, halogen, C$_1$-C$_6$alkyl, or C$_1$-C$_6$haloalkyl. In some embodiments of a compound of Formula (III), (IIIa), or (IIIb), R$^Y$ is hydrogen, halogen, or $C_1$-$C_6$alkyl. In some embodiments of a compound of Formula (III), (IIIa), or (IIIb), $R^Y$ is hydrogen or halogen. In some embodiments of a compound of Formula (III), (IIIa), or (IIIb), $R^Y$ is hydrogen.

In some embodiments of a compound of Formula (III), (IIIa), or (IIIb), or a pharmaceutically acceptable salt, or stereoisomer thereof, wherein L is absent, —O—, —C($R^3$)$_2$, or —C($R^3$)$_2$O—. In some embodiments of a compound of Formula (III), (IIIa), or (IIIb), L is absent, —O—, or —C($R^3$)$_2$. In some embodiments of a compound of Formula (III), (IIIa), or (IIIb), L is absent or —O—. In some embodiments of a compound of Formula (III), (IIIa), or (IIIb), L is —O— or —C($R^3$)$_2$O—. In some embodiments of a compound of Formula (III), (IIIa), or (IIIb), L is absent. In some embodiments of a compound of Formula (III), (IIIa), or (IIIb), L is —O—. In some embodiments of a compound of Formula (III), (IIIa), or (IIIb), L is —C($R^3$)$_2$.

In some embodiments of a compound of Formula (III), (IIIa), or (IIIb), $R^2$ is hydrogen, $C_1$-$C_6$alkyl, or $C_1$-$C_6$haloalkyl. In some embodiments of a compound of Formula (III), (IIIa), or (IIIb), $R^2$ is hydrogen or $C_1$-$C_6$alkyl. In some embodiments of a compound of Formula (III), (IIIa), or (IIIb), $R^2$ is hydrogen.

In some embodiments of a compound of Formula (III), (IIIa), or (IIIb), each $R^3$ is independently hydrogen, $C_1$-$C_6$alkyl, or $C_1$-$C_6$haloalkyl. In some embodiments of a compound of Formula (III), (IIIa), or (IIIb), each $R^3$ is independently hydrogen or $C_1$-$C_6$alkyl. In some embodiments of a compound of Formula (III), (IIIa), or (IIIb), each $R^3$ is hydrogen.

In some embodiments of a compound of Formula (III), (IIIa), or (IIIb), Ring A is cycloalkyl or heterocycloalkyl. In some embodiments of a compound of Formula (III), (IIIa), or (IIIb), Ring A is cycloalkyl. In some embodiments of a compound of Formula (III), (IIIa), or (IIIb), Ring A is heterocycloalkyl. In some embodiments of a compound of Formula (III), (IIIa), or (IIIb), Ring A is aryl or heteroaryl. In some embodiments of a compound of Formula (III), (IIIa), or (IIIb), Ring A is phenyl. In some embodiments of a compound of Formula (III), (IIIa), or (IIIb), Ring A is heteroaryl. In some embodiments of a compound of Formula (III), (IIIa), or (IIIb), Ring A is 5- or 6-membered heteroaryl.

In some embodiments of a compound of Formula (III), (IIIa), or (IIIb), each $R^1$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more $R^{1a}$. In some embodiments of a compound of Formula (III), (IIIa), or (IIIb), each $R^1$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (III), (IIIa), or (IIIb), each $R^1$ is independently halogen, —CN, —OH, —OR$^a$, —NR$^c$R$^d$, $C_1$-$C_6$alkyl, or $C_1$-$C_6$haloalkyl. In some embodiments of a compound of Formula (III), (IIIa), or (IIIb), each $R^1$ is independently halogen, —OR$^a$, $C_1$-$C_6$alkyl, or $C_1$-$C_6$haloalkyl. In some embodiments of a compound of Formula (III), (IIIa), or (IIIb), each $R^1$ is independently halogen, $C_1$-$C_6$alkyl, or $C_1$-$C_6$haloalkyl. In some embodiments of a compound of Formula (III), (IIIa), or (IIIb), each $R^1$ is independently $C_1$-$C_6$haloalkyl.

In some embodiments of a compound of Formula (III), (IIIa), or (IIIb), each $R^{1a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two $R^{1a}$ on the same atom are taken together to form an oxo. In some embodiments of a compound of Formula (III), (IIIa), or (IIIb), each $R^{1a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (III), (IIIa), or (IIIb), each $R^{1a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (III), (IIIa), or (IIIb), each $R^{1a}$ is independently halogen, $C_1$-$C_6$alkyl, or $C_1$-$C_6$haloalkyl.

In some embodiments of a compound of Formula (III), (IIIa), or (IIIb), n is 0, 1, 2, or 3. In some embodiments of a compound of Formula (III), (IIIa), or (IIIb), n is 0, 1, or 2. In some embodiments of a compound of Formula (III), (IIIa), or (IIIb), n is 0 or 1. In some embodiments of a compound of Formula (III), (IIIa), or (IIIb), n is 1 or 2. In some embodiments of a compound of Formula (III), (IIIa), or (IIIb), n is 0. In some embodiments of a compound of Formula (III), (IIIa), or (IIIb), n is 1. In some embodiments of a compound of Formula (III), (IIIa), or (IIIb), n is 2. In some embodiments of a compound of Formula (III) (IIIa), or (IIIb), n is 3.

In some embodiments of a compound of Formula (III) (IIIa), or (IIIb),

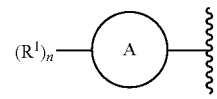

is

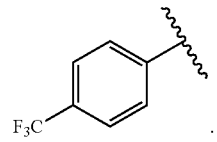

.

In some embodiments of a compound of Formula (III), (IIIa), or (IIIb), each $R^{13}$ is independently hydrogen, halogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R. In some embodiments of a compound of Formula (III), (IIIa), or (IIIb), each $R^{13}$ is independently hydrogen, halogen, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one or more R. In some embodiments of a compound of Formula (III), (IIIa), or (IIIb), each $R^{13}$ is independently hydrogen, $C_1$-$C_6$alkyl, $C_1$-$C_6$haloalkyl, or $C_1$-$C_6$hydroxyalkyl. In some embodiments of a compound of Formula (III), (IIIa), or (IIIb), two $R^{13}$ on the same carbon are taken together to form an $C_2$-$C_6$ alkylidenyl. In some embodiments of a compound of Formula (III), (IIIa), or (IIIb), two $R^{13}$ on adjacent carbons are taken together to form a double bond. In some embodiments of a compound of Formula (III), (IIIa), or (IIIb), two $R^{13}$ on the same carbon are taken together to form a cycloalkyl or heterocycloalkyl, each optionally substituted with one or more R. In some embodiments of a compound of Formula (III), (IIIa), or (IIIb), two $R^{13}$ on the same carbon are taken together to form a cycloalkyl optionally substituted with one or more R.

In some embodiments of a compound of Formula (III), (IIIa), or (IIIb), p is 2 or 3. In some embodiments of a compound of Formula (III), (IIIa), or (IIIb), p is 2. In some embodiments of a compound of Formula (III), (IIIa), or (IIIb), p is 3. In some embodiments of a compound of Formula (III), (IIIa), or (IIIb), p is 4.

In some embodiments of a compound of Formula (III), (IIIa), or (IIIb), $R^{14}$ and $R^{15}$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl; wherein each alkyl, cycloalkyl, and heterocycloalkyl is independently optionally substituted with one or more R.

In some embodiments of a compound of Formula (III), (IIIa), or (IIIb), $R^{14}$ and $R^{15}$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl; wherein each alkyl is independently optionally substituted with one or more R.

In some embodiments of a compound of Formula (III), (IIIa), or (IIIb), $R^{14}$ and $R^{15}$ are independently hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (III), (IIIa), or (IIIb), $R^{14}$ and $R^{15}$ are independently hydrogen, $C_1$-$C_6$alkyl, or $C_1$-$C_6$haloalkyl. In some embodiments of a compound of Formula (III), (IIIa), or (IIIb), $R^{14}$ and $R^{15}$ are independently hydrogen or $C_1$-$C_6$alkyl. In some embodiments of a compound of Formula (III), (IIIa), or (IIIb), $R^{14}$ and $R^{15}$ are taken together to form a heterocycloalkyl optionally substituted with one or more R.

In some embodiments of a compound of Formula (III), (IIIa), or (IIIb),

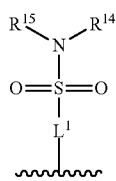

is

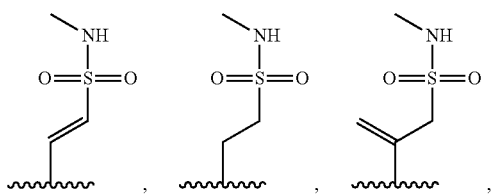

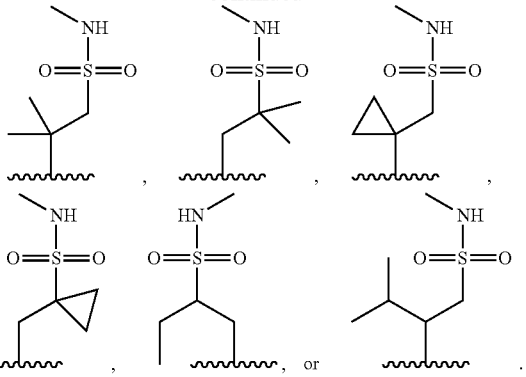

In some embodiments of a compound of Formula (III), (IIIa), or (IIIb), Ring B is a 5-membered heteroaryl. In some embodiments of a compound of Formula (III), (IIIa), or (IIIb), Ring B is pyrrolyl, furanyl, thiophenyl, imidazolyl, pyrazolyl, thiazolyl, oxazolyl, or triazolyl. In some embodiments of a compound of Formula (III), (IIIa), or (IIIb), Ring B is imidazolyl, pyrazolyl, thiazolyl, or oxazolyl. In some embodiments of a compound of Formula (III), (IIIa), or (IIIb), Ring B is pyrazolyl. In some embodiments of a compound of Formula (III), (IIIa), or (IIIb), Ring B is a 6-membered heteroaryl. In some embodiments of a compound of Formula (III), (IIIa), or (IIIb), Ring B is a pyridinyl, pyrimidinyl, or pyrazinyl. In some embodiments of a compound of Formula (III), (IIIa), or (IIIb), Ring B is a pyridinyl. In some embodiments of a compound of Formula (III), (IIIa), or (IIIb), Ring B is a 5-membered heterocycloalkyl.

In some embodiments of a compound of Formula (III), (IIIa), or (IIIb), each $R^{12}$ is independently halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (III), (IIIa), or (IIIb), each $R^{12}$ is independently halogen, —CN, —OH, —$OR^a$, —$NR^cR^d$, $C_1$-$C_6$alkyl, $C_1$-$C_6$haloalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (III), (IIIa), or (IIIb), each $R^{12}$ is independently halogen, —CN, —OH, $C_1$-$C_6$alkyl, $C_1$-$C_6$haloalkyl, cycloalkyl, or heterocycloalkyl. In some embodiments of a compound of Formula (III), (IIIa), or (IIIb), each $R^{12}$ is independently —CN, $C_1$-$C_6$alkyl, or $C_1$-$C_6$haloalkyl. In some embodiments of a compound of Formula (III), (IIIa), or (IIIb), each $R^{12}$ is independently $C_1$-$C_6$alkyl.

In some embodiments of a compound of Formula (III), (IIIa), or (IIIb), m is 0 or 1. In some embodiments of a compound of Formula (III), (IIIa), or (IIIb), m is 1 or 2. In some embodiments of a compound of Formula (III), (IIIa), or (IIIb), m is 0. In some embodiments of a compound of Formula (III), (IIIa), or (IIIb), m is 1. In some embodiments of a compound of Formula (III), (IIIa), or (IIIb), m is 2. In some embodiments of a compound of Formula (III), (IIIa), or (IIIb), m is 3.

In some embodiments of a compound of Formula (III), (IIIa), or (IIIb),

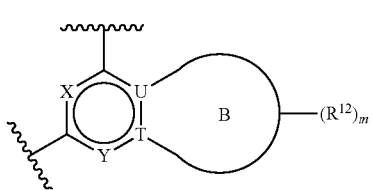

is

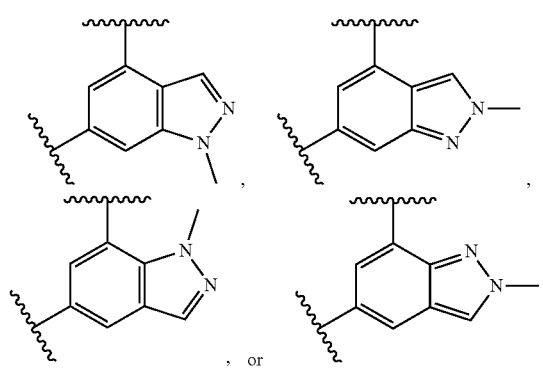

, or

Also disclosed herein is a compound of Formula (IV), or a pharmaceutically acceptable salt, or stereoisomer thereof:

Formula (IV)

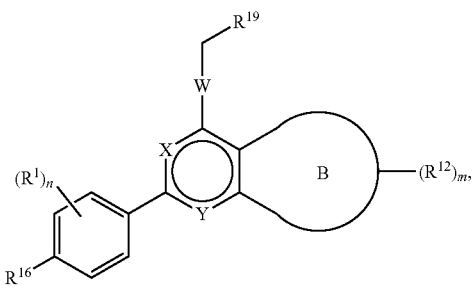

wherein:
X is —N— or —CR$^X$—;
R$^X$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
Y is —N— or —CR$^Y$—;
R$^Y$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
W is —C(R$^{17}$)$_2$—, —O—, or —NR$^{18}$—;
each R$^{17}$ is independently hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;
or two R$^{17}$ on the same carbon are taken together to form an oxo;
or two R$^{17}$ on the same carbon are taken together to form a cycloalkyl or heterocycloalkyl; each optionally substituted with one or more R;
R$^{18}$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;
R$^{19}$ is —C(=O)OR$^9$, —C(=O)NR$^{10}$R$^{11}$, —S(=O)$_2$NR$^{10}$R$^{11}$, —P(=O)(OR$^{10}$)(OR$^{11}$), or —B(OR$^{10}$)(OR$^{11}$);
R$^9$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R$^{9a}$;
each R$^{9a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
or two R$^{9a}$ on the same atom are taken together to form an oxo;
R$^{10}$ and R$^{11}$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R$^{10a}$;
or R$^{10}$ and R$^{11}$ are taken together with the atom to which they are attached to form a heterocycloalkyl optionally substituted with one or more R$^{10b}$;
each R$^{10a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)($R^b$)$_2$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{10a}$ on the same atom are taken together to form an oxo;

each $R^{10b}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{10b}$ on the same atom are taken together to form an oxo;

each $R^1$ is independently halogen, —CN, —OH, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

n is 0, 1, 2, 3, or 4;

$R^{16}$ is $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

Ring B is a 5-membered heteroaryl or 5-membered heterocycloalkyl;

each $R^{12}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{12}$ on the same atom are taken together to form an oxo;

or two $R^{12}$ on the same carbon are taken together to form a cycloalkyl or heterocycloalkyl; each optionally substituted with one or more R;

or two $R^{12}$ on different atoms are taken together to form a cycloalkyl, heterocycloalkyl, aryl, or heteroaryl; each optionally substituted with one or more R;

m is 0, 1, 2, 3, 4, 5, or 6;

or one $R^{12}$ and R are taken together to form a cycloalkyl, heterocycloalkyl, aryl, or heteroaryl; each optionally substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —SF$_5$, —SH, —S(=O)$C_1$-$C_3$alkyl, —S(=O)$_2$$C_1$-$C_3$alkyl, —S(=O)$_2$NH$_2$, —S(=O)$_2$NH$C_1$-$C_3$alkyl, —S(=O)$_2$N($C_1$-$C_3$alkyl)$_2$, —S(=O)(=NC$_1$-$C_3$alkyl)($C_1$-$C_3$alkyl), —NH$_2$, —NH$C_1$-$C_3$alkyl, —N($C_1$-$C_3$alkyl)$_2$, —N=S(=O)($C_1$-$C_3$alkyl)$_2$, —C(=O)$C_1$-$C_3$alkyl, —C(=O)OH, —C(=O)O$C_1$-$C_3$alkyl, —C(=O)NH$_2$, —C(=O)NH$C_1$-$C_3$alkyl, —C(=O)N($C_1$-$C_3$alkyl)$_2$, —P(=O)($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl;

or two R on the same atom form an oxo.

In some embodiments of a compound of Formula (IV), X is —N—. In some embodiments of a compound of Formula (IV), X is —CR$^X$—.

In some embodiments of a compound of Formula (IV), $R^X$ is hydrogen, halogen, $C_1$-$C_6$alkyl, or $C_1$-$C_6$haloalkyl. In some embodiments of a compound of Formula (IV), $R^X$ is hydrogen.

In some embodiments of a compound of Formula (IV), Y is —N—. In some embodiments of a compound of Formula (IV), Y is —CR$^Y$—.

In some embodiments of a compound of Formula (IV), $R^Y$ is hydrogen, halogen, $C_1$-$C_6$alkyl, or $C_1$-$C_6$haloalkyl. In some embodiments of a compound of Formula (IV), $R^Y$ is hydrogen.

In some embodiments of a compound of Formula (IV), W is —C($R^{17}$)$_2$—. In some embodiments of a compound of Formula (IV), W is —O—. In some embodiments of a compound of Formula (IV), W is NR$^{18}$—.

In some embodiments of a compound of Formula (IV), each $R^{17}$ is independently hydrogen, halogen, $C_1$-$C_6$alkyl, or $C_1$-$C_6$haloalkyl. In some embodiments of a compound of Formula (IV), each $R^{17}$ is hydrogen.

In some embodiments of a compound of Formula (IV), $R^{18}$ is hydrogen, $C_1$-$C_6$alkyl, or $C_1$-$C_6$haloalkyl. In some embodiments of a compound of Formula (IV), $R^{18}$ is hydrogen.

In some embodiments of a compound of Formula (IV), $R^{19}$ is —C(=O)OR$^9$, —C(=O)NR$^{10}$R$^{11}$ or —S(=O)$_2$NR$^{10}$R$^{11}$. In some embodiments of a compound of Formula (IV), $R^{19}$ is —C(=O)OR$^9$. In some embodiments of a compound of Formula (IV), $R^{19}$ is —C(=O)NR$^{10}$R$^{11}$. In some embodiments of a compound of Formula (IV), $R^{19}$ is —S(=O)$_2$NR$^{10}$R$^{11}$.

In some embodiments of a compound of Formula (IV), $R^9$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, cycloalkyl, heterocycloalkyl, aryl, and heteroaryl is independently optionally substituted with one or more R$^{9a}$. In some embodiments of a compound of Formula (IV), $R^9$ is hydrogen, C$_1$-C$_6$alkyl, C$_1$-C$_6$haloalkyl, cycloalkyl, heterocycloalkyl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, cycloalkyl, heterocycloalkyl, aryl, and heteroaryl is independently optionally substituted with one or more R$^{9a}$. In some embodiments of a compound of Formula (IV), $R^9$ is hydrogen, C$_1$-C$_6$alkyl, C$_1$-C$_6$haloalkyl, cycloalkyl, or heterocycloalkyl, wherein each alkyl, cycloalkyl, and heterocycloalkyl is independently optionally substituted with one or more R$^{9a}$. In some embodiments of a compound of Formula (IV), $R^9$ is hydrogen, C$_1$-C$_6$alkyl, C$_1$-C$_6$haloalkyl, cycloalkyl, or heterocycloalkyl. In some embodiments of a compound of Formula (IV), $R^9$ is hydrogen, C$_1$-C$_6$alkyl, or C$_1$-C$_6$haloalkyl. In some embodiments of a compound of Formula (IV), $R^9$ is hydrogen or C$_1$-C$_6$alkyl. In some embodiments of a compound of Formula (IV), $R^9$ is hydrogen.

In some embodiments of a compound of Formula (IV), each R$^{9a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl; wherein each alkyl, cycloalkyl, and heterocycloalkyl is independently optionally substituted with one or more R; or two R$^{9a}$ on the same atom are taken together to form an oxo. In some embodiments of a compound of Formula (IV), each R$^{9a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (IV), each R$^{9a}$ is independently halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (IV), each R$^{9a}$ is independently halogen, C$_1$-C$_6$alkyl, or C$_1$-C$_6$haloalkyl.

In some embodiments of a compound of Formula (IV), $R^{10}$ and $R^{11}$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, cycloalkyl, heterocycloalkyl, aryl, and heteroaryl is independently optionally substituted with one or more R$^{10}$. In some embodiments of a compound of Formula (IV), $R^{10}$ and $R^{11}$ are each independently hydrogen, C$_1$-C$_6$alkyl, C$_1$-C$_6$hydroxyalkyl, C$_1$-C$_6$aminoalkyl, C$_1$-C$_6$heteroalkyl, C$_1$-C$_6$alkylene(aryl), or C$_1$-C$_6$alkylene(heteroaryl), wherein each alkyl, alkylene, aryl, and heteroaryl is independently optionally substituted with one or more R$^{10a}$. In some embodiments of a compound of Formula (IV), $R^{10}$ and $R^{11}$ are each independently hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (IV), $R^{10}$ and $R^{11}$ are each independently hydrogen, C$_1$-C$_6$alkyl, C$_1$-C$_6$hydroxyalkyl, or C$_1$-C$_6$heteroalkyl. In some embodiments of a compound of Formula (IV), $R^{10}$ and $R^{11}$ are each independently hydrogen or C$_1$-C$_6$alkyl.

In some embodiments of a compound of Formula (IV), each R$^{10a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl; wherein each alkyl, cycloalkyl, and heterocycloalkyl is independently optionally substituted with one or more R; or two R$^{10a}$ on the same atom are taken together to form an oxo. In some embodiments of a compound of Formula (IV), each R$^{10a}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (IV), each R$^{10a}$ is independently halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (IV), each R$^{10a}$ is independently halogen, C$_1$-C$_6$alkyl, or C$_1$-C$_6$haloalkyl.

In some embodiments of a compound of Formula (IV), $R^{10}$ and $R^{11}$ are taken together with the atom to which they are attached to form a heterocycloalkyl optionally substituted with one or more R$^{10b}$.

In some embodiments of a compound of Formula (IV), each R$^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl; wherein each alkyl, cycloalkyl, and heterocycloalkyl is independently optionally substituted with one or more R; or two R$^{10b}$ on the same atom are taken together to form an oxo. In some embodiments of a compound of Formula (IV), each R$^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (IV), each R$^{10b}$ is independently halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl. In some embodiments of a compound of Formula (IV), each R$^{10b}$ is independently halogen, C$_1$-C$_6$alkyl, or C$_1$-C$_6$haloalkyl. In some embodiments of a compound of Formula (IV), each R$^{10b}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (IV),

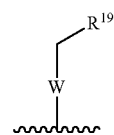

is

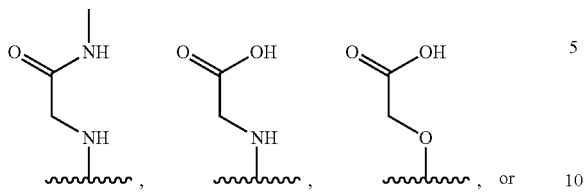, or

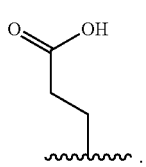.

In some embodiments of a compound of Formula (IV), each $R^{10b}$ is independently —OH, —OR$^a$, or —NR$^c$R$^d$.

In some embodiments of a compound of Formula (IV), $R^{16}$ is C$_1$-C$_6$alkyl or C$_1$-C$_6$haloalkyl. In some embodiments of a compound of Formula (IV), $R^{16}$ is C$_1$-C$_6$haloalkyl.

In some embodiments of a compound of Formula (IV), Ring B is a 5-membered heteroaryl. In some embodiments of a compound of Formula (IV), Ring B is pyrrolyl, furanyl, thiophenyl, imidazolyl, pyrazolyl, thiazolyl, oxazolyl, or triazolyl. In some embodiments of a compound of Formula (IV), Ring B is imidazolyl, pyrazolyl, thiazolyl, or oxazolyl. In some embodiments of a compound of Formula (IV), Ring B is pyrazolyl. In some embodiments of a compound of Formula (IV), Ring B is a 5-membered heterocycloalkyl.

In some embodiments of a compound of Formula (IV), each $R^{12}$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (IV), each $R^{12}$ is independently halogen, —CN, —OH, —OR$^a$, —NR$^c$R$^d$, C$_1$-C$_6$alkyl, C$_1$-C$_6$haloalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (IV), each $R^{12}$ is independently halogen, —CN, —OH, C$_1$-C$_6$alkyl, C$_1$-C$_6$haloalkyl, cycloalkyl, or heterocycloalkyl. In some embodiments of a compound of Formula (IV), each $R^{12}$ is independently —CN, C$_1$-C$_6$alkyl, or C$_1$-C$_6$haloalkyl. In some embodiments of a compound of Formula (IV), each $R^{12}$ is independently C$_1$-C$_6$alkyl.

In some embodiments of a compound of Formula (IV), m is 0 or 1. In some embodiments of a compound of Formula (IV), m is 1 or 2. In some embodiments of a compound of Formula (IV), m is 0. In some embodiments of a compound of Formula (IV), m is 1. In some embodiments of a compound of Formula (IV), m is 2. In some embodiments of a compound of Formula (IV), m is 3.

In some embodiments of a compound of Formula (IV),

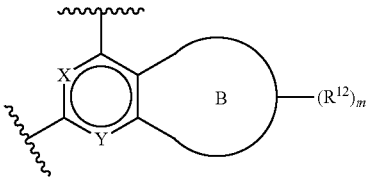

is

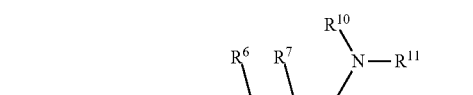

Disclosed herein is a compound of Formula (V), or a pharmaceutically acceptable salt, or stereoisomer thereof:

Formula (V)

wherein:
X is —N— or —CR$^X$—;
R$^X$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;
Y is —N— or —CR$^Y$—;
R$^Y$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

Ring A is cycloalkyl, heterocycloalkyl, aryl, or heteroaryl;

each $R^1$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more $R^{1a}$;

or two $R^1$ on the same atom are taken together to form an oxo;

each $R^{1a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SR$^a$, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{1a}$ on the same atom are taken together to form an oxo;

n is 0, 1, 2, 3, or 4;

L is absent, —O—, —S—, —NR$^2$—, —C(R$^3$)$_2$—, —C(R$^3$)$_2$—C(R$^3$)$_2$—, —C(R$^3$)=C(R$^3$)—, —C(R$^3$)$_2$O—, —OC(R$^3$)$_2$—, —C(R$^3$)$_2$S—, —SC(R$^3$)$_2$—, —C(R$^3$)$_2$NR$^2$—, or —NR$^2$C(R$^3$)$_2$—;

$R^2$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;

each $R^3$ is independently hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more R;

or two $R^3$ on the same carbon are taken together to form an oxo;

or two $R^3$ on the same carbon are taken together to form a cycloalkyl or heterocycloalkyl; each optionally substituted with one or more R;

or two $R^3$ on different carbons are taken together to form a cycloalkyl, heterocycloalkyl, aryl, or heteroaryl; each optionally substituted with one or more R;

$R^4$, $R^5$, $R^6$, and $R^7$ are each independently hydrogen, halogen, or C$_1$-C$_6$alkyl;

$R^{10}$ is hydrogen or C$_1$-C$_6$alkyl and $R^{11}$ is a bicyclic heterocycloalkyl optionally substituted with one or more $R^{10a}$;

or $R^{10}$ and $R^{11}$ are taken together with the atom to which they are attached to form a bicyclic heterocycloalkyl optionally substituted with one or more $R^{10b}$;

each $R^{10a}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{10a}$ on the same atom are taken together to form an oxo;

each $R^{10b}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{10b}$ on the same atom are taken together to form an oxo;

U is —C— or —N—;

T is —C— or —N—;

provided that U and T are not both —N—; and provided that U and T are both —C— when Ring B is a phenyl or 6-membered heteroaryl;

Ring B is a phenyl, 5- or 6-membered heteroaryl, or 5-membered heterocycloalkyl;

each $R^{12}$ is independently halogen, —CN, —NO$_2$, —OH, —OR$^a$, —OC(=O)R$^a$, —OC(=O)OR$^b$, —OC(=O)NR$^c$R$^d$, —SF$_5$, —SH, —SW, —S(=O)R$^a$, —S(=O)$_2$R$^a$, —S(=O)$_2$NR$^c$R$^d$, —S(=O)(=NR$^b$)R$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —N=S(=O)(R$^b$)$_2$, —C(=O)R$^a$, —C(=O)OR$^b$, —C(=O)NR$^c$R$^d$, —P(=O)(R$^b$)$_2$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R;

or two $R^{12}$ on the same atom are taken together to form an oxo;

or two $R^{12}$ on the same carbon are taken together to form a cycloalkyl or heterocycloalkyl; each optionally substituted with one or more R;

or two $R^{12}$ on different atoms are taken together to form a cycloalkyl, heterocycloalkyl, aryl, or heteroaryl; each optionally substituted with one or more R;

m is 0, 1, 2, 3, 4, 5, or 6;

or one $R^{12}$ and R are taken together to form a cycloalkyl, heterocycloalkyl, aryl, or heteroaryl; each optionally substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —SF$_5$, —SH, —S(=O)$C_1$-$C_3$alkyl, —S(=O)$_2$$C_1$-$C_3$alkyl, —S(=O)$_2$NH$_2$, —S(=O)$_2$NH$C_1$-$C_3$alkyl, —S(=O)$_2$N($C_1$-$C_3$alkyl)$_2$, —S(=O)(=N$C_1$-$C_3$alkyl)($C_1$-$C_3$alkyl), —NH$_2$, —NH$C_1$-$C_3$alkyl, —N($C_1$-$C_3$alkyl)$_2$, —N=S(=O)($C_1$-$C_3$alkyl)$_2$, —C(=O)$C_1$-$C_3$alkyl, —C(=O)OH, —C(=O)O$C_1$-$C_3$alkyl, —C(=O)NH$_2$, —C(=O)NH$C_1$-$C_3$alkyl, —C(=O)N($C_1$-$C_3$alkyl)$_2$, —P(=O)($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl;

or two R on the same atom form an oxo.

In some embodiments of a compound of Formula (V), the compound is of Formula (Va):

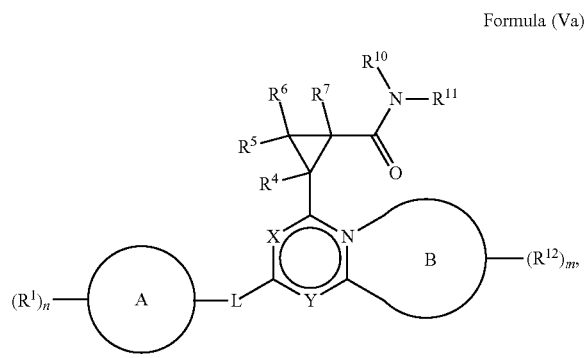

Formula (Va)

wherein Ring B is a 5-membered heteroaryl or 5-membered heterocycloalkyl.

In some embodiments of a compound of Formula (V), the compound is of Formula (Vb):

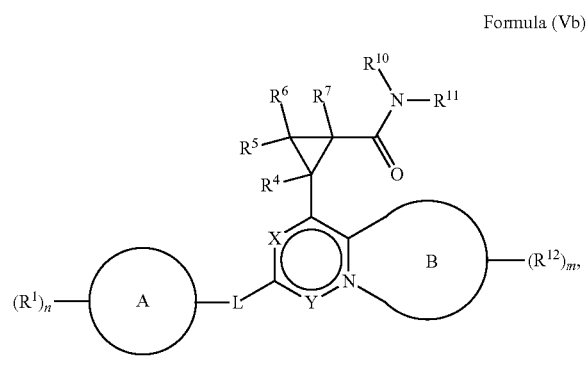

Formula (Vb)

wherein Ring B is a 5-membered heteroaryl or 5-membered heterocycloalkyl.

In some embodiments of a compound of Formula (V), the compound is of Formula (Vc):

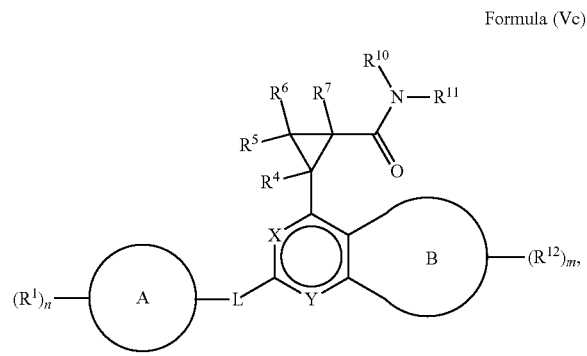

Formula (Vc)

wherein Ring B is a phenyl, 5- or 6-membered heteroaryl or 5-membered heterocycloalkyl.

In some embodiments of a compound of Formula (V) or (Va)-(Vc),

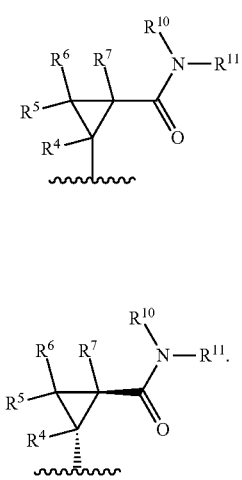

is

In some embodiments of a compound of Formula (V) or (Va)-(Vc),

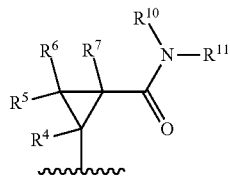

is

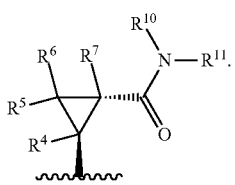

In some embodiments of a compound of Formula (V) or (Va)-(Vc), X is —N—. In some embodiments of a compound of Formula (V) or (Va)-(Vc), X is —CR$^X$—.

In some embodiments of a compound of Formula (V) or (Va)-(Vc), R$^X$ is hydrogen, halogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (V) or (Va)-(Vc), R$^X$ is hydrogen, halogen, $C_1$-$C_6$alkyl, or $C_1$-$C_6$haloalkyl. In some embodiments of a compound of Formula (V) or (Va)-(Vc), R$^X$ is hydrogen, halogen, or $C_1$-$C_6$alkyl. In some embodiments of a compound of Formula (V) or (Va)-(Vc), R$^X$ is hydrogen or halogen. In some embodiments of a compound of Formula (V) or (Va)-(Vc), R$^X$ is hydrogen.

In some embodiments of a compound of Formula (V) or (Va)-(Vc), Y is —N—. In some embodiments of a compound of Formula (V) or (Va)-(Vc), Y is —CR$^Y$—.

In some embodiments of a compound of Formula (V) or (Va)-(Vc), R$^Y$ is hydrogen, halogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (V) or (Va)-(Vc), R, is hydrogen, halogen, $C_1$-$C_6$alkyl, or $C_1$-$C_6$haloalkyl. In some embodiments of a compound of Formula (V) or (Va)-(Vc), R$^Y$ is hydrogen, halogen, or $C_1$-$C_6$alkyl. In some embodiments of a compound of Formula (V) or (Va)-(Vc), R$^Y$ is hydrogen or halogen. In some embodiments of a compound of Formula (V) or (Va)-(Vc), R$^Y$ is hydrogen.

In some embodiments of a compound of Formula (V) or (Va)-(Vc), L is absent, —O—, —C(R$^3$)$_2$, or —C(R$^3$)$_2$O—. In some embodiments of a compound of Formula (V) or (Va)-(Vc), L is absent, —O—, or —C(R$^3$)$_2$. In some embodiments of a compound of Formula (V) or (Va)-(Vc), L is absent or —O—. In some embodiments of a compound of Formula (V) or (Va)-(Vc), L is —O— or —C(R$^3$)$_2$O—. In some embodiments of a compound of Formula (V) or (Va)-(Vc), L is absent. In some embodiments of a compound of Formula (V) or (Va)-(Vc), L is —O—. In some embodiments of a compound of Formula (V) or (Va)-(Vc), L is —C(R$^3$)$_2$.

In some embodiments of a compound of Formula (V) or (Va)-(Vc), R$^2$ is hydrogen, $C_1$-$C_6$alkyl, or $C_1$-$C_6$haloalkyl. In some embodiments of a compound of Formula (V) or (Va)-(Vc), R$^2$ is hydrogen or $C_1$-$C_6$alkyl. In some embodiments of a compound of Formula (V) or (Va)-(Vc), R$^2$ is hydrogen.

In some embodiments of a compound of Formula (V) or (Va)-(Vc), each R$^3$ is independently hydrogen, $C_1$-$C_6$alkyl, or $C_1$-$C_6$haloalkyl. In some embodiments of a compound of Formula (V) or (Va)-(Vc), each R$^3$ is independently hydrogen or $C_1$-$C_6$alkyl. In some embodiments of a compound of Formula (V) or (Va)-(Vc), each R$^3$ is hydrogen.

In some embodiments of a compound of Formula (V) or (Va)-(Vc), Ring A is cycloalkyl or heterocycloalkyl. In some embodiments of a compound of Formula (V) or (Va)-(Vc), Ring A is cycloalkyl. In some embodiments of a compound of Formula (V) or (Va)-(Vc), Ring A is heterocycloalkyl. In some embodiments of a compound of Formula (V) or (Va)-(Vc), Ring A is aryl or heteroaryl. In some embodiments of a compound of Formula (V) or (Va)-(Vc), Ring A is phenyl. In some embodiments of a compound of Formula (V) or (Va)-(Vc), Ring A is heteroaryl. In some embodiments of a compound of Formula (V) or (Va)-(Vc), Ring A is 5- or 6-membered heteroaryl.

In some embodiments of a compound of Formula (V) or (Va)-(Vc), each R$^1$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R$^{1a}$. In some embodiments of a compound of Formula (V) or (Va)-(Vc), each R$^1$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (V) or (Va)-(Vc), each R$^1$ is independently halogen, —CN, —OH, —OR$^a$, —NR$^c$R$^d$, $C_1$-$C_6$alkyl, or $C_1$-$C_6$haloalkyl. In some embodiments of a compound of Formula (V) or (Va)-(Vc), each R$^1$ is independently halogen, —OR$^a$, $C_1$-$C_6$alkyl, or $C_1$-$C_6$haloalkyl. In some embodiments of a compound of Formula (V) or (Va)-(Vc), each R$^1$ is independently halogen, $C_1$-$C_6$alkyl, or $C_1$-$C_6$haloalkyl. In some embodiments of a compound of Formula (V) or (Va)-(Vc), each R$^1$ is independently halogen or $C_1$-$C_6$haloalkyl. In some embodiments of a compound of Formula (V) or (Va)-(Vc), each R$^1$ is independently $C_1$-$C_6$haloalkyl. In some embodiments of a compound of Formula (V) or (Va)-(Vc), each R$^1$ is independently halogen.

In some embodiments of a compound of Formula (V) or (Va)-(Vc), each R$^{1a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two R$^{1a}$ on the same atom are taken together to form an oxo. In some embodiments of a compound of Formula (V) or (Va)-(Vc), each R$^{1a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (V) or (Va)-(Vc), each R$^{1a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (V) or (Va)-(Vc), each $R^{1a}$ is independently halogen, $C_1$-$C_6$alkyl, or $C_1$-$C_6$haloalkyl.

In some embodiments of a compound of Formula (V) or (Va)-(Vc), n is 0, 1, 2, or 3. In some embodiments of a compound of Formula (V) or (Va)-(Vc), n is 0, 1, or 2. In some embodiments of a compound of Formula (V) or (Va)-(Vc), n is 0 or 1. In some embodiments of a compound of Formula (V) or (Va)-(Vc), n is 1 or 2. In some embodiments of a compound of Formula (V) or (Va)-(Vc), n is 0. In some embodiments of a compound of Formula (V) or (Va)-(Vc), n is 1. In some embodiments of a compound of Formula (V) or (Va)-(Vc), n is 2. In some embodiments of a compound of Formula (V) or (Va)-(Vc), n is 3.

In some embodiments of a compound of Formula (V) or (Va)-(Vc),

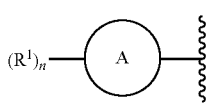

is

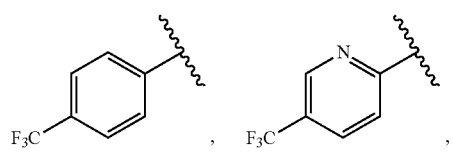
,
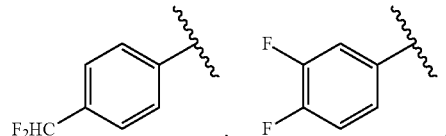
,
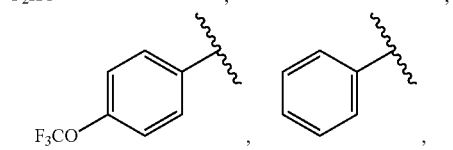
,

,
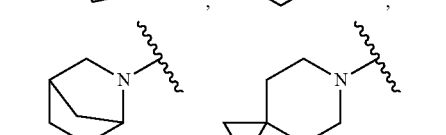
,
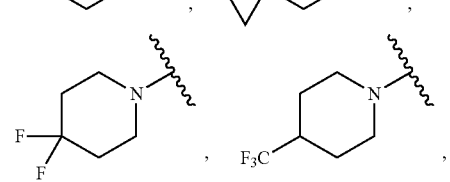
,
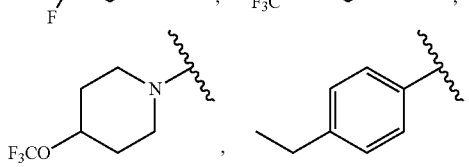
,
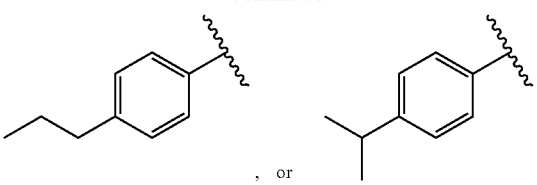

In some embodiments of a compound of Formula (V) or (Va)-(Vc),

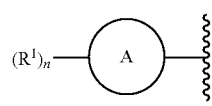

is

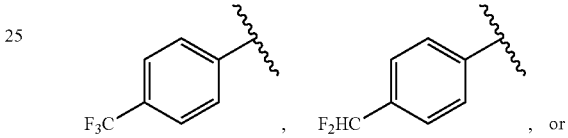
,
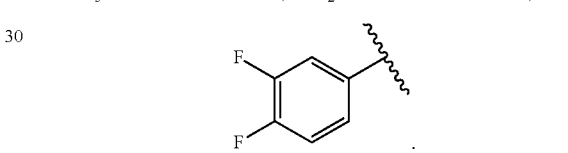
.

In some embodiments of a compound of Formula (V) or (Va)-(Vc),

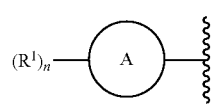

is

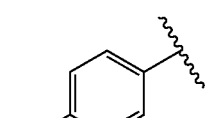
.

In some embodiments of a compound of Formula (V) or (Va)-(Vc),

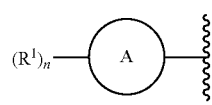

is

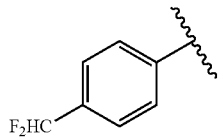

In some embodiments of a compound of Formula (V) or (Va)-(Vc),

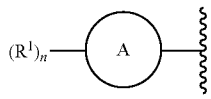

is

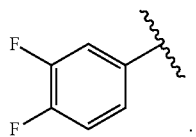

In some embodiments of a compound of Formula (V) or (Va)-(Vc), $R^4$ is hydrogen or $C_1$-$C_6$alkyl. In some embodiments of a compound of Formula (V) or (Va)-(Vc), $R^4$ is hydrogen.

In some embodiments of a compound of Formula (V) or (Va)-(Vc), $R^5$ is hydrogen or $C_1$-$C_6$alkyl. In some embodiments of a compound of Formula (V) or (Va)-(Vc), $R^5$ is hydrogen.

In some embodiments of a compound of Formula (V) or (Va)-(Vc), $R^6$ is hydrogen or $C_1$-$C_6$alkyl. In some embodiments of a compound of Formula (V) or (Va)-(Vc), $R^6$ is hydrogen.

In some embodiments of a compound of Formula (V) or (Va)-(Vc), $R^7$ is hydrogen or $C_1$-$C_6$alkyl. In some embodiments of a compound of Formula (V) or (Va)-(Vc), $R^7$ is hydrogen.

In some embodiments of a compound of Formula (V) or (Va)-(Vc), $R^{10}$ is hydrogen and $R^{11}$ is bicyclic heterocycloalkyl optionally substituted with one or more $R^{10a}$. In some embodiments of a compound of Formula (V) or (Va)-(Vc), $R^{10}$ is hydrogen and $R^{11}$ is fused bicyclic heterocycloalkyl optionally substituted with one or more $R^{10a}$. In some embodiments of a compound of Formula (V) or (Va)-(Vc), $R^{10}$ is hydrogen and $R^{11}$ is bridged bicyclic heterocycloalkyl optionally substituted with one or more $R^{10a}$. In some embodiments of a compound of Formula (V) or (Va)-(Vc), $R^{10}$ is hydrogen and $R^{11}$ is bicyclic spiroheterocycloalkyl optionally substituted with one or more $R^{10a}$.

In some embodiments of a compound of Formula (V) or (Va)-(Vc), $R^{10}$ is hydrogen and $R^{11}$ is

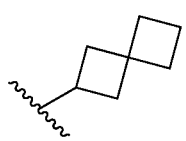 [SMILES: *C1CC2(CCC2)C1]

or

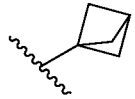

each optionally substituted with one or more $R^{10a}$.

In some embodiments of a compound of Formula (V) or (Va)-(Vc), each $R^{10a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two $R^{10a}$ on the same atom are taken together to form an oxo. In some embodiments of a compound of Formula (V) or (Va)-(Vc), each $R^{10a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (V) or (Va)-(Vc), each $R^{10a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (V) or (Va)-(Vc), each $R^{10a}$ is independently halogen, $C_1$-$C_6$alkyl, or $C_1$-$C_6$haloalkyl. In some embodiments of a compound of Formula (V) or (Va)-(Vc), each $R^{10a}$ is independently halogen, —CN, —OH, —OR$^a$, —NR$^c$R$^d$, $C_1$-$C_6$alkyl, or $C_1$-$C_6$haloalkyl. In some embodiments of a compound of Formula (V) or (Va)-(Vc), each $R^{10a}$ is independently halogen, —OH, —OR$^a$, $C_1$-$C_6$alkyl, or $C_1$-$C_6$haloalkyl. In some embodiments of a compound of Formula (V) or (Va)-(Vc), each $R^{10a}$ is independently halogen, —OH, $C_1$-$C_6$alkyl, or $C_1$-$C_6$haloalkyl. In some embodiments of a compound of Formula (V) or (Va)-(Vc), each $R^{10a}$ is independently —OH, $C_1$-$C_6$alkyl, or $C_1$-$C_6$haloalkyl. In some embodiments of a compound of Formula (V) or (Va)-(Vc), each $R^{10a}$ is independently —OH.

In some embodiments of a compound of Formula (V) or (Va)-(Vc), $R^{10}$ and $R^{11}$ are taken together with the atom to which they are attached to form a bicyclic heterocycloalkyl optionally substituted with one or more $R^{10b}$. In some embodiments of a compound of Formula (V) or (Va)-(Vc), $R^{10}$ and $R^{11}$ are taken together with the atom to which they are attached to form a fused bicyclic heterocycloalkyl optionally substituted with one or more $R^{10b}$. In some embodiments of a compound of Formula (V) or (Va)-(Vc), $R^{10}$ and $R^{11}$ are taken together with the atom to which they are attached to form a bridged bicyclic heterocycloalkyl optionally substituted with one or more $R^{10b}$. In some embodiments of a compound of Formula (V) or (Va)-(Vc), $R^{10}$ and $R^{11}$ are taken together with the atom to which they are attached to form a bicyclic spiroheterocycloalkyl optionally substituted with one or more $R^{10b}$. In some embodiments of a compound of Formula (V) or (Va)-(Vc), $R^{10}$ and $R^{11}$ are taken together with the atom to which they are attached to form

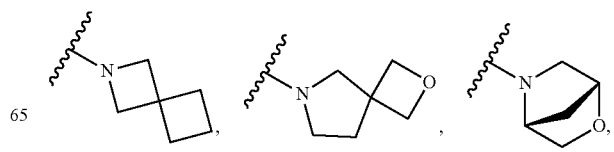

-continued

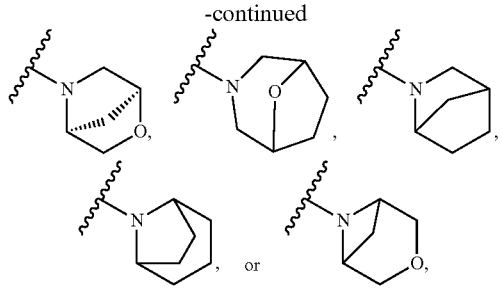

each optionally substituted with one or more $R^{10b}$. In some embodiments of a compound of Formula (V) or (Va)-(Vc), $R^{10}$ and $R^{11}$ are taken together with the atom to which they are attached to form

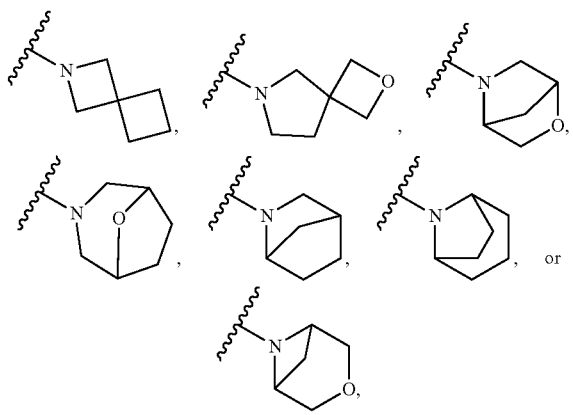

each optionally substituted with one or more $R_{10b}$.

In some embodiments of a compound of Formula (V) or (Va)-(Vc), each $R^{10b}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently optionally substituted with one or more R; or two $R^{10b}$ on the same atom are taken together to form an oxo. In some embodiments of a compound of Formula (V) or (Va)-(Vc), each $R^{10b}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (V) or (Va)-(Vc), each $R^{10b}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound of Formula (V) or (Va)-(Vc), each $R^{10b}$ is independently halogen, $C_1$-$C_6$alkyl, or $C_1$-$C_6$haloalkyl. In some embodiments of a compound of Formula (V) or (Va)-(Vc), each $R^{10b}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl. In some embodiments of a compound of Formula (V) or (Va)-(Vc), each $R^{10b}$ is independently —OH, —OR$^a$, or —NR$^c$R$^d$. In some embodiments of a compound of Formula (V) or (Va)-(Vc), each $R^{10b}$ is independently —OH, $C_1$-$C_6$alkoxyl, or amino. In some embodiments of a compound of Formula (V) or (Va)-(Vc), each $R^{10b}$ is independently —OH. In some embodiments of a compound of Formula (V) or (Va)-(Vc), at least one $R^{10b}$ is —OH.

In some embodiments of a compound of Formula (V) or (Va)-(Vc),

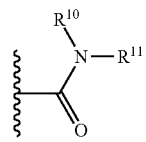

is

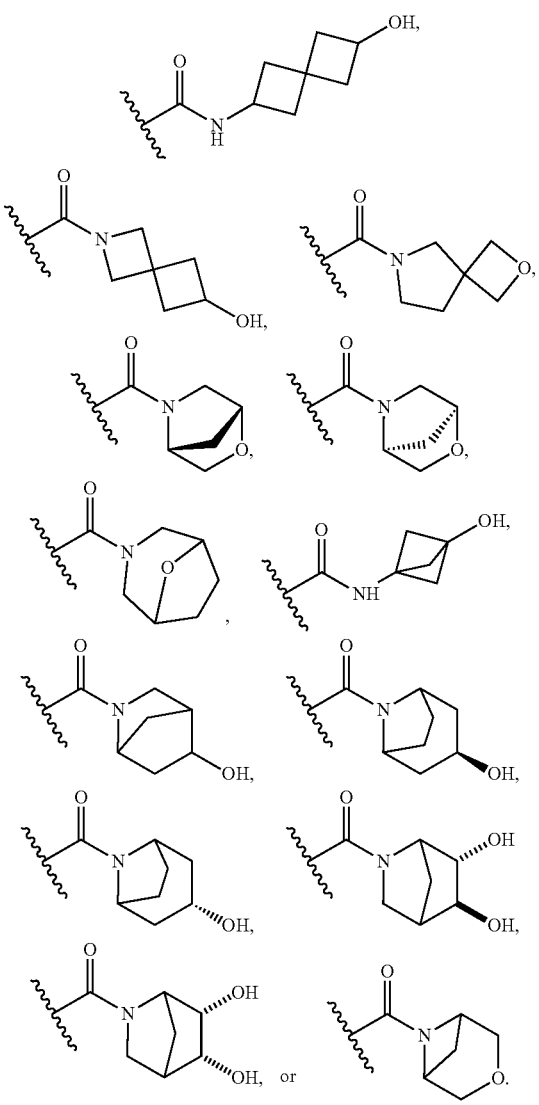

In some embodiments of a compound of Formula (V) or (Va)-(Vc),

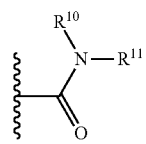

is

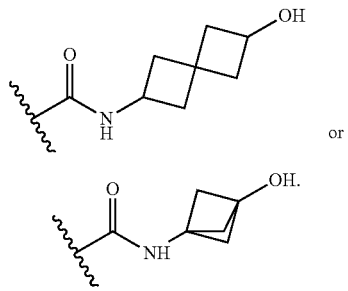

or

In some embodiments of a compound of Formula (V) or (Va)-(Vc),

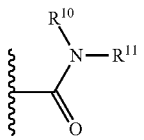

is

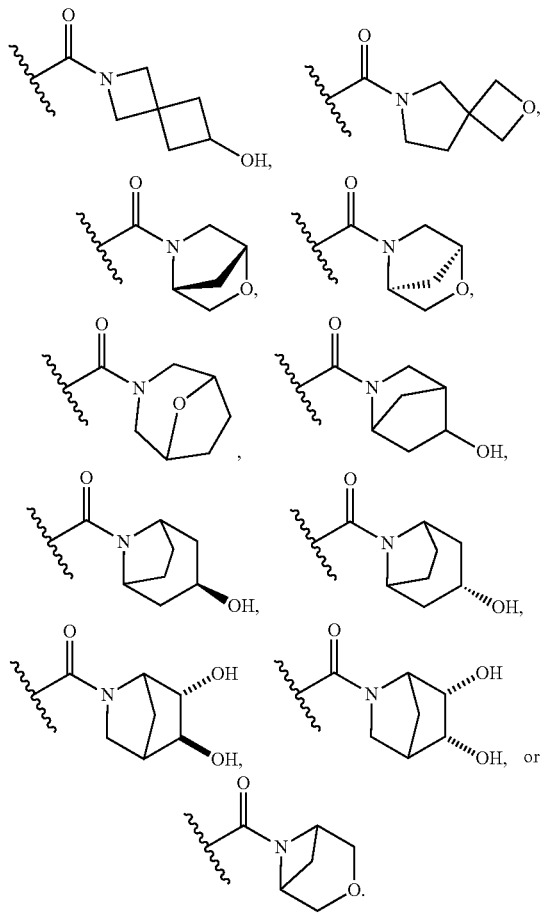

In some embodiments of a compound of Formula (V) or (Va)-(Vc),

is

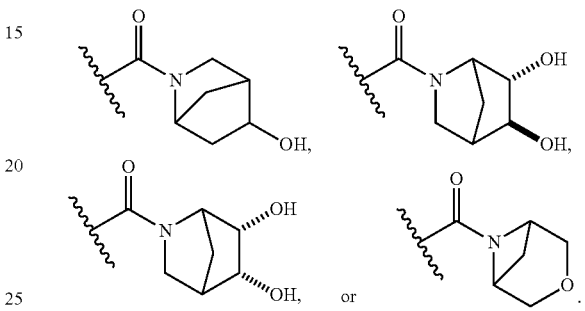

In some embodiments of a compound of Formula (V) or (Va)-(Vc), Ring B is a 5-membered heteroaryl or 5-membered heterocycloalkyl. In some embodiments of a compound of Formula (V) or (Va)-(Vc), Ring B is a phenyl. In some embodiments of a compound of Formula (V) or (Va)-(Vc), Ring B is a 5- or 6-membered heteroaryl. In some embodiments of a compound of Formula (V) or (Va)-(Vc), Ring B is a 5-membered heteroaryl. In some embodiments of a compound of Formula (V) or (Va)-(Vc), Ring B is pyrrolyl, furanyl, thiophenyl, imidazolyl, pyrazolyl, thiazolyl, oxazolyl, or triazolyl. In some embodiments of a compound of Formula (V) or (Va)-(Vc), Ring B is imidazolyl, pyrazolyl, thiazolyl, or oxazolyl. In some embodiments of a compound of Formula (V) or (Va)-(Vc), Ring B is pyrazolyl. In some embodiments of a compound of Formula (V) or (Va)-(Vc), Ring B is a 6-membered heteroaryl. In some embodiments of a compound of Formula (V) or (Va)-(Vc), Ring B is a pyridinyl, pyrimidinyl, or pyrazinyl. In some embodiments of a compound of Formula (V) or (Va)-(Vc), Ring B is a pyridinyl. In some embodiments of a compound of Formula (V) or (Va)-(Vc), Ring B is a 5-membered heterocycloalkyl.

In some embodiments of a compound of Formula (V) or (Va)-(Vc), each $R^{12}$ is independently halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (V) or (Va)-(Vc), each $R^{12}$ is independently halogen, —CN, —OH, —$OR^a$, —$NR^cR^d$, $C_1$-$C_6$alkyl, $C_1$-$C_6$haloalkyl, cycloalkyl, heterocycloalkyl, aryl, or heteroaryl; wherein each alkyl, cycloalkyl, heterocycloalkyl, aryl, and heteroaryl is independently optionally substituted with one or more R. In some embodiments of a compound of Formula (V) or (Va)-(Vc), each $R^{12}$ is independently halogen, —CN, —OH, $C_1$-$C_6$alkyl, $C_1$-$C_6$haloalkyl, cycloalkyl, or heterocycloalkyl. In some embodiments of a compound of Formula (V) or (Va)-(Vc), each $R^{12}$ is independently —CN, $C_1$-$C_6$alkyl, or $C_1$-$C_6$haloalkyl. In some embodiments of a compound of Formula (V) or (Va)-(Vc), each $R^{12}$ is independently $C_1$-$C_6$alkyl.

In some embodiments of a compound of Formula (V) or (Va)-(Vc), m is 0 or 1. In some embodiments of a compound of Formula (V) or (Va)-(Vc), m is 1 or 2. In some embodiments of a compound of Formula (V) or (Va)-(Vc), m is 0. In some embodiments of a compound of Formula (V) or (Va)-(Vc), m is 1. In some embodiments of a compound of Formula (V) or (Va)-(Vc), m is 2. In some embodiments of a compound of Formula (V) or (Va)-(Vc), m is 3.

In some embodiments of a compound of Formula (V) or (Va)-(Vc),

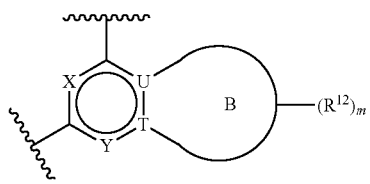

is

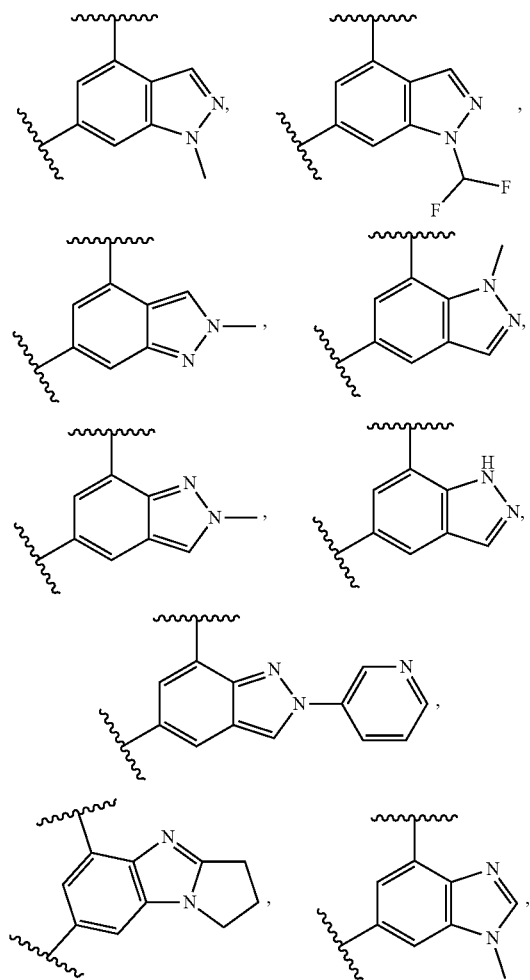

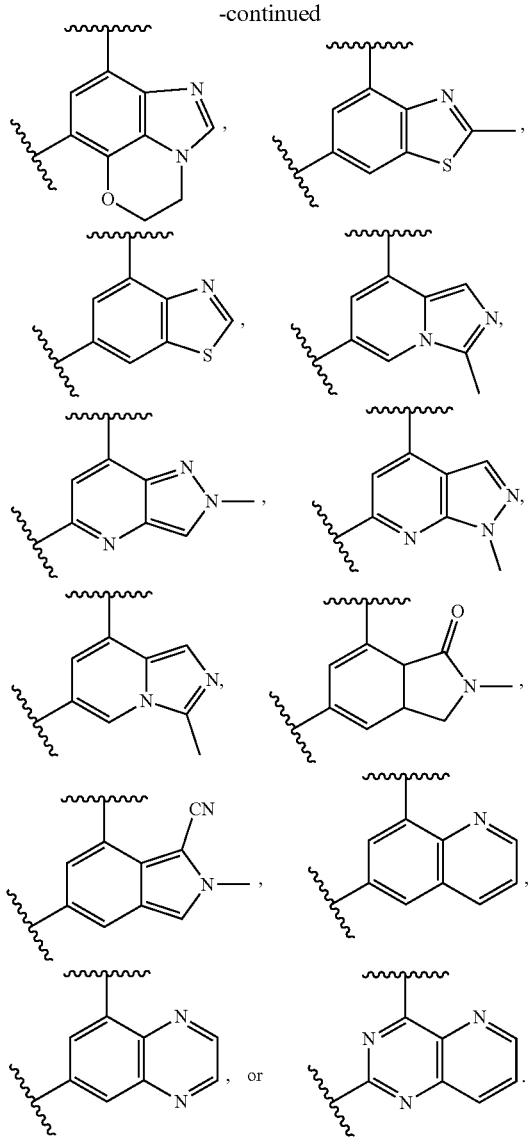

In some embodiments of a compound of Formula (V) or (Va)-(Vc),

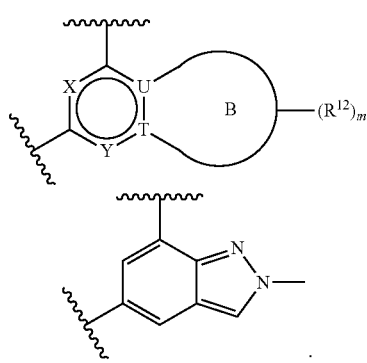

In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more R. In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl, wherein each alkyl, cycloalkyl, heterocycloalkyl, aryl, and heteroaryl is independently optionally substituted with one or more R. In some embodiments of a compound disclosed herein, each $R^a$ is independently $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkylene, cycloalkyl, heterocycloalkyl, aryl, and heteroaryl is independently optionally substituted with one or more R. In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl.

In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more R. In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl, wherein each alkyl, cycloalkyl, heterocycloalkyl, aryl, and heteroaryl is independently optionally substituted with one or more R. In some embodiments of a compound disclosed herein, each $R^b$ is independently hydrogen, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkylene, cycloalkyl, heterocycloalkyl, aryl, and heteroaryl is independently optionally substituted with one or more R. In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound disclosed herein, each $R^b$ is independently hydrogen, $C_1$-$C_6$alkyl, or $C_1$-$C_6$haloalkyl. In some embodiments of a compound disclosed herein, each $R^b$ is independently hydrogen or $C_1$-$C_6$alkyl. In some embodiments of a compound disclosed herein, each $R^b$ is hydrogen. In some embodiments of a compound disclosed herein, each $R^b$ is independently $C_1$-$C_6$alkyl.

In some embodiments of a compound disclosed herein, $R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, cycloalkyl, heterocycloalkyl, aryl, and heteroaryl is independently optionally substituted with one or more R. In some embodiments of a compound disclosed herein, $R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl, wherein each alkyl, cycloalkyl, heterocycloalkyl, aryl, and heteroaryl is independently optionally substituted with one or more R. In some embodiments of a compound disclosed herein, each $R^b$ is independently hydrogen, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkylene, cycloalkyl, heterocycloalkyl, aryl, and heteroaryl is independently optionally substituted with one or more R. In some embodiments of a compound disclosed herein, $R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound disclosed herein, $R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of a compound disclosed herein, $R^c$ and $R^d$ are each independently hydrogen, $C_1$-$C_6$alkyl, or $C_1$-$C_6$haloalkyl. In some embodiments of a compound disclosed herein, $R^c$ and $R^d$ are each independently hydrogen or $C_1$-$C_6$alkyl. In some embodiments of a compound disclosed herein, $R^c$ and $R^d$ are each hydrogen. In some embodiments of a compound disclosed herein, $R^c$ and $R^d$ are each independently $C_1$-$C_6$alkyl.

In some embodiments of a compound disclosed herein, $R^c$ and $R^d$ are taken together with the atom to which they are attached to form a heterocycloalkyl optionally substituted with one or more R.

In some embodiments of a compound disclosed herein, each R is independently halogen, —CN, —OH, —SF$_5$, —NH$_2$, —NHC$_1$-C$_3$alkyl, —N(C$_1$-C$_3$alkyl)$_2$, —C(=O)C$_1$-C$_3$alkyl, —C(=O)OH, —C(=O)OC$_1$-C$_3$alkyl, —C(=O)NH$_2$, —C(=O)NHC$_1$-C$_3$alkyl, —C(=O)N(C$_1$-C$_3$alkyl)$_2$, —P(=O)(C$_1$-C$_3$alkyl)$_2$, C$_1$-C$_3$alkyl, C$_1$-C$_3$alkoxy, C$_1$-C$_3$haloalkyl, C$_1$-C$_3$haloalkoxy, C$_1$-C$_3$hydroxyalkyl, C$_1$-C$_3$aminoalkyl, C$_1$-C$_3$heteroalkyl, or C$_3$-C$_6$cycloalkyl; or two R on the same atom form an oxo. In some embodiments of a compound disclosed herein, each R is independently halogen, —CN, —OH, —SF$_5$, —NH$_2$, —NHC$_1$-C$_3$alkyl, —N(C$_1$-C$_3$alkyl)$_2$, —P(=O)(C$_1$-C$_3$alkyl)$_2$, C$_1$-C$_3$alkyl, C$_1$-C$_3$alkoxy, or C$_1$-C$_3$haloalkyl; or two R on the same atom form an oxo. In some embodiments of a compound disclosed herein, each R is independently halogen, —CN, —OH, —NH$_2$, C$_1$-C$_3$alkyl, or C$_1$-C$_3$haloalkyl; or two R on the same atom form an oxo. In some embodiments of a compound disclosed herein, each R is independently halogen, C$_1$-C$_3$alkyl, or C$_1$-C$_3$haloalkyl; or two R on the same atom form an oxo.

In some embodiments of a compound disclosed herein, one or more of R, $R^1$, $R^{1a}$, $R^2$, $R^3$, $R^4$, $R^5$, $R^6$, $R^7$, $R^8$, $R^9$, $R^{9a}$, $R^{10}$, $R^{10a}$, $R^{10b}$, $R^{11}$, $R^{12}$, $R^{13}$, $R^{14}$, $R^{15}$, $R^{16}$, $R^{17}$, $R^{18}$, $R^{19}$, $R^X$, $R^Y$, $R^a$, $R^b$, $R^c$, and $R^d$ groups comprise deuterium at a percentage higher than the natural abundance of deuterium.

In some embodiments of a compound disclosed herein, one or more $^1$H are replaced with one or more deuteriums in one or more of the following groups R, $R^1$, $R^{1a}$, $R^2$, $R^3$, $R^4$, $R^5$, $R^6$, $R^7$, $R^8$, $R^9$, $R^{9a}$, $R^{10}$, $R^{10a}$, $R^{10b}$, $R^{11}$, $R^{12}$, $R^{13}$, $R^{14}$, $R^{15}$, $R^{16}$, $R^{17}$, $R^{18}$, $R^{19}$, $R^X$, $R^Y$, $R^a$, $R^b$, $R^c$, and $R^d$.

In some embodiments of a compound disclosed herein, the abundance of deuterium in each of R, $R^1$, $R^{1a}$, $R^2$, $R^3$, $R^4$, $R^5$, $R^6$, $R^7$, $R^8$, $R^9$, $R^{9a}$, $R^{10}$, $R^{10a}$, $R^{10b}$, $R^{11}$, $R^{12}$, $R^{13}$, $R^{14}$, $R^{15}$, $R^{16}$, $R^{17}$, $R^{18}$, $R^{19}$, $R^X$, $R^Y$, $R^a$, $R^b$, $R^c$, and $R^d$ is independently at least 1%, at least 10%, at least 20%, at least 30%, at least 40%, at least 50%, at least 60%, at least 70%, at least 80%, at least 90%, or 100% by molar.

In some embodiments of a compound disclosed herein, one or more $^1$H of Ring A or Ring B are replaced with one or more deuteriums.

Any combination of the groups described above for the various variables is contemplated herein. Throughout the specification, groups and substituents thereof are chosen by one skilled in the field to provide stable moieties and compounds.

In some embodiments the compound disclosed herein, or a pharmaceutically acceptable salt, or stereoisomer thereof, is one of the compounds in Table 1.

TABLE 1

| Example | Chirality Comments | Structure |
|---------|-------------------|-----------|
| 1 | Trans racemic | 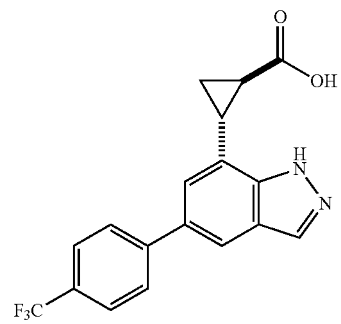 |
| 2 | Trans racemic | 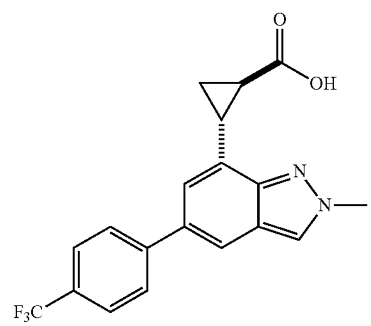 |
| 3 | Trans racemic | 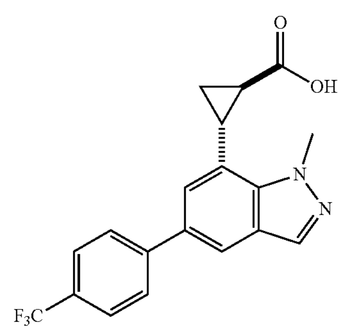 |
| 4 | Trans racemic | 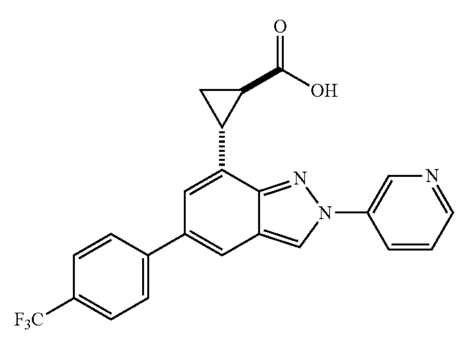 |

TABLE 1-continued

| Example | Chirality Comments | Structure |
|---|---|---|
| 5 | Trans racemic | 4-(trans-2-carboxycyclopropyl)-6-(4-trifluoromethylphenyl)-1H-indazole |
| 6 | Trans racemic | 4-(trans-2-carboxycyclopropyl)-6-(4-trifluoromethylphenyl)-2-methyl-2H-indazole |
| 7 | Trans racemic | 4-(trans-2-carboxycyclopropyl)-6-(4-trifluoromethylphenyl)-1-methyl-1H-indazole |
| 8 | Cis racemic | 4-(cis-2-carboxycyclopropyl)-6-(4-trifluoromethylphenyl)-1-methyl-1H-indazole |

TABLE 1-continued

| Example | Chirality Comments | Structure |
|---|---|---|
| 9 | Trans racemic | 4-(cyclopropanecarboxylic acid)-6-(4-trifluoromethylphenyl)-1-(difluoromethyl)-1H-indazole |
| 10 | Trans racemic | 4-(cyclopropanecarboxylic acid)-6-(4-trifluoromethoxyphenyl)-1-methyl-1H-indazole |
| 11 | Trans racemic | 4-(N-methylcyclopropanecarboxamide)-6-(4-isopropylphenyl)-1-methyl-1H-indazole |
| 12 | Trans racemic | 7-(cyclopropanecarboxylic acid)-5-(4-trifluoromethoxyphenyl)-2-methyl-2H-indazole |

TABLE 1-continued

| Example | Chirality Comments | Structure |
|---|---|---|
| 13 | Trans racemic | 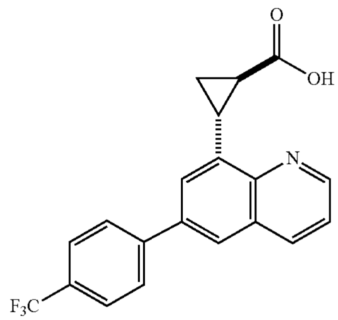 |
| 14 | Trans racemic | 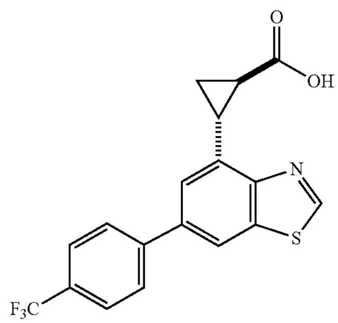 |
| 15 | Trans racemic | 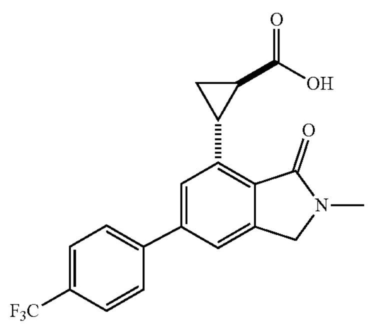 |
| 16 | Trans racemic | 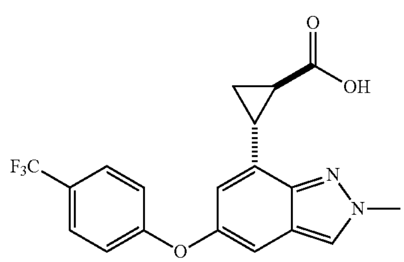 |
| 16a and 16b | Pure enantiomers (configuration arbitrarily assigned) | trans, enantiomer |

&

TABLE 1-continued

| Example | Chirality Comments | Structure |
|---------|-------------------|-----------|
|  |  | *trans, enantiomer* |
| 17 | Trans racemic | 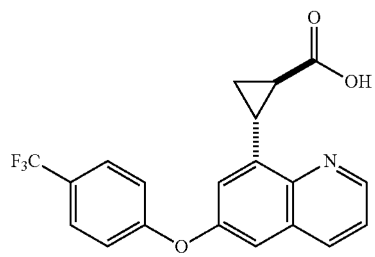 |
| 18 | Trans racemic | 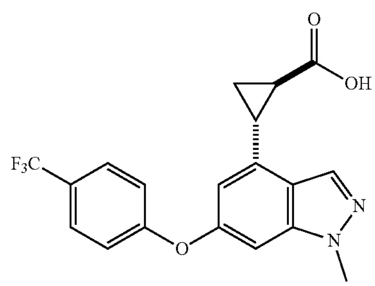 |
| 19 | Trans racemic | 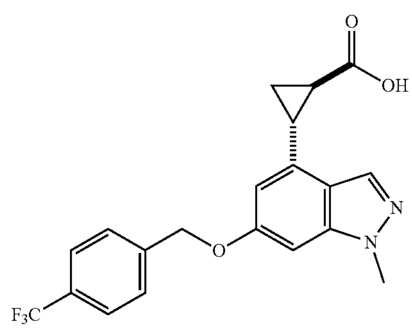 |
| 20 | Trans racemic | 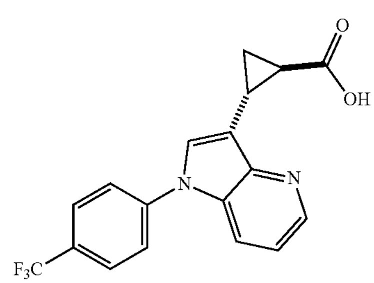 |

TABLE 1-continued
| Example | Chirality Comments | Structure |
|---|---|---|
| 21 | Trans racemic | 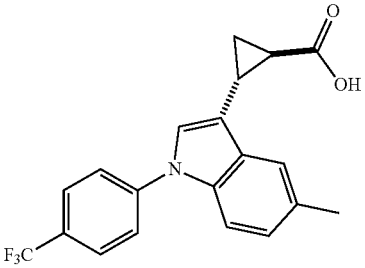 |
| 22 | Trans racemic | 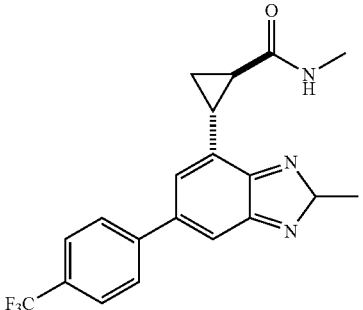 |
| 23 | Trans racemic | 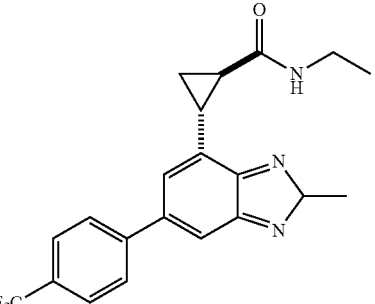 |
| 24 | Trans racemic | 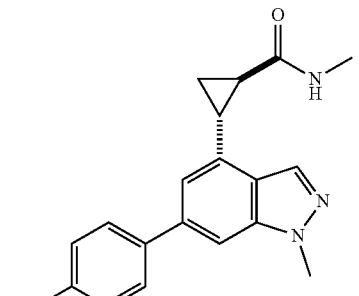 |
| 25 | Trans racemic | 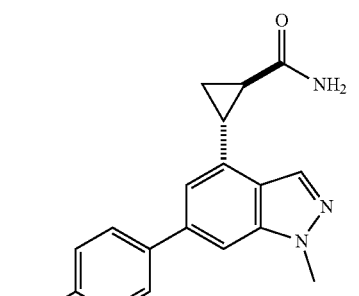 |

TABLE 1-continued

| Example | Chirality Comments | Structure |
|---|---|---|
| 26 | Trans racemic | 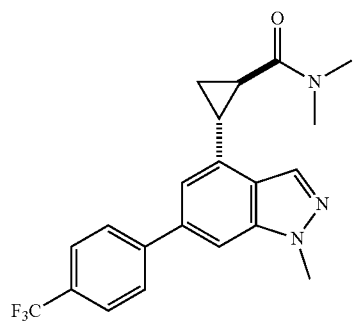 |
| 27 | Trans racemic | 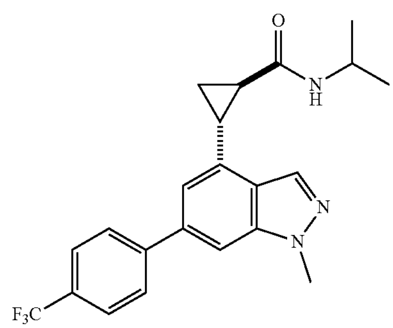 [SMILES: CC(C)NC(=O)[C@@H]1C[C@H]1c1cc(-c2ccc(C(F)(F)F)cc2)cc2c1cnn2C] |
| 28 | Trans racemic | 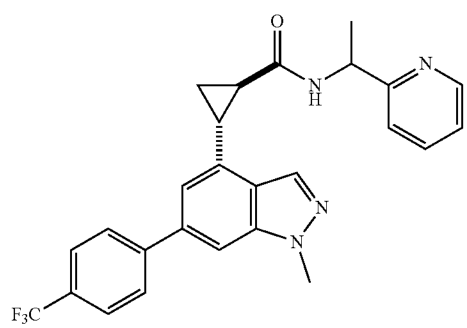 [SMILES: CC(NC(=O)[C@@H]1C[C@H]1c1cc(-c2ccc(C(F)(F)F)cc2)cc2c1cnn2C)c1ccccn1] |
| 29 | Trans racemic | 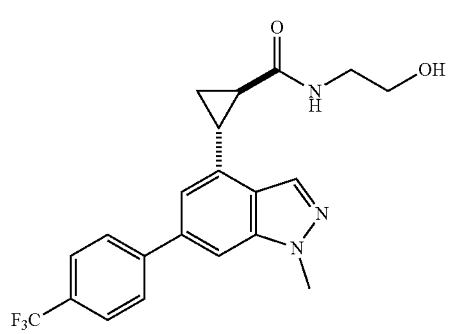 [SMILES: Cn1ncc2c([C@@H]3C[C@H]3C(=O)NCCO)cc(-c3ccc(C(F)(F)F)cc3)cc21] |

TABLE 1-continued
| Example | Chirality Comments | Structure |
|---|---|---|
| 30 | Trans racemic | 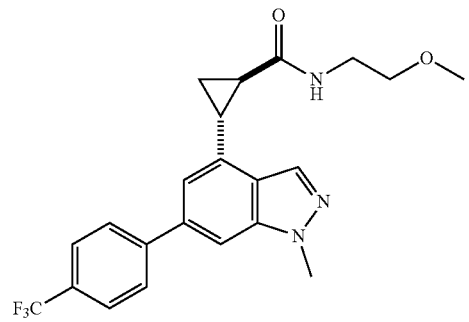 [SMILES: COCCNC(=O)[C@@H]1C[C@H]1c1cc(-c2ccc(C(F)(F)F)cc2)cc2c1cnn2C] |
| 31 | Trans racemic | 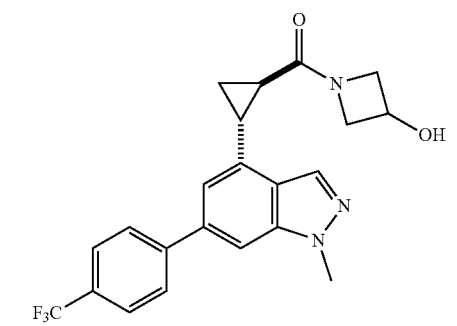 [SMILES: Cn1ncc2c([C@@H]3C[C@H]3C(=O)N3CC(O)C3)cc(-c3ccc(C(F)(F)F)cc3)cc21] |
| 32 | Trans racemic | 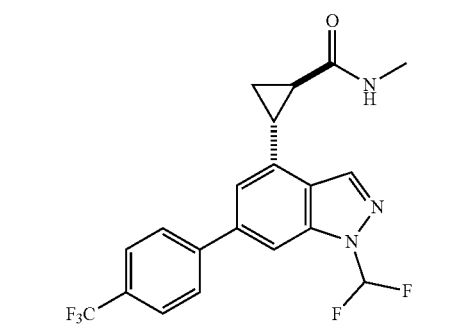 [SMILES: CNC(=O)[C@@H]1C[C@H]1c1cc(-c2ccc(C(F)(F)F)cc2)cc2c1cnn2C(F)F] |
| 33 | Trans racemic | 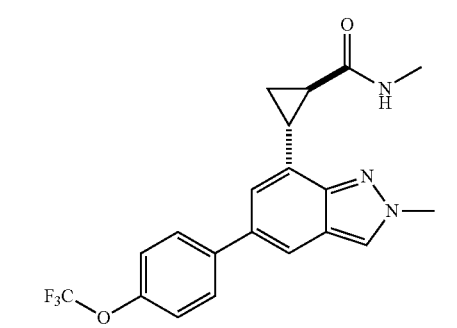 |
| 34 | Trans racemic | 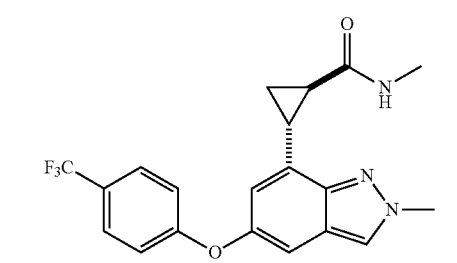 |

TABLE 1-continued
| Example | Chirality Comments | Structure |
|---|---|---|
| 34a and 34b | Pure enantiomers (configuration arbitrarily assigned) | 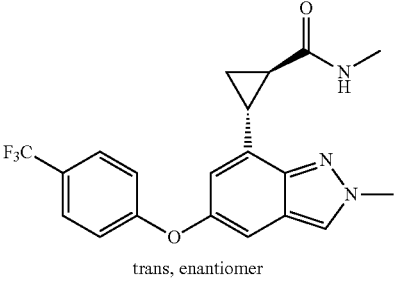 [SMILES: CNC(=O)[C@@H]1C[C@H]1c1cc(Oc2ccc(C(F)(F)F)cc2)cc2cn(C)nc12] trans, enantiomer<br><br>&<br><br>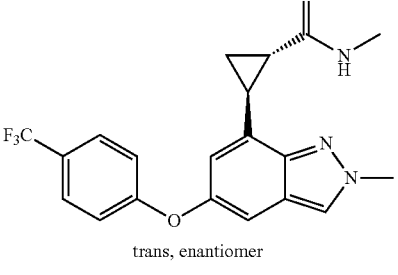 trans, enantiomer |
| 35 | Trans racemic | 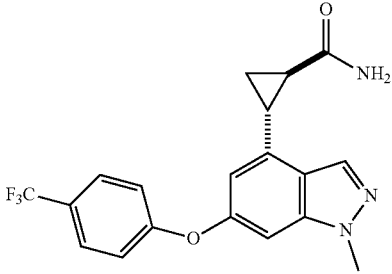 |
| 36 | Trans racemic | 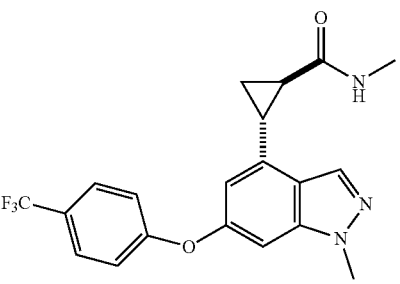 |
| 37 | Trans racemic | 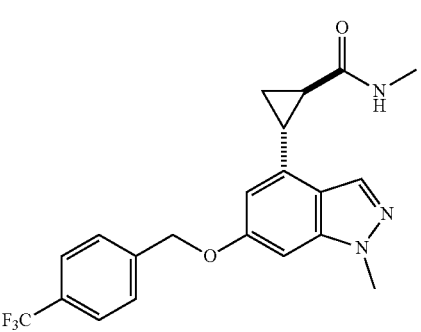 |

TABLE 1-continued
| Example | Chirality Comments | Structure |
|---|---|---|
| 38 | Trans racemic | 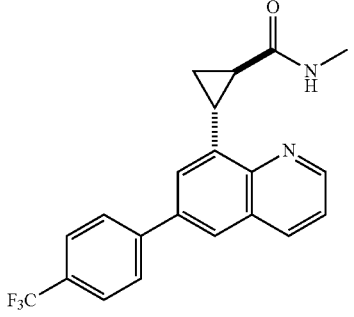 |
| 39 | Trans racemic | 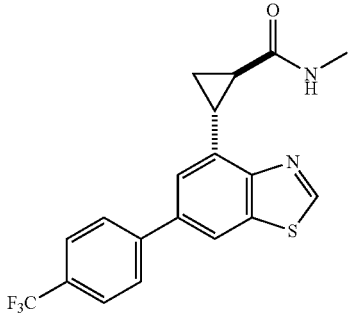 |
| 40 | NA | 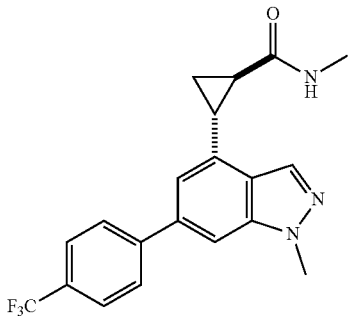 |
| 41 | NA | 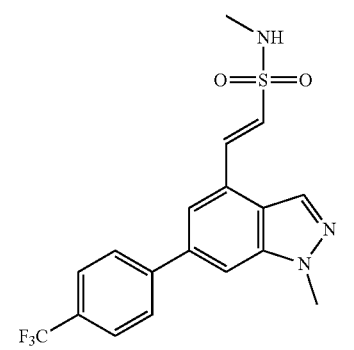 [SMILES: CNS(=O)(=O)/C=C/c1cc(-c2ccc(C(F)(F)F)cc2)cc2c1cnn2C] |

TABLE 1-continued

| Example | Chirality Comments | Structure |
|---------|-------------------|-----------|
| 42 | NA | 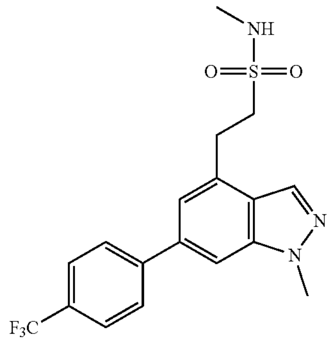 [SMILES: CNS(=O)(=O)CCc1cc(-c2ccc(C(F)(F)F)cc2)cc2c1cnn2C] |
| 43 | NA | 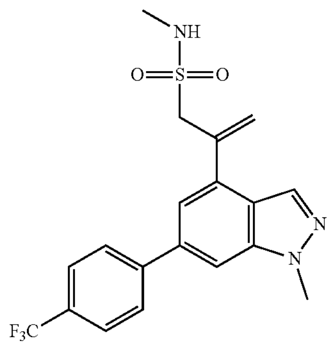 [SMILES: C=C(CS(=O)(=O)NC)c1cc(-c2ccc(C(F)(F)F)cc2)cc2c1cnn2C] |
| 44 | NA | 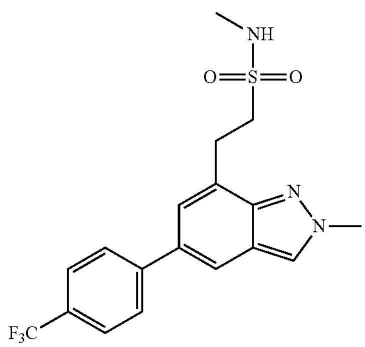 [SMILES: CNS(=O)(=O)CCc1cc(-c2ccc(C(F)(F)F)cc2)cc2cn(C)nc12] |
| 45 | NA | 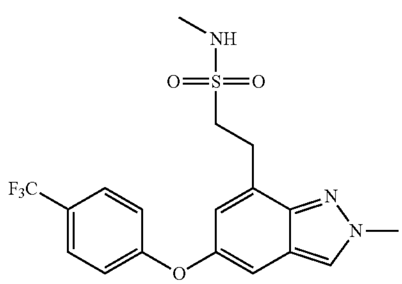 [SMILES: CNS(=O)(=O)CCc1cc(Oc2ccc(C(F)(F)F)cc2)cc2cn(C)nc12] |
| 46 | NA | 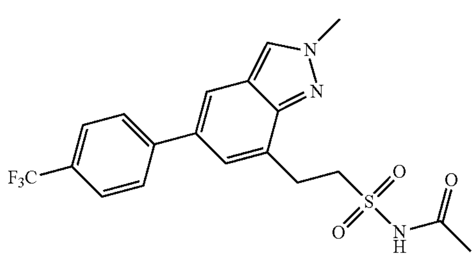 [SMILES: CC(=O)NS(=O)(=O)CCc1cc(-c2ccc(C(F)(F)F)cc2)cc2cn(C)nc12] |

TABLE 1-continued
| Example | Chirality Comments | Structure |
|---|---|---|
| 47 | NA | 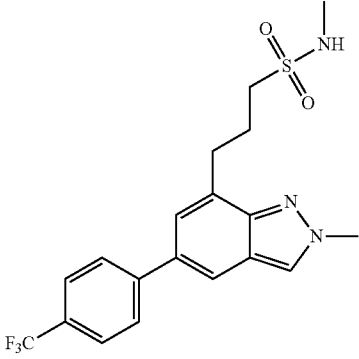 [SMILES: CNS(=O)(=O)CCCc1cc(-c2ccc(C(F)(F)F)cc2)cc2cn(C)nc12] |
| 48 | NA | 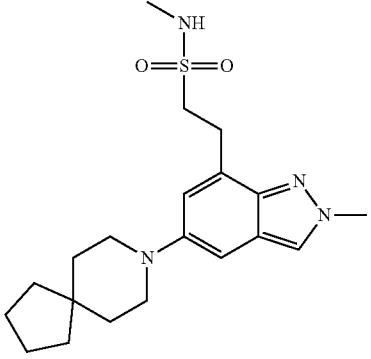 [SMILES: CNS(=O)(=O)CCc1cc(N2CCC3(CCCC3)CC2)cc2cn(C)nc12] |
| 49 | NA | 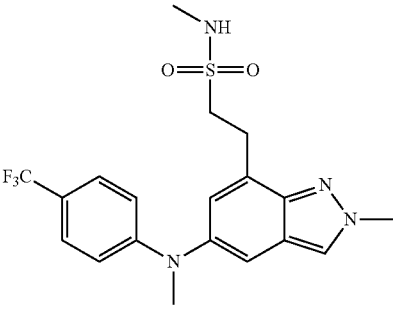 [SMILES: CNS(=O)(=O)CCc1cc(N(C)c2ccc(C(F)(F)F)cc2)cc2cn(C)nc12] |
| 50 | Trans racemic | 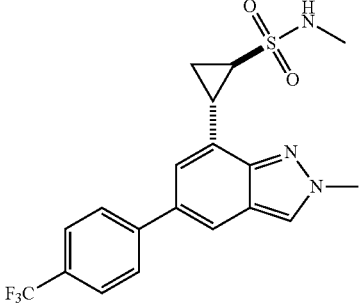 |

TABLE 1-continued

| Example | Chirality Comments | Structure |
|---|---|---|
| 51 | Trans racemic | 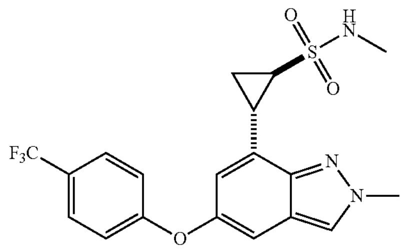 |
| 52 or 53 | Pure enantiomers (configuration arbitrarily assigned) | trans, enantiomer  &  trans, enantiomer |
| 54 | Pure trans enantiomer (unknown configuration) | 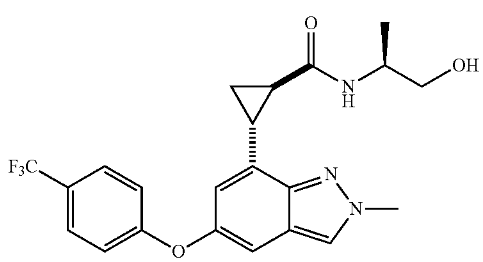 |
| 55 | Pure trans enantiomer (unknown configuration) | 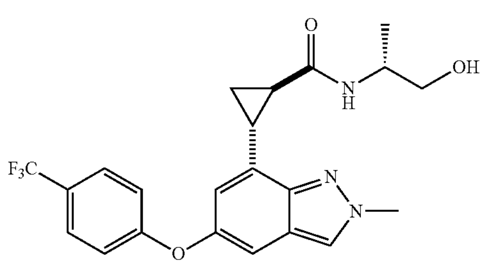 |

TABLE 1-continued

| Example | Chirality Comments | Structure |
|---|---|---|
| 56 | Trans racemic | 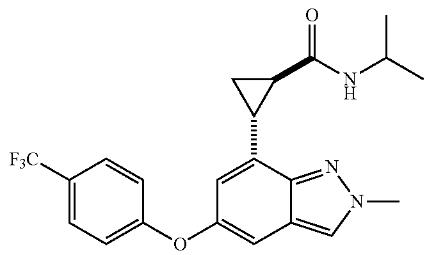 |
| 56a and 56b | Pure enantiomers (configuration arbitrarily assigned) | trans, enantiomer & trans, enantiomer |
| 57 | Trans racemic | 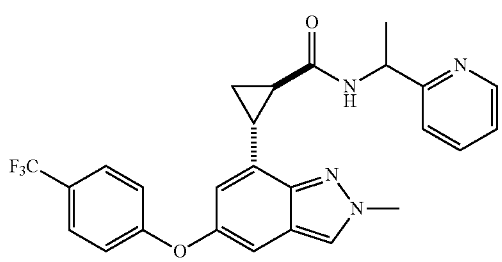 |
| 58a and 58b | Pure enantiomers (configuration arbitrarily assigned) | trans, enantiomer & |

TABLE 1-continued

| Example | Chirality Comments | Structure |
|---------|--------------------|-----------|
|  |  | trans, enantiomer |
| 59a and 59b | Pure enantiomers (configuration arbitrarily assigned) | trans, enantiomer<br><br>&<br><br>trans, enantiomer |
| 60 | Pure trans enantiomer (unknown configuration) | 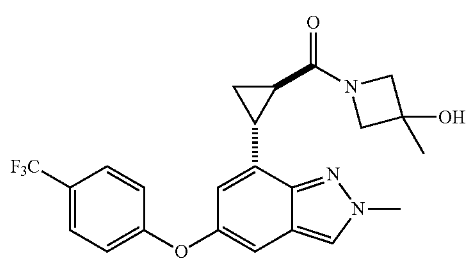 [SMILES: Cn1cc2cc(Oc3ccc(C(F)(F)F)cc3)cc([C@@H]3C[C@H]3C(=O)N3CC(C)(O)C3)c2n1] |
| 61 | Pure trans enantiomer (unknown configuration) | 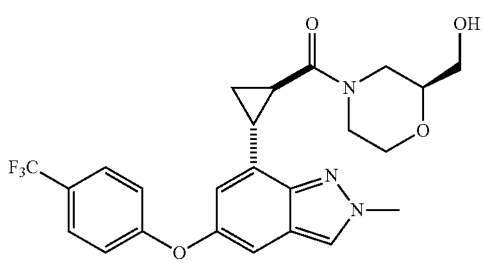 [SMILES: Cn1cc2cc(Oc3ccc(C(F)(F)F)cc3)cc([C@@H]3C[C@H]3C(=O)N3CCO[C@H](CO)C3)c2n1] |

TABLE 1-continued

| Example | Chirality Comments | Structure |
|---|---|---|
| 62 | Pure trans enantiomer (unknown configuration) | 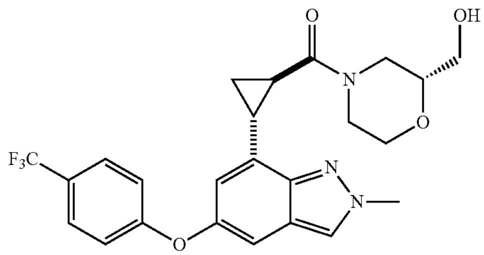 [SMILES: Cn1cc2cc(Oc3ccc(C(F)(F)F)cc3)cc([C@@H]3C[C@H]3C(=O)N3CCO[C@@H](CO)C3)c2n1] |
| 63 | Pure trans enantiomer (unknown configuration) | 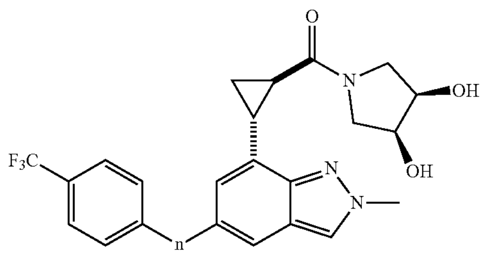 |
| 64 | Pure trans enantiomer (unknown configuration) | 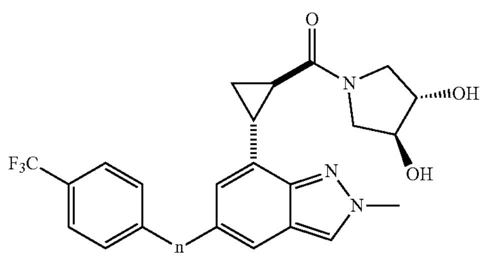 |
| 65 | Pure trans enantiomer (unknown configuration) | 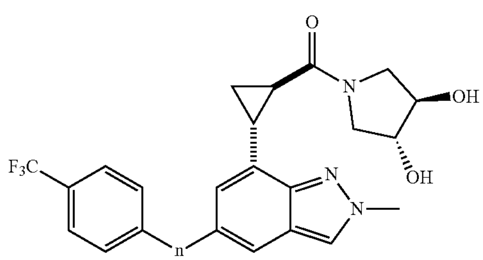 |
| 66 | Pure trans enantiomer (unknown configuration) | 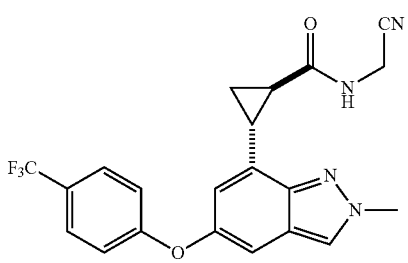 [SMILES: Cn1cc2cc(Oc3ccc(C(F)(F)F)cc3)cc([C@@H]3C[C@H]3C(=O)NCC#N)c2n1] |
| 67 | Pure trans enantiomer (unknown configuration) | 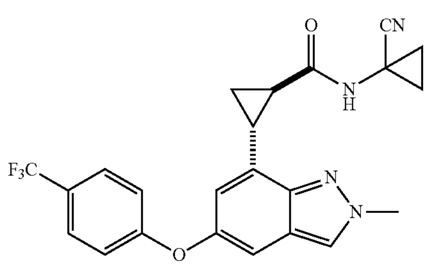 [SMILES: Cn1cc2cc(Oc3ccc(C(F)(F)F)cc3)cc([C@@H]3C[C@H]3C(=O)NC3(C#N)CC3)c2n1] |

TABLE 1-continued
| Example | Chirality Comments | Structure |
|---|---|---|
| 68 | Pure trans enantiomer (unknown configuration) | 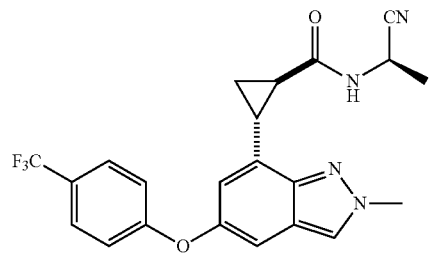 [SMILES: C[C@H](C#N)NC(=O)[C@@H]1C[C@H]1c1cc(Oc2ccc(C(F)(F)F)cc2)cc2cn(C)nc12] |
| 69 | Pure trans enantiomer (unknown configuration) | 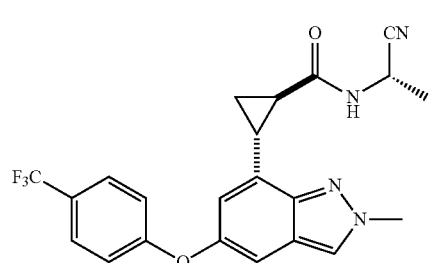 |
| 70 | Pure trans enantiomer (unknown configuration) | 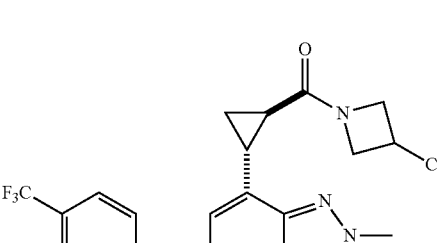 |
| 71 | Pure trans enantiomer (unknown configuration) | 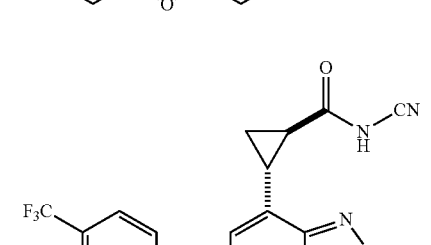 |
| 72 | Pure trans enantiomer (unknown configuration) | 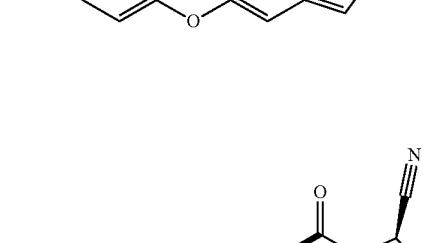 |

TABLE 1-continued
| Example | Chirality Comments | Structure |
|---|---|---|
| 73 | Pure trans enantiomer (unknown configuration) | 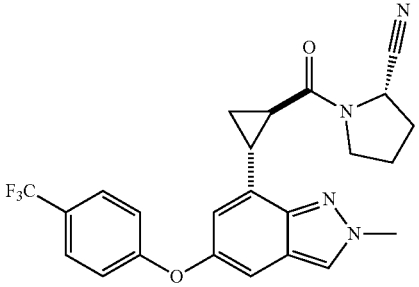 |
| 74 | Pure trans enantiomer (unknown configuration) | 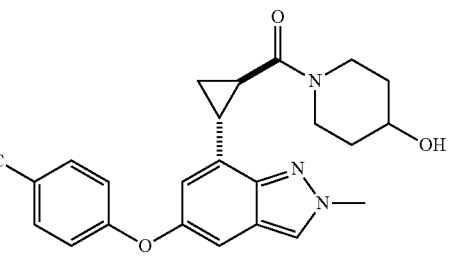 |
| 75a and 75b | Pure enantiomers (configuration arbitrarily assigned) | 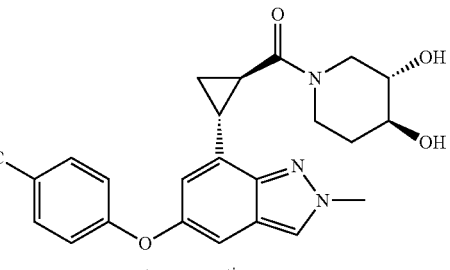
trans, enantiomer
&
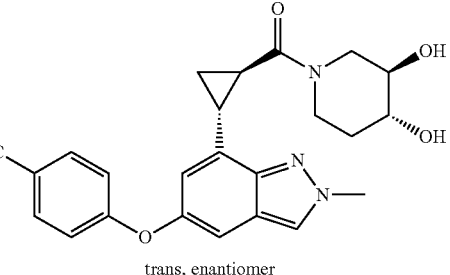
trans, enantiomer
or
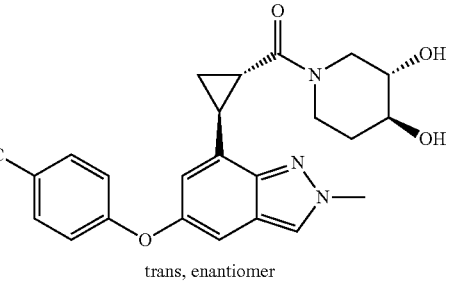
trans, enantiomer
& |

TABLE 1-continued

| Example | Chirality Comments | Structure |
|---|---|---|
| | | [Structure: trans, enantiomer — cyclopropyl carbonyl-(3,4-dihydroxy)piperidine attached to 5-(4-trifluoromethylphenoxy)-2-methyl-2H-indazol-7-yl] |
| 76a and 76b | Pure enantiomers (configuration arbitrarily assigned) | [Structure: trans, enantiomer — cyclopropyl-N-methylcarboxamide on 5-(4-trifluoromethylphenoxy)-2-(CD₃)-2H-indazol-7-yl] <br><br> & <br><br> [Structure: trans, enantiomer — opposite enantiomer of above] |
| 77 | Pure trans enantiomer (unknown configuration) | [Structure: cyclopropyl-N-methylcarboxamide on 5-(4-trifluoromethylphenoxy)-2-(CD₃)-2H-indazol-7-yl] |
| 78 | Trans racemic | [Structure: cyclopropyl-N-methylcarboxamide on 5-(4-trifluoromethylphenoxy)-2-cyclopropyl-2H-indazol-7-yl] |

TABLE 1-continued

| Example | Chirality Comments | Structure |
|---|---|---|
| 79 | Trans racemic | 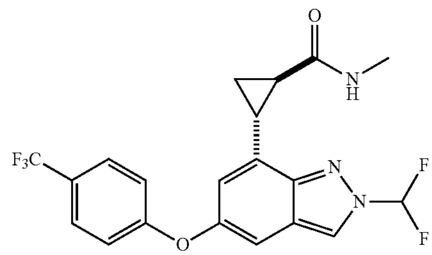 |
| 80 | Trans racemic | 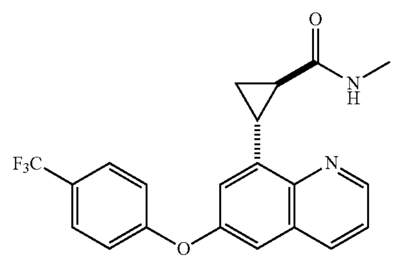 |
| 81 | Trans racemic | 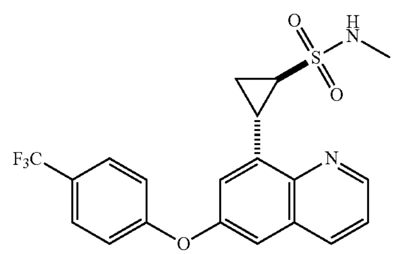 |
| 82 | Trans racemic | 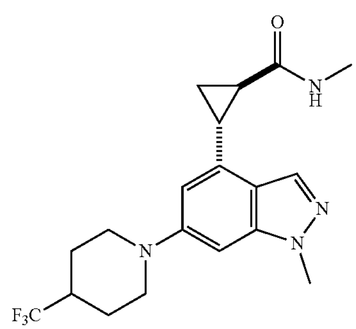 |
| 83 | Trans racemic | 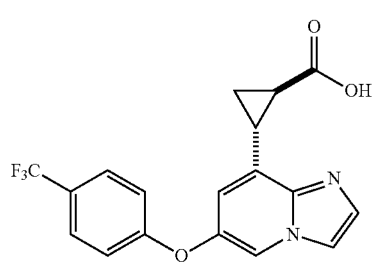 |

TABLE 1-continued
| Example | Chirality Comments | Structure |
|---|---|---|
| 84 | Trans racemic | 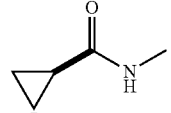 |
| 85a and 85b | Pure enantiomers (configuration arbitrarily assigned) | 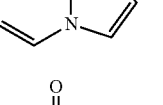
*trans*, enantiomer
&
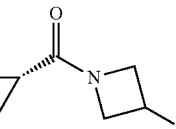
*trans*, enantiomer |
| 86 | Pure trans enantiomer (unknown configuration) | 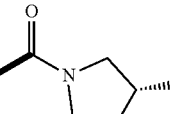 |
| 87a and 87b | Pure enantiomers (configuration arbitrarily assigned) | 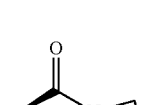
*trans*, enantiomer
& |

TABLE 1-continued
| Example | Chirality Comments | Structure |
|---|---|---|
| | | 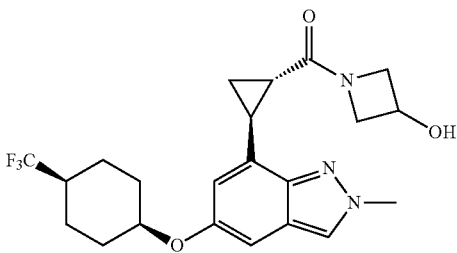
trans, enantiomer |
| 88a and 88b | Pure enantiomers (configuration arbitrarily assigned) | 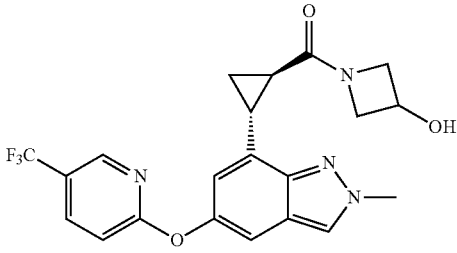
trans, enantiomer
&
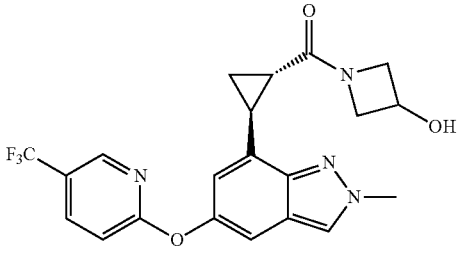
trans, enantiomer |
| 89a and 89b | Pure enantiomers (configuration arbitrarily assigned) | 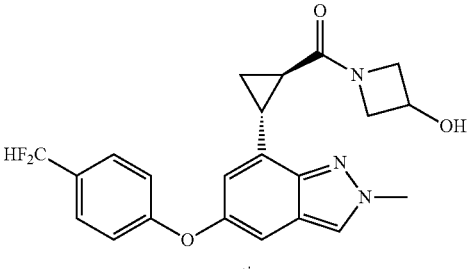
trans, enantiomer
&
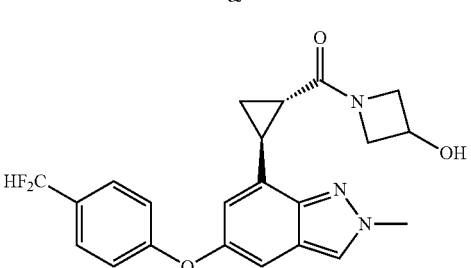
trans, enantiomer |

TABLE 1-continued
| Example | Chirality Comments | Structure |
|---|---|---|
| 90a and 90b | Pure enantiomers (configuration arbitrarily assigned) | 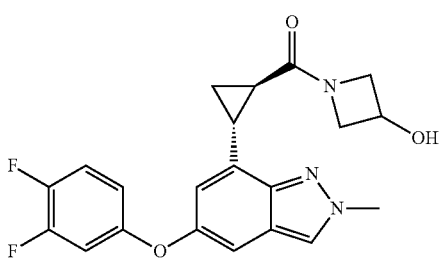 *trans*, enantiomer<br><br>&<br><br>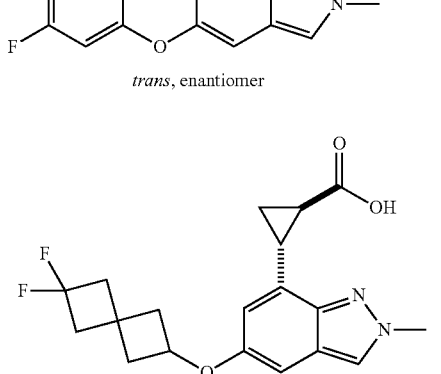 *trans*, enantiomer |
| 93 | Trans racemic | 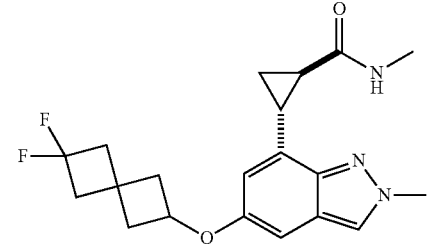 |
| 94 | Trans racemic | 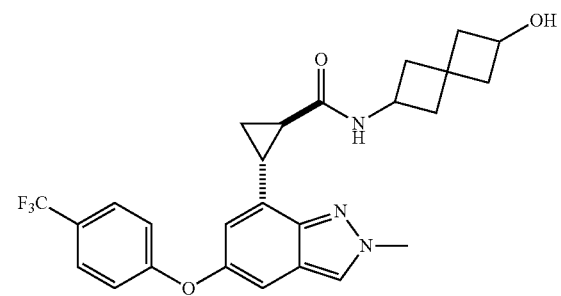 |
| 95 | Pure trans enantiomer (unknown configuration) | 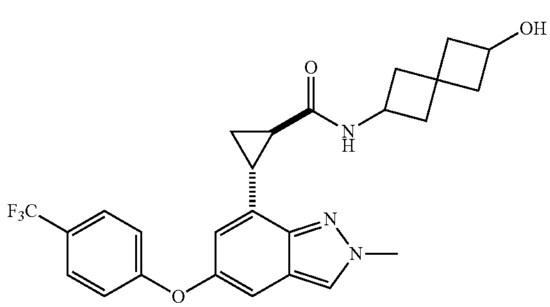 |

TABLE 1-continued

| Example | Chirality Comments | Structure |
|---|---|---|
| 96 | Pure trans enantiomer (unknown configuration) | 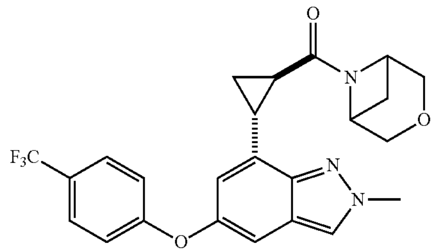 |
| 97 | Pure trans enantiomer (unknown configuration) | 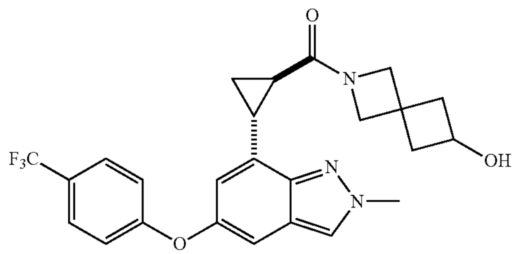 |
| 98 | Pure trans enantiomer (unknown configuration) | 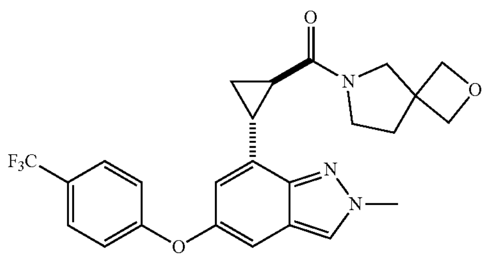 |
| 102 | Pure trans enantiomer (unknown configuration) | 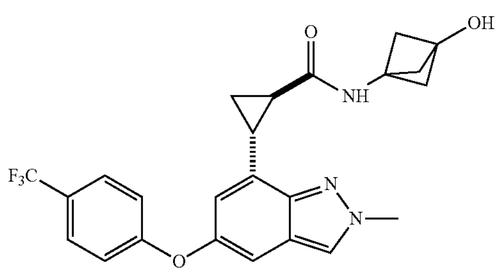 |
| 103a and 103b | Pure enantiomers (configuration arbitrarily assigned) | diastereoisomer |

&

TABLE 1-continued
| Example | Chirality Comments | Structure |
|---|---|---|
| | | 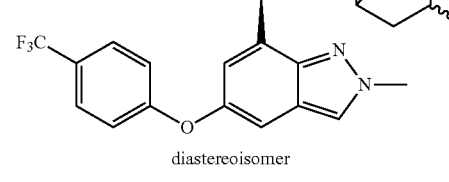<br>diastereoisomer |
| 103c | Pure trans enantiomer (unknown configuration) | 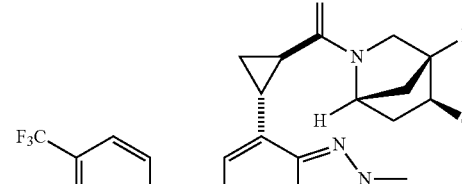 |
| 103d | Pure trans enantiomer (unknown configuration) | 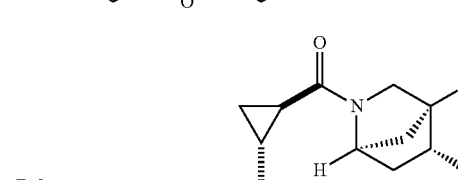 |
| 103e | Pure trans enantiomer (unknown configuration) | 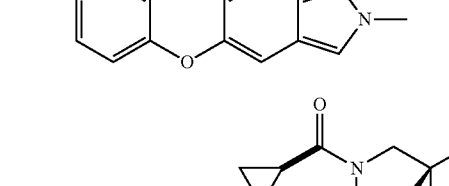 |
| 103f | Pure trans enantiomer (unknown configuration) | 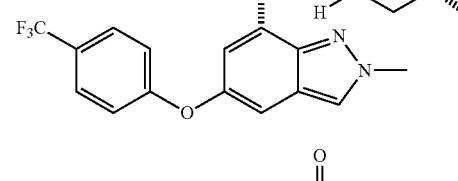 |
| 104 | Pure trans enantiomer (unknown configuration) | 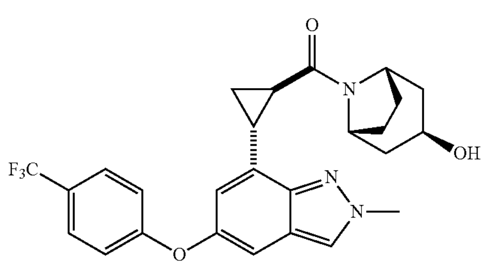 |

TABLE 1-continued

| Example | Chirality Comments | Structure |
|---|---|---|
| 105 | Pure trans enantiomer (unknown configuration) | 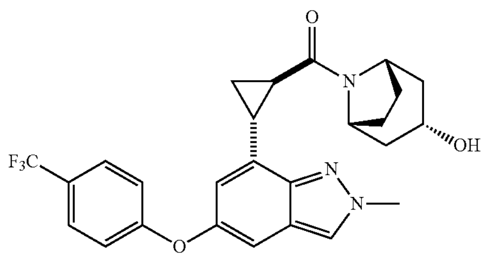 |
| 106 | Pure trans enantiomer (unknown configuration) | 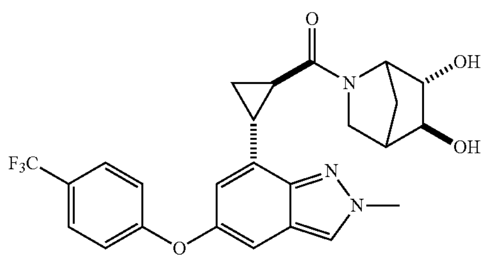 |
| 107 | Pure trans enantiomer (unknown configuration) | 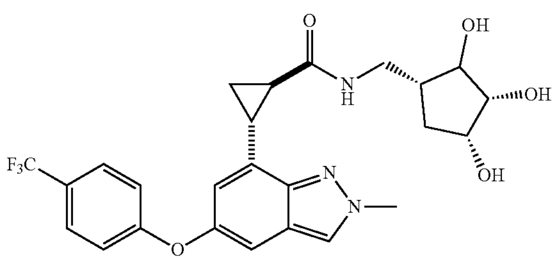 |
| 108a and 108b | Pure enantiomers (configuration arbitrarily assigned) | trans, enantiomer & trans, enantiomer |

TABLE 1-continued
| Example | Chirality Comments | Structure |
|---|---|---|
| 109a and 109b | Pure enantiomers (configuration arbitrarily assigned) | 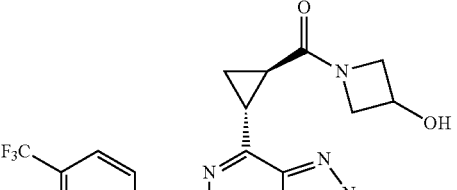<br>trans, enantiomer<br>&<br>trans, enantiomer |
| 110 | Pure trans enantiomer (unknown configuration) | 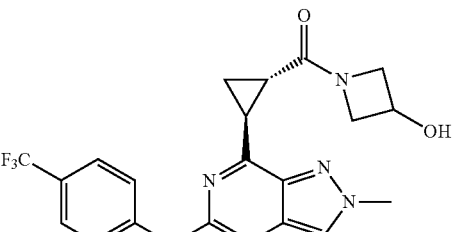 |
| 111 | Pure trans enantiomer (unknown configuration) | 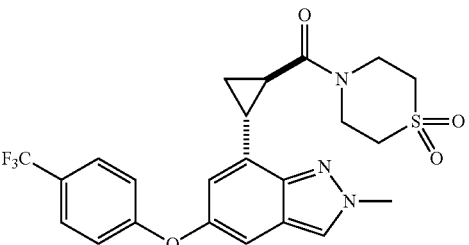 |
| 112a and 112b | Pure enantiomers (configuration arbitrarily assigned) | 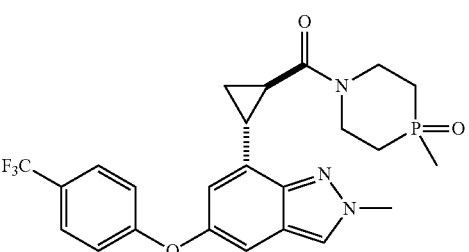<br>trans, enantiomer<br>& |

TABLE 1-continued
| Example | Chirality Comments | Structure |
|---|---|---|
| | | 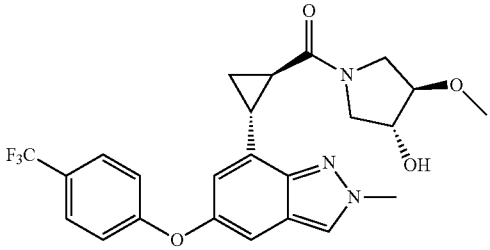trans, enantiomer<br>or<br>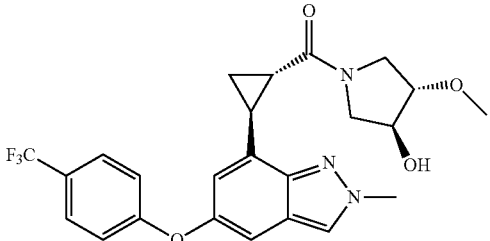trans, enantiomer<br>&<br>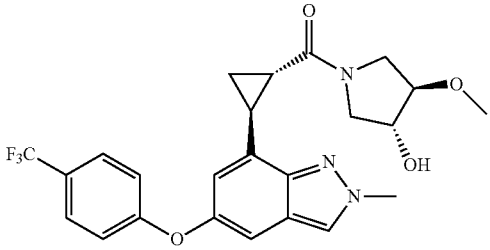trans, enantiomer |
| 113 | Pure trans enantiomer (unknown configuration) | 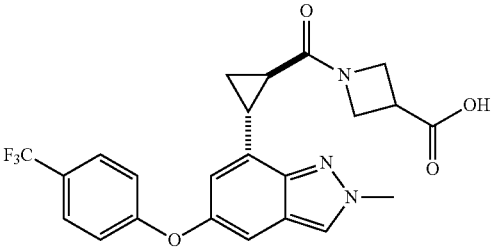 |
| 114 | Pure trans enantiomer (unknown configuration) | 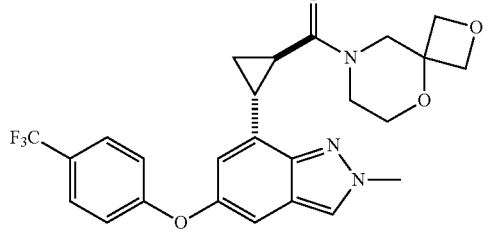 |

TABLE 1-continued
| Example | Chirality Comments | Structure |
|---|---|---|
| 115 | Pure trans enantiomer (unknown configuration) | 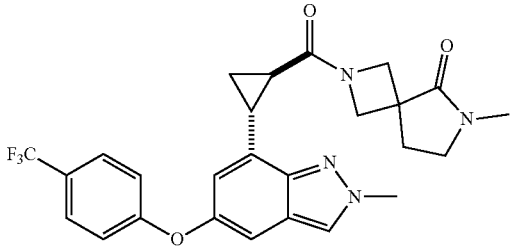 |
| 116a | Pure trans enantiomer (unknown configuration) | 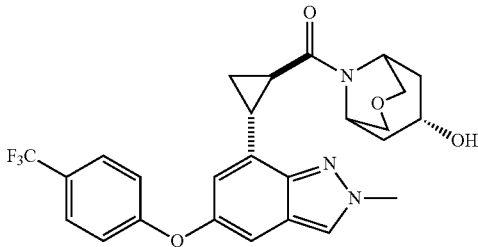 |
| 116b | Pure trans enantiomer (unknown configuration) | 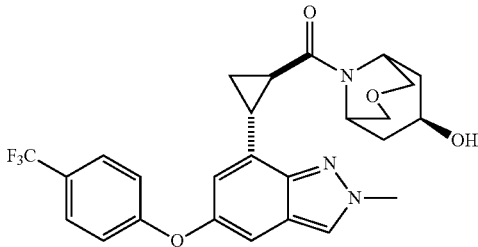 |
| 117 | Pure trans enantiomer (unknown configuration) | 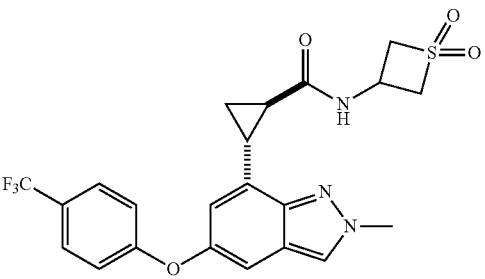 |
| 118 | Pure trans enantiomer (unknown configuration) | 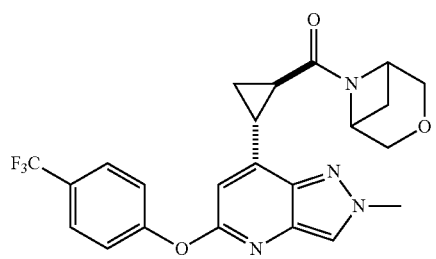 |
| 119 | Pure trans enantiomer (unknown configuration) | 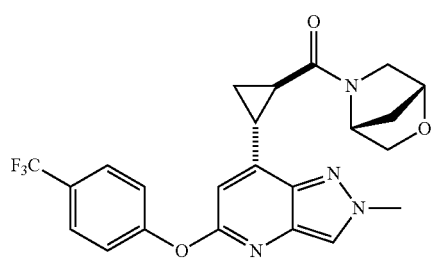 |

TABLE 1-continued

| Example | Chirality Comments | Structure |
|---|---|---|
| 120 | Pure trans enantiomer (unknown configuration) | 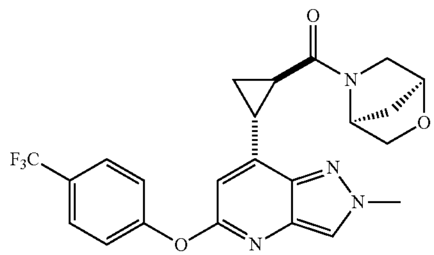 |
| 121 | Pure trans enantiomer (unknown configuration) | 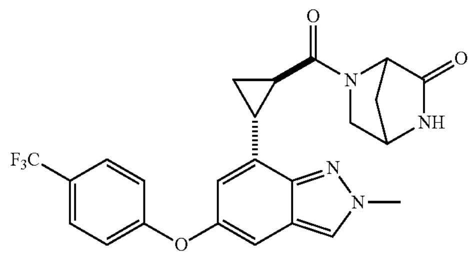 |
| 122 | Pure trans enantiomer (unknown configuration) | 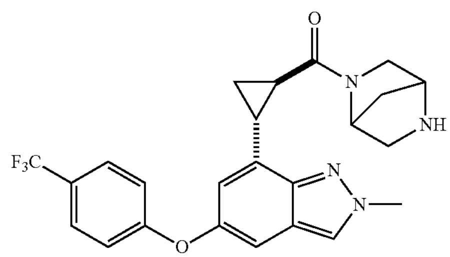 |
| 123 | Pure trans enantiomer (unknown configuration) | 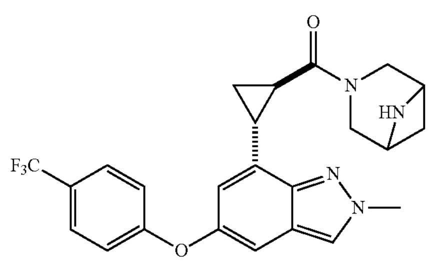 |
| 124 | Pure trans enantiomer (unknown configuration) | 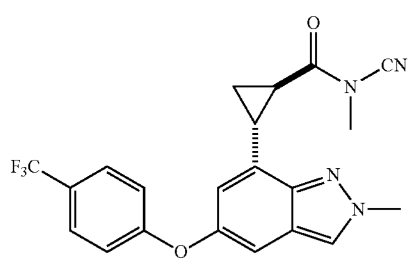 |
| 125 | Pure trans enantiomer (unknown configuration) | 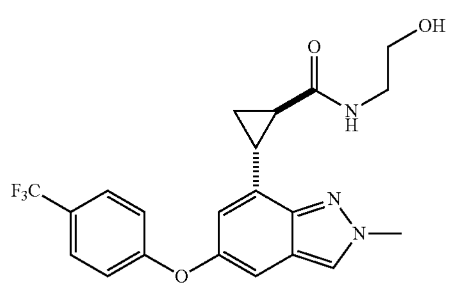 |

TABLE 1-continued

| Example | Chirality Comments | Structure |
|---|---|---|
| 126 | Pure trans enantiomer (unknown configuration) | 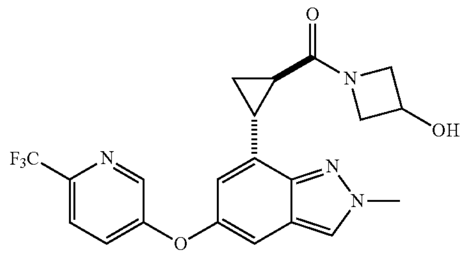 |
| 127 | Pure trans enantiomer (unknown configuration) | 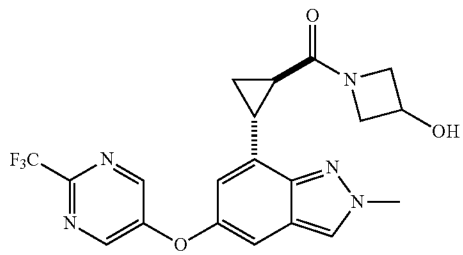 |
| 128 | Pure trans enantiomer (unknown configuration) | 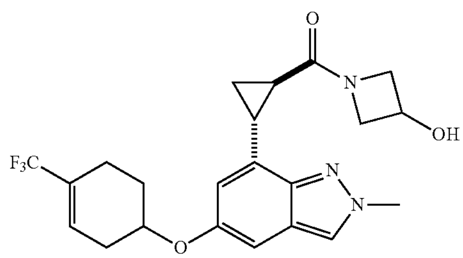 |
| 129 | Pure trans enantiomer (unknown configuration) | 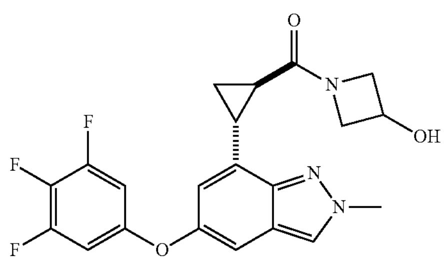 |
| 130 | Pure trans enantiomer (unknown configuration) | 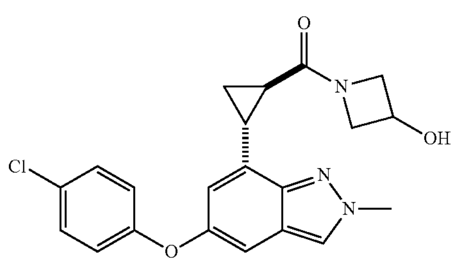 |
| 131 | Pure trans enantiomer (unknown configuration) | 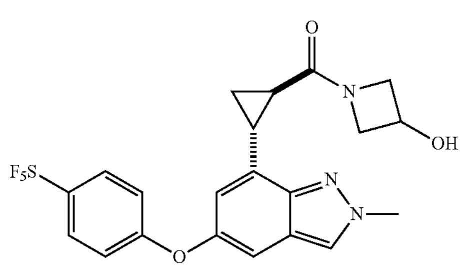 |

TABLE 1-continued
| Example | Chirality Comments | Structure |
|---|---|---|
| 132 | Pure trans enantiomer (unknown configuration) | 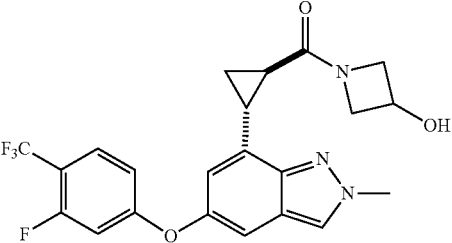 [SMILES: Cn1cc2cc(Oc3ccc(C(F)(F)F)c(F)c3)cc([C@@H]3C[C@H]3C(=O)N3CC(O)C3)c2n1] |
| 133 | Pure trans enantiomer (unknown configuration) | 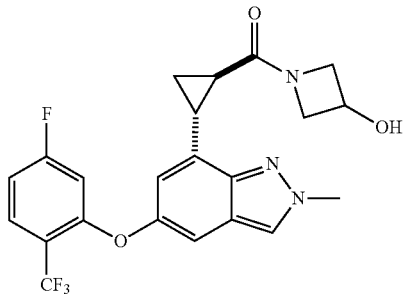 [SMILES: Cn1cc2cc(Oc3cc(F)ccc3C(F)(F)F)cc([C@@H]3C[C@H]3C(=O)N3CC(O)C3)c2n1] |
| 134 | Pure trans enantiomer (unknown configuration) | 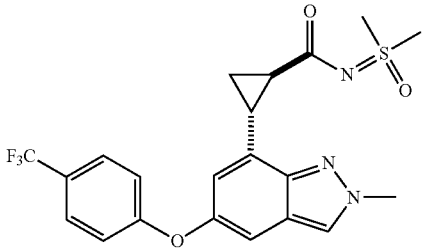 [SMILES: Cn1cc2cc(Oc3ccc(C(F)(F)F)cc3)cc([C@@H]3C[C@H]3C(=O)N=S(C)(C)=O)c2n1] |
| 135 | Pure trans enantiomer (unknown configuration) | 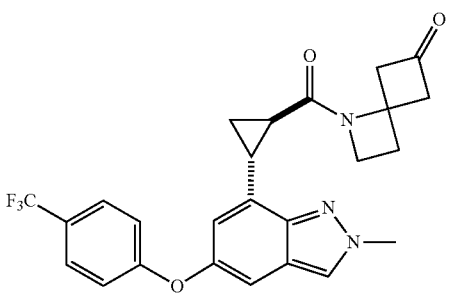 [SMILES: Cn1cc2cc(Oc3ccc(C(F)(F)F)cc3)cc([C@@H]3C[C@H]3C(=O)N3CCC34CC(=O)C4)c2n1] |
| 136 | Pure trans enantiomer (unknown configuration) | 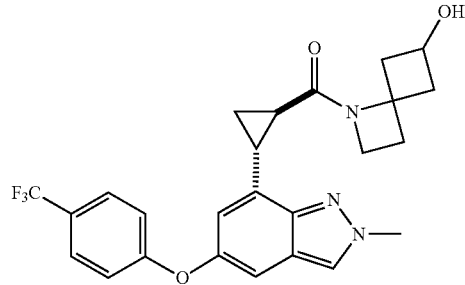 [SMILES: Cn1cc2cc(Oc3ccc(C(F)(F)F)cc3)cc([C@@H]3C[C@H]3C(=O)N3CCC34CC(O)C4)c2n1] |

TABLE 1-continued

| Example | Chirality Comments | Structure |
|---|---|---|
| 137 | Pure trans enantiomer (unknown configuration) | 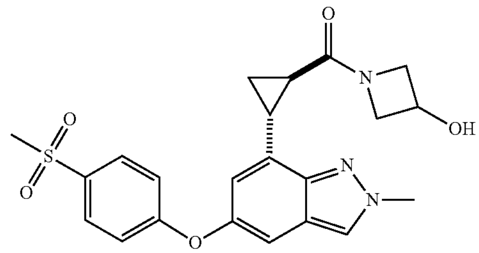 [SMILES: Cn1cc2cc(Oc3ccc(S(C)(=O)=O)cc3)cc([C@@H]3C[C@H]3C(=O)N3CC(O)C3)c2n1] |
| 138 | Pure trans enantiomer (unknown configuration) | 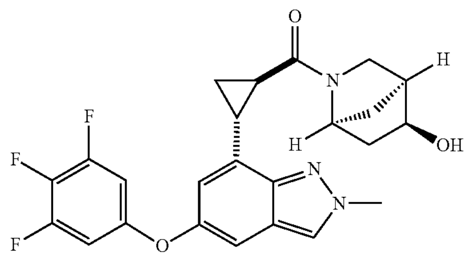 [SMILES: Cn1cc2cc(Oc3cc(F)c(F)c(F)c3)cc([C@@H]3C[C@H]3C(=O)N3C[C@@H]4C[C@H]3C[C@@H]4O)c2n1] |
| 139 | Pure trans enantiomer (unknown configuration) | 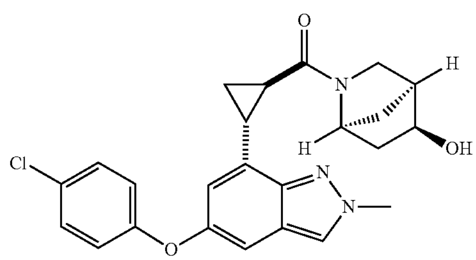 [SMILES: Cn1cc2cc(Oc3ccc(Cl)cc3)cc([C@@H]3C[C@H]3C(=O)N3C[C@@H]4C[C@H]3C[C@@H]4O)c2n1] |
| 140 | Pure trans enantiomer (unknown configuration) | 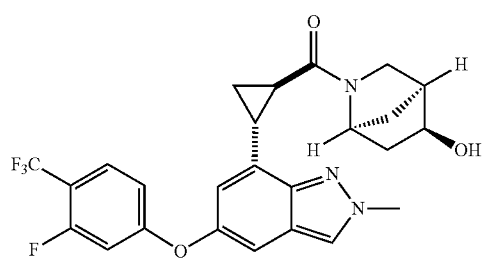 [SMILES: Cn1cc2cc(Oc3ccc(C(F)(F)F)c(F)c3)cc([C@@H]3C[C@H]3C(=O)N3C[C@@H]4C[C@H]3C[C@@H]4O)c2n1] |
| 141 | Pure trans enantiomer (unknown configuration) | 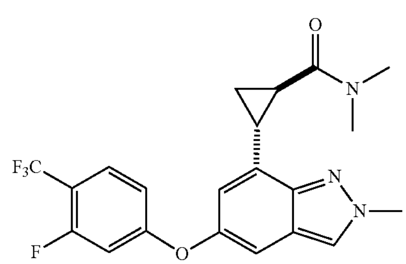 [SMILES: CN(C)C(=O)[C@@H]1C[C@H]1c1cc(Oc2ccc(C(F)(F)F)c(F)c2)cc2cn(C)nc12] |
| 142 | NA | 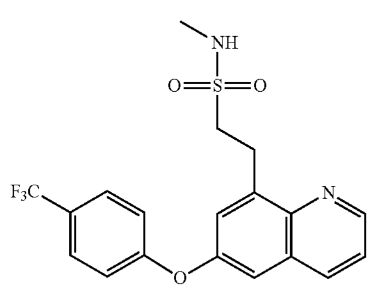 [SMILES: CNS(=O)(=O)CCc1cc(Oc2ccc(C(F)(F)F)cc2)cc2cccnc12] |

TABLE 1-continued

| Example | Chirality Comments | Structure |
|---------|---------------------|-----------|
| 143 | NA | 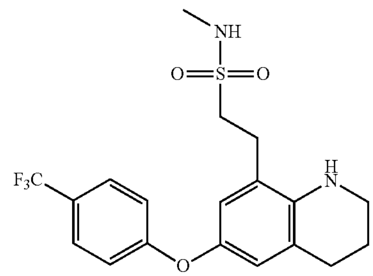 [SMILES: CNS(=O)(=O)CCc1cc(Oc2ccc(C(F)(F)F)cc2)cc2c1NCCC2] |
| 144 | Trans racemic | 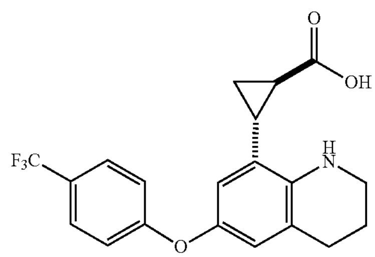 [SMILES: O=C(O)[C@@H]1C[C@H]1c1cc(Oc2ccc(C(F)(F)F)cc2)cc2c1NCCC2] |
| 145 | Trans racemic | 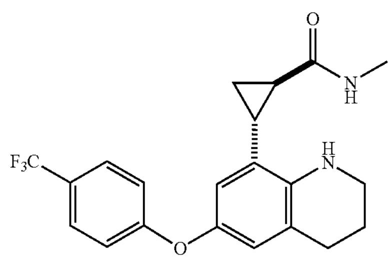 [SMILES: CNC(=O)[C@@H]1C[C@H]1c1cc(Oc2ccc(C(F)(F)F)cc2)cc2c1NCCC2] |
| 146 | Trans racemic | 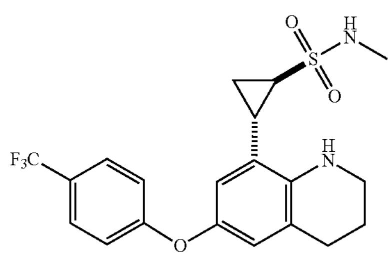 [SMILES: CNS(=O)(=O)[C@@H]1C[C@H]1c1cc(Oc2ccc(C(F)(F)F)cc2)cc2c1NCCC2] |

In some embodiments the compound disclosed herein, or a pharmaceutically acceptable salt, or stereoisomer thereof, is one of the compounds in Table 2.

TABLE 2

-continued

153
-continued
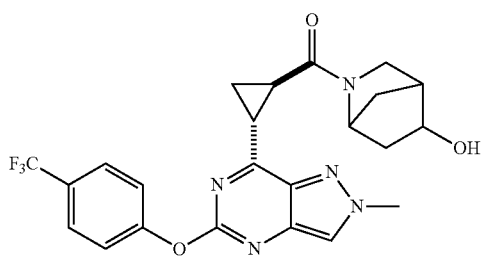
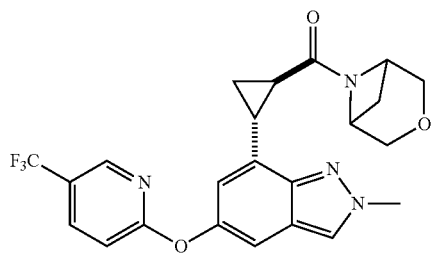
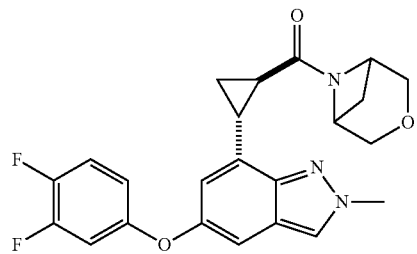
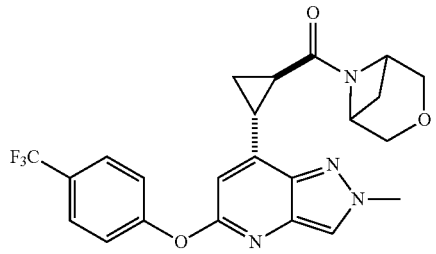
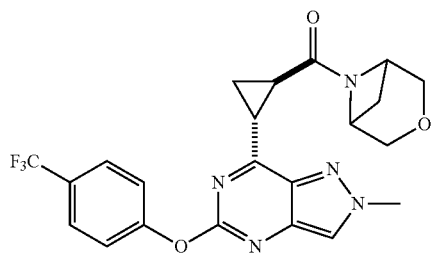
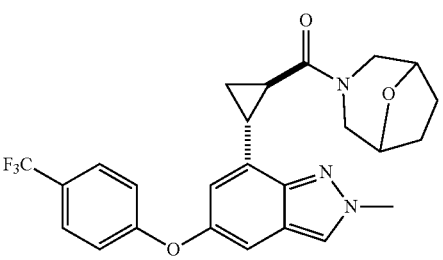
154
-continued
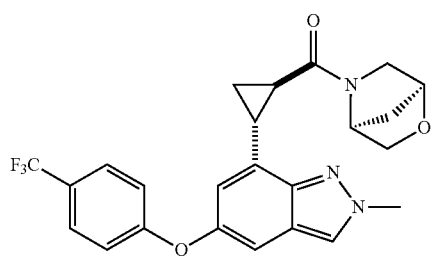
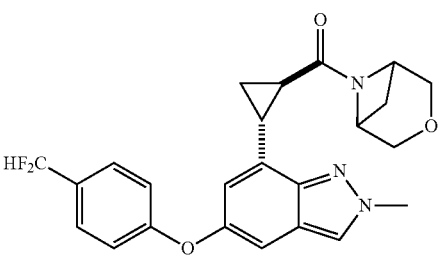
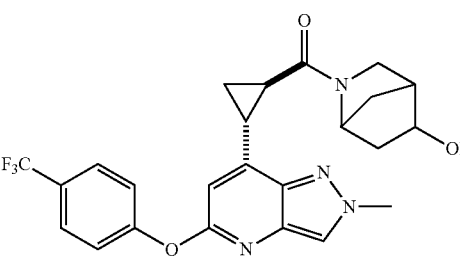
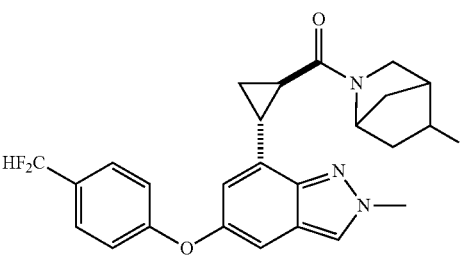
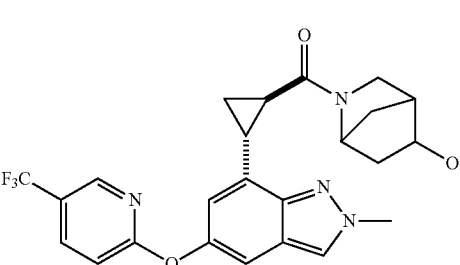
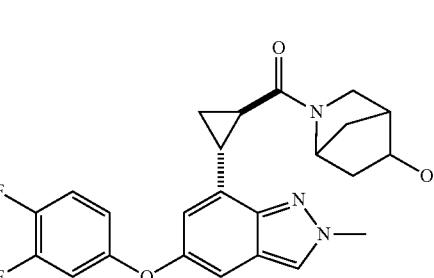

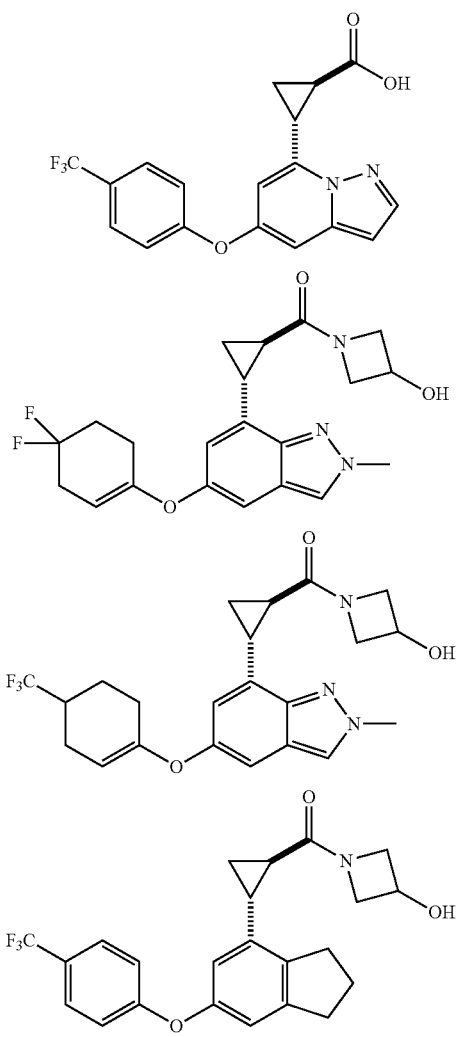
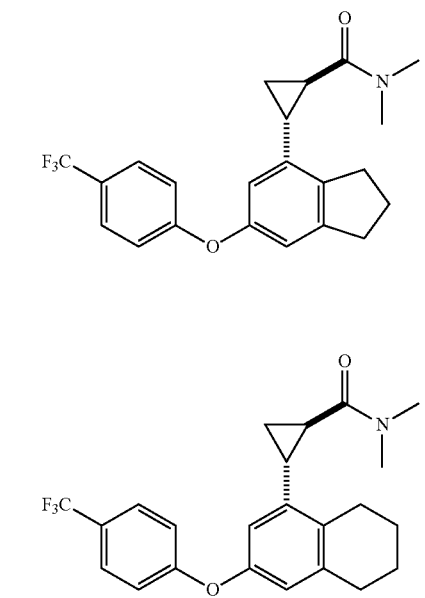
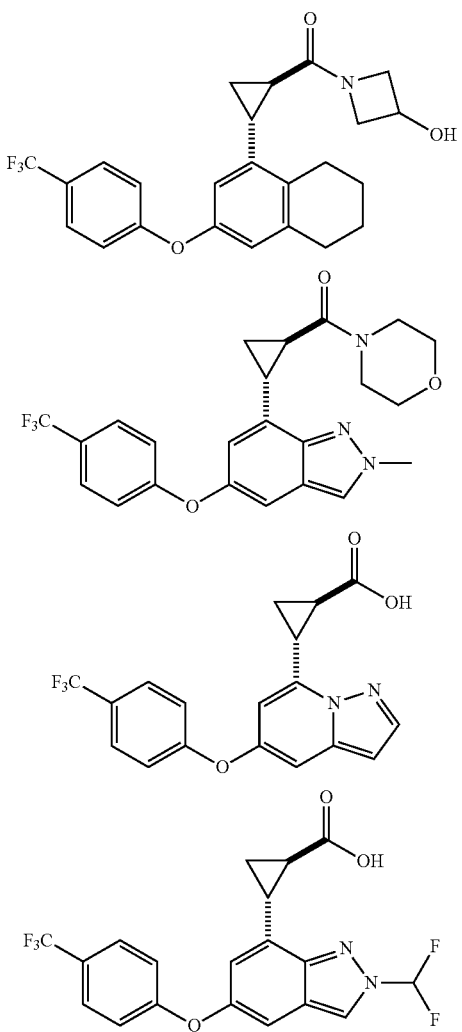
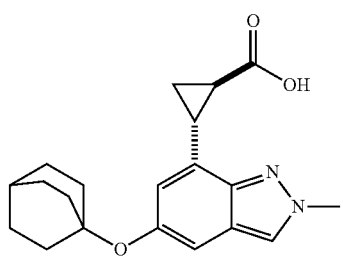
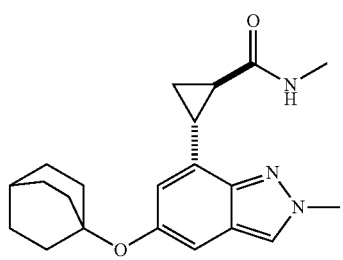

157
-continued
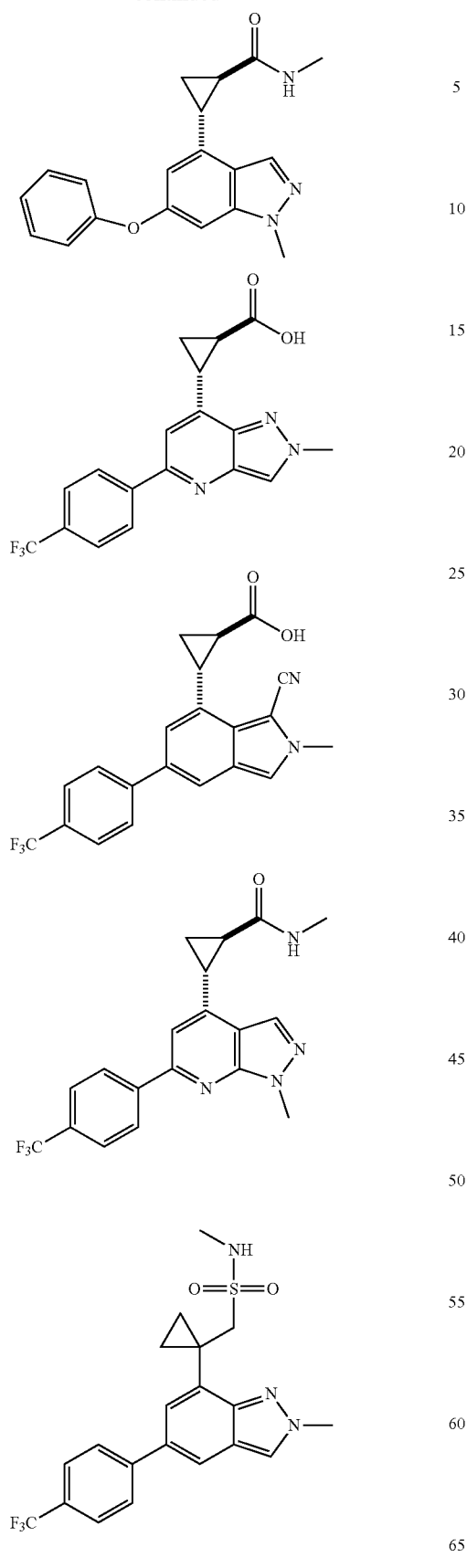
158
-continued
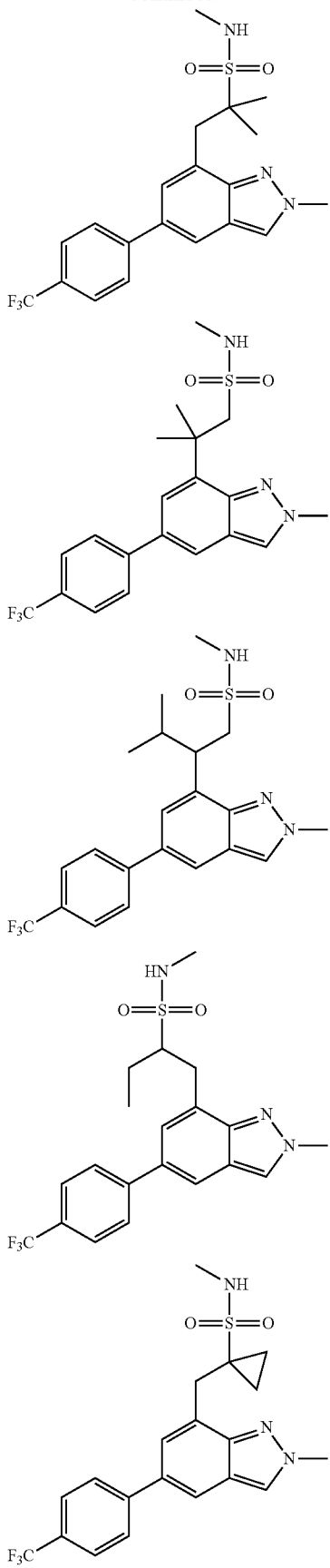

159
-continued
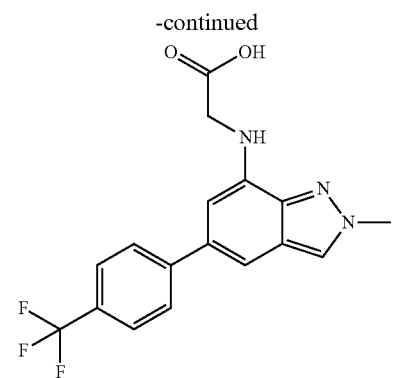
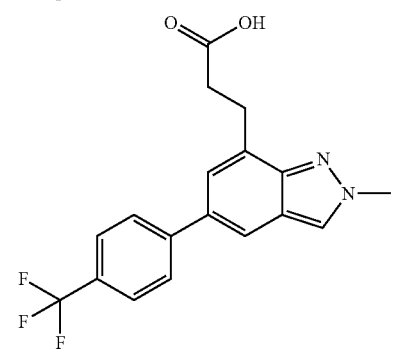
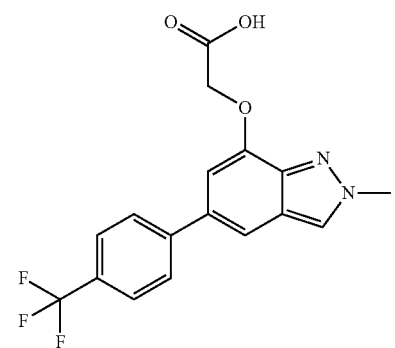
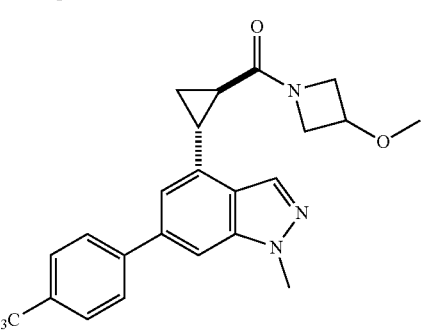
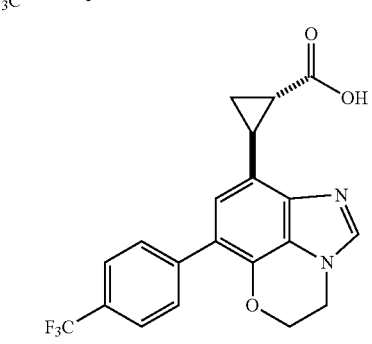
160
-continued
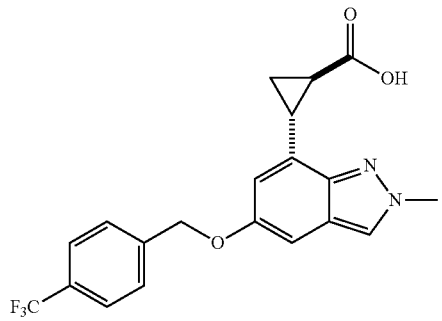
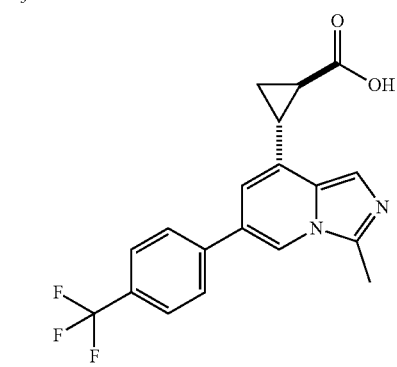
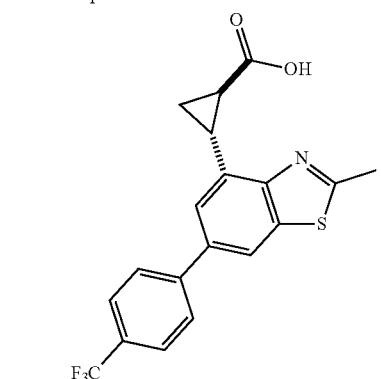
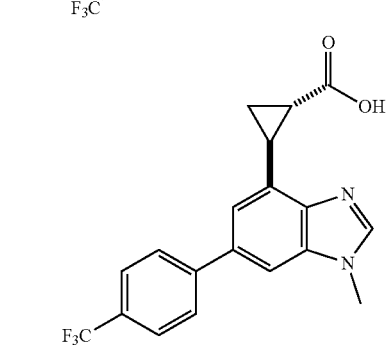
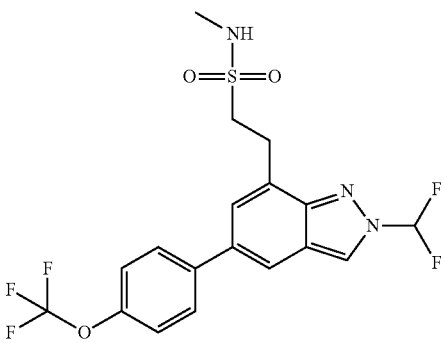

-continued
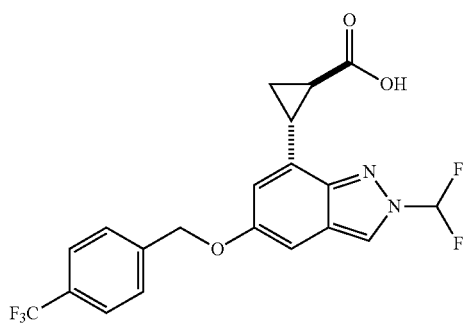
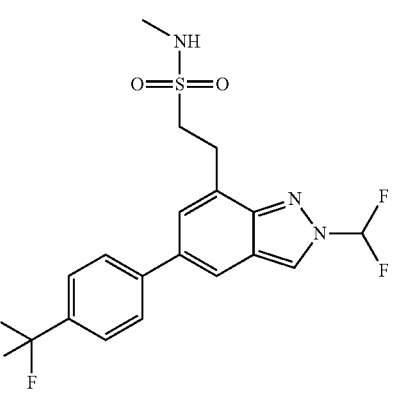
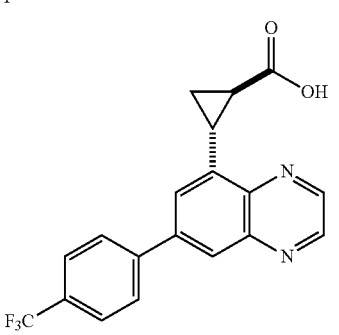
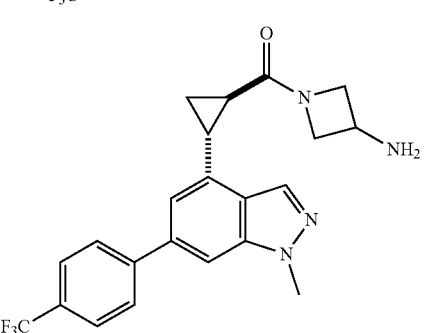
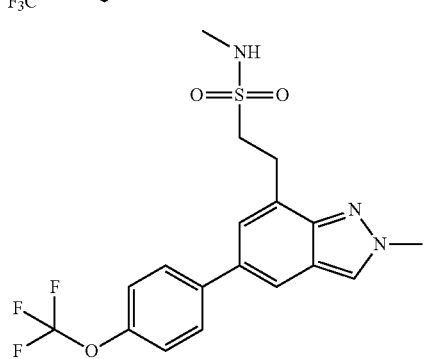
-continued
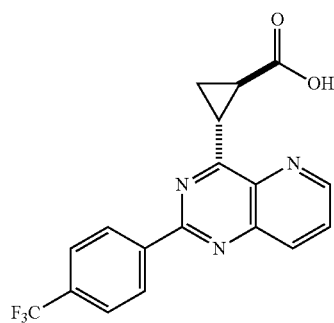
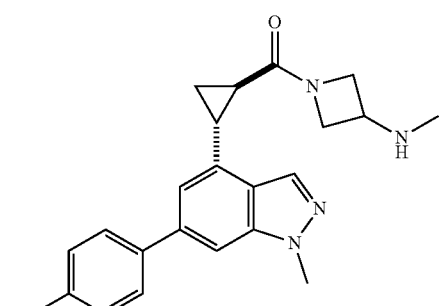
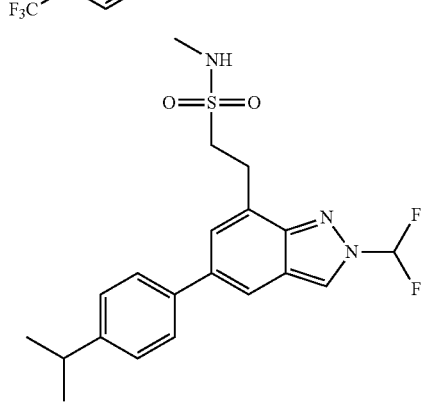
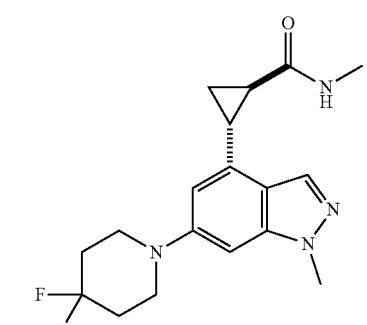
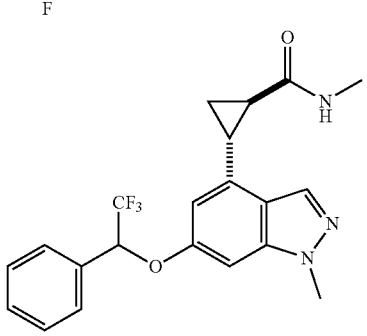

163
-continued
164
-continued
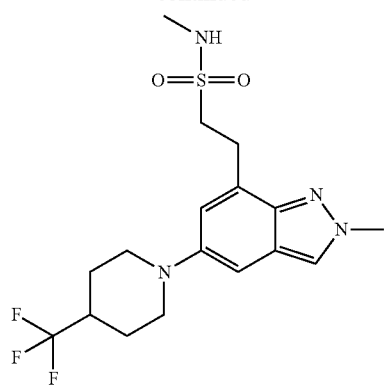
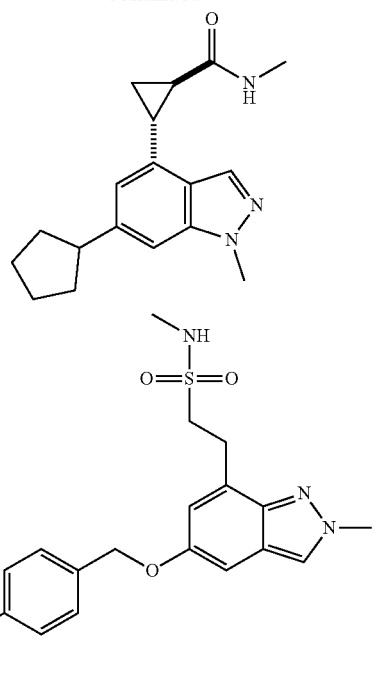
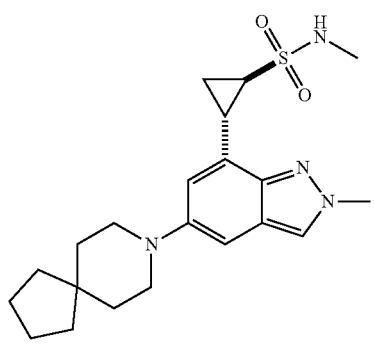
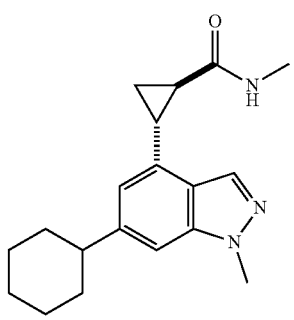
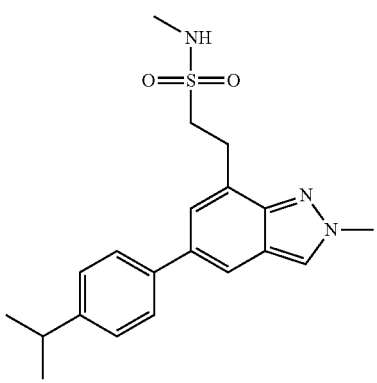

165
-continued
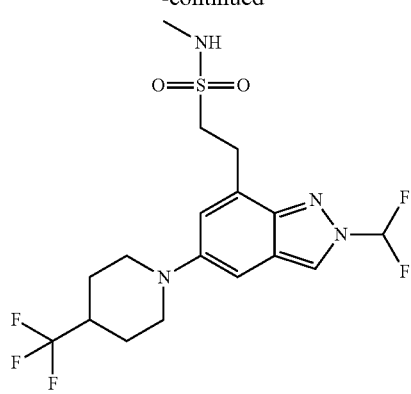
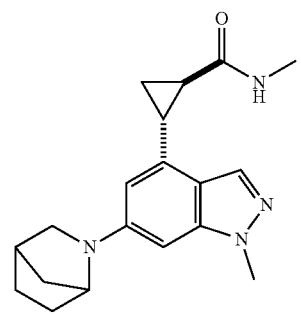
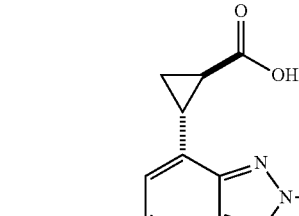
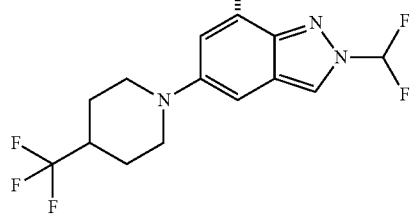
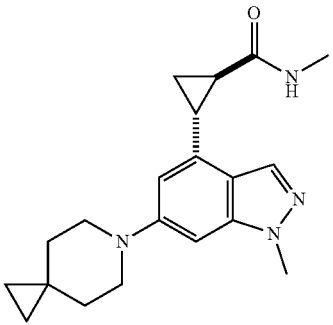
166
-continued
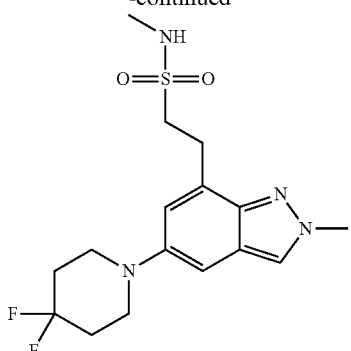
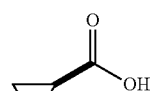
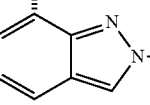
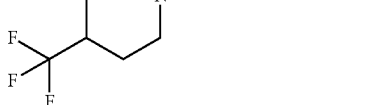
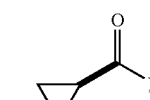
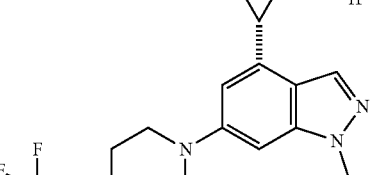
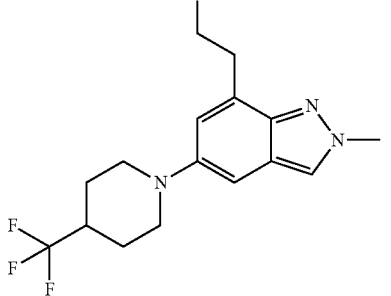
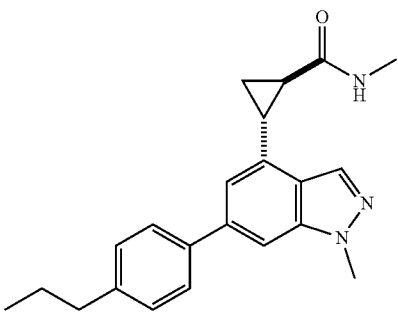

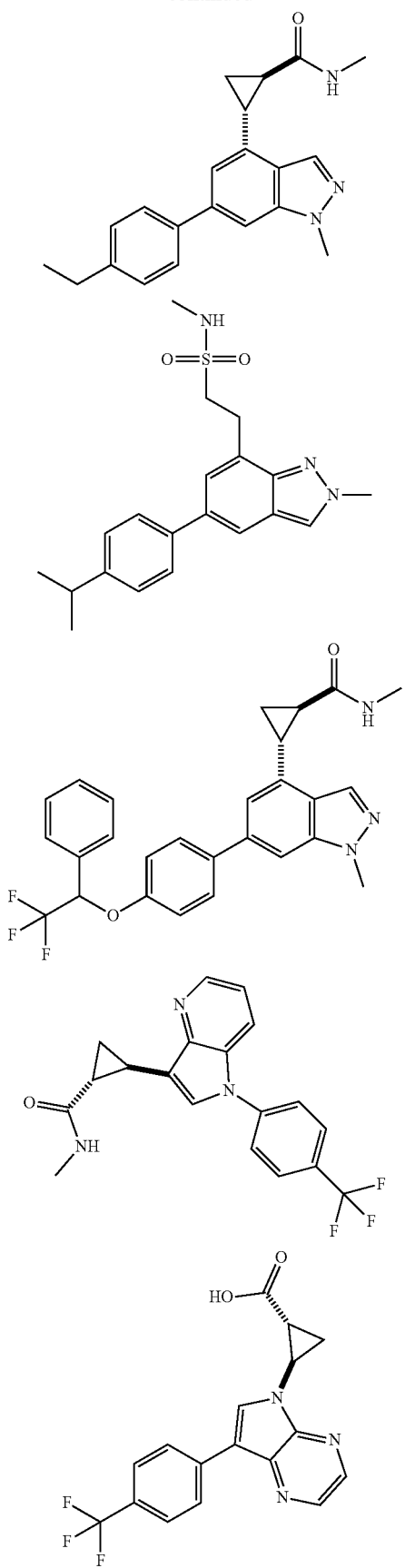
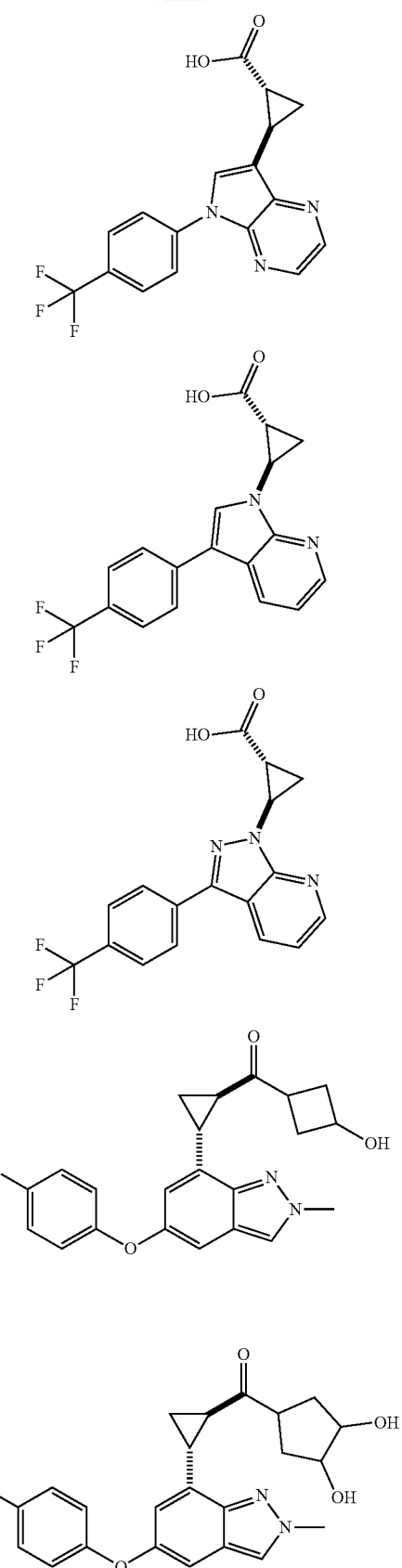

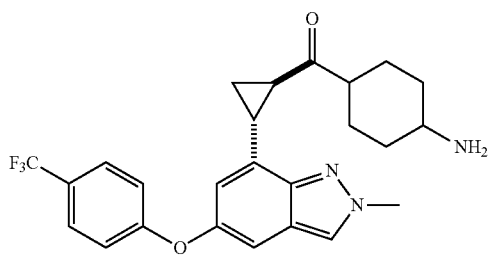

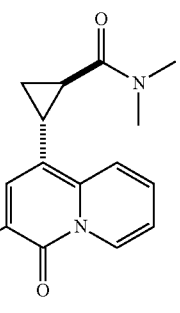

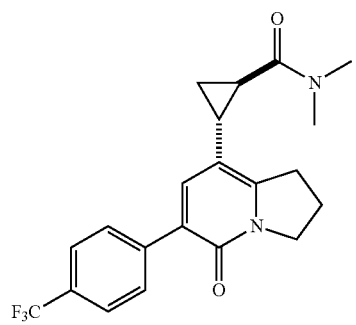

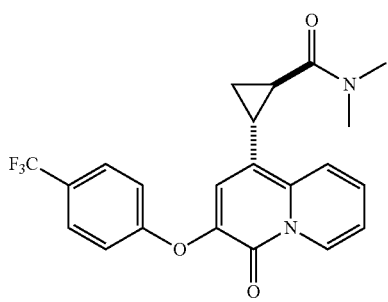

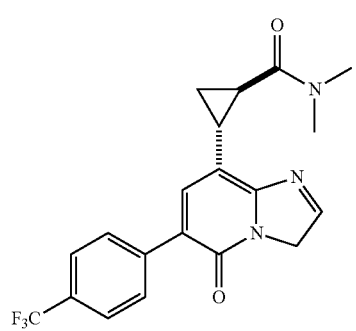

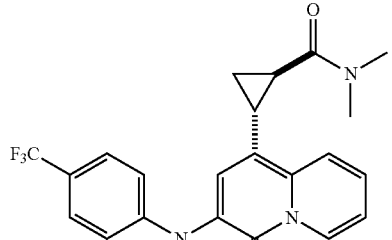

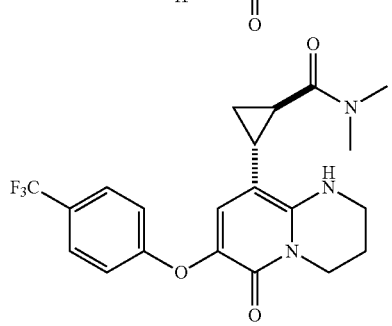

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Unless explained otherwise, in the present disclosure, bonds represented by solid wedge lines ( ◢ ) and dashed wedge lines ( ◁ ) are used to indicate absolute configuration of a chiral center, bonds represented by solid lines ( ◢ ) and dashed lines ( ◁ ) are used to indicate relative configuration of a chiral center, and a bond represented by a wavy line ( ∿ ) is used to indicate (1) a solid wedge line (⬩) or a dashed wedge line (⬩) or (2) a solid line (⬩) or a dashed line (⬩).

Isotopically Enriched Compounds

Unless otherwise stated, compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1H$ (protium), $^2H$ (deuterium), and $^3H$ (tritium). Protium is the most abundant isotope of hydrogen in nature. Enriching for deuterium may afford some therapeutic advantages, such as increased in vivo half-life and/or exposure, or may provide a compound useful for investigating in vivo routes of drug elimination and metabolism.

For example, the compounds described herein may be artificially enriched in one or more particular isotopes. In some embodiments, the compounds described herein may be artificially enriched in one or more isotopes that are not predominantly found in nature. In some embodiments, the compounds described herein may be artificially enriched in one or more isotopes selected from deuterium ($^2H$), tritium ($^3H$), iodine-125 ($^{125}I$), or carbon-14 ($^{14}C$). In some embodiments, the compounds described herein are artificially enriched in one or more isotopes selected from $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{131}I$, and $^{125}I$. In some embodiments, the abundance of the enriched isotopes is independently at least 1%, at least 10%, at least 20%, at least 30%, at least 40%, at least 50%, at least 60%, at least 70%, at least 80%, at least 90%, or 100% by molar.

In some embodiments, the compound is deuterated in at least one position. In some embodiments, the compounds disclosed herein have some or all of the $^1H$ atoms replaced with $^2H$ atoms.

The methods of synthesis for deuterium-containing compounds are known in the art and include, by way of non-limiting example only, the procedure described in U.S. Pat. Nos. 5,846,514 and 6,334,997, and the following synthetic methods. For example, deuterium substituted compounds may be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undecanoate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein are methods of treating a disease in a subject in need thereof, the method comprising administering to the subject an effective amount of a TEAD inhibitor described herein, or a pharmaceutically acceptable salt, or stereoisomer thereof, or a composition described herein.

In some embodiments, the disease is mediated by TEAD activity.

In some embodiments, the disease is an advanced solid tumor. In some embodiments, the disease is a solid tumor. In some embodiments, the disease is cancer or a proliferative disorder. In some embodiments, the cancer is associated with increased TEAD expression. In some embodiments, the cancer is associated with increased TEAD activity.

In some embodiments, the cancer is a cancer in which YAP is localized in the nucleus of cells of the cancer.

In some embodiments, the increased TEAD expression or increased TEAD activity is increased TEAD1 expression or increased TEAD1 activity. In some embodiments, the increased TEAD expression or increased TEAD activity is increased TEAD2 expression or increased TEAD2 activity. In some embodiments, the increased TEAD expression or increased TEAD activity is increased TEAD3 expression or increased TEAD3 activity. In some embodiments, the increased TEAD expression or increased TEAD activity is increased TEAD4 expression or increased TEAD4 activity.

In some embodiments, the disease is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hemangioendothelioma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, or Wilms' tumor.

Also disclosed herein is a method of treating a cancer in a subject in need thereof, the method comprising administering an effective amount of a compound disclosed herein, or a pharmaceutically acceptable salt, or stereoisomer thereof, to the subject in need thereof, or a pharmaceutical composition disclosed herein.

In some embodiments of a method of treating cancer, the cancer is mesothelioma. In some embodiments of a method of treating cancer, the cancer is NF2 deficient mesothelioma.

In some embodiments of a method of treating cancer, the cancer is epithelioid hemangioendothelioma.

In some embodiments of a method of treating cancer, the cancer is a liquid tumor. In some embodiments of a method of treating cancer, the cancer is a solid tumor.

The method of claim 222, wherein the solid tumor has a NF2 mutation, a LATS1 mutation, a LATS2 mutation, or any combination thereof. In some embodiments of a method of treating cancer, the solid tumor has a NF2 mutation. In some embodiments of a method of treating cancer, the solid tumor has a LATS1 mutation. In some embodiments of a method of treating cancer, the solid tumor has a LATS2 mutation. In some embodiments of a method of treating cancer, the solid tumor has a YAP1/TAZ gene fusion.

Also disclosed herein is a method of treating a disease in which Hippo pathway inhibition is beneficial in a subject in need thereof, the method comprising administering an effective amount of a compound disclosed herein, or a pharmaceutically acceptable salt, or stereoisomer thereof, to the subject in need thereof, or a pharmaceutical composition disclosed herein.

Dosing

In certain embodiments, the compositions containing the compound(s) described herein are administered for therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage, or the frequency of administration, or both, is reduced, as a function of the symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In some embodiments, doses employed for adult human treatment are typically in the range of 0.01 mg-5000 mg per day. In some embodiments, the daily dosages appropriate for the compound described herein, or a pharmaceutically acceptable salt thereof, are from about 0.01 to about 50 mg/kg per body weight. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In some embodiments, the compounds described herein are administered to animals.

In another aspect, provided herein are pharmaceutical compositions comprising a compound described herein, or a pharmaceutically acceptable salt, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Combination

Disclosed herein are methods of treating a disease or disorder associated with TEAD using a compound disclosed herein, or a pharmaceutically acceptable salt, or stereoisomer thereof, in combination with an additional therapeutic agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

In some embodiments, the additional therapeutic agent is an anti-cancer agent.

EXAMPLES

The following examples are offered to illustrate, but not to limit the claimed invention. The following examples further illustrate the invention but, of course, should not be construed as in any way limiting its scope.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Example 1

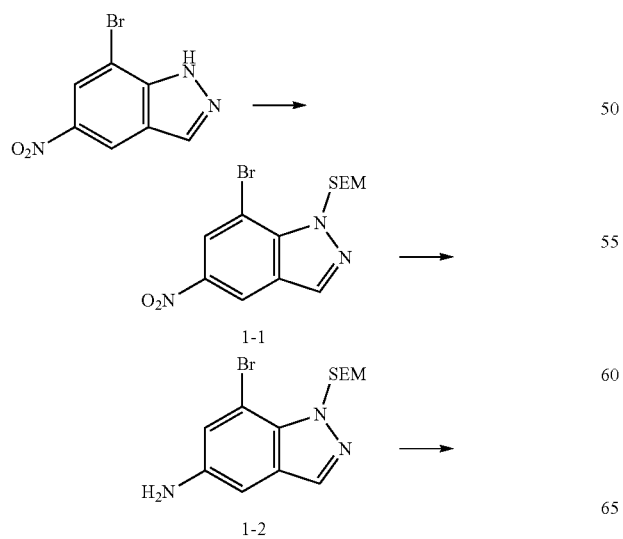

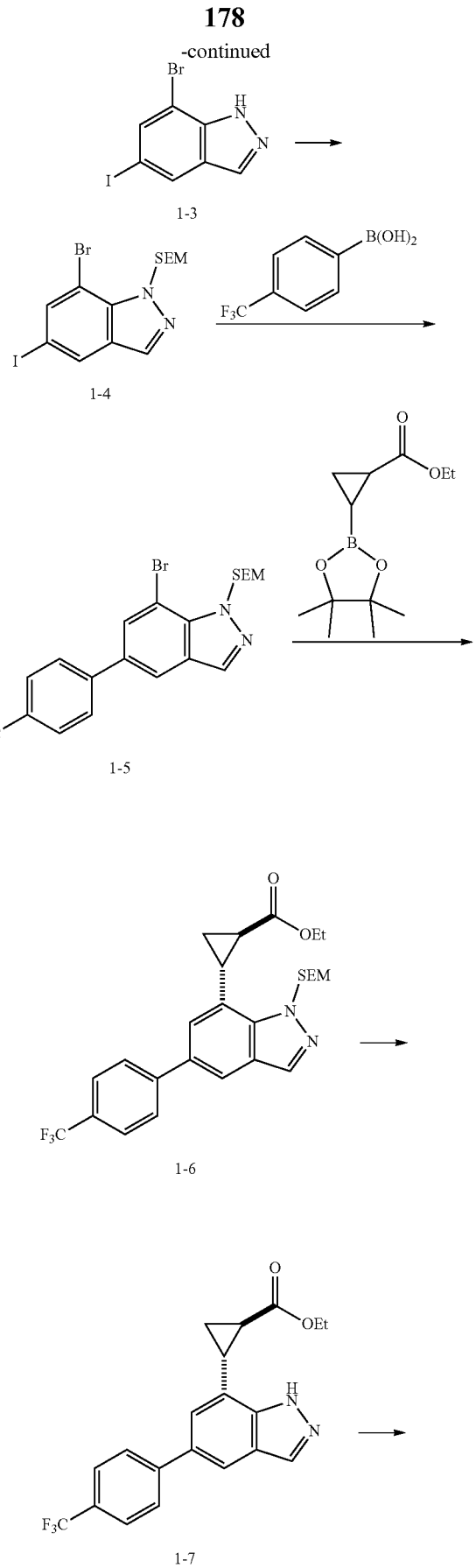

-continued

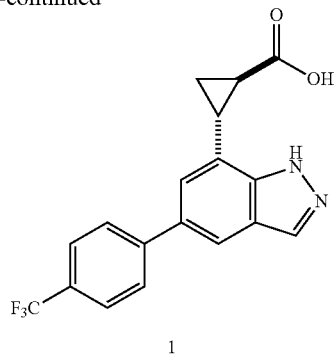

1

Step 1: Preparation of Compound 1-1

To a solution of 7-bromo-5-nitro-1H-indazole (9.80 g, 40.49 mmol) in THF (10.0 mL) was added NaH (1.94 g, 48.5 mmol) at 0° C. The mixture was warmed to 25° C. and stirred for 30 mins, then cooled to 0° C. and SEM-Cl (8.10 g, 48.5 mmol, 8.6 mL) was added. The mixture was then stirred at 25° C. for 3 hrs and filtered. The reaction mixture was poured into $H_2O$ (200 mL), then extracted with EtOAc (40 mL×5). The organic layer was washed with brine (60 mL×2), dried over $Na_2SO_4$, filtered and concentrated. The residue was purified by column chromatography to give Compound 1-1 (13.0 g, 34.9 mmol, 86.2% yield). $^1$HNMR (400 MHz, DMSO-$d_6$) δ 9.17 (s, 1H), 9.02 (d, J=2.0 Hz, 1H), 8.33 (d, J=2.0 Hz, 1H), 5.91 (s, 2H), 3.77-3.68 (m, 2H), 3.37 (s, 2H), 0.98-0.89 (m, 2H), 0.01 (s, 9H).

Step 2: Preparation of Compound 1-2

To a mixture of Compound 1-1 (4.00 g, 10.7 mmol) and $NH_4Cl$ (4.02 g, 75.2 mmol) in EtOH (15 mL) and $H_2O$ (15 mL) was added Fe (4.20 g, 75.2 mmol) in three portions. The mixture was stirred at 80° C. for 3 hrs and the iron powder was removed by filtration. Ethanol was removed and the residue was extracted with EtOAc (50 mL×2) and $H_2O$ (100 mL). The organic layer was dried with $Na_2SO_4$ and concentrated. Compound 1-2 (3.50 g, 10.2 mmol, 76.1% yield) was by column chromatography purification. LCMS: 342.0 [M+H]$^+$.

Step 3: Preparation of Compound 1-3

A mixture of Compound 1-2 (3.00 g, 8.76 mmol) in HCl (12 M, 14.6 mL) and $H_2O$ (15.0 mL) was cooled to 0° C., $NaNO_2$ (1.81 g, 26.2 mmol) was added. The reaction was stirred for 30 min to 0° C., a mixture of NaI (9.20 g, 61.3 mmol) and CuI (834 mg, 4.38 mmol) in $H_2O$ (5.0 mL) was added dropwise and the mixture was stirred at 25° C. for 2 hrs. The mixture was quenched with $Na_2S_2O_3$ (aq., 30 mL), neutralized with $Na_2CO_3$ (aq., 30 mL), and extracted with EtOAc (30 mL×2). The organic layer was dried over $Na_2SO_4$ and concentrated. The residue was purified by HPLC to give Compound 1-3 (700 mg, 2.16 mmol, 24.5% yield). LCMS: 322.8 [M+H]$^+$.

Step 4: Preparation of Compound 1-4

To a solution of Compound 1-3 (700 mg, 2.17 mmol) in THF (10.0 mL) was added NaH (173 mg, 4.34 mmol, 60.0% purity) in portions at 0° C. After stirring at 25° C. for 0.5 hr, SEM-Cl (542 mg, 3.25 mmol, 575 μL) was added dropwise and the resulting mixture was stirred at 25° C. for 1 hr. The mixture was added $NH_4Cl$ (aq., 30 mL) and extracted with EtOAc (30 mL×2). The organic layer was dried over $Na_2SO_4$, filtered and concentrated. The residue was purified by column chromatography to give Compound 1-4 (600 mg, 1.32 mmol, 60.8% yield). LCMS: 455.0 [M+H]$^+$.

Step 5: Preparation of Compound 1-5

A mixture of Compound 1-4 (600 mg, 1.32 mmol), (4-(trifluoromethyl)phenyl)boronic acid (226 mg, 1.19 mmol), Pd(dppf)Cl$_2$ (96.8 mg, 1.32 mmol), and $K_2CO_3$ (365 mg, 2.65 mmol) in dioxane (10 mL) and $H_2O$ (3 mL) was stirred at 80° C. for 3 hrs under $N_2$ atmosphere. The reaction was extracted with EtOAc (10 mL×2) and $H_2O$ (10 mL). The organic layer was dried with $Na_2SO_4$, concentrated, and the residue was purified by column chromatography to give Compound 1-5 (500 mg, 1.06 mmol, 80.3% yield). LCMS: 473.0 [M+H]$^+$.

Step 6: Preparation of Compound 1-6

A mixture of Compound 1-5 (700 mg, 1.48 mmol), ethyl 2-(4,4,5,5-tetramethyl-1,3,2-dioxaborolan-2-yl)cyclopropane-1-carboxylate (356 mg, 1.48 mmol), Pd(dppf)Cl$_2$ (108 mg, 1.48 mmol) and $K_2CO_3$ (615 mg, 4.45 mmol) in dioxane (10 mL) and $H_2O$ (2 mL) was stirred at 90° C. for 2 hrs under $N_2$ atmosphere. The reaction was extracted with EtOAc (50 mL×2) and $H_2O$ (50 mL). The organic layer was dried with $Na_2SO_4$, concentrated and the residue was purified by column chromatography to give Compound 1-6 (250 mg, 0.49 mmol, 33.18% yield). LCMS: 505.3 [M+H]$^+$.

Step 7: Preparation of Compound 1-7

A solution of Compound 1-6 (150 mg, 0.30 μmol) in TFA (0.5 mL) and DCM (1.5 mL) was stirred at 25° C. for 3 hrs. The mixture was concentrated, and the residue was added EtOH (2.0 mL) and $NH_3 \cdot H_2O$ (0.5 mL). The mixture was stirred at 25° C. for 0.5 hr and concentrated to give Compound 1-7 (100 mg, crude). LCMS: 375.2 [M+H]$^+$.

Step 8: Preparation of Example 1

To a solution of Compound 1-7 (40.0 mg, 106 μmol) in dioxane (3.0 mL) and $H_2O$ (1.0 mL) was added LiOH·$H_2O$ (13.4 mg, 320 μmol) and the mixture as stirred at 25° C. for 1 hr. The reaction was neutralized with HCl (1 M) to pH around 7, poured into $H_2O$ (10 mL), extracted with EtOAc (10 mL×3). The combined organic layers were washed with brine (20 mL), dried over $Na_2SO_4$ and concentrated. The residue was purified by prep-HPLC to give Example 1 (12.5 mg, 36.1 μmol, 33.8% yield). LCMS: 347.2 [M+H]$^+$. $^1$HNMR (400 MHz, METHANOL-$d_4$) δ 8.16 (s, 1H), 7.95 (d, J=1.5 Hz, 1H), 7.86-7.83 (m, 2H), 7.75-7.72 (m, 2H), 7.36 (s, 1H), 2.92-2.87 (m, 1H), 2.12-2.08 (m, 1H), 1.72-1.68 (m, 1H), 1.58-1.53 (m, 1H).

Example 2 & Example 3

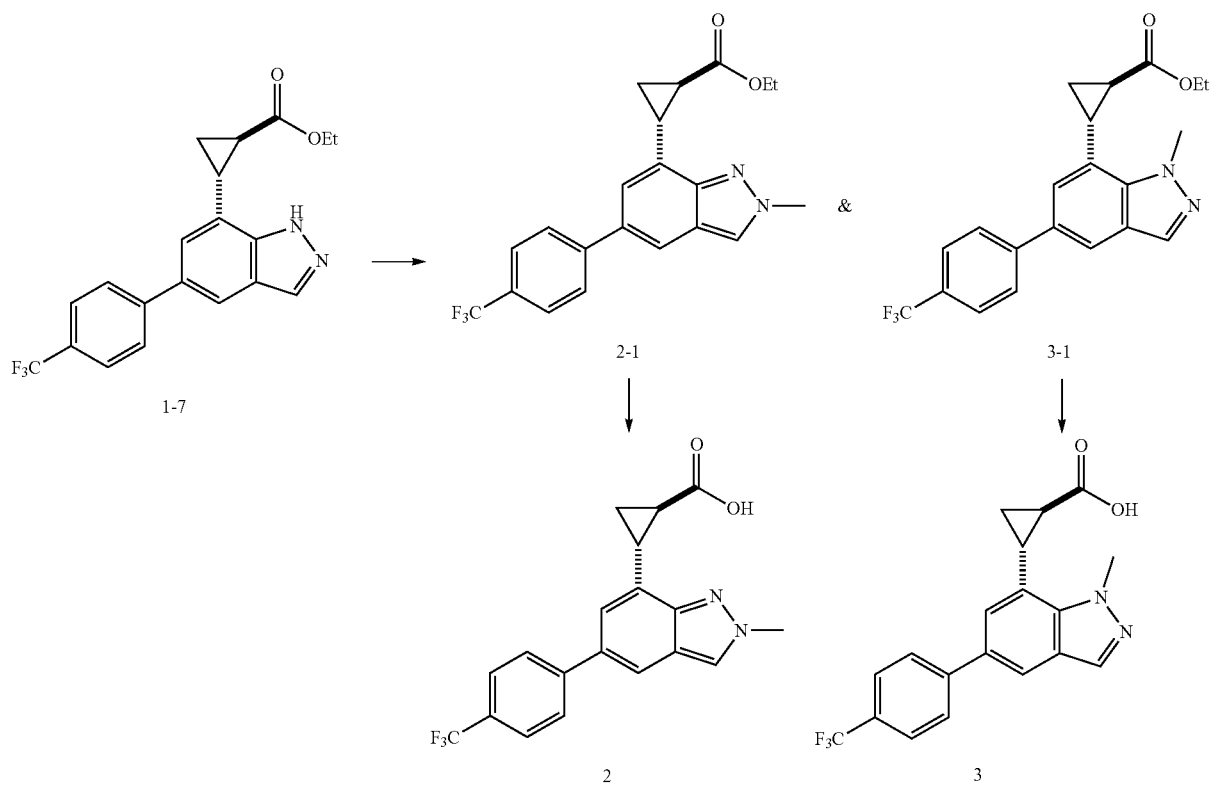

Step 1: Preparation of Compound 2-1 and Compound 3-1

To a solution of Compound 1-7 (100 mg, 267 µmol) in THF (2 mL) was added NaH (21.3 mg, 534 µmol, 60.0% purity) in portions at 0° C. After stirring at 25° C. for 1 hr, MeI (75.8 mg, 534 µmol, 33.2 µL) was added dropwise and the resulting mixture was stirred at 25° C. for 1 hr. The mixture was added aq. NH₄Cl (10 mL) and extracted with EtOAc (20 mL×3). The organic layer was dried over Na₂SO₄, filtered and concentrated. The residue was purified by prep-HPLC to give the mixture of Compound 2-1 (40.0 mg, 102 µmol, 38.1% yield) and Compound 3-1 (50 mg, 126 µmol, 47.31% yield).

Compound 2-1: LCMS: 389.2 [M+H]⁺. ¹HNMR (400 MHz, CHLOROFORM-d) δ 7.92 (s, 1H), 7.68 (s, 5H), 7.21 (s, 1H), 4.21-4.17 (m, 5H), 3.05-2.99 (m, 1H), 2.61-2.49 (m, 1H), 1.92-1.79 (m, 1H), 1.79-1.66 (m, 1H), 1.31-1.27 (m, 3H).

Compound 3-1: LCMS: 389.2 [M+H]⁺. ¹HNMR (400 MHz, CHLOROFORM-d) δ 8.01 (s, 1H), 7.78 (s, 1H), 7.68 (s, 4H), 7.30 (s, 1H), 4.37 (s, 3H), 4.30-4.15 (m, 2H), 3.10-3.05 (m, 1H), 2.13-1.97 (m, 1H), 1.75-1.72 (m, 1H), 1.63-1.53 (m, 1H), 1.35-1.31 (m, 3H).

Step 2: Preparation of Example 2

To a solution of Compound 2-1 (50.0 mg, 0.129 mmol) in dioxane (3 mL) and H₂O (1 mL) was added LiOH·H₂O (20.0 mg, 0.386 mmol), and the reaction was stirred at 25° C. for 2 hr. The reaction was neutralized with HCl (1 M) to pH around 7, poured into H₂O (10 mL), and extracted with EtOAc (10 mL×3). The combined organic layers were washed with brine (20 mL), dried over Na₂SO₄, and concentrated and the residue was purified by prep-HPLC to give Example 2 (20.0 mg, 0.055 mmol, 53.8% yield). LCMS: 361.1 [M+H]⁺. ¹HNMR (400 MHz, METHANOL-d₄) δ 8.25 (s, 1H), 7.84-7.80 (m, 3H), 7.73-07.71 (m, 2H), 7.28-7.27 (m, 1H), 4.24 (s, 3H), 3.01-2.96 (m, 1H), 2.30-2.25 (m, 1H), 1.82-1.78 (m, 1H), 1.66-1.61 (m, 1H).

Step 3: Preparation of Example 3

Example 3 (21.2 mg, 0.059 mmol, 45.6% yield) was prepared according to the similar procedures as Example 2 starting from Compound 3-1 (50.0 mg, 0.129 mmol). LCMS: 361.1 [M+H]⁺. ¹HNMR (400 MHz, METHANOL-d₄) δ 8.05 (s, 1H), 7.93-7.92 (m, 1H), 7.84-7.82 (m, 2H), 7.74-7.72 (m, 2H), 7.46-7.45 (m, 1H), 4.38 (s, 3H), 3.12-3.07 (m, 1H), 2.02-1.98 (m, 1H), 1.71-1.67 (m, 2H).

Example 4

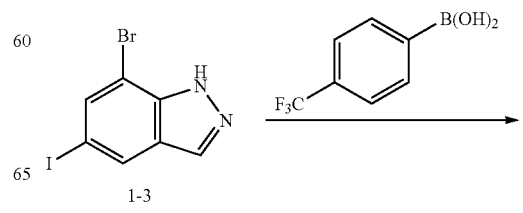

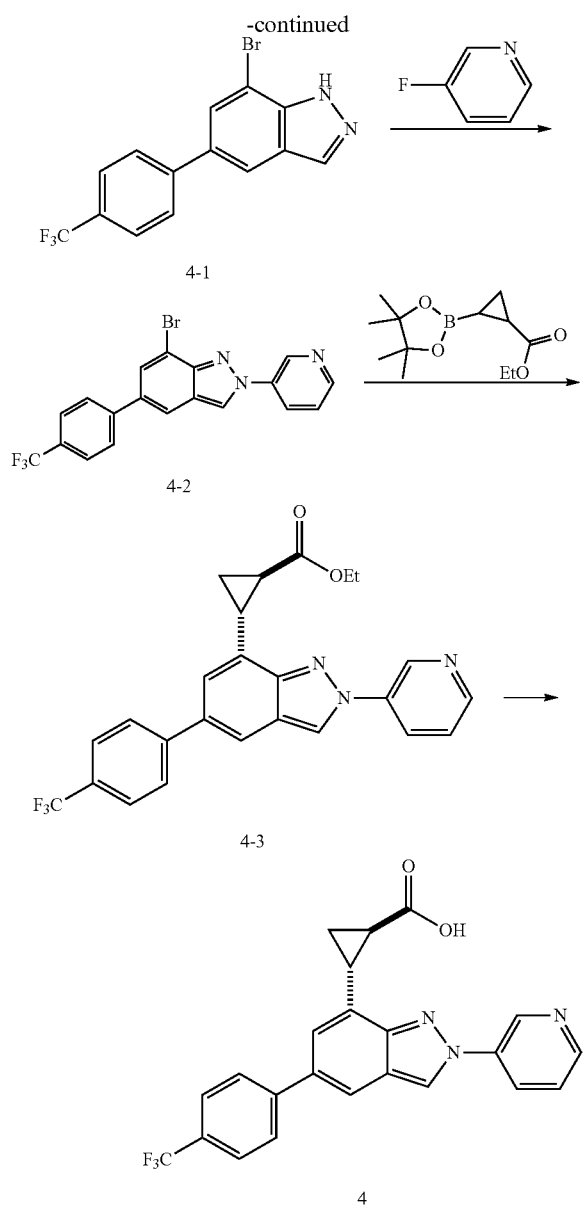

4-1

4-2

4-3

4

Step 1: Preparation of Compound 4-1

A mixture of Compound 1-3 (1.20 g, 8.85 mmol), (4-(trifluoromethyl)phenyl)boronic acid (2.52 g, 7.21 mmol), K₂CO₃ (3.67 g, 26.5 mmol) and Pd(dppf)Cl₂ (0.65 g, 0.885 mmol) in dioxane (20.0 mL) and H₂O (5.0 mL) was degassed and purged with N₂ for 3 times, and then the mixture was stirred at 100° C. for 3 hrs under N₂ atmosphere. The reaction mixture was diluted with water (20.0 mL) and extracted with EtOAc (30.0 mL×2). The combined organic layers were washed with brine (100 mL), dried over with Na₂SO₄, filtered and concentrated. The residue was purified by column chromatography to give Compound 4-1 (2.70 g, 9.27 mmol, crude). LCMS: 341.0 [M+H]⁺.

Step 2: Preparation of Compound 4-2

A mixture of Compound 4-1 (1.20 g, 3.51 mmol), 3-fluoropyridine (6.83 g, 70.3 mmol), K₂CO₃ (0.97 g, 7.035 mmol) in DMF (20 mL) was degassed and purged with N₂ for 3 times, and then stirred at 120° C. for 2 hrs under microwave condition. The mixture was diluted with water (20 mL) and extracted with EtOAc (30 mL×2). The combined organic layers were washed with brine (100 mL), dried over Na₂SO₄, filtered and concentrated. The residue was purified by column chromatography to give Compound 4-2 (400 mg, 9.27 mmol, crude). LCMS: 419.2 [M+H]⁺.

Step 3: Preparation of Compound 4-3

A mixture of Compound 4-2 (400 mg, 9.27 mmol), ethyl 2-(4,4,5,5-tetramethyl-1,3,2-dioxaborolan-2-yl)cyclopropane-1-carboxylate (0.90 g, 3.73 mmol), K₂CO₃ (1.03 g, 7.46 mmol) and Pd(dppf)Cl₂ (0.18 g, 0.25 mmol) in dioxane (10.0 mL) and H₂O (2.00 mL) was degassed and purged with N₂ for 3 times, then the mixture was stirred at 100° C. for 3 hrs under N₂ atmosphere. The reaction mixture was diluted with water (10.0 mL) and extracted with EtOAc (20.0 mL×3). The combined organic layers were washed with brine (50.0 mL), dried over with Na₂SO₄, filtered and concentrated. The residue was purified by prep-HPLC to give Compound 4-3 (150 mg, 0.33 mmol, crude). LCMS: 452.1[M+H]⁺.

Step 4: Preparation of Example 4

To a solution of Compound 4-3 (150 mg, 0.64 mmol) in THF (5.0 mL) was added a solution of LiOH (54.0 mg, 1.29 mmol) in H₂O (5.0 mL). The mixture was stirred at 65° C. for 24 hrs. The reaction mixture was diluted with water (5.0 mL) and extracted with EtOAc (10.0 mL×3). The combined organic layers were washed with brine (20.0 mL), dried over with Na₂SO₄, filtered and concentrated. The residue was purified by reversed-phase HPLC to give Example 9 (30.0 mg, 0.07 mmol, 21.2% yield). LCMS: 424.3 [M+H]⁺.
¹HNMR (400 MHz, DMSO-d₆) δ 9.36 (d, J=2.5 Hz, 1H), 9.30 (s, 1H), 8.70-8.68 (m, 1H), 8.54-8.51 (m, 1H), 8.02-8.00 (m, 3H), 7.83-7.81 (m, 2H), 7.69-7.66 (m, 1H), 7.48-7.47 (m, 1H), 2.99-2.94 (m, 1H), 2.48-2.44 (m, 1H), 1.97-1.92 (m, 1H), 1.58-1.53 (m, 1H).

Example 5

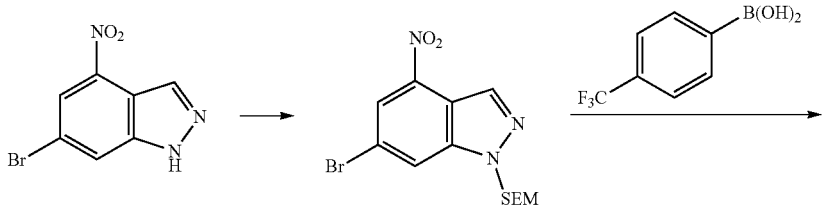

5-1

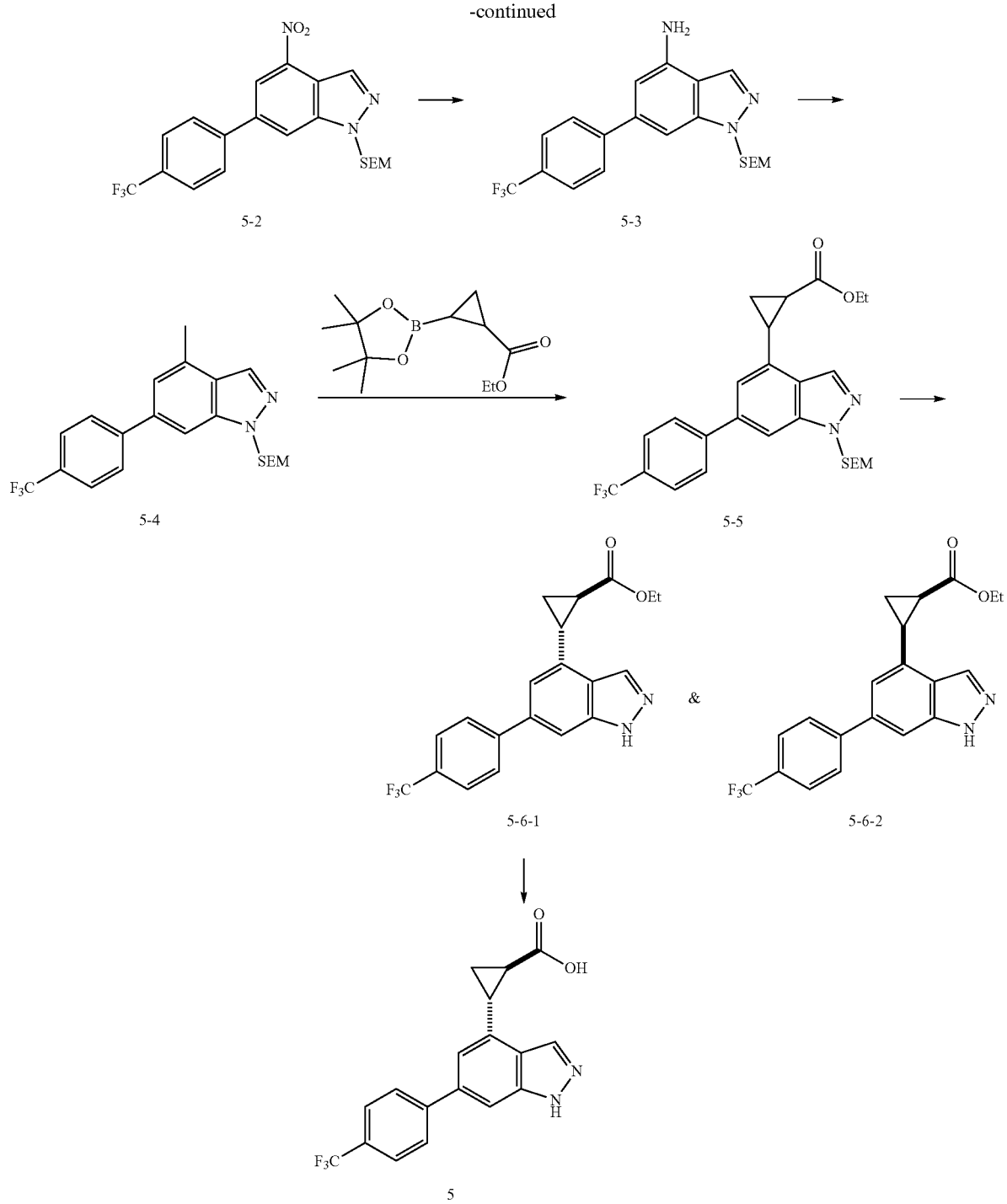

Step 1: Preparation of Compound 5-1

To a solution of 6-bromo-4-nitro-1H-indazole (9.00 g, 37.2 mmol) in THF (90.0 mL) was added portion-wise NaH (2.97 g, 74.4 mmol, 60.0% purity) at 0-10° C. and the mixture was stirred at 25° C. for 1 h. SEM-Cl (9.30 g, 55.8 mmol, 9.87 mL) was added dropwise and the mixture was stirred at 25° C. for 1 h. The mixture was poured into aqueous NH$_4$Cl (100 mL) and extracted with EtOAc (100 mL), the organic layer was dried over Na$_2$SO$_4$, filtered and concentrated. The residue was purified by column chromatography to give Compound 5-1 (9.69 g, 26.0 mmol, 70.0% yield). LCMS: 374.1[M+H]$^+$.

Step 2: Preparation of Compound 5-2

A mixture of Compound 5-1 (9.00 g, 24.2 mmol), Pd(dppf)Cl$_2$ (1.77 g, 2.42 mmol), (4-(trifluoromethyl)phenyl)boronic acid (4.59 g, 24.2 mmol) and Na$_2$CO$_3$ (7.69 g, 72.5 mmol) in dioxane (50.0 mL) and H$_2$O (20.0 mL) was stirred at 80° C. for 2 hrs under N$_2$ atmosphere. The mixture was poured into H$_2$O (100 mL) and extracted with EtOAc (100 mL). The combined organic layers were dried over Na₂SO₄ and concentrated. The residue was purified by column chromatography to give Compound 5-2 (9.20 g, 21.0 mmol, 87.0% yield). LCMS: 438.3 [M+H]⁺.

Step 3: Preparation of Compound 5-3

To a solution of Pd/C (0.50 g, 10% purity) in MeOH (20.0 mL), was added Compound 5-2 (2.00 g, 4.57 mmol), and the mixture was stirred at 25° C. for 2 hrs under H₂ (15.0 psi) atmosphere. The mixture was filtered through celite, and the solvent was removed to give crude Compound 5-3 (2.10 g, crude). LCMS: 408.2 [M+H]⁺.

Step 4: Preparation of Compound 5-4

To a solution of Compound 5-3 in HCl (10 mL) and H₂O (10 mL) was added NaNO₂ (508 mg, 7.36 mmol) at 0° C. After stirring for 0.5 h, a mixture of CuI (234 mg, 1.23 mmol) and NaI (1.84 g, 12.3 mmol) in H₂O (1.00 mL) was added dropwise and the mixture was stirred at 0° C. for 0.5 h. The mixture was quenched with aqueous Na₂S₂O₃ (20.0 mL), neutralized with aqueous Na₂CO₃ (20.0 mL), and extracted with EtOAc (60.0 mL), the organic layer was dried over Na₂SO₄ and concentrated. The residue was purified by column chromatography to give Compound 5-4. LCMS: 518.8 [M+H]⁺.

Step 5: Preparation of Compound 5-5

A mixture of Compound 5-4 (550 mg, 1.06 mmol), ethyl 2-(4,4,5,5-tetramethyl-1,3,2-dioxaborolan-2-yl)cyclopropane-1-carboxylate (382 mg, 1.59 mmol), Pd(dppf)Cl₂ (77.6 mg, 106 µmol) and Na₂CO₃ (337 mg, 3.18 mmol) in dioxane (10.0 mL) and H₂O (5.00 mL) was stirred at 85° C. for 10 hrs under N₂ atmosphere. The mixture was poured into the water (200 mL), extracted with EtOAc (40 mL), the organic layer was washed with brine (40 mL), dried over with Na₂SO₄, filtered and concentrated. The residue was purified by column chromatography to give Compound 5-5. LCMS: 505.2 [M+H]⁺.

Step 6: Preparation of Compound 5-6-1 and Compound 5-6-2

To a solution of Compound 5-5 (750 mg, 1.49 mmol) in DCM (4 mL) was added TFA (2.31 g, 20.3 mmol, 1.50 mL). The mixture was stirred at 25° C. for 10 hrs and concentrated to give a residue, which was purified by prep-HPLC to give Compound 5-6-1 (100 mg, 267 µmol, 17.97% yield) and Compound 5-6-2 (40.0 mg, 0.11 mmol, 7.38% yield).

Compound 5-6-1: LCMS: 375.2[M+H]⁺. ¹HNMR (400 MHz, CHLOROFORM-d) δ 8.23 (s, 1H), 7.75-7.70 (m, 4H), 7.51 (s, 1H), 7.31 (s, 1H), 3.86-3.76 (m, 2H), 2.91-2.87 (m, 1H), 2.34-2.30 (m, 1H), 1.90-1.88 (m, 1H), 0.90-0.87 (m, 3H).

Compound 5-6-2: LCMS: 375.2[M+H]⁺. ¹HNMR (400 MHz, CHLOROFORM-d) δ 8.15 (s, 1H), 7.68-7.60 (m, 4H), 7.44 (s, 1H), 7.23 (s, 1H), 3.83-3.64 (m, 2H), 2.80 (q, J=8.4 Hz, 1H), 2.28-2.22 (m, 1H), 1.83-1.78 (m, 1H), 1.48-1.43 (m, 1H), 0.81 (t, J=7.1 Hz, 3H).

Step 7: Preparation of Example 5

To a solution of Compound 5-6-1 (20.0 mg, 53.4 µmol) in EtOH (2.00 mL) and H₂O (1 mL) was added LiOH·H₂O (2.24 mg, 53.4 µmol). The mixture was stirred at 25° C. for 2 hrs and concentrated to give a residue, which was purified by prep-HPLC to give Example 5. LCMS: 347.2[M+H]⁺. ¹HNMR (400 MHz, METHANOL-d₄) δ 8.19 (d, J=1.0 Hz, 1H), 7.88-7.86 (m, 2H), 7.77-7.75 (m, 2H), 7.66 (s, 1H), 7.15 (s, 1H), 2.93-2.87 (m, 1H), 2.14-2.06 (m, 1H), 1.72-1.60 (m, 2H).

Example 6 & Example 7

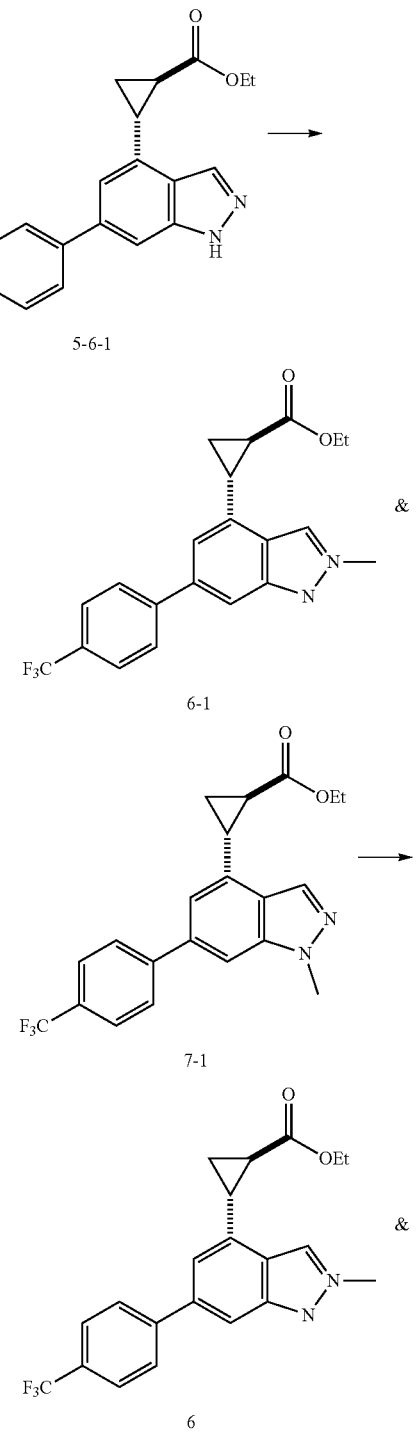

189
-continued

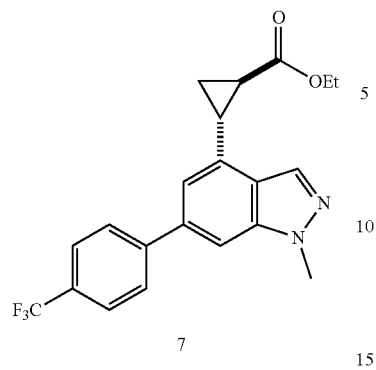

7

Step 1: Preparation of Compound 6-1 and Compound 7-1

The mixture of Compound 6-1 and Compound 7-1 (20.0 mg, 51.5 μmol, 32.1% yield) was prepared according to the similar procedures as Compound 2-1 and 3-1 starting from Compound 5-6-1 (60.0 mg, 155 μmol). LCMS: 389.2[M+H]+.

Step 2: Preparation of Example 6 and Example 7

Example 6 (15.0 mg, 41.5 μmol, 46.1%) and Example 7 (10.0 mg, 27.8 μmol, 30.8% yield) was prepared according to the similar procedures as Example 2 and Example 3 starting from Compound 6-1 and Compound 7-1 (35.0 mg, 90 μmol).

Example 6 LCMS: 361.2 [M+H]+. $^1$HNMR (400 MHz, METHANOL-$d_4$) δ 8.35 (s, 1H), 7.86-7.84 (m, 2H), 7.76-7.74 (m, 2H), 7.71 (s, 1H), 7.10 (s, 1H), 4.24 (s, 3H), 2.81-2.76 (m, 1H), 2.10-2.05 (m, 1H), 1.67-1.57 (m, 2H).

Example 7 LCMS: 361.1 [M+H]+. $^1$HNMR (400 MHz, METHANOL-$d_4$) δ 8.41 (s, 1H), 8.13 (s, 1H), 7.90-7.88 (m, 2H), 7.77-7.75 (m, 2H), 7.67 (s, 1H), 7.13 (s, 1H), 4.11 (s, 3H), 2.89-2.80 (m, 1H), 2.09-2.02 (m, 1H), 1.69-1.63 (m, 1H), 1.59-1.50 (m, 1H).

Example 8

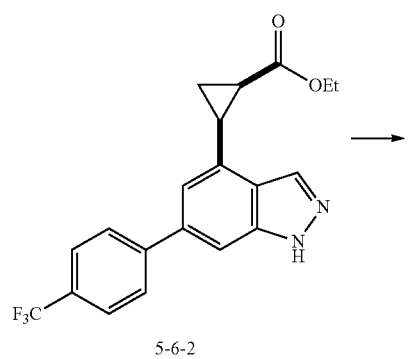

5-6-2

190
-continued

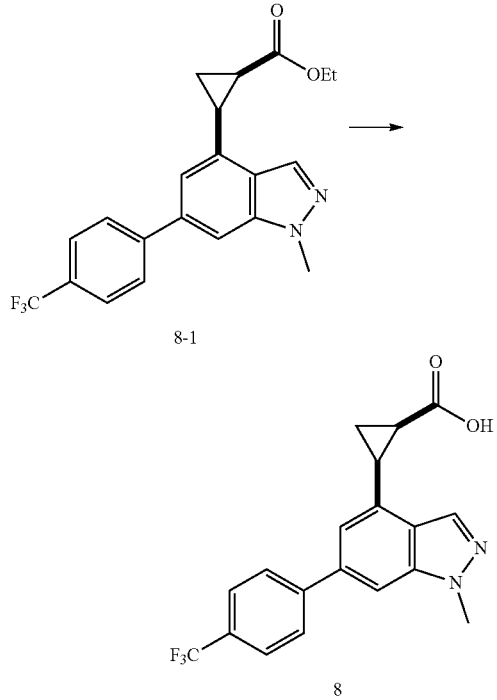

8-1

8

Example 8 (30.0 mg, 0.08 mmol, 80.8%) was prepared according to the similar procedures as Example 6 and Example 7 starting from Compound 5-6-2 (40.0 mg, 0.11 mmol). LCMS: 361.1 [M+H]+. $^1$HNMR (400 MHz, METHANOL-$d_4$) δ 8.19 (s, 1H), 7.94-7.91 (m, 2H), 7.79-7.77 (m, 2H), 7.69 (s, 1H), 7.35 (s, 1H), 2.98-2.92 (m, 1H), 2.35-2.30 (m, 1H), 1.84-1.80 (m, 1H), 1.57-1.52 (m, 1H).

Example 9

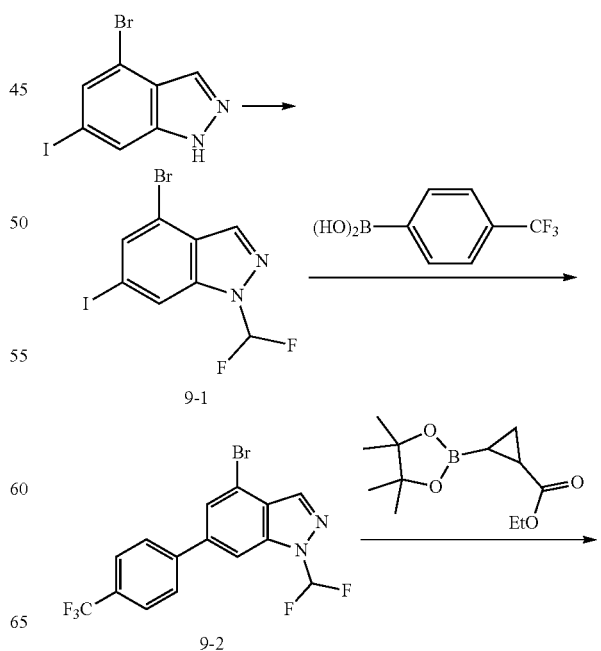

9-1

9-2

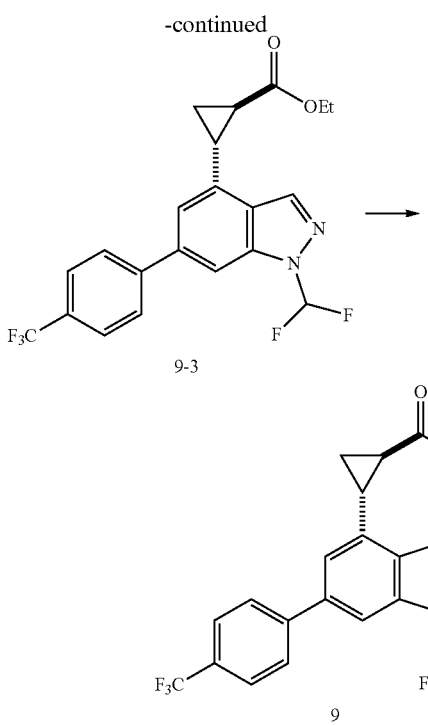

Step 1: Preparation of Compound 9-1

To a solution 4-bromo-6-iodo-1H-indazole (600 mg, 1.86 mmol), and KF (432 mg, 7.43 mmol) in ACN (10.0 mL) at 25° C. for 2 hrs under $N_2$ was added diethyl (bromodifluoromethyl) phosphonate (992 mg, 3.72 mmol). The mixture was stirred at 25° C. for 5 hrs. The reaction mixture was poured into the water (50 mL), extracted with EtOAc (20 mL×2). The organic layer was washed with brine (20 mL×2), dried over $Na_2SO_4$, filtered, and concentrated. The residue was purified by prep-TLC to give Compound 9-1 (200 mg, 0.54 mmol, 28.9%). LCMS: 374.8 [M+H]$^+$.

Step 2: Preparation of Compound 9-2

To a solution of Compound 9-1 (200 mg, 0.54 mmol), (4-(trifluoromethyl)phenyl)boronic acid (91.7 mg, 0.48 mmol) and Pd(dppf)Cl$_2$ (39.2 mg, 0.05 mmol) in dioxane (6 mL) and H$_2$O (2 mL) were added Na$_2$CO$_3$ (114 mg, 1.07 mmol). The reaction was stirred at 80° C. for 2 hrs. The mixture was poured into the water (50 mL), extracted with EtOAc (20 mL×2). The organic layer was washed with brine (20 mL×2), dried over Na$_2$SO$_4$, filtered and concentrated. The residue was purified by prep-TLC to give Compound 9-2 (140 mg, 0.36 mmol, 66.7%). LCMS: 392.8 [M+H]$^+$.

Step 3: Preparation of Compound 9-3

To a solution of Compound 9-2 (140 mg, 0.36 mmol), ethyl 2-(4,4,5,5-tetramethyl-1,3,2-dioxaborolan-2-yl)cyclopropane-1-carboxylate (129 mg, 0.54 mmol) and Pd(dppf)Cl$_2$ (26.2 mg, 0.04 mmol) in dioxane (3 mL) and H$_2$O (1 mL) were added K$_2$CO$_3$ (98.9 mg, 0.72 mmol), and the reaction was stirred at 80° C. for 2 hrs under N$_2$. The mixture was poured into the water (50 mL), extracted with EtOAc (20 mL×2). The organic layer was washed with brine (20 mL×2), dried over Na$_2$SO$_4$, filtered, and concentrated. The residue was purified by prep-HPLC to give Compound 9-3 (30.0 mg, 0.07 mmol, 19.8%). LCMS: 425.1 [M+H]$^+$.

Step 4: Preparation of Example 9

To a solution of Compound 9-3 (30.0 mg, 0.07 mmol) in EtOH (4 mL) and H$_2$O (2 mL) were added LiOH (5.93 mg, 0.14 mmol). The mixture was stirred at 60° C. for 30 min and concentrated. The residue was purified by prep-HPLC to give Example 9 (11.8 mg, 0.03 mmol, 42.5%). LCMS: 397.2 [M+H]$^+$. $^1$HNMR (400 MHz, METHANOL-d$_4$) δ 8.42-8.41 (m, 1H), 8.00-7.71 (m, 6H), 7.32 (s, 1H), 2.96-2.94 (m, 1H), 2.18-2.14 (m, 1H), 1.75-1.72 (m, 1H), 1.69-1.64 (m, 1H).

Example 10

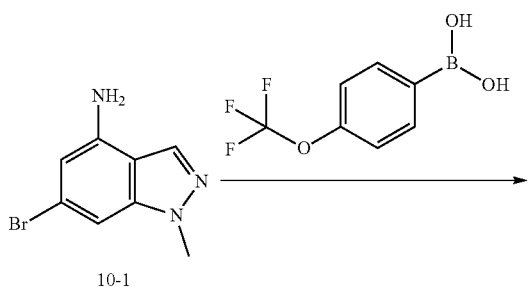

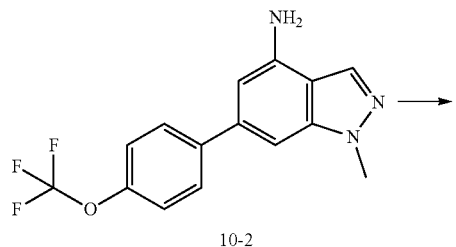

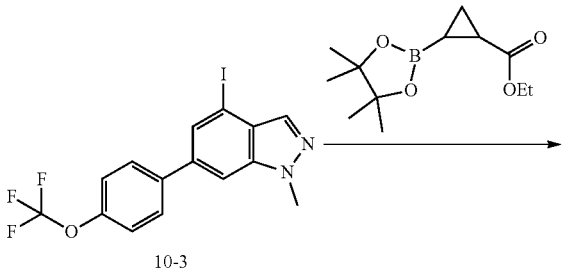

-continued

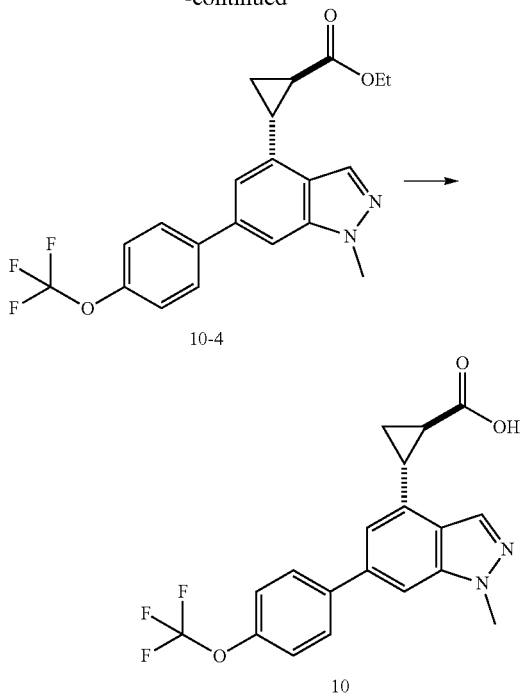

10-4

10

Step 1: Preparation of Compound 10-1

To a solution of 6-bromo-1-methyl-4-nitroindazole (10 g, 39.05 mmol) in EtOH (100 mL) was added a solution of $NH_4Cl$ (10.44 g, 195.27 mmol) in $H_2O$ (50 mL) and Fe (10.90 g, 195.27 mmol). The mixture was stirred at 60° C. for 3 hrs. The reaction mixture was diluted with water (5 mL) and extracted with EtOAc (100 mL×3). The combined organic layers were washed with brine (200 mL), dried over with $Na_2SO_4$, filtered and concentrated. The residue was purified by column chromatography to give Compound 10-1 (4.2 g, 18.577 mmol, 47.57%). LCMS: 226.1 [M+H]$^+$.

Step 2: Preparation of Compound 10-2

To a solution of Compound 10-1 (450 mg, 1.99 mmol), (4-(trifluoromethoxy)phenyl)boronic acid (615 mg, 3.00 mmol) and Pd(dppf)Cl$_2$ (146 mg, 0.20 mmol) in dioxane (3 mL) and $H_2O$ (1 mL) were added $K_2CO_3$ (825 mg, 5.97 mmol), and the reaction was stirred at 80° C. for 2 hrs. The mixture was poured into water (50 mL) and extracted with EtOAc (20 mL×2) The organic layer was washed with brine (20 mL×2), dried over with $Na_2SO_4$, filtered and concentrated. The residue was purified by column chromatography to give Compound 10-2 (600 mg, 1.95 mmol, 98.1%). LCMS: 308.3 [M+H]$^+$.

Step 3: Preparation of Compound 10-3

To a solution of Compound 10-2 (400 mg, 1.30 mmol) in HCl (1 mL) and $H_2O$ (1 mL) were added slowly sodium nitrite (180 mg, 2.60 mmol) in $H_2O$ (1 mL) at 0° C. The reaction was stirred at 0° C. for 30 min, then added slowly CuI (18.6 mg, 0.10 mmol) and KI (648 mg, 3.91 mmol) at 0° C. The reaction was stirred at 0° C. for 1 hr. The reaction mixture was poured into the water (50 mL), extracted with EtOAc (20 mL×2), the organic layer was washed with brine (20 mL×2), dried over with $Na_2SO_4$, filtered and concentrated. The residue was purified by column chromatography to give Compound 10-3 (200 mg, 0.478 mmol, 36.74%). LCMS: 419.2 [M+H]$^+$.

Step 4: Preparation of Compound 10-4

To a solution of Compound 10-3 (200 mg, 0.48 mmol), ethyl 2-(4,4,5,5-tetramethyl-1,3,2-dioxaborolan-2-yl)cyclopropane-1-carboxylate (172 mg, 0.72 mmol) and Pd(dppf)Cl$_2$ (70.0 mg, 0.10 mmol) in dioxane (4 mL) and $H_2O$ (1 mL) were added $K_2CO_3$ (198 mg, 1.44 mmol), and the reaction was stirred at 80° C. for 2 hrs under $N_2$. The mixture was poured into the water (50 mL), extracted with EtOAc (20 mL×2). The organic layer was washed with brine (20 mL×2), dried over with $Na_2SO_4$, filtered and concentrated. The residue was purified by prep-TLC to give Compound 10-4 (30 mg, 0.074 mmol, 15.51%). LCMS: 405.2[M+H]$^+$.

Step 5: Preparation of Example 10

To a solution of Compound 10-4 (50.0 mg, 0.12 mmol) in EtOH (4.0 mL) and $H_2O$ (2.0 mL) were added LiOH (10.4 mg, 0.25 mmol) and the reaction was stirred at 25° C. for 2 hrs. The mixture was concentrated and the residue was purified by prep-HPLC to give Example 10 (10.0 mg, 0.03 mmol). LCMS: 377.2 [M+H]$^+$. $^1$HNMR (400 MHz, METHANOL-d$_4$) δ 8.13 (s, 1H), 7.83-7.81 (m, 2H), 7.65 (s, 1H), 7.40-7.38 (m, 2H), 7.13 (s, 1H), 4.13 (s, 3H), 2.91-2.86 (m, 1H), 2.13-2.08 (m, 1H), 1.72-1.61 (m, 2H).

Example 11

Example 11 (10.0 mg, 0.03 mmol) was prepared according to the similar procedures as Example 10 by replacing (4-(trifluoromethyl)phenyl)boronic acid with (4-isopropylphenyl)boronic acid. LCMS: 335.1[M+H]$^+$. $^1$HNMR (400 MHz, METHANOL-d$_4$) δ 8.11 (s, 1H), 7.66-7.64 (m, 2H), 7.60 (s, 1H), 7.37-7.35 (m, 2H), 7.13 (s, 1H), 4.12 (s, 3H), 3.01-2.94 (m, 1H), 2.90-2.85 (m, 1H), 2.11-2.06 (m, 1H), 1.71-1.60 (m, 2H), 1.32 (d, J=6.9 Hz, 6H).

Example 12

Example 12 (30 mg, 0.138 mmol) was prepared according to the similar procedures as Example 10 by 6-bromo-1-methyl-4-nitroindazole with 5-bromo-2-methyl-7-nitro-2H-indazole. LCMS: 377.2 [M+H]$^+$. $^1$HNMR (400 MHz, METHANOL-d$_4$) δ 8.23 (s, 1H), 7.77-7.71 (m, 3H), 7.34 (d, J=8.1 Hz, 2H), 7.24-7.23 (m, 1H), 4.25 (s, 3H), 3.02-2.97 (m, 1H), 2.30-2.25 (m, 1H), 1.82-1.78 (m, 1H), 1.67-1.62 (m, 1H).

Example 13

Example 13 (10 mg, 0.028 mmol) was prepared according to the similar procedures as Example 10 by replacing 6-bromo-1-methyl-4-nitroindazole with 8-bromo-6-nitroquinoline. LCMS: 358.4 [M+H]$^+$. $^1$HNMR (400 MHz, METHANOL-d$_4$) δ 8.96-8.95 (m, 1H), 8.43-8.40 (m, 1H), 8.11-8.10 (m, 1H), 7.99-7.97 (m, 2H), 7.82-7.80 (m, 2H), 7.69-7.68 (m, 1H), 7.60-7.57 (m, 1H), 3.68-3.63 (m, 1H), 2.16-2.14 (m, 1H), 1.79-1.75 (m, 1H), 1.71-1.66 (m, 1H).

Example 14

Example 14 (15 mg, 41.3 μmol) was prepared according to the similar procedures as Example 10 by replacing 6-bromo-1-methyl-4-nitroindazole with 4-bromo-6-nitrobenzo[d]thiazole. LCMS: 364.3 [M+H]+. ¹HNMR (400 MHz, METHANOL-d₄) δ 9.28 (s, 1H), 8.25 (s, 1H), 7.92-7.90 (m, 2H), 7.79-7.77 (m, 2H), 7.70 (s, 1H), 3.27-3.21 (m, 1H), 2.40-2.38 (m, 1H), 1.92-1.87 (m, 1H), 1.64-1.59 (m, 1H).

Example 15

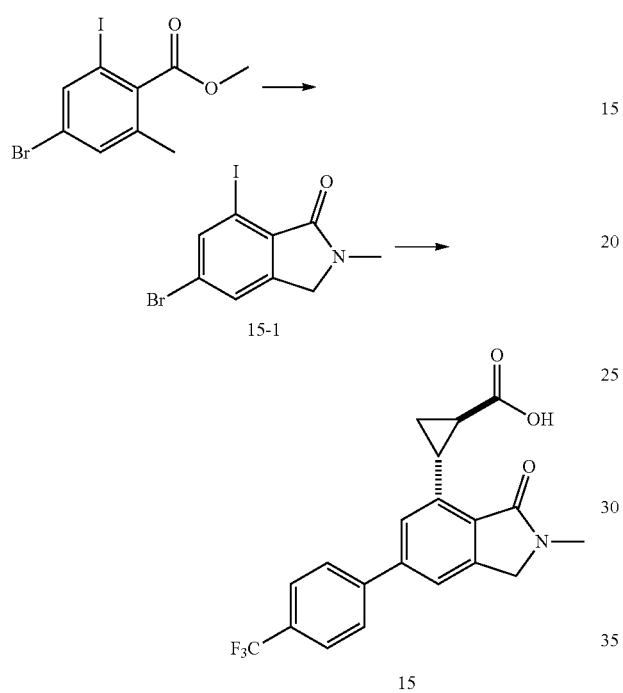

Step 1: Preparation of Compound 15-1

To a solution of methyl 4-bromo-2-iodo-6-methylbenzoate (3.00 g, 8.45 mmol) in CCl₄ (30.0 mL) was added NBS (3.31 g, 18.5 mmol) and benzoic peroxyanhydride (1.02 g, 4.22 mmol). The mixture was stirred at 80° C. for 7 hrs. The reaction mixture was diluted with water (20 mL) and extracted with EtOAc (30 mL×3). The combined organic layers were washed with brine (100 mL), dried over with Na₂SO₄, filtered and concentrated. The residue was purified by column chromatography to give methyl 4-bromo-2-(bromomethyl)-6-iodobenzoate (3.20 g, 7.38 mmol, 87.3%). LCMS: 433.9 [M+H]+. To a solution of 4-bromo-2-(bromomethyl)-6-iodobenzoate (3.20 g, 7.37 mmol) in THF (30 mL) was added methanamine (0.60 g, 18.43 mmol). The mixture was stirred and heated at 50° C. 8 hrs. The reaction mixture was diluted with H₂O (50 mL) and extracted EtOAc (80 mL×2). The combined organic layers were washed with brine (20 mL×2), dried over Na₂SO₄, filtered and concentrated. The residue was purified by column chromatography to give Compound 15-1 (1.10 g, 3.12 mmol, 42.4%). LCMS: 351.8 [M+H]+.

Step 2: Preparation of Example 15

Example 15 (15.0 mg, 0.04 mmol) was prepared according to the similar procedures as Example 10 by replacing Compound 10-3 with Compound 15-1. LCMS: 398.2 [M+Na]+. ¹HNMR: (400 MHz, METHANOL-d₄) δ 7.87-7.85 (m, 2H), 7.79-7.77 (m, 2H), 7.68 (s, 1H), 7.26 (s, 1H), 4.52 (s, 2H), 3.90-3.85 (m, 1H), 3.20 (s, 3H), 2.03-1.99 (m, 1H), 1.71-1.66 (m, 1H), 1.61-1.56 (m, 1H).

Example 16, Example 16a and 16b

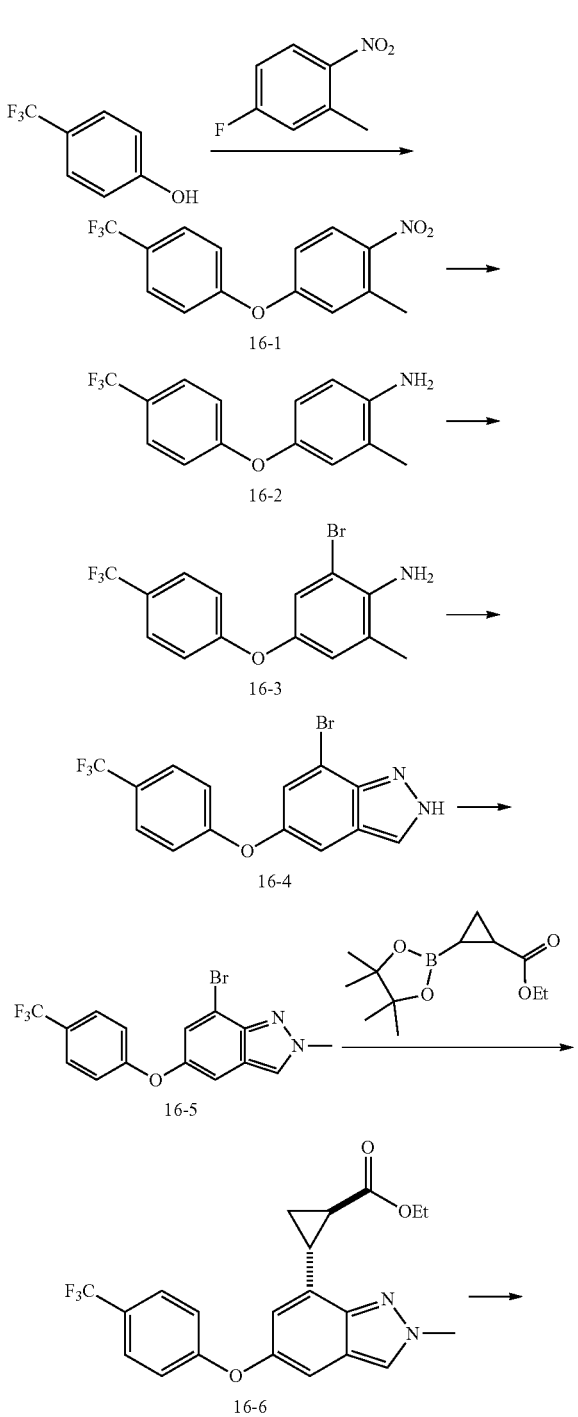

-continued

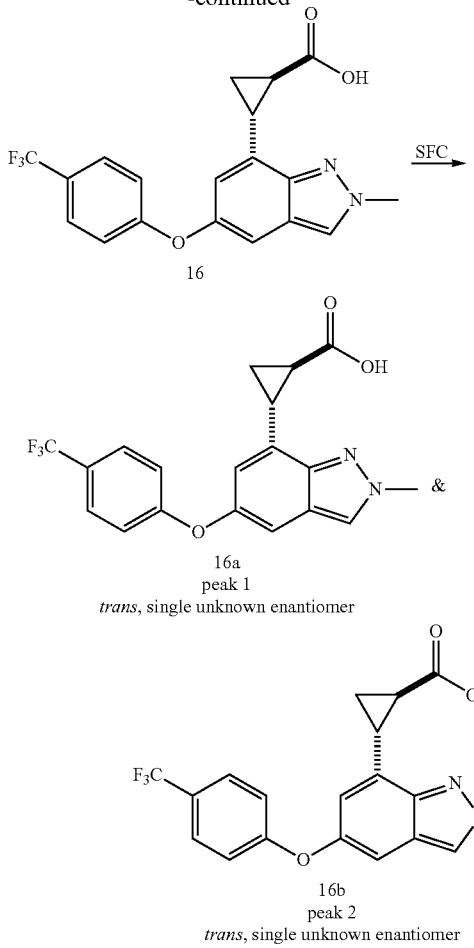

16

16a
peak 1
*trans*, single unknown enantiomer 16b
peak 2
*trans*, single unknown enantiomer Step 1: Preparation of Compound 16-1

To a solution of 4-(trifluoromethyl)phenol (15.7 g, 96.7 mmol) and 4-fluoro-2-methyl-1-nitrobenzene (10.0 g, 64.5 mmol) in DMF (20 mL) were added $K_2CO_3$ (8.90 g, 64.5 mmol), and the reaction was stirred at 80° C. for 5 hrs. The mixture was poured into water (200 mL), extracted with EtOAc (40 mL×3). The organic layer was washed with brine (100 mL×2), dried over with $Na_2SO_4$, filtered and concentrated. The residue was purified by column chromatography to give Compound 16-1 (8.00 g, 26.9 mmol, 41.7%).

Step 2: Preparation of Compound 16-2

To a solution of Compound 16-1 (6000 mg, 20.2 mmol) and $NH_4Cl$ (3240 mg, 60.6 mmol) in EtOH (60 mL) and $H_2O$ (30 mL) were added Fe (3380 mg, 60.6 mmol), and the reaction was stirred at 60° C. for 2 hrs. The mixture was filtered and concentrated. The residue was poured into $H_2O$ (50 mL), extracted with EtOAc (20 mL×2). The organic layer was washed with brine (20 mL×2), dried over with $Na_2SO_4$, filtered and concentrated. The residue was purified by column chromatography to give Compound 16-2 (5.20 g, 19.5 mmol, 96.4%). LCMS: 268.1[M+H]⁺.

Step 3: Preparation of Compound 16-3

To a solution of Compound 16-2 (5.20 g, 19.5 mmol) in ACN (60 mL) were added NBS (6.90 g, 38.9 mmol), and the reaction was stirred at 0° C. for 1 hr. The mixture was concentrated, and the residue was purified by column chromatography to give Compound 16-3 (4.60 g, 13.3 mmol, 68.3%). LCMS: 347.9 [M+H]⁺.

Step 4: Preparation of Compound 16-4

To a solution of Compound 16-3 (4.60 g, 13.3 mmol) in AcOH (38 mL) and $H_2O$ (10 mL) was added $NaNO_2$ (0.90 g, 13.3 mmol) at 0° C. The mixture was stirred at 20° C. for 2 hrs. The mixture was concentrated and diluted with $H_2O$ (200 mL), extracted with EtOAc (40 mL×3). The combined organic layers were washed with brine (120 mL×2), dried over with $Na_2SO_4$, filtered and concentrated. The residue was purified by column chromatography to give Compound 16-4 (4.00 g, 11.2 mmol, 84.3%). LCMS: 358.9 [M+H]⁺.

Step 5: Preparation of Compound 16-5

To a solution of Compound 16-4 (3.00 g, 8.40 mmol) in EtOAc (30 mL) was added trimethyloxonium tetrafluoroborate (1.50 g, 10.1 mmol), and the reaction was stirred at 20° C. for 2 hrs. The reaction mixture was concentrated. The residue was purified by column chromatography to give Compound 16-5 (2.50 g, 6.74 mmol, 80.2%). LCMS: 371.1 [M+H]⁺.

Step 6: Preparation of Compound 16-6

To a solution of Compound 16-5 (250 mg, 0.67 mmol), ethyl 2-(4,4,5,5-tetramethyl-1,3,2-dioxaborolan-2-yl)cyclopropane-1-carboxylate (162 mg, 0.67 mmol) and Pd(dppf)$Cl_2$ (493 mg, 0.67 mmol) in dioxane (6 mL) and $H_2O$ (2 mL) were added $K_2CO_3$ (93.1 mg, 0.67 mmol), and the reaction was stirred at 80° C. for 2 hrs under $N_2$. The mixture was poured into $H_2O$ (50 mL), extracted with EtOAc (20 mL×2). The organic layer was washed with brine (20 mL×3), dried over with $Na_2SO_4$, filtered and concentrated. The residue was purified by prep-TLC to give Compound 16-6 (100 mg, 0.25 mmol, 36.7%). LCMS: 405.0 [M+H]⁺.

Step 7: Preparation of Example 16

To a solution of Compound 16-6 (60.0 mg, 0.15 mmol) in EtOH (3 mL) and $H_2O$ (1 mL) were added LiOH (12.5 mg, 0.30 mmol), and the reaction was stirred at 25° C. for 2 hrs. The mixture was concentrated. The residue was purified by prep-HPLC to give Example 16 (20.0 mg, 0.05 mmol, 35.8%) LCMS: 377.3 [M+H]⁺. ¹HNMR (400 MHz, METHANOL-d4) δ 8.14 (s, 1H), 7.61 (d, J=8.5 Hz, 2H), 7.17 (d, J=2.1 Hz, 1H), 7.06 (d, J=8.5 Hz, 2H), 6.75 (d, J=1.9 Hz, 1H), 4.22 (s, 3H), 2.94-2.91 (m, 1H), 2.24-2.13 (m, 1H), 1.69-1.67 (m, 1H), 1.62-1.58 (m, 1H)

Step 8: Chiral Separation of Example 16a and 16b

Racemic Example 16 (60 mg, 0.16 mmol) was separated by SFC (column: DAICEL CHIRALPAK AD 250 mm*30 mm, 10 um; mobile phase:[CO2-EtOH]; gradient: 20%-20% B over 2.5 min) to give Example 16a (24 mg, 0.07 mmol, 43.8%) Retention time: 1.24 min. LCMS: 377.1 [M+H]⁺. ¹HNMR (400 MHz, METHANOL-d4) δ 8.12 (s, 1H), 7.61 (d, J=8.6 Hz, 2H), 7.15 (d, J=1.9 Hz, 1H), 7.06 (d, J=8.6 Hz, 2H), 6.74 (d, J=1.8 Hz, 1H), 4.22 (s, 3H), 2.98-2.88 (m, 1H), 2.23-2.15 (m, 1H), 1.68-1.58 (m, 2H)

And Example 16b (19 mg, 0.05 mmol, 31.6%) Retention time: 1.41 min. LCMS: 377.1 [M+H]⁺. ¹HNMR (400 MHz, METHANOL-d4) δ 8.11 (s, 1H), 7.62 (d, J=8.5 Hz, 2H), 7.15-7.03 (m, 3H), 6.77 (s, 1H), 4.22 (s, 3H), 2.89-2.82 (m, 1H), 2.14-2.05 (m, 1H), 1.54 (dt, J=9.0, 4.5 Hz, 1H), 1.38 (dd, J=16.7, 7.8 Hz, 1H).

Example 17

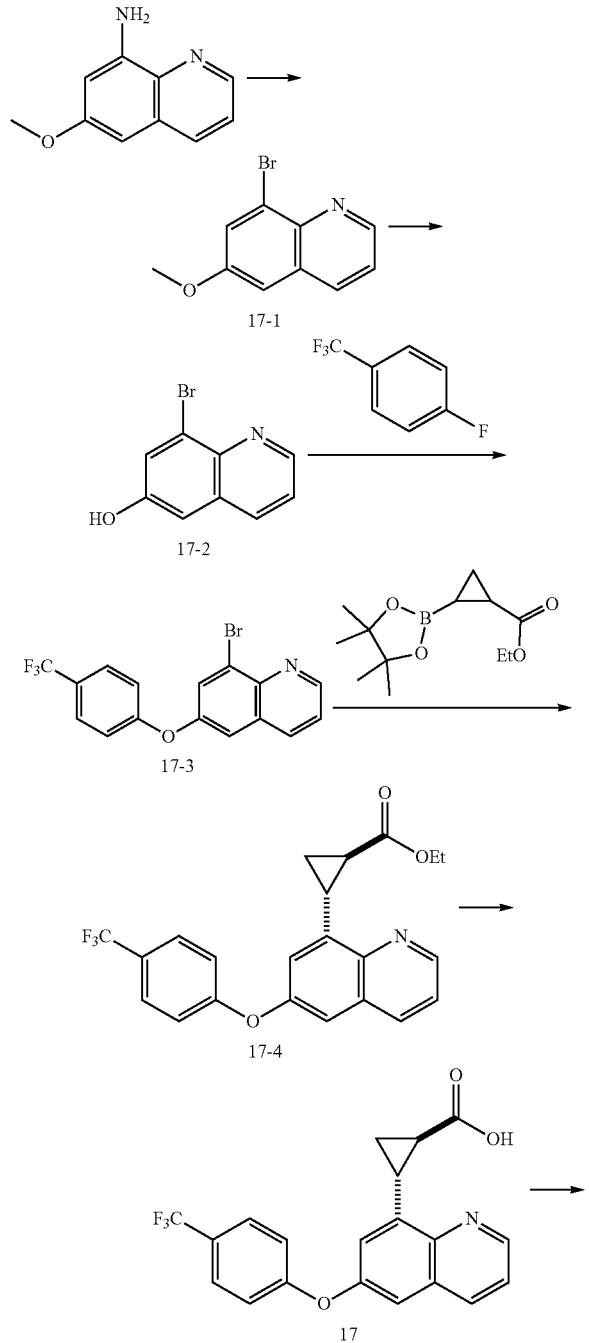

Step 1: Preparation of Compound 17-1

To a solution of 6-methoxyquinolin-8-amine (4.00 g, 23.0 mmol) in ACN (50 mL) was added CuBr$_2$ (0.10 g, 18.3 mmol). After stirring at room temperature for 30 min, 2-methyl-2-(nitrosooxy)propane (2.37 g, 23.0 mmol) was slowly added. The mixture was then stirred at 60° C. for 2 hrs. The mixture was poured into H$_2$O (50 mL) and extracted with EtOAc (20 mL×2). The organic layer was washed with brine (20 mL×2), dried over Na$_2$SO$_4$, filtered and concentrated. The residue was purified by column chromatography to give Compound 17-1 (500 mg, 2.10 mmol, 9.10%). LCMS: 240.1 [M+H]$^+$.

Step 2: Preparation of Compound 17-2

To a solution of Compound 17-1 (500 mg, 2.10 mmol) in DCM (15 mL) was added tribromoborane (526 mg, 2.10 mmol) at 0° C. The mixture was stirred at 25° C. for 3 hrs, filtered and concentrated to give Compound 17-2 (400 mg, 1.78 mmol, 85.0%). LCMS: 224.1 [M+H]$^+$.

Step 3: Preparation of Compound 17-3

To a solution of Compound 17-2 (400 mg, 1.78 mmol) and 1-fluoro-4-(trifluoromethyl)benzene (586 mg, 3.57 mmol) in DMF (5 mL) was added Cs$_2$CO$_3$ (1.75 g, 5.36 mmol). The reaction was stirred at 110° C. for 10 hrs. The mixture was poured into H$_2$O (50 mL) and extracted with EtOAc (20 mL×2). The organic layer was washed with brine (20 mL×2), dried over with Na$_2$SO$_4$, filtered and concentrated. The residue was purified by column chromatography to give Compound 17-3 (250 mg, 0.68 mmol, 38.0%). LCMS: 370.1 [M+H]$^+$.

Step 4: Preparation of Compound 17-4

To a solution of Compound 17-3 (200 mg, 0.54 mmol), ethyl 2-(4,4,5,5-tetramethyl-1,3,2-dioxaborolan-2-yl)cyclopropane-1-carboxylate (130 mg, 0.54 mmol) and Pd(dppf)Cl$_2$ (397 mg, 0.54 mmol) in dioxane (4 mL) and H$_2$O (1 mL) was added K$_2$CO$_3$ (75.1 mg, 0.54 mmol), the reaction was stirred at 80° C. for 2 hrs. The mixture was poured into the water (50 mL), extracted with EtOAc (20 mL×2), the organic layer was washed with brine (20 mL×2), dried over Na$_2$SO$_4$, filtered and concentrated. The residue was purified by prep-TLC to give Compound 17-4 (60.0 mg, 0.15 mmol, 27.5%).

Step 5: Preparation of Example 17

To a solution of Compound 17-4 (100 mg, 0.25 mmol) in EtOH (4 mL) and H$_2$O (2 mL) were added LiOH (10.5 mg, 0.25 mmol), the reaction was stirred at 25° C. for 2 hrs. The mixture was concentrated. The residue was purified by prep-HPLC to give Example 17 (20.0 mg, 0.05 mmol, 21.5%). LCMS: 374.2 [M+H]$^+$. $^1$HNMR (400 MHz, CHLOROFORM-d) 9.03 (s, 1H), 8.16-8.14 (m, 1H), 7.68-7.66 (m, 2H), 7.54-7.53 (m, 1H), 7.24-7.20 (m, 2H), 7.16-7.14 (m, 2H), 3.74-3.69 (m, 1H), 1.98-1.94 (m, 1H), 1.90-1.86 (m, 1H), 1.64-1.59 (m, 1H).

Example 18

Example 18 (38.7 mg, 0.103 mmol) was prepared according to the similar procedures as Example 17 by replacing 8-bromo-6-(4-(trifluoromethyl)phenoxy)quinoline with 4-bromo-1-methylindazol-6-ol. LCMS: 377.2 [M+H]$^+$. $^1$HNMR (400 MHz, METHANOL-d$_4$) δ 8.13 (s, 1H), 7.69-7.67 (m, 2H), 7.16-7.09 (m, 3H), 6.65 (s, 1H), 4.02-3.98 (m, 3H), 2.85 (s, 1H), 2.03 (brs, 1H), 1.66 (brs, 1H), 1.54 (brs, 1H).

Example 19

Example 19 (20.0 mg, 0.051 mmol) was prepared according to the similar procedures as Example 17 by replacing 8-bromo-6-(4-(trifluoromethyl)phenoxy)quinoline with 4-bromo-1-methylindazol-6-ol and 1-fluoro-4-(trifluoromethyl)benzene with 1-(chloromethyl)-4-(trifluoromethyl)benzene. LCMS: 391.4 [M+H]$^+$. $^1$H NMR (400 MHz, DMSO-d$_6$) δ 8.03 (s, 1H), 7.76 (dd, J=26.2, 8.2 Hz, 4H), 7.09 (s, 1H), 6.57-6.56 (m, 1H), 5.30 (s, 2H), 3.99 (s, 3H), 2.70-2.66 (m, 1H), 2.02-1.92 (m, 1H), 1.53-1.49 (m, 2H).

Example 20

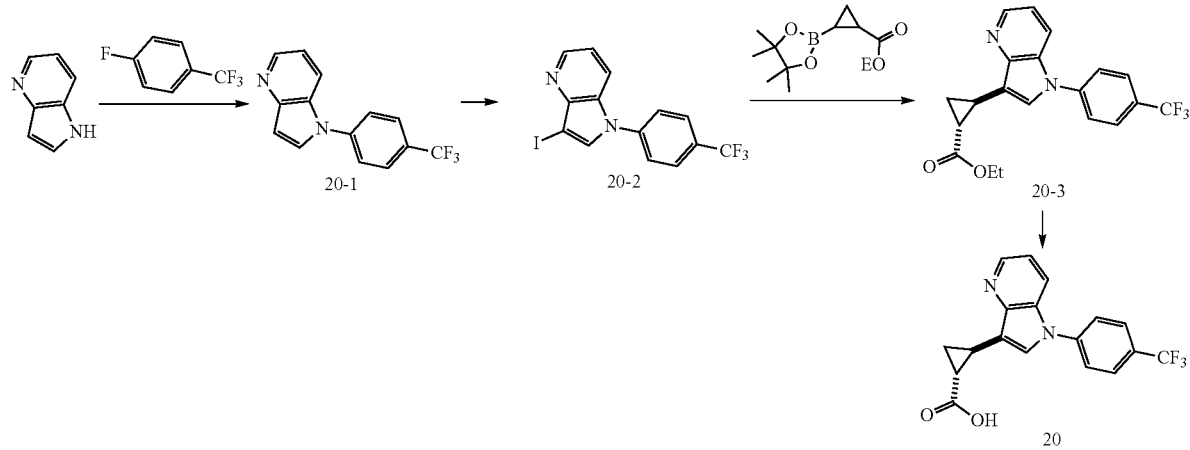

Step 1: Preparation of Compound 20-1

To a solution of 1H-pyrrolo[3,2-b]pyridine (4.00 g, 33.8 mmol) in DMF (40.0 mL) were added 1-fluoro-4-(trifluoromethyl) benzene (6.11 g, 37.2 mmol) and Cs$_2$CO$_3$ (33.0 g, 101 mmol) under N$_2$. The reaction was stirred at 80° C. for 3 hrs. The mixture was diluted with water (50 mL) and extracted with EtOAc (50 mL×3). The organic layer was washed with brine (50 mL×3), dried over with Na$_2$SO$_4$, filtered to give Compound 20-1. LCMS: 263.1 [M+H]$^+$.

Step 2: Preparation of Compound 20-2

To a solution of Compound 20-1 (1.00 g, 3.81 mmol) in DMF (15 mL) and ACN (15 mL) were added NIS (1.72 g, 7.62 mmol) under N$_2$ and the reaction was stirred at 25° C. for 12 hrs. The mixture was diluted with H$_2$O (30 mL) and extracted with EtOAc (20 mL×3). The organic layer was dried over with Na$_2$SO$_4$, filtered and concentrated. The residue was purified by column chromatography to give Compound 20-2. LCMS: 389.3 [M+H]$^+$.

Step 3: Preparation of Compound 20-3

To a solution of Compound 20-2 (860 mg, 2.21 mmol) and ethyl 2-(4,4,5,5-tetramethyl-1,3,2-dioxaborolan-2-yl) cyclopropane-1-carboxylate (798 mg, 3.32 mmol) in dioxane (10 mL) and H$_2$O (2 mL) was added K$_2$CO$_3$ (918 mg, 6.64 mmol) and Pd(dppf)Cl$_2$ (162 mg, 0.22 mmol). The mixture was degassed and purged with N$_2$ for 3 times and stirred at 100° C. for 12 hrs. The mixture was diluted with H$_2$O (5 mL) and extracted with EtOAc (10 mL×4). The organic layer was dried over with Na$_2$SO$_4$, filtered and concentrated. The residue was purified by reversed-phase HPLC to give Compound 20-3. LCMS: 375.1 [M+H]$^+$.

Step 4: Preparation of Example 20

To a solution of Compound 20-3 (50.0 mg, 0.13 mmol) in THF (0.5 mL) and H$_2$O (0.5 mL) were added LiOH·H$_2$O (16.8 mg, 0.401 mmol) under N$_2$ at 25° C. The reaction was stirred at 40° C. for 3 hrs. 2M HCl was added to adjust pH to around 6, then added EtOAc (10 mL). The organic phase was collected, the aqueous layer was extracted with EtOAc (10.0 mL×4). The combined organic layer was washed with H$_2$O (5 mL) and brine (5 mL), dried over with Na$_2$SO$_4$, filtered and concentrated. The residue was purified by reversed-phase HPLC to give Example 20. LCMS: 347.1 [M+H]$^+$. $^1$HNMR (400 MHz, DMSO-d$_6$) δ 8.45 (dd, J=4.6, 1.1 Hz, 1H), 8.06 (dd, J=8.4, 1.1 Hz, 1H), 7.99 (s, 1H), 7.93 (d, J=8.6 Hz, 2H), 7.85 (d, J=8.5 Hz, 2H), 7.27 (dd, J=8.4, 4.6 Hz, 1H), 2.67-2.59 (m, 1H), 2.22-2.13 (m, 1H), 1.69 (td, J=8.1, 3.6 Hz, 1H), 1.46-1.39 (m, 1H).

Example 21

Example 21 (20.0 mg, 0.051 mmol) was prepared according to the similar procedures as Example 20 by replacing 1H-pyrrolo[3,2-b]pyridine with 5-methyl-1H-indole. LCMS: 358.1 [M−H]$^−$. $^1$HNMR (400 MHz, METHANOL-d$_4$) δ 7.85-7.83 (m, 2H), 7.74-7.72 (m, 2H), 7.54-7.49 (m, 2H), 7.34 (s, 1H), 7.11 (d, J=8.5 Hz, 1H), 2.60-2.55 (m, 1H), 2.48 (s, 3H), 1.89-1.84 (m, 1H), 1.60-1.55 (m, 1H), 1.48-1.43 (m, 1H)

Example 22

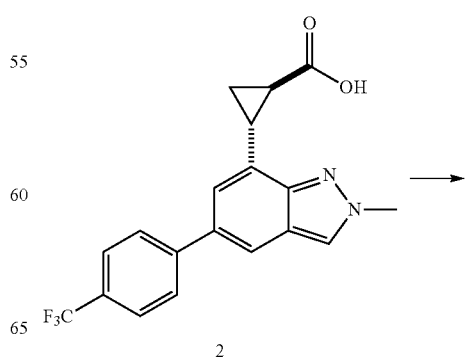

-continued

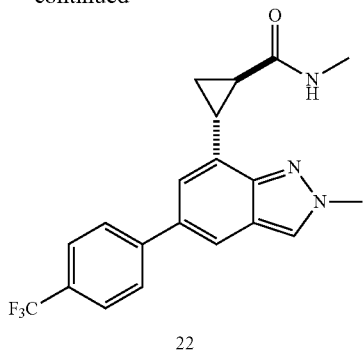

22

To a solution of Example 2 (20.0 mg, 55.5 μmol), HATU (158 mg, 0.42 mmol) and TEA (0.06 mL, 0.42 mmol) in DMF (1.0 mL) were added methanamine (17.2 mg, 0.56 mmol). The mixture was stirred at 25° C. for 2 hrs under $N_2$ and then poured into $H_2O$ (50 mL), extracted with EtOAc (20 mL×2). The organic layer was washed with brine (20 mL×2), dried over $Na_2SO_4$, filtered, and concentrated. The residue was purified by prep-HPLC to give Example 22 (15.96 mg, 42.7 μmol, 76.9% yield). LCMS: 374.2 [M+H]$^+$. $^1$H NMR (400 MHz, METHANOL-d$_4$) δ 8.26 (s, 1H), 7.85-7.84 (m, 3H), 7.75-7.73 (m, 2H), 7.29-7.28 (m, 1H), 4.25 (s, 3H), 2.92-2.87 (m, 1H), 2.80 (s, 3H), 2.33-2.29 (m, 1H), 1.71-1.66 (m, 1H), 1.64-1.59 (m, 1H).

Compounds in Table 3 below were prepared in accordance with the synthetic sequence in Example 22 using the corresponding starting materials.

TABLE 3

| Ex. | Starting material | MW [M + H]$^+$ & $^1$H NMR |
|---|---|---|
| 23 | Example 2 & EtNH$_2$ | LCMS: 388.4 [M + H]$^+$. $^1$HNMR (400 MHz, METHANOL-d$_4$) δ 8.25 (s, 1H), 7.85-7.83 (m, 3H), 7.75-7.73 (m, 2H), 7.28 (s, 1H), 4.25 (s, 3H), 3.31-3.22 (m, 2H), 2.92-2.87 (m, 1H), 2.35-2.30 (m, 1H), 1.69-1.65 (m, 1H), 1.64-1.59 (m, 1H), 1.17 (t, J = 7.3 Hz, 3H). |
| 24 | Example 7 & MeNH$_2$ | LCMS: 374.3 [M + H]$^+$. $^1$HNMR (400 MHz, METHANOL-d$_4$) δ 8.13 (s, 1H), 7.92-7.90 (m, 2H), 7.79-7.77 (m, 2H), 7.69 (s, 1H), 7.15 (s, 1H), 4.12 (s, 3H), 2.82-2.78 (m, 4H), 2.15-2.10 (m, 1H), 1.67-1.62 (m, 1H), 1.55-1.51 (m, 1H). |
| 25 | Example 7 & NH$_4$OH | LCMS: 360.0 [M + H]$^+$. $^1$HNMR (400 MHz, METHANOL-d$_4$) δ 8.15 (s, 1H), 7.94-7.92 (m, 2H), 7.80-7.78 (m, 2H), 7.71 (s, 1H), 7.18 (s, 1H), 4.14 (s, 3H), 2.85-2.80 (m, 1H), 2.22-2.18 (m, 1H), 1.68-1.63 (m, 1H), 1.59-1.54 (m, 1H) |
| 26 | Example 7 & dimethylamine | LCMS: 388.0 [M + H]$^+$. $^1$HNMR (400 MHz, METHANOL-d$_4$) δ 8.17-8.16 (m, 1H), 7.95-7.93 (m, 2H), 7.80-7.78 (m, 2H), 7.71 (s, 1H), 7.19 (s, 1H), 4.14 (s, 3H), 3.21 (s, 3H), 3.04 (s, 3H), 2.88-2.83 (m, 1H), 2.48-2.43 (m, 1H), 1.70-1.63 (m, 2H) |
| 27 | Example 7 & propan-2-amine | LCMS: 402.0 [M + H]$^+$. $^1$HNMR (400 MHz, METHANOL-d$_4$) δ 8.13 (s, 1H), 7.93-7.91 (m, 2H), 7.80-7.78 (m, 2H), 7.70 (s, 1H), 7.17 (s, 1H), 4.13 (s, 3H), 4.09-4.03 (m, 1H), 2.82-2.78 (m, 1H), 2.16-2.05 (m, 1H), 1.66-1.62 (m, 1H), 1.54-1.49 (m, 1H), 1.21-1.19 (m, 6H). |
| 28 | Example 7 & 1-(pyridin-2-yl)ethan-1-amine | LCMS: 465.3 [M + H]$^+$. $^1$HNMR (400 MHz, METHANOL-d$_4$) δ 8.58-8.57 (m, 1H), 8.16-8.09 (m, 1H), 8.03-7.96 (m, 1H), 7.94-7.92 (m, 2H), 7.80-7.78 (m, 2H), 7.72 (s, 1H), 7.58 (dd, J = 11.1, 8.1 Hz, 1H), 7.48-7.43 (m, 1H), 7.19 (d, J = 5.0 Hz, 1H), 5.17-5.12 (m, 1H), 4.14 (s, 3H), 2.86-2.73 (m, 1H), 2.34-2.27 (m, 1H), 1.69-1.54 (m, 5H). |
| 29 | Example 7 & 2-aminoethan-1-ol | LCMS: 404.2 [M + H]$^+$. $^1$HNMR (400 MHz, METHANOL-d$_4$) δ 8.15 (s, 1H), 7.94-7.92 (m, 2H), 7.80-7.78 (m, 2H), 7.70 (s, 1H), 7.18 (s, 1H), 4.13 (s, 3H), 3.66 (t, J = 5.8 Hz, 2H), 3.43-3.39 (m, 2H), 2.85-2.80 (m, 1H), 2.23-2.19 (m, 1H), 1.69-1.64 (m, 1H), 1.56-1.52 (m, 1H) |
| 30 | Example 7 & 2-methoxyethan-1-amine | LCMS: 418.1 [M + H]$^+$. $^1$HNMR (400 MHz, METHANOL-d$_4$) δ 8.38-8.36 (m, 1H), 8.15-8.14 (m, 1H), 7.93-7.91 (m, 2H), 7.79-7.77 (m, 2H), 7.70 (s, 1H), 7.17 (s, 1H), 4.13 (s, 3H), 3.53-3.44 (m, 4H), 3.38 (s, 3H), 2.84-2.79 (m, 1H), 2.22-2.17 (m, 1H), 1.68-1.63 (m, 1H), 1.56-1.51 (m, 1H) |
| 31 | Example 7 & azetidin-3-ol | LCMS: 416.3 [M + H]$^+$. $^1$HNMR (400 MHz, METHANOL-d$_4$) δ 8.04 (d, J = 9.1 Hz, 1H), 7.66 (s, 4H), 7.33 (s, 1H), 6.94-6.93 (m, 1H), 4.68-4.62 (m, 1H), 4.43-4.34 (m, 1H), 4.29-4.25 (m, 1H), 4.06-4.00 (m, 4H), 3.91 - 3.86 (m, 1H), 2.85-2.81 (m, 1H), 1.81-1.77 (m, 2H), 1.50-1.43 (m, 1H). |
| 32 | Example 9 & MeNH$_2$ | LCMS: 410.2 [M + H]$^+$. $^1$HNMR (400 MHz, METHANOL-d$_4$) δ 8.39 (s, 1H), 8.01-7.68 (m, 6H), 7.31 (s, 1H), 2.91-2.78 (m, 4H), 2.20-2.11 (m, 1H), 1.73-1.66 (m, 1H), 1.59-1.52 (m, 1H). |
| 33 | Example 12 & MeNH$_2$ | LCMS: 390.1 [M + H]$^+$. $^1$HNMR (400 MHz, METHANOL-d$_4$) δ 8.23 (s, 1H), 7.76-7.72 (m, 3H), 7.36-7.34 (m, 2H), 7.24 (s, 1H), 4.24 (s, 3H), 2.91-2.86 (m, 1H), 2.80 (s, 3H), 2.31-2.27 (m, 1H), 1.68-1.59 (m, 2H). |
| 34 | Example 16 & MeNH$_2$ | LCMS: 390.0 [M + H]$^+$. $^1$HNMR (400 MHz, METHANOL-d$_4$) δ 8.14 (s, 1H), 7.64-7.62 (m, 2H), 7.18-7.17 (m, 1H), 7.08-7.06 (m, 2H), 6.75-6.74 (m, 1H), 4.23 (s, 3H), 2.90-2.82 (m, 1H), 2.78 (s, 3H), 2.24-2.19 (m, 1H), 1.61-1.52 (m, 2H). |
| 34a | Example 16a & MeNH$_2$ | LCMS: 390.4 [M + H]$^+$. $^1$HNMR (400 MHz, METHANOL-d$_4$) δ 8.14 (s, 1H), 7.64-7.61 (m, 2H), 7.18-7.17 (m, 1H), 7.08-7.05 (m, 2H), 6.75 - 6.74 (m, 1H), 4.23 (s, 3H), 2.90-2.82 (m, 1H), 2.78 (s, 3H), 2.24-2.19 (m, 1H), 1.61-1.52 (m, 2H). |
| 34b | Example 16b & MeNH$_2$ | LCMS: 390.4 [M + H]$^+$. $^1$HNMR (400 MHz, METHANOL-d$_4$) δ 8.12 (s, 1H), 7.63-7.60 (m, 2H), 7.16-7.15 (m, 1H), 7.06-7.03 (m, 2H), 6.73 - 6.72 (m, 1H), 4.20 (s, 3H), 2.85-2.82 (m, 1H), 2.76 (s, 3H), 2.22-2.18 (m, 1H), 1.58-1.51 (m, 2H). |

TABLE 3-continued

| Ex. | Starting material | MW [M + H]⁺ & ¹H NMR |
|---|---|---|
| 35 | Example 18 & NH₄Cl | LCMS: 376.4 [M + H]⁺. ¹HNMR (400 MHz, METHANOL-d₄) δ 8.13-8.12 (m, 1H), 7.69-7.67 (m, 2H), 7.16-7.13 (m, 2H), 7.09 (s, 1H), 6.65-6.64 (m, 1H), 4.00 (s, 3H), 2.79-2.75 (m, 1H), 2.13-2.09 (m, 1H), 1.63-1.59 (m, 1H), 1.45-1.40 (m, 1H). |
| 36 | Example 18 & MeNH₂ | LCMS: 390.4 [M + H]⁺. ¹HNMR (400 MHz, DMSO-d₆) δ 8.14 (s, 1H), 8.09-8.08 (m, 1H), 7.73 (d, J = 8.7 Hz, 2H), 7.27 (s, 1H), 7.14 (d, J = 8.5 Hz, 2H), 6.63-6.62 (m, 1H), 3.98 (s, 3H), 2.64-2.57 (m, 4H), 2.11-2.07 (m, 1H), 1.47-1.43 (m, 1H), 1.38-1.33 (m, 1H). |
| 37 | Example 19 & MeNH₂ | LCMS: 404.1 [M + H]⁺. ¹H NMR (400 MHz, DMSO-d₆) δ 8.13-8.12 (m, 1H), 8.02 (s, 1H), 7.80 (dd, J = 29.6, 8.1 Hz, 4H), 7.12 (s, 1H), 6.58 (s, 1H), 5.33 (s, 2H), 4.01 (s, 3H), 2.69-2.68 (m, 3H), 2.13-2.09 (m, 1H), 1.49-1.45 (m, 1H), 1.41-1.36 (m, 1H), 1.29 (s, 2H). |
| 38 | Example 13 & MeNH₂ | LCMS: 371.2 [M + H]⁺. ¹HNMR (400 MHz, METHANOL-d₄) δ 8.99-8.98 (m, 1H), 8.53 (d, J = 8.1 Hz, 1H), 8.17-8.16 (m, 1H), 8.00-7.98 (m, 2H), 7.84-7.82 (m, 1H), 7.77-7.76 (m, 1H), 7.68-7.65 (m, 1H), 3.51-3.46 (m, 1H), 2.83 (s, 3H), 2.21-2.16 (m, 1H), 1.78-1.73 (m, 1H), 1.56-1.51 (m, 1H). |
| 39 | Example 14 & MeNH₂ | LCMS: 377.4 [M + H]⁺. ¹HNMR (400 MHz, DMSO-d₆) δ 9.39 (s, 1H), 8.35 (s, 1H), 7.99-7.90 (m, 3H), 7.87-7.85 (m, 2H), 7.66 (s, 1H), 3.12-3.02 (m, 1H), 2.40-2.31 (m, 3H), 2.27-2.18 (m, 1H), 1.82-1.73 (m, 1H), 1.45-1.36 (m, 1H) |
| 52 | Example 16a & Methan-d₃-amine | LCMS: 393.2 [M + H]⁺. ¹HNMR (400 MHz, DMSO-d₆) δ 8.15 (s, 1H), 7.64-7.61 (m, 2H), 7.18-7.17 (m, 1H), 7.07-7.05 (m, 2H), 6.74 (d, J = 2.0 Hz, 1H), 4.22 (s, 3H), 2.87-2.83 (m, 1H), 2.24-2.19 (m, 1H), 1.60-1.54 (m, 2H) |
| 53 | Example 16b & Methan-d₃-amine | LCMS: 393.2 [M + H]⁺. ¹HNMR (400 MHz, DMSO-d₆) δ 8.14 (s, 1H), 7.65-7.61 (m, 2H), 7.18-7.17 (m, 1H), 7.07-7.05 (m, 2H), 6.74-6.73 (m, 1H), 4.22 (s, 3H), 2.87-2.83 (m, 1H), 2.23-2.21 (m, 1H), 1.59-1.54 (m, 2H) |
| 54 | Example 16b & (S)-2-aminopropan-1-ol | LCMS: 434.3 [M + H]⁺. ¹HNMR (400 MHz, METHANOL-d₄) δ 8.12 (s, 1H), 7.62-7.59 (m, 2H), 7.15 (m, 1H), 7.06-7.03 (m, 2H), 6.72-6.71 (m, 1H), 4.20 (s, 3H), 3.98-3.96 (m, 1H), 3.53-3.44 (m, 2H), 2.86-2.84 (m, 1H), 2.26-2.22 (m, 1H), 1.58-1.49 (m, 2H), 1.15 (d, J = 6.9 Hz, 3H) |
| 55 | Example 16b & (R)-2-aminopropan-1-ol | LCMS: 434.3 [M + H]⁺. ¹HNMR (400 MHz, METHANOL-d₄) δ 8.14 (s, 1H), 7.63-7.61 (m, 2H), 7.17 (m, 1H), 7.07-7.05 (m, 2H), 6.75-6.74 (m, 1H), 4.22 (s, 3H), 4.05-3.95 (m, 1H), 3.53-3.47 (m, 2H), 2.91-2.87 (m, 1H), 2.28-2.23 (m, 1H), 1.61-1.46 (m, 2H), 1.16 (d, J = 6.9 Hz, 3H) |
| 56 | Example 16 & propan-2-amine | LCMS: 418.4 [M + H]⁺. ¹HNMR (400 MHz, METHANOL-d₄) δ 8.14 (s, 1H), 7.63-7.61 (m, 2H), 7.16 (d, J = 2.1 Hz, 1H), 7.07-7.05 (m, 2H), 6.73 (m, 1H), 4.22 (s, 3H), 4.07-3.96 (m, 1H), 2.87-2.85 (m, 1H), 2.23-2.21 (m, 1H), 1.59-1.56 (m, 1H), 1.52-1.49 (m, 1H), 1.16 (d, J = 6.5 Hz, 6H) |
| 56a | Example 16a & propan-2-amine | LCMS: 418.4 [M + H]⁺. ¹HNMR (400 MHz, METHANOL-d₄) δ 8.13 (s, 1H), 7.62-7.59 (m, 2H), 7.15 (d, J = 2.1 Hz, 1H), 7.05-7.03 (m, 2H), 6.71-6.70 (m, 1H), 4.21 (s, 3H), 4.05-3.92 (m, 1H), 2.88-2.79 (m, 1H), 2.25-2.17 (m, 1H), 1.57-1.42 (m, 2H), 1.49 (ddd, J = 4.0, 6.3, 8.3 Hz, 1H), 1.14 (d, J = 6.6 Hz, 6H) |
| 56b | Example 16b & propan-2-amine | LCMS: 418.4 [M + H]⁺. ¹HNMR (400 MHz, METHANOL-d₄) δ 8.15 (s, 1H), 7.64-7.61 (m, 2H), 7.17 (m, 1H), 7.07-7.05 (m, 2H), 6.73-6.72 (m, 1H), 4.22 (s, 3H), 4.05-3.95 (m, 1H), 2.90-2.82 (m, 1H), 2.26-2.18 (m, 1H), 1.61-1.47 (m, 2H), 1.16 (d, J = 6.6 Hz, 6H) |
| 57 | Example 16 & 1-(pyridin-2-yl)ethan-1-amine | LCMS: 481.4 [M + H]⁺. ¹HNMR (400 MHz, METHANOL-d₄) δ 8.55 (s, 1H), 8.16-8.15 (m, 1H), 8.04-7.95 (m, 1H), 7.67-7.60 (m, 2H), 7.57-7.55 (m, 1H), 7.46-7.44 (m, 1H), 7.20-7.18 (m, 1H), 7.10-7.08 (m, 2H), 6.77 (s, 1H), 5.13-5.09 (m, 1H), 4.23-4.22 (m, 3H), 2.91-2.79 (m, 1H), 2.39-2.36 (m, 1H), 1.60-1.55 (m, 2H), 1.53-1.51 (m, 3H) |
| 58a | Example 16a & azetidin-3-ol | LCMS: 432.4 [M + H]⁺. ¹HNMR (400 MHz, METHANOL-d₄) δ 8.37 (s, 1H), 7.68-7.62 (m, 2H), 7.28-7.24 (m, 1H), 7.12-7.09 (m, 2H), 6.98-6.97 (m, 1H), 4.64-4.57 (m, 1H), 4.56-4.45 (m, 1H), 4.30 (s, 3H), 4.26-4.21 (m, 1H), 4.12-3.99 (m, 1H), 3.88-3.75 (m, 1H), 2.82-2.73 (m, 1H), 2.20-2.11 (m, 1H), 1.65-1.55 (m, 2H) |
| 58b | Example 16b & azetidin-3-ol | LCMS: 432.4 [M + H]⁺. ¹HNMR (400 MHz, METHANOL-d₄) δ 8.55-8.46 (m, 1H), 7.66-7.64 (m, 2H), 7.32-7.26 (m, 1H), 7.12-7.10 (m, 2H), 7.07-7.02 (m, 1H), 4.66-4.57 (m, 1H), 4.55-4.46 (m, 1H), 4.4 (s, 3H), 4.29-4.21 (m, 1H), 4.14-3.98 (m, 1H), 3.92-3.72 (m, 1H), 2.80-2.68 (m, 1H), 2.18-2.11 (m, 1H), 1.69-1.49 (m, 2H) |
| 59a | Example 16a & (R)-2-amino-2-(pyridin-2-yl)ethan-1-ol | LCMS: 497.3 [M + H]⁺. ¹HNMR (400 MHz, METHANOL-d₄) δ 8.80-8.75 (m, 1H), 8.66-8.60 (m, 1H), 8.30-8.26 (m, 1H), 8.20-8.14 (m, 1H), 8.04-7.98 (m, 1H), 7.67-7.60 (m, 2H), 7.24-7.23 (m, 1H), 7.11-7.04 (m, 2H), 6.90-6.85 (m, 1H), 5.22-5.15 (m, 1H), 4.26 (s, 3H), 4.04-3.95 (m, 2H), 2.81-2.72 (m, 1H), 2.44-2.36 (m, 1H), 1.64-1.56 (m, 2H) |
| 59b | Example 16b & (R)-2-amino-2-(pyridin-2-yl)ethan-1-ol | LCMS: 497.5 [M + H]⁺. ¹HNMR (400 MHz, METHANOL-d₄) δ 8.82-8.77 (m, 1H), 8.67-8.64 (m, 1H), 8.33 (s, 1H), 8.19-8.12 (m, 1H), 8.07-8.00 (m, 1H), 7.66-7.62 (m, 2H), 7.26-7.25 (m, 1H), 7.10-7.07 (m, 2H), 6.94-6.90 (m, 1H), 5.21-5.16 (m, 1H), 4.29 (s, 3H), 4.01-3.96 (m, 2H), 2.89-2.82 (m, 1H), 2.48-2.40 (m, 1H), 1.65-1.52 (m, 2H) |

TABLE 3-continued

| Ex. | Starting material | MW [M + H]⁺ & ¹H NMR |
|---|---|---|
| 60 | Example 16b & 3-methylazetidin-3-ol | LCMS: 446.3 [M + H]⁺. ¹HNMR (400 MHz, METHANOL-d₄) δ 8.22-8.14 (m, 1H), 7.65-7.62 (m, 2H), 7.20-7.18 (m, 1H), 7.14-7.05 (m, 2H), 6.82-6.81 (m, 1H), 4.30-4.24 (m, 3H), 4.21-4.11 (m, 2H), 3.98-3.87 (m, 2H), 2.85-2.75 (m, 1H), 2.20-2.11 (m, 1H), 1.70-1.61 (m, 2H), 1.55-1.46 (m, 3H) |
| 61 | Example 16b & (S)-morpholin-2-ylmethanol | LCMS: 476.3 [M + H]⁺. ¹HNMR (400 MHz, METHANOL-d₄) δ 8.20-8.12 (m, 1H), 7.65-7.61 (m, 2H), 7.18 (s, 1H), 7.11-7.05 (m, 2H), 6.84-6.81 (m, 1H), 4.47-4.35 (m, 1H), 4.24 (s, 3H), 4.14-4.07 (m, 1H), 4.01-3.91 (m, 1H), 3.64-3.58 (m, 2H), 3.50-3.40 (m, 2H), 3.16-3.05 (m, 1H), 2.95-2.78 (m, 2H), 2.64-2.45 (m, 1H), 1.71-1.61 (m, 2H) |
| 62 | Example 16b & (R)-morpholin-2-ylmethanol | LCMS: 476.4 [M + H]⁺. ¹HNMR (400 MHz, METHANOL-d₄) δ 8.17 (s, 1H), 7.65-7.61 (m, 2H), 7.20-7.17 (m, 1H), 7.13-7.04 (m, 2H), 6.88-6.80 (m, 1H), 4.50-4.32 (m, 1H), 4.23 (s, 3H), 4.09-3.87 (m, 2H), 3.68-3.58 (m, 2H), 3.57-3.45 (m, 2H), 3.17-2.92 (m, 1H), 2.87-2.67 (m, 2H), 2.64-2.48 (m, 1H), 1.70-1.61 (m, 2H) |
| 63 | Example 16b & (3R,4S)-pyrrolidine-3,4-diol | LCMS: 462.3 [M + H]⁺. ¹HNMR (400 MHz, METHANOL-d₄) δ 8.16-8.11 (m, 1H), 7.76-7.63 (m, 2H), 7.18-7.13 (m, 1H), 7.09-7.01 (m, 2H), 6.84-6.78 (m, 1H), 4.27-4.14 (m, 5H), 3.89-3.81 (m, 1H), 3.67-3.53 (m, 2H), 3.50-3.40 (m, 1H), 2.85-2.74 (m, 1H), 2.44-2.31 (m, 1H), 1.67-1.63 (m, 2H) |
| 64 | Example 16b & (3S,4S)-pyrrolidine-3,4-diol | LCMS: 462.4 [M + H]⁺. ¹HNMR (400 MHz, METHANOL-d₄) δ 8.16 (s, 1H), 7.64-7.59 (m, 2H), 7.19-7.15 (m, 1H), 7.09 -7.04 (m, 2H), 6.86-6.80 (m, 1H), 4.21 (s, 3H), 4.13-4.07 (m, 2H), 3.95-3.86 (m, 1H), 3.69-3.60 (m, 2H), 3.56-3.47 (m, 1H), 2.85-2.75 (m, 1H), 2.46-2.36 (m, 1H), 1.74-1.58 (m, 2H) |
| 65 | Example 16b & (3R,4R)-pyrrolidine-3,4-diol | LCMS: 462.1 [M + H]⁺. ¹HNMR (400 MHz, METHANOL-d₄) δ 8.14 (s, 1H), 7.65-7.60 (m, 2H), 7.19-7.14 (m, 1H), 7.09 -7.01 (m, 2H), 6.84-6.80 (m, 1H), 4.21 (s, 3H), 4.18-4.06 (m, 2H), 3.91-3.85 (m, 1H), 3.71-3.54 (m, 3H), 2.90-2.81 (m, 1H), 2.47-2.35 (m, 1H), 1.68-1.59 (m, 2H) |
| 66 | Example 16b & aminoacetonitrile | LCMS: 415.3 [M + H]⁺. ¹HNMR (400 MHz, METHANOL-d₄) δ 8.13 (s, 1H), 7.64-7.56 (m, 2H), 7.17-7.15 (m, 1H), 7.09 -7.01 (m, 2H), 6.75-6.71 (m, 1H), 4.22-4.17 (m, 5H), 2.94-2.83 (m, 1H), 2.29-2.21 (m, 1H), 1.66-1.59 (m, 2H) |
| 67 | Example 16b & 1-amino-cyclopropane-1-carbonitrile | LCMS: 441.5 [M + H]⁺. ¹HNMR (400 MHz, METHANOL-d₄) δ 8.21-8.09 (m, 1H), 7.65-7.59 (m, 2H), 7.19-7.17 (m, 1H), 7.09-7.01 (m, 2H), 6.77-6.74 (m, 1H), 4.25-4.19 (m, 5H), 2.95-2.88 (m, 1H), 2.25-2.19 (m, 1H), 1.66-1.60 (m, 2H), 1.52-1.46 (m, 2H), 1.32-1.21 (m, 2H) |
| 68 | Example 16b & (R)-2-amino-propanenitrile | LCMS: 428.9 [M + H]⁺. ¹HNMR (400 MHz, METHANOL-d₄) δ 8.15 (s, 1H), 7.66-7.60 (m, 2H), 7.21-7.19 (m, 1H), 7.11-7.08 (m, 2H), 6.79-6.75 (m, 1H), 4.85-4.84 (m, 1H), 4.23 (s, 3H), 2.97-2.87 (m, 1H), 2.34-2.25 (m, 1H), 1.65-1.60 (m, 2H), 1.57-1.52 (m, 3H) |
| 69 | Example 16b & (S)-2-amino-propanenitrile | LCMS: 429.1 [M + H]⁺. ¹HNMR (400 MHz, METHANOL-d₄) δ 8.12 (s, 1H), 7.73-7.60 (m, 2H), 7.18-7.14 (m, 1H), 7.06-7.02 (m, 2H), 6.75-6.72 (m, 1H), 4.83-4.80 (m, 1H), 4.20 (s, 3H), 2.91-2.82 (m, 1H), 2.28-2.19 (m, 1H), 1.66-1.58 (m, 2H), 1.54-1.49 (m, 3H) |
| 70 | Example 16b & azetidine-3-carbonitrile | LCMS: 441.4 [M + H]⁺. ¹HNMR (400 MHz, METHANOL-d₄) δ 8.19-8.15 (m, 1H), 7.68-7.60 (m, 2H), 7.22-7.17 (m, 1H), 7.13-7.04 (m, 2H), 6.85-6.80 (m, 1H), 4.66-4.48 (m, 2H), 4.40-4.30 (m, 1H), 4.26-4.20 (m, 3H), 3.84-3.68 (m, 1H), 2.88-2.75 (m, 1H), 2.16-1.98 (m, 1H), 1.70-1.59 (m, 2H) |
| 71 | Example 16b & azanecarbonitrile | LCMS: 401.2 [M + H]⁺. ¹HNMR (400 MHz, METHANOL-d₄) δ 8.16 (s, 1H), 7.64-7.57 (m, 2H), 7.23-7.16 (m, 1H), 7.10-7.01 (m, 2H), 6.82-6.74 (m, 1H), 4.23 (s, 3H), 2.99-2.90 (m, 1H), 2.38-2.23 (m, 1H), 1.87-1.75 (m, 1H), 1.71-1.63 (m, 1H) |
| 72 | Example 16b & (2R)-tetrahydropyrrole-2-carbonitrile | LCMS: 455.1 [M + H]⁺. ¹HNMR (400 MHz, METHANOL-d₄) δ 8.23-8.10 (m, 1H), 7.67-7.60 (m, 2H), 7.24-7.17 (m, 1H), 7.13-7.05 (m, 2H), 6.93-6.84 (m, 1H), 4.81-4.76 (m, 1H), 4.23 (s, 3H), 3.91-3.80 (m, 1H), 3.76-3.63 (m, 1H), 2.93 -2.81 (m, 1H), 2.55-2.45 (m, 1H), 2.39-2.25 (m, 2H), 2.23-2.11 (m, 2H), 1.81-1.63 (m, 2H) |
| 73 | Example 16b & (2S)-tetrahydropyrrole-2-carbonitrile | LCMS: 455.3 [M + H]⁺. ¹HNMR (400 MHz, METHANOL-d₄) δ 8.22-8.07 (m, 1H), 7.67-7.55 (m, 2H), 7.21-7.18 (m, 1H), 7.10-7.01 (m, 2H), 6.87-6.79 (m, 1H), 4.84-4.78 (m, 1H), 4.23 (s, 3H), 3.87-3.80 (m, 1H), 3.72-3.63 (m, 1H), 2.90-2.80 (m, 1H), 2.47-2.13 (m, 5H), 1.74-1.64 (m, 2H) |
| 74 | Example 16b & hexahydropyridin-4-ol | LCMS: 460.4 [M + H]⁺. ¹HNMR (400 MHz, METHANOL-d₄) δ 8.13 (s, 1H), 7.64-7.59 (m, 2H), 7.18-7.12 (m, 1H), 7.08 -7.00 (m, 2H), 6.83-6.79 (m, 1H), 4.25-4.21 (m, 3H), 4.14-3.96 (m, 2H), 3.87-3.80 (m, 1H), 3.46-3.36 (m, 1H), 3.29-3.10 (m, 1H), 2.82-2.76 (m, 1H), 2.63-2.58 (m, 1H), 1.95-1.75 (m, 2H), 1.68-1.60 (m, 2H), 1.57-1.42 (m, 2H) |
| 75a | Example 16b & trans-piperidine-3,4-diol | LCMS: 476.4 [M + H]⁺. ¹HNMR (400 MHz, METHANOL-d₄) δ 8.13 (s, 1H), 7.65-7.58 (m, 2H), 7.18-7.14 (m, 1H), 7.09-7.03 (m, 2H), 6.82 (br s, 1H), 4.26-4.18 (m, 3H), 4.12-3.92 (m, 2H), 3.65-3.52 (m, 1H), 3.51-3.42 (m, 1H), 3.29-3.10 (m, 2H), 2.84-2.72 (m, 1H), 2.66-2.53 (m, 1H), 2.04-1.90 (m, 1H), 1.69-1.56 (m, 2H), 1.54-1.42 (m, 1H) |
| 75b | Example 16b & trans-piperidine-3,4-diol | LCMS: 476.4 [M + H]⁺. ¹HNMR (400 MHz, METHANOL-d₄) δ 8.19-8.14 (m, 1H), 7.66-7.59 (m, 2H), 7.22-7.17 (m, 1H), 7.11-7.03 (m, 2H), 6.90-6.80 (m, 1H), 4.25-4.20 (m, 3H), 4.10-3.92 (m, 1H), 3.85-3.67 (m, 1H), 3.60-3.46 (m, 2H), 3.44-3.35 (m, 1H), 3.31-3.20 (m, 1H), 2.82-2.70 (m, 1H), 2.61-2.40 (m, 1H), 2.10-1.86 (m, 1H), 1.71-1.43 (m, 3H) |

TABLE 3-continued

| Ex. | Starting material | MW [M + H]+ & 1H NMR |
|---|---|---|
| 77 | Compound 76-3b & azetidin-3-ol | LCMS: 435.2 [M + H]+. 1HNMR (400 MHz, METHANOL-$d_4$) δ 8.17-8.14 (m, 1H), 7.68-7.53 (m, 2H), 7.22-7.15 (m, 1H), 7.12-7.00 (m, 2H), 6.83-6.77 (m, 1H), 4.67-4.54 (m, 1H), 4.54-4.42 (m, 1H), 4.29-4.18 (m, 1H), 4.10-4.00 (m, 1H), 3.87-3.74 (m, 1H), 2.85-2.74 (m, 1H), 2.20-2.07 (m, 1H), 1.67-1.51 (m, 2H) |
| 80 | Example 17 & MeNH$_2$ | LCMS: 387.0 [M + H]+. 1HNMR (400 MHz, METHANOL-$d_4$) δ 8.91-8.81 (m, 1H), 8.24-8.17 (m, 1H), 7.73-7.65 (m, 2H), 7.57-7.47 (m, 1H), 7.36-7.29 (m, 1H), 7.25-7.10 (m, 3H), 3.60-3.49 (m, 1H), 2.78 (s, 3H), 2.08-1.95 (m, 1H), 1.72-1.61 (m, 1H), 1.44-1.33 (m, 1H) |
| 84 | Example 83 & MeNH$_2$ | LCMS: 376.3 [M + H]+. 1HNMR (400 MHz, METHANOL-$d_4$) δ 8.31-8.27 (m, 1H), 7.77-7.74 (m, 1H), 7.59-7.53 (m, 2H), 7.50-7.47 (m, 1H), 7.07-7.01 (m, 2H), 6.76-6.73 (m, 1H), 2.83-2.77 (m, 1H), 2.65 (s, 3H), 2.07-2.00 (m, 1H), 1.56-1.48 (m, 1H), 1.39-1.32 (m, 1H) |
| 94 | Example 93 & MeNH$_2$ | LCMS: 376.4 [M + H]+. 1HNMR (400 MHz, METHANOL-$d_4$) δ 7.96 (s, 1H), 6.68-6.65 (m, 1H), 6.59-6.56 (m, 1H), 4.71 -4.60 (m, 1H), 4.16 (s, 3H), 2.81-2.75 (m, 4H), 2.74-2.57 (m, 6H), 2.34-2.26 (m, 2H), 2.17-2.11 (m, 1H), 1.60-1.45 (m, 2H) |
| 95 | Example 16b & 6-aminospiro[3.3]heptan-2-ol | LCMS: 486.4 [M + H]+. 1HNMR (400 MHz, METHANOL-$d_4$) δ 8.42-8.32 (m, 1H), 8.14 (s, 1H), 7.66-7.60 (m, 2H), 7.17-7.15 (m, 1H), 7.09-7.02 (m, 2H), 6.74-6.70 (m, 1H), 4.22 (s, 3H), 4.13-4.06 (m, 1H), 2.90-2.79 (m, 1H), 2.50-2.34 (m, 2H), 2.35-2.18 (m, 3H), 2.02-1.87 (m, 4H), 1.64-1.49 (m, 2H) |
| 96 | Example 16b & 3-oxa-6-azabicyclo[3.1.1]heptane | LCMS: 458.2 [M + H]+. 1HNMR (400 MHz, METHANOL-$d_4$) δ 8.13 (s, 1H), 7.65-7.59 (m, 2H), 7.17-7.15 (m, 1H), 7.10-7.01 (m, 2H), 6.79-6.74 (m, 1H), 4.60-4.52 (m, 1H), 4.41-4.32 (m, 1H), 4.30-4.10 (m, 5H), 3.94-3.70 (m, 2H), 3.00-2.92 (m, 1H), 2.74-2.66 (m, 1H), 2.31-2.15 (m, 1H), 1.97-1.91 (m, 1H), 1.74-1.54 (m, 2H) |
| 97 | Example 16b & 2-azaspiro[3.3]heptan-6-ol | LCMS: 472.3 [M + H]+. 1HNMR (400 MHz, METHANOL-$d_4$) δ 8.13 (s, 1H), 7.64-7.56 (m, 2H), 7.17-7.15 (m, 1H), 7.07-7.02 (m, 2H), 6.78-6.75 (m, 1H), 4.27-4.19 (m, 5H), 4.15-3.90 (m, 3H), 2.83-2.74 (m, 1H), 2.59-2.49 (m, 2H), 2.15-2.05 (m, 3H), 1.65-1.50 (m, 2H) |
| 98 | Example 16b & 2-oxa-6-azaspiro[3.4]octane | LCMS: 472.4 [M + H]+. 1HNMR (400 MHz, METHANOL-$d_4$) δ 8.16-8.10 (m, 1H), 7.65-7.59 (m, 2H), 7.20-7.12 (m, 1H), 7.10-7.03 (m, 2H), 6.85-6.76 (m, 1H), 4.71-4.57 (m, 4H), 4.25-4.19 (m, 3H), 3.99-3.84 (m, 1H), 3.74-3.65 (m, 2H), 3.52-3.46 (m, 1H), 2.85-2.75 (m, 1H), 2.39-2.33 (m, 1H), 2.30-2.15 (m, 2H), 1.65-1.59 (m, 2H) |
| 102 | Example 16b & 3-aminobicyclo[1.1.1]pentan-1-ol | LCMS: 458.1 [M + H]+. 1HNMR (400 MHz, METHANOL-$d_4$) δ 8.12 (s, 1H), 7.64-7.56 (m, 2H), 7.17-7.12 (m, 1H), 7.06-6.99 (m, 2H), 6.73-6.69 (m, 1H), 4.20 (s, 3H), 2.84-2.77 (m, 1H), 2.22-2.11 (m, 7H), 1.57-1.47 (m, 2H) |
| 103c | Example 16b & (1R,4R,5S)-2-azabicyclo[2.2.1]heptan-5-ol | LCMS: 472.1 [M + H]+. 1HNMR (400 MHz, METHANOL-$d_4$) δ 8.15-8.10 (m, 1H), 7.64-7.57 (m, 2H), 7.17-7.14 (m, 1H), 7.08-7.03 (m, 2H), 6.84-6.80 (m, 1H), 4.46-4.31 (m, 1H), 4.24-4.17 (m, 3H), 3.95-3.76 (m, 1H), 3.49-3.24 (m, 1H), 2.84-2.76 (m, 1H), 2.66-2.59 (m, 1H), 2.44-2.37 (m, 1H), 2.15-2.03 (m, 1H), 1.84-1.60 (m, 4H), 1.68-1.57 (m, 3H), 1.42-1.34 (m, 1H), 1.30-1.26 (m, 1H) |
| 103d | Example 16b & (1S,4S,5R)-2-azabicyclo[2.2.1]heptan-5-ol | LCMS: 472.1 [M + H]+. 1HNMR (400 MHz, METHANOL-$d_4$) δ 8.16-8.10 (m, 1H), 7.69-7.57 (m, 2H), 7.18-7.13 (m, 1H), 7.11-7.01 (m, 2H), 6.84-6.69 (m, 1H), 4.52-4.45 (m, 1H), 4.35-4.30 (m, 1H), 4.24-4.18 (m, 3H), 4.04-3.80 (m, 1H), 3.45-3.21 (m, 1H), 2.84-2.80 (m, 1H), 2.45-2.34 (m, 1H), 2.10-1.94 (m, 1H), 1.83-1.71 (m, 1H), 1.68-1.57 (m, 3H), 1.40-1.29 (m, 2H) |
| 103e | Example 16b & (1R,4R,5R)-2-azabicyclo[2.2.1]heptan-5-ol | LCMS: 472.1 [M + H]+. 1HNMR (400 MHz, METHANOL-$d_4$) δ 8.14-8.11 (m, 1H), 7.65-7.59 (m, 2H), 7.18-7.13 (m, 1H), 7.11-7.01 (m, 2H), 6.84-6.69 (m, 1H), 4.58-4.48 (m, 1H), 4.23-4.17 (m, 3H), 4.03-3.95 (m, 1H), 3.51-3.25 (m, 1H), 3.24-3.00 (m, 1H), 2.86-2.76 (m, 1H), 2.54-2.45 (m, 1H), 2.43-2.22 (m, 1H), 2.16-2.02 (m, 1H), 1.93-1.82 (m, 1H), 1.68-1.51 (m, 3H), 1.50-1.35 (m, 1H) |
| 103f | Example 16b & (1S,4S,5S)-2-azabicyclo[2.2.1]heptan-5-ol | LCMS: 472.3 [M + H]+. 1HNMR (400 MHz, METHANOL-$d_4$) δ 8.14 (s, 1H), 7.70-7.53 (m, 2H), 7.21-7.13 (m, 1H), 7.11-6.99 (m, 2H), 6.84-6.70 (m, 1H), 4.57-4.42 (m, 1H), 4.25-4.18 (m, 3H), 4.05-3.93 (m, 1H), 3.53-3.33 (m, 1H), 3.20-2.93 (m, 1H), 2.84-2.70 (m, 1H), 2.54-2.47 (m, 1H), 2.44-2.07 (m, 2H), 1.93-1.84 (m, 1H), 1.73-1.45 (m, 3H), 1.61-1.21 (m, 1H) |
| 104 | Example 16b & (1R,3S,5S)-8-azabicyclo[3.2.1]octan-3-ol | LCMS: 486.2 [M + H]+. 1HNMR (400 MHz, METHANOL-$d_4$) δ 8.15 (s, 1H), 7.66-7.60 (m, 2H), 7.19-7.16 (m, 1H), 7.11-7.06 (m, 2H), 6.84-6.80 (m, 1H), 4.64-4.53 (m, 1H), 4.50-4.43 (m, 1H), 4.24-4.17 (m, 3H), 4.12-4.05 (m, 1H), 2.89-2.76 (m, 1H), 2.53-2.48 (m, 1H), 2.36-2.04 (m, 5H), 1.97-1.59 (m, 5H) |
| 105 | Example 16b & (1R,3R,5S)-8-azabicyclo[3.2.1]octan-3-ol | LCMS: 486.3 [M + H]+. 1HNMR (400 MHz, METHANOL-$d_4$) δ 8.14 (s, 1H), 7.65-7.59 (m, 2H), 7.19-7.14 (m, 1H), 7.10-7.04 (m, 2H), 6.85-6.80 (m, 1H), 4.66-4.56 (m, 1H), 4.55-4.50 (m, 1H), 4.23-4.17 (m, 3H), 4.17-4.04 (m, 1H), 2.91-2.76 (m, 1H), 2.56-2.48 (m, 1H), 2.11-1.85 (m, 4H), 1.84-1.52 (m, 6H) |

TABLE 3-continued

| Ex. | Starting material | MW [M + H]+ & 1H NMR |
|---|---|---|
| 110 | Example 16b & thiomorpholine 1,1-dioxide | LCMS: 494.2 [M + H]+. 1HNMR (400 MHz, METHANOL-d4) δ 8.26-8.14 (m, 1H), 7.66-7.60 (m, 2H), 7.23-7.19 (m, 1H), 7.12-7.06 (m, 2H), 6.88-6.79 (m, 1H), 4.44-4.26 (m, 2H), 4.25 (s, 3H), 4.05-3.98 (m, 1H), 3.88-3.78 (m, 1H), 3.45-3.38 (m, 1H), 3.28-3.24 (m, 1H), 3.18-3.05 (m, 2H), 2.87-2.79 (m, 1H), 2.54-2.46 (m, 1H), 1.78-1.65 (m, 2H) |
| 111 | Example 16b & 4-methyl-1,4-azaphosphinane 4-oxide | LCMS: 492.4 [M + H]+. 1HNMR (400 MHz, METHANOL-d4) δ 8.15 (s, 1H), 7.65-7.59 (m, 2H), 7.20-7.16 (m, 1H), 7.08-7.03 (m, 2H), 6.86-6.81 (m, 1H), 4.26-4.19 (m, 3H), 4.18-3.94 (m, 2H), 3.94-3.65 (m, 2H), 2.85-2.76 (m, 1H), 2.63-2.53 (m, 1H), 2.15-1.84 (m, 4H), 1.71-1.60 (m, 5H) |
| 112a | Example 16b & trans-4-methoxypyrrolidin-3-ol | LCMS: 476.2 [M + H]+. 1HNMR (400 MHz, METHANOL-d4) δ 8.15-8.11 (m, 1H), 7.65-7.59 (m, 2H), 7.19-7.16 (m, 1H), 7.08-7.03 (m, 2H), 6.84-6.80 (m, 1H), 4.28-4.25 (m, 1H), 4.21 (s, 3H), 3.85-3.72 (m, 3H), 3.66-3.51 (m, 3H), 3.39-3.36 (m, 3H), 2.90-2.82 (m, 1H), 2.45-2.37 (m, 1H), 1.69-1.56 (m, 2H) |
| 112b | Example 16b & trans-4-methoxypyrrolidin-3-ol | LCMS: 476.1 [M + H]+. 1HNMR (400 MHz, METHANOL-d4) δ 8.13 (s, 1H), 7.64-7.59 (m, 2H), 7.19-7.15 (m, 1H), 7.10-7.04 (m, 2H), 6.84-6.80 (m, 1H), 4.26-4.23 (m, 1H), 4.21 (s, 3H), 3.87-3.66 (m, 3H), 3.65-3.47 (m, 3H), 3.38-3.32 (m, 3H), 2.84-2.75 (m, 1H), 2.43-2.34 (m, 1H), 1.70-1.58 (m, 2H) |
| 114 | Example 16b & 2,5-dioxa-8-azaspiro[3.5]nonane | LCMS: 488.3 [M + H]+. 1HNMR (400 MHz, METHANOL-d4) δ 8.44-8.31 (m, 1 H), 7.68-7.58 (m, 2 H), 7.29-7.22 (m, 1 H), 7.13-7.05 (m, 2 H), 7.05-6.92 (m, 1 H), 4.53-4.37 (m, 2 H), 4.34-4.24 (m, 3 H), 4.09-3.39 (m, 8 H), 2.88-2.77 (m, 1 H), 2.75-2.43 (m, 1 H), 1.73-1.53 (m, 2 H) |
| 115 | Example 16b & 6-methyl-2,6-diazaspiro[3.4]octan-5-one | LCMS: 499.2 [M + H]+. 1HNMR (400 MHz, METHANOL-d4) δ 8.16-8.12 (m, 1H), 7.64-7.57 (m, 2 H), 7.18-7.15 (m, 1 H), 7.08-7.03 (m, 2 H), 6.82-6.78 (m, 1 H), 4.47-4.41 (m, 1 H), 4.26-4.14 (m, 5 H), 3.98-3.88 (m, 1 H), 2.90-2.77 (m, 4 H), 2.45-2.35 (m, 2 H), 2.25-2.12 (m, 1 H), 1.76-1.56 (m, 2H) |
| 116a | Example 16b & (7-endo)-3-Oxa-9-azabicyclo[3.3.1]nonan-7-ol | LCMS: 502.2 [M + H]+. 1HNMR (400 MHz, METHANOL-d4) δ 8.14 (s, 1H), 7.64-7.58 (m, 2H), 7.18-7.15 (m, 1H), 7.09-7.04 (m, 2H), 6.84-6.79 (m, 1H), 4.63-4.55 (m, 1H), 4.37-4.30 (m, 1H), 4.25-4.18 (m, 3H), 3.96-3.69 (m, 5H), 2.87-2.76 (m, 1H), 2.54-2.41 (m, 1H), 2.35-2.13 (m, 2H), 1.92-1.75 (m, 2H), 1.71-1.58 (m, 2H) |
| 116b | Example 16b & (7-exo)-3-Oxa-9-azabicyclo[3.3.1]nonan-7-ol | LCMS: 502.2 [M + H]+. 1HNMR (400 MHz, METHANOL-d4) δ 8.13 (s, 1H), 7.64-7.58 (m, 2H), 7.17-7.14 (m, 1H), 7.08-7.02 (m, 2H), 6.84-6.81 (m, 1H), 4.61-4.51 (m, 1H), 4.35-4.28 (m, 1H), 4.24-4.18 (m, 3H), 3.90-3.73 (m, 3H), 3.72-3.59 (m, 2H), 2.87-2.76 (m, 1H), 2.60-2.46 (m, 1H), 2.24-2.02 (m, 2H), 1.72-1.56 (m, 4H) |
| 117 | Example 16b & 3-aminothietane 1,1-dioxide | LCMS: 480.0 [M + H]+. 1HNMR (400 MHz, METHANOL-d4) δ 8.97 (br s, 1H), 8.31 (s, 1H), 7.73-7.68 (m, 2H), 7.25-7.22 (m, 1H), 7.11-7.05 (m, 2H), 6.81-6.77 (m, 1H), 4.57-4.48 (m, 2H), 4.43-4.34 (m, 1H), 4.18 (s, 3H), 4.07-3.99 (m, 2H), 2.76-2.67 (m, 1H), 2.39-2.29 (m, 1H), 1.72-1.64 (m, 1H), 1.44-1.35 (m, 1H) |
| 118 | Compound108-8b & 3-oxa-6-azabicyclo[3.1.1]heptane | LCMS: 459.2 [M + H]+. 1HNMR (400 MHz, METHANOL-d4) δ 8.06 (s, 1H), 7.75-7.70 (m, 2H), 7.38-7.29 (m, 2H), 6.88-6.82 (m, 1H), 4.64-4.57 (m, 1H), 4.42-4.35 (m, 1H), 4.28-4.21 (m, 1H), 4.18 (s, 3H), 4.02-3.95 (m, 1H), 3.88-3.76 (m, 2H), 2.99-2.79 (m, 1H), 2.78-2.66 (m, 1H), 2.58-2.49 (m, 1H), 1.97-1.85 (m, 2H), 1.82-1.64 (m, 1H) |
| 119 | Compound108-8b & (1R,4R)-2-oxa-5-azabicyclo[2.2.1]heptane | LCMS: 459.2 [M + H]+. 1HNMR (400 MHz, METHANOL-d4) δ 8.10-8.02 (m, 1 H), 7.78-7.66 (m, 2 H), 7.37-7.27 (m, 2 H), 6.91-6.81 (m, 1 H), 4.70-4.60 (m, 1 H), 4.17 (s, 3 H), 3.93-3.78 (m, 2 H), 3.73-3.52 (m, 1 H), 3.49-3.37 (m, 1 H), 2.92-2.75 (m, 2 H), 2.63-2.52 (m, 1 H), 2.01-1.89 (m, 2 H), 1.89-1.81 (m, 1 H), 1.80-1.69 (m, 1 H) |
| 120 | Compound108-8b & (1S,4S)-2-oxa-5-azabicyclo[2.2.1]heptane | LCMS: 459.2 [M + H]+. 1HNMR (400 MHz, METHANOL-d4) δ 8.07-8.04 (m, 1H), 7.75-7.70 (m, 2H), 7.35-7.30 (m, 2H), 6.88-6.85 (m, 1H), 4.68-4.64 (m, 1H), 4.20-4.12 (m, 3H), 3.82-3.79 (m, 1H), 3.76-3.58 (m, 2H), 3.46-3.41 (m, 1H), 2.95-2.74 (m, 2H), 2.65-2.57 (m, 1H), 2.01-1.83 (m, 3H), 1.78-1.64 (m, 1H) |
| 121 | Example 16b & 2,5-diazabicyclo[2.2.1]heptan-3-one | LCMS: 471.1 [M + H]+. 1HNMR (400 MHz, METHANOL-d4) δ 8.17-8.13 (m, 1H), 7.71-7.52 (m, 2H), 7.23-7.16 (m, 1H), 7.14-7.02 (m, 2H), 6.94-6.76 (m, 1H), 4.30-4.19 (m, 4H), 3.61-3.48 (m, 1H), 3.40-3.35 (m, 1H), 3.01-2.88 (m, 1H), 2.74-2.64 (m, 1H), 2.38-2.28 (m, 1H), 2.17-1.87 (m, 2H), 1.73-1.54 (m, 2H) |
| 122 | Example 16b & 2,5-diazabicyclo[2.2.1]heptane | LCMS: 457.1 [M + H]+. 1HNMR (400 MHz, METHANOL-d4) δ 8.47 (br s, 1H), 8.19-8.12 (m, 1H), 7.65-7.57 (m, 2H), 7.21-7.16 (m, 1H), 7.09-7.00 (m, 2H), 6.86 (s, 1H), 4.44-4.33 (m, 2H), 4.27-4.13 (m, 5H), 4.12-3.85 (m, 2H), 3.05-2.96 (m, 1H), 2.91-2.78 (m, 1H), 2.52-2.41 (m, 1H), 2.00-1.85 (m, 1H), 1.77-1.64 (m, 2H) |

TABLE 3-continued

| Ex. | Starting material | MW [M + H]+ & 1H NMR |
|---|---|---|
| 123 | Example 16b & tert-butyl 3,6-diazabicyclo[3.1.1 ]heptane-6-carboxylate (After amide coupling, a de-boc-protection in HCl condition was preformed) | LCMS: 457.3 [M + H]+. 1HNMR (400 MHz, METHANOL-d4) δ 8.20-8.12 (m, 1H), 7.66-7.57 (m, 2H), 7.21-7.16 (m, 1H), 7.09-7.01 (m, 2H), 6.88-6.80 (m, 1H), 5.04-4.92 (m, 1H), 4.45-4.37 (m, 1H), 4.26-4.18 (m, 3H), 3.92-3.35 (m, 4H), 2.92-2.75 (m, 1H), 2.46-2.07 (m, 2H), 2.05-1.91 (m, 1H), 1.75-1.55 (m, 2H) |
| 125 | Example 16b & 2-aminoethan-1-ol | LCMS: 420.1 [M + H]+. 1HNMR (400 MHz, METHANOL-d4) δ 8.11 (s, 1 H), 7.64-7.56 (m, 2 H), 7.17-7.13 (m, 1 H), 7.07-7.00 (m, 2 H), 6.76-6.70 (m, 1 H), 4.20 (s, 3 H), 3.65-3.58 (m, 2 H), 3.37-3.32 (m, 2 H), 2.90-2.81 (m, 1 H), 2.29-2.21 (m, 1 H), 1.62-1.45 (m, 2 H) |
| 134 | Example 16b & (Dimethyl-sulfinylidene)amine | LCMS: 452.2 [M + H]+. 1HNMR (400 MHz, METHANOL-d4) δ 8.13 (s, 1H), 7.66-7.56 (m, 2H), 7.18-7.13 (m, 1H), 7.09-7.00 (m, 2H), 6.76-6.65 (m, 1H), 4.21 (s, 3H), 3.38-3.34 (m, 6H), 2.97-2.86 (m, 1H), 2.28-2.22 (m, 1H), 1.65-1.57 (m, 2H) |
| 135 | Example 16b & 1-azaspiro[3.3]hep-tan-6-one | LCMS: 470.0 [M + H]+. 1HNMR (400 MHz, METHANOL-d4) δ 8.12 (s, 1H), 7.56-7.66 (m, 2H), 7.13-7.19 (m, 1H), 6.99-7.10 (m, 2H), 6.68-6.75 (m, 1H), 5.92-6.04 (m, 1H), 4.18-4.23 (m, 3H), 3.50-3.59 (m, 2H), 3.16-3.24 (m, 2H), 2.79-2.90 (m, 3H), 2.15-2.22 (m, 1H), 1.49-1.60 (m, 2H) |
| 136 | Example 16b & 1-azaspiro[3.3]hep-tan-6-ol | LCMS: 472.1 [M + H]+. 1HNMR (400 MHz, METHANOL-d4) δ 8.11-8.19 (m, 1H), 7.55-7.68 (m, 2H), 7.14-7.21 (m, 1H), 7.01-7.10 (m, 2H), 6.76-6.93 (m, 1H), 4.23 (s, 3H), 4.12-4.18 (m, 1H), 3.97-4.05 (m, 1H), 3.83-3.94 (m, 1H), 2.80-2.99 (m, 3H), 2.64-2.76 (m, 1H), 2.50-2.59 (m, 2H), 2.30-2.48 (m, 3H), 1.57-1.73 (m, 1H) |

Example 40

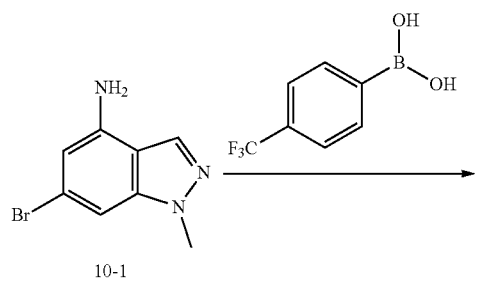

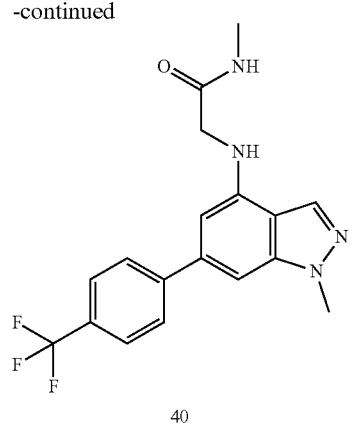

Step 1: Preparation of Compound 40-1

A mixture of Compound 10-1 (2.00 g, 8.846 mmol), (2.52 g, 13.3 mmol), $K_2CO_3$ (3.67 g, 26.5 mmol) and Pd(dppf)Cl$_2$ (0.65 g, 0.885 mmol) in dioxane (20 mL) and $H_2O$ (5 mL) was degassed and purged with $N_2$ for 3 times, then the mixture was stirred at 100° C. for 3 hrs under $N_2$ atmosphere. The mixture was diluted with water (20 mL) and extracted with EtOAc (30 mL×3). The organic layer was washed with brine (100 mL), dried over with $Na_2SO_4$, filtered and concentrated. The residue was purified by column chromatography to give Compound 40-1 (2.70 g, 9.27 mmol, crude). LCMS: 292.2 [M+H]+.

Step 2: Preparation of Compound 40-2

To a solution of Compound 40-1 (2.70 g, 9.27 mmol) in $H_2O$ (10 mL) was added HCl (15.5 mL, 185 mmol) and a solution of sodium nitrite (1.92 g, 27.8 mmol) in $H_2O$ (10 mL). The mixture was stirred at 0° C. for 0.5 hr. Potassium iodide (7.69 g, 46.3 mmol) and iodocopper(I) (0.88 g, 4.64 mmol) in H₂O (10 mL) was added to the mixture and which was stirred at 25° C. for 2 hrs. The mixture was quenched with Na₂SO₃ (30 mL) and extracted with EtOAc (50 mL×3). The organic layer was washed with NaHCO₃ (100 mL×2), dried over with Na₂SO₄, filtered and concentrated. The residue was purified by column chromatography to give Compound 40-2 (2.20 g, 5.47 mmol, 59.0%).

Step 3: Preparation of Example 40

To a solution of Compound 40-2 (30.0 mg, 0.06 mmol) in DCM (1.0 mL) was added TFA (0.3 mL, 0.06 mmol) and the mixture was stirred at 25° C. for 6 hrs under N₂ atmosphere. The mixture was concentrated and the residue was purified by reversed-phase HPLC to give Example 40 (6.14 mg, 0.02 mmol, 26.4%). LCMS: 410.0 [M+H]⁺. ¹HNMR (400 MHz, METHANOL-d₄) δ 8.21 (s, 1H), 7.98-7.96 (m, 2H), 7.83-7.79 (m, 3H), 7.63 (s, 1H), 5.93 (s, 1H), 7.85 (s, 1H), 4.45 (s, 2H), 4.16 (s, 3H), 3.51-3.43 (m, 5H), 2.65 (s, 3H).

Example 41 & Example 42

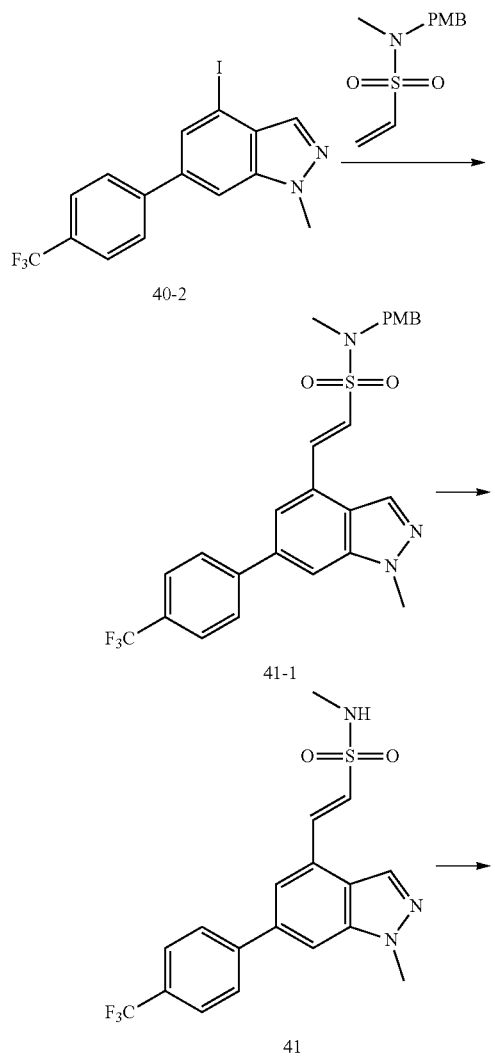

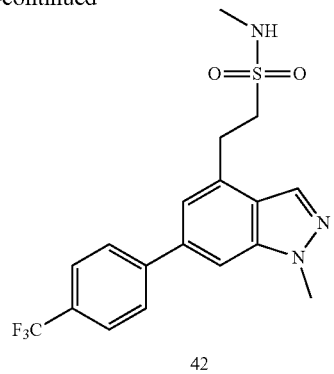

Step 1: Preparation of Compound 41-1

To a solution of 1-(4-methoxyphenyl)-N-methylmethanamine (1.50 g, 9.92 mmol) in DCM (10 ml) was added TEA (4.83 mL, 34.7 mmol), followed by addition 2-chloroethane-1-sulfonyl chloride (1.78 g, 10.9 mmol) at 0° C. The mixture was stirred for 2 hrs. The mixture was diluted with water (50 mL) and extracted with EtOAc (50 mL×3). The combined organic layers were washed with brine (100 mL), dried over with Na₂SO₄, filtered and concentrated. The residue was purified by column chromatography to give N-(4-methoxybenzyl)-N-methylethenesulfonamide (2.00 g, 8.28 mmol, 83.5%). ¹HNMR (400 MHz, METHANOL-d4) δ 7.36-7.22 (m, 2H), 6.97-6.90 (m, 2H), 6.73-6.58 (m, 1H), 6.20 (d, J=16.5 Hz, 1H), 6.12-6.04 (m, 1H), 4.18 (s, 2H), 3.85-3.76 (m, 3H), 2.65 (s, 3H)

To a solution of Compound 40-2 (150 mg, 0.37 mmol), N-(4-methoxybenzyl)-N-methylethenesulfonamide (135 mg, 0.56 mmol) and Pd(OAc)₂ (8.37 mg, 0.04 mmol) in DMF (4 mL) were added TEA (0.16 mL, 1.12 mmol). The reaction was stirred at 80° C. for 2 hrs. The reaction mixture was poured into the H₂O (50 mL), extracted with EtOAc (20 mL×2). The organic layer was washed with brine (20 mL×2), dried over with Na₂SO₄, filtered and concentrated. The residue was purified by prep-TLC to give Compound 41-1 (80.0 mg, 0.16 mmol, 41.6%). LCMS: 516.1 [M+H]⁺.

Step 2: Preparation of Example 41

To a solution of compound 41-1 (100 mg, 0.194 mmol) in DCM (3 mL) was added TFA (1 mL). The mixture was stirred at 25° C. for 2 hrs under N₂ atmosphere. The mixture was concentrated. The crude product was purified by reversed-phase HPLC to give Example 41 (40.0 mg, 0.101 mmol, 52.1%). LCMS: 396.1 [M+H]⁺. ¹HNMR (400 MHz, METHANOL-d₄) δ 8.37-8.34 (m, 1H), 8.02-7.96 (m, 3H), 7.85-7.77 (m, 4H), 7.30-7.24 (m, 1H), 4.19 (s, 3H), 2.72 (s, 3H)

Step 3: Preparation of Example 42

To a solution of Example 41 (15.0 mg, 0.04 mmol) in MeOH (2 mL) was added Pd/C (20.0 mg, 10% purity) under Ar atmosphere. The suspension was degassed and purged with H₂ (0.01 g, 6.01 mmol) for 3 times. The mixture was stirred under H₂ (30 Psi) at 20° C. for 10 hrs. The mixture was filtered, and the cake was washed with THF (5 mL×3), then the filtrate was concentrated. The crude was purified by reversed-phase HPLC to give Example 42 (8.63 mg, 0.02 mmol, 57.2%). LCMS: 398.1 [M+H]⁺. ¹HNMR (400 MHz, METHANOL-d₄) δ 8.15 (s, 1H), 7.94 (d, J=8.3 Hz, 2H), 7.80-7.72 (m, 3H), 7.40 (s, 1H), 4.13 (s, 3H), 3.51-3.43 (m, 5H), 2.74 (s, 3H).

Example 43

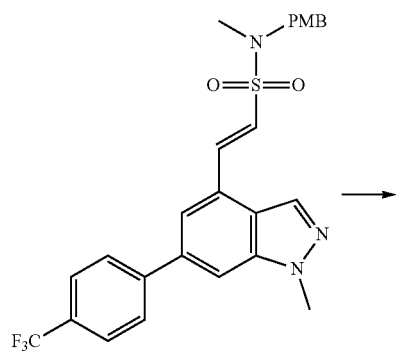

41-1

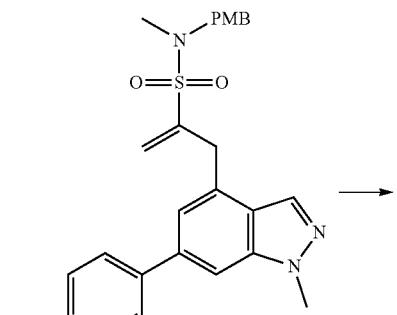

43-1

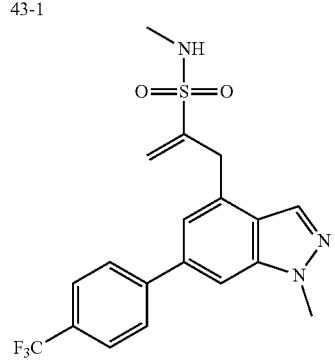

43

Step 1: Preparation of Compound 43-1

To a solution of trimethylsulfoxide iodide (128 mg, 0.58 mmol) in DMSO (5 mL) were added NaH (23.2 mg 0.58 mmol). After stirring at 25° C. for 0.5 hr, a solution of Compound 41-1 (100 mg, 0.19 mmol) in DMSO (5 mL) was added under N₂. The reaction was stirred at 25° C. for 10 hrs. The mixture was poured into the H₂O (50 mL), extracted with EtOAc (10 mL×5). The organic layer was washed with brine (10 mL×2), dried over with Na₂SO₄, filtered and concentrated to give Compound 43-1 (30.0 mg, crude). LCMS: 530.1 [M+H]⁺.

Step 2: Preparation of Example 43

To a solution of Compound 43-1 (50.0 mg, 0.12 mmol), 2-amino-N-methylacetamide (16.4 mg, 0.19 mmol), Pd₂(dba)₃ (22.8 mg, 0.03 mmol) and Xantphos (36.0 mg, 0.06 mmol) in toluene (4 mL) were added Cs₂CO₃ (122 mg, 0.37 mmol), and the reaction was stirred at 100° C. for 6 hrs under N₂. The mixture was poured into H₂O (50 mL), extracted with EtOAc (20 mL×2), the organic layer was washed with brine (20 mL×2), dried over Na₂SO₄, filtered and concentrated. The residue was purified by prep-HPLC to give Example 43 (8.19 mg, 0.03 mmol, 26.05%). LCMS: 263.4 [M+H]⁺. ¹HNMR (400 MHz, DMSO-d₆) δ 8.16 (s, 1H), 7.94-7.88 (m, 3H), 7.85-7.79 (m, 2H), 7.14 (s, 1H), 6.22 (s, 1H), 4.00 (s, 4H), 3.88 (s, 3H), 2.61 (d, J=4.6 Hz, 3H)

Example 44

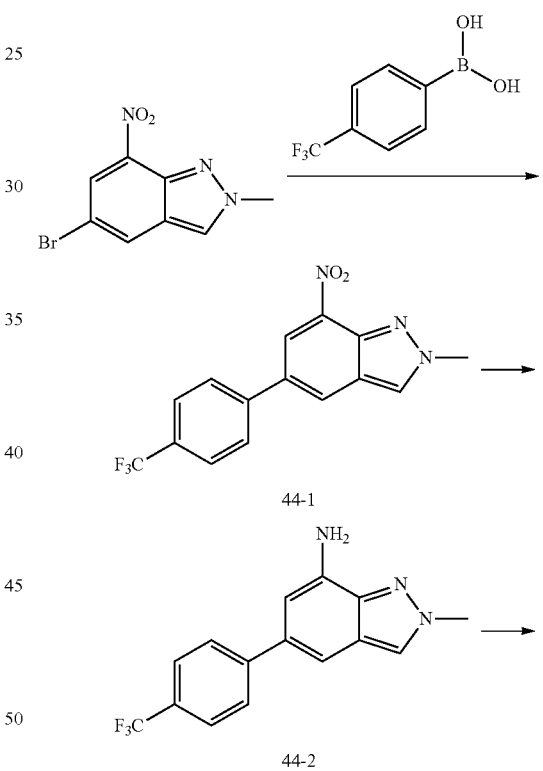

44-1

44-2

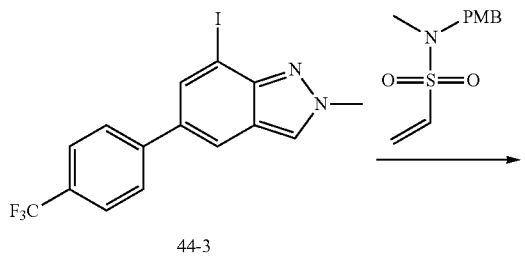

44-3

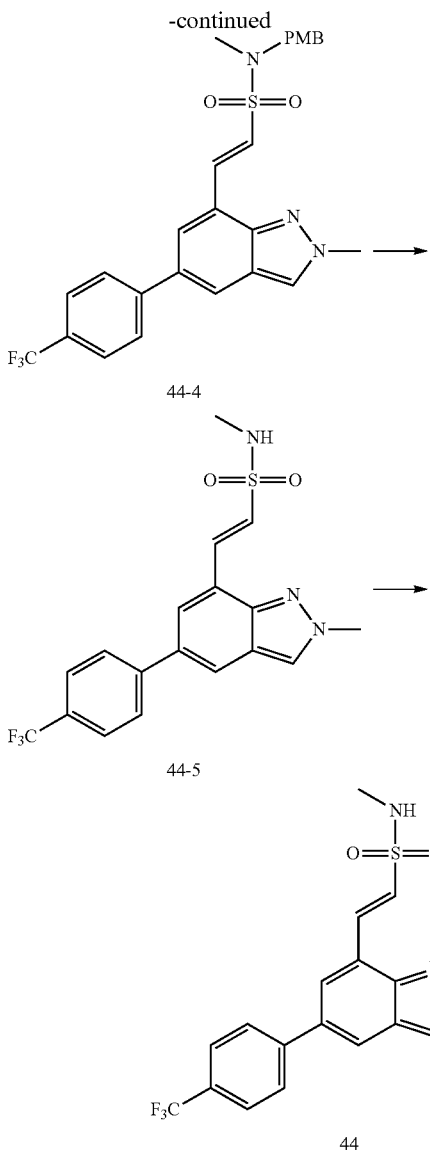

44-4

44-5

44

Step 1: Preparation of Compound 44-1

To a solution of 5-bromo-2-methyl-7-nitro-2H-indazole (1.00 g, 3.91 mmol), (4-(trifluoromethyl)phenyl)boronic acid (1.11 g, 5.86 mmol), and Pd(dppf)Cl$_2$ (285 mg, 0.39 mmol) in dioxane (20 mL) and H$_2$O (5 mL) was added K$_2$CO$_3$ (1.62 mg, 11.7 mmol). The reaction was stirred at 80° C. for 2 hrs under N$_2$. The mixture was poured into H$_2$O (100 mL), extracted with EtOAc (30 mL×3), the organic layer was washed with brine (50 mL×2), dried over with Na$_2$SO$_4$, filtered and concentrated. The residue was purified by column chromatography to give Compound 44-1 (1.00 g, 3.11 mmol, 79.7%). LCMS: 322.3 [M+H]$^+$.

Step 2: Preparation of Compound 44-2

To a solution of Pd/C (331 mg, 10%) in MeOH (10 mL) were added Compound 44-1 (1.00 mg, 3.11 mmol), the reaction was stirred at 25° C. for 3 hrs. The mixture was filtered and concentrated to give Compound 44-2 (650 mg, 2.23 mmol, 71.7%). LCMS: 292.1 [M+H]$^+$.

Step 3: Preparation of Compound 44-3

To a solution of Compound 44-2 (450 mg, 1.55 mmol) in H$_2$O (2 mL) and concentrated HCl (2.0 mL) were added slowly sodium nitrite (128 mg, 1.85 mmol) in H$_2$O (2.0 mL) at 0° C., the reaction was stirred at 0° C. for 30 min. Potassium iodide (769 mg, 4.63 mmol) in H$_2$O (2 mL) was added slowly, the mixture was stirred for 1 hrs at 25° C. The mixture was poured into H$_2$O (50 mL) and extracted with EtOAc (20 mL×2). The organic layer was washed with brine (50 mL×2), dried over with Na$_2$SO$_4$, filtered and concentrated. The residue was purified by column chromatography to give Compound 44-3 (300 mg, 0.75 mmol, 48.29%). LCMS: 402.9 [M+H]$^+$.

Step 4: Preparation of Compound 44-4

To a solution of Compound 44-3 (150 mg, 0.37 mmol), N-(4-methoxybenzyl)-N-methylethenesulfonamide (135 mg, 0.56 mmol) and Pd(OAc)$_2$ (8.37 mg, 0.04 mmol) in DMF (4 mL) were added TEA (0.16 mL, 1.12 mmol), the reaction was stirred at 80° C. for 2 hrs. The mixture was poured into H$_2$O (50 mL), extracted with EtOAc (20 mL×2), the organic layer was washed with brine (20 mL×2), dried over with Na$_2$SO$_4$, filtered and concentrated. The residue was purified by prep-TLC to give Compound 44-4 (80.0 mg, 0.16 mmol, 41.6%). LCMS: 516.1 [M+H]$^+$.

Step 5: Preparation of Compound 44-5

To a solution of Compound 44-4 (60 mg, 0.12 mmol) in DCM (3 mL) were added TFA (0.20 mL, 0.04 mmol), the reaction was stirred at 25° C. for 2 hrs. The mixture was poured into H$_2$O (50 mL), extracted with DCM (20 mL×3). The organic layer was washed with brine (20 mL×2), dried over with Na$_2$SO$_4$, filtered and concentrated to give Compound 44-5 (50.0 mg, 0.13 mmol, crude). LCMS: 396.2 [M+H]$^+$

Step 5: Preparation of Example 44

To a solution of Pd/C (13.5 mg, 10% purity) in MeOH (2 mL) was added Compound 44-5 (50.0 mg, 0.13 mmol), and the reaction was stirred at 25° C. for 2 hrs under H$_2$. The mixture was filtered, the liquid phase was concentrated. The residue was purified by prep-HPLC to give Example 44 (10.0 mg, 0.03 mmol, 19.9%). LCMS: 398.2 [M+H]$^+$. $^1$HNMR (400 MHz, METHANOL-d$_4$) δ 8.30 (s, 1H), 7.93-7.91 (m, 1H), 7.87 (d, J=8.1 Hz, 2H), 7.75 (d, J=8.3 Hz, 2H), 7.52 (s, 1H), 4.60 (s, 1H), 4.27 (s, 3H), 3.65-3.58 (m, 2H), 3.53-3.44 (m, 2H), 2.77 (s, 3H).

Example 45

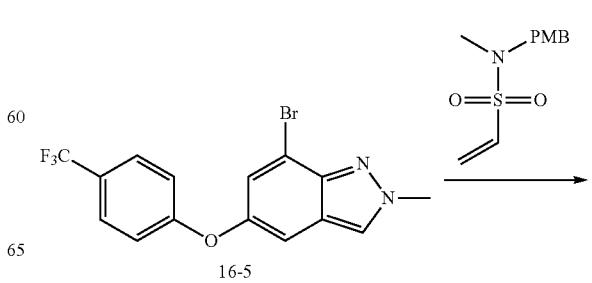

16-5

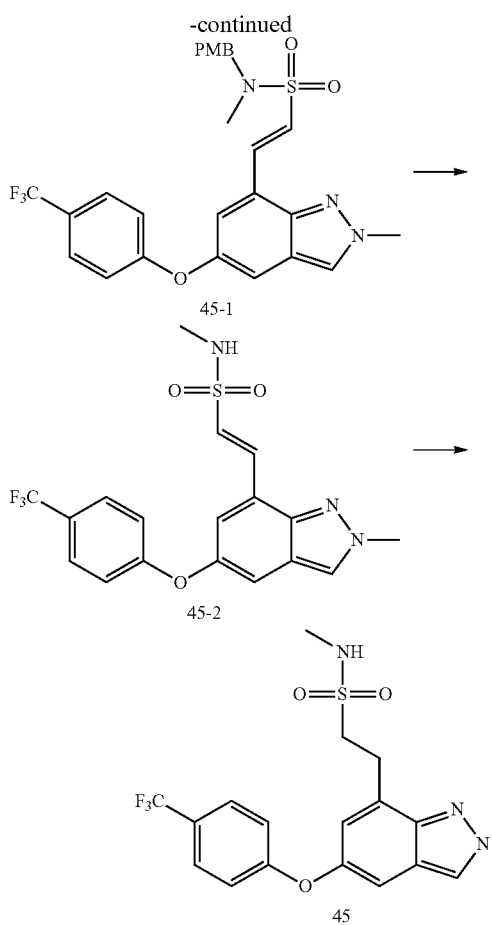

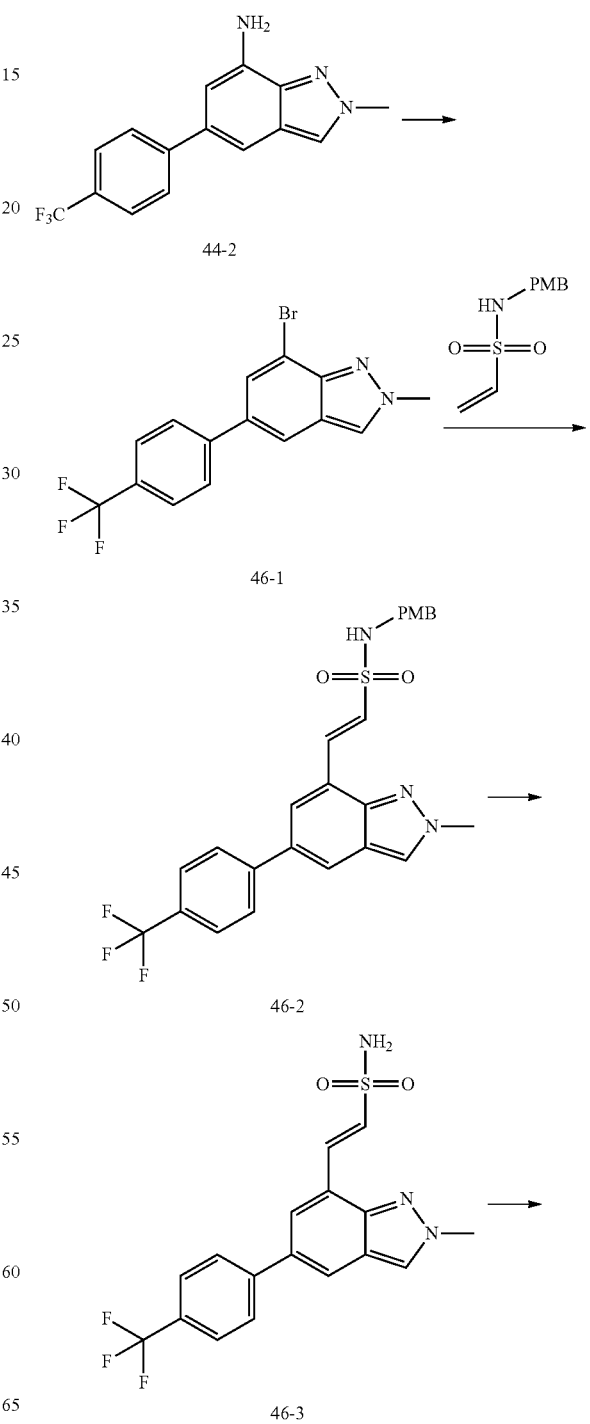

reversed-phase HPLC to give Example 45 (35.3 mg, 0.08 mmol, 29.5%) as a white solid. LCMS: 414.2 [M+H]$^+$. $^1$HNMR (400 MHz, METHANOL-d$_4$) δ 8.17 (s, 1H), 7.63 (d, J=8.6 Hz, 2H), 7.24 (d, J=2.1 Hz, 1H), 7.10 (d, J=8.6 Hz, 2H), 6.99-6.98 (m, 1H), 4.24 (s, 3H), 3.59-3.53 (m, 2H), 3.43-3.39 (m, 2H), 2.75 (s, 3H).

Example 46

Step 1: Preparation of Compound 45-1

To a solution of Compound 16-5 (200 mg, 0.54 mmol), N-(4-methoxybenzyl)-N-methylethenesulfonamide (195 mg, 0.81 mmol) and palladium(0) bis[tris(2-methylprop-2-yl)phosphane](27.5 mg, 0.05 mmol) in DMF (2 mL) was added TEA (0.22 mL, 1.62 mmol), the reaction was stirred at 100° C. for 2 hrs. under microwave condition. The mixture was poured into H$_2$O (50 mL), extracted with EtOAc (20 mL×2), the organic layer was washed with brine (20 mL×2), dried over with Na$_2$SO$_4$, filtered and concentrated. The residue was purified by column chromatography to give Compound 45-1 (190 mg, 0.36 mmol, 66.3%). LCMS: 554.2 [M+Na]$^+$.

Step 2: Preparation of Compound 45-2

To a solution of Compound 45-1 (200 mg, 0.38 mmol) in DCM (5 mL) was added TFA (0.50 mL, 0.38 mmol). The mixture was stirred for 2 hrs and concentrated to give Compound 45-2 (120 mg, 0.29 mmol, 77.5%). LCMS: 412.0 [M+H]$^+$.

Step 3: Preparation of Example 45

A mixture of Compound 45-2 (120 mg, 0.29 mmol) and Pd/C (310 mg, 10% purity) in MeOH (10 ml) was degassed and purged with H$_2$ for 3 times, the mixture was stirred at 25° C. for 3 hrs under H$_2$ atmosphere. The mixture was filtered and concentrated. The residue was purified by

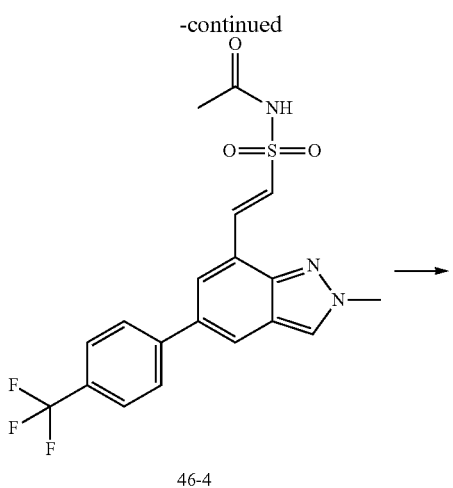

46-4

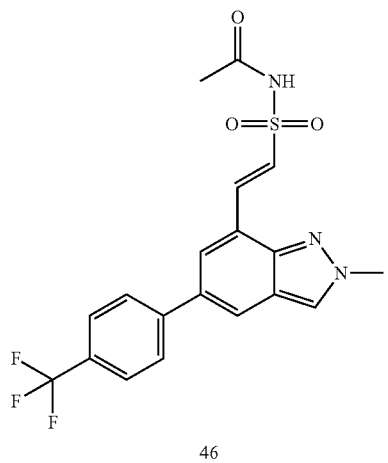

46

Step 1: Preparation of Compound 46-1

A mixture of Compound 44-2 (2 g, 6.87 mmol) and bromine (10 mL) in $H_2O$ (10 mL) was cooled to 0° C., then sodium nitrite (0.5 g, 6.87 mmol) in $H_2O$ (10 ml) was added, stirred at 0° C. for 15 mins, then sodium nitrite (0.5 g, 6.87 mmol) and bromocopper(I) (1.1 g, 7.55 mmol) in HBr (10 mL) was added slowly. The mixture was stirred at 25° C. for 12 hrs and saturated $NaHCO_3$ water solution was added to adjust pH to around 7, then extracted with EtOAc (5 mL×3), dried over with $Na_2SO_4$, filtered and concentrated. The residue was purified by column chromatography to give Compound 46-1 (1 g, 2.82 mmol, 41.0%). LCMS: 356.9 $[M+H]^+$.

Step 2: Preparation of Compound 46-2

A mixture of Compound 46-1 (100 mg, 0.282 mmol), N-[(4-methoxyphenyl)methyl]ethenesulfonamide (83.2 mg, 0.366 mmol), palladium(0) bis[tris(2-methylprop-2-yl)phosphane] (14.4 mg, 0.028 mmol), TEA (0.120 mL, 0.845 mmol) in DMF (1 mL) was stirred at 120° C. for 2 hrs under microwave condition. The reaction was quenched by $H_2O$ (1 mL), extracted with EtOAc (1 mL×3), washed with brine (1 mL×3), dried over with $Na_2SO_4$, filtered and concentrated. The residue was purified by Prep-TLC to give Compound 46-2 (70 mg, 0.140 mmol, 49.6%). LCMS: 502.0 $[M+H]^+$.

Step 3: Preparation of Compound 46-3

To a solution of Compound 46-2 (70 mg, 0.140 mmol) in DCM (0.5 mL) was added TFA (0.5 mL), stirred at 40° C. for 2 hrs. Saturated $NaHCO_3$ water solution was added to the mixture to adjust pH to around 8, extracted with DCM (1 mL×3), dried over with $Na_2SO_4$, filtered and concentrated to give crude Compound 46-3 (60 mg, 0.157 mmol). LCMS: 763.3 $[2M+H]^+$.

Step 3: Preparation of Compound 46-4

To a solution of Compound 46-3 (60 mg, 0.157 mmol) in 0.25 mL DCM was added acetyl chloride (38.5 mg, 0.472 mmol) in 1 mL DCM and TEA (0.11 mL, 0.787 mmol) at 0° C., the mixture was stirred at 25° C. for 5 hrs and quenched by adding saturated $NaHCO_3$ water solution (1 mL), then extracted with DCM (1 mL×3), dried over with $Na_2SO_4$, filtered and concentrated. The residue was purified by Prep-TLC to give Compound 46-4 (20.0 mg, 0.047 mmol, 30.0%). LCMS: 424.1 $[M+H]^+$.

Step 4: Preparation of Example 46

A mixture of Compound 46-4 (20.0 mg, 0.047 mmol) and Pd/C (2.00 mg, 10% purity) in MeOH (0.20 mL) was stirred at 25° C. under $H_2$ atmosphere. The reaction was filtered and concentrated, purified by Prep-HPLC to give Example 46 (2.26 mg, 0.005 mmol, 28.2%). LCMS: 426.1 $[M+H]^+$. $^1$HNMR (400 MHz, METHANOL-$d_4$) δ 8.28 (s, 1H), 7.92-7.89 (m, 1H), 7.89-7.84 (m, 2H), 7.76-7.70 (m, 2H), 7.51-7.48 (m, 1H), 4.25 (s, 3H), 3.95-3.86 (m, 2H), 3.57-3.45 (m, 2H), 2.66 (s, 3H).

Example 47

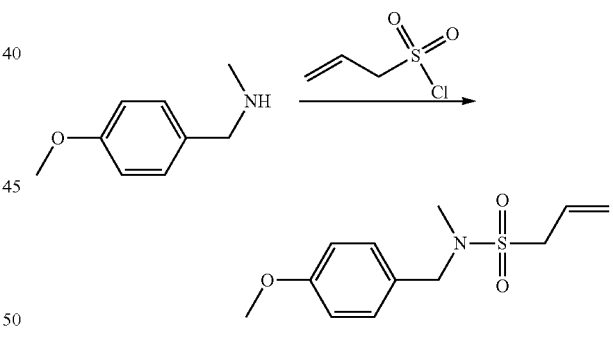

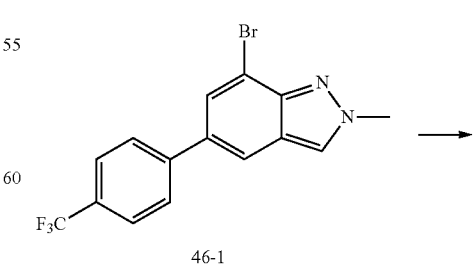

46-1

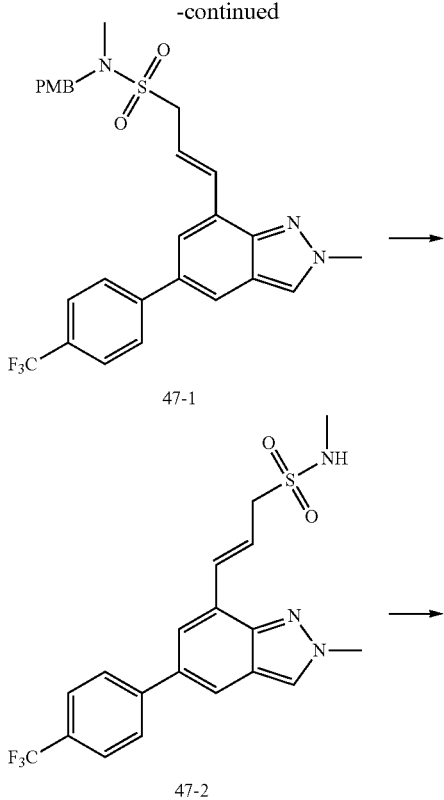

47-1

47-2 tography to give Compound 47-1 (88.0 mg, 0.166 mmol, 59.0%). LCMS: 530.4 [M+H]+.

Step 2: Preparation of Compound 47-2

A mixture of Compound 47-1 (88.0 mg, 0.166 mmol) and TFA (1 mL, 0.161 mmol) in DCM (1 mL) was degassed and purged with $N_2$ for 3 times, the mixture was stirred at 25° C. for 2 hrs under $N_2$ atmosphere. Saturated $NaHCO_3$ water solution was added to the mixture to adjust pH to around 7. 10 mL water was added and extracted with EtOAc (2 mL×3), dried over with $Na_2SO_4$, filtered and concentrated to give Compound 47-2 (63.0 mg, 0.15 mmol, 92.6%). LCMS: 410.3 [M+H]+;

Step 3: Preparation of Example 47

To a solution of Compound 47-2 (63.0 mg, 0.15 mmol) in MeOH (2 mL) was added Pd/C (30 mg, 10% purity) under $N_2$ atmosphere. The suspension was degassed and purged with $H_2$ for 3 times, stirred under $H_2$ (15 Psi) at 25° C. for 12 hrs. The reaction was filtered and concentrated, purified by Prep-HPLC to give Example 47 (23.8 mg, 0.06 mmol, 37.6%). LCMS: 412.3 [M+H]+. $^1$HNMR (400 MHz, METHANOL-$d_4$) δ 8.29 (s, 1H), 7.91-7.84 (m, 3H), 7.78-7.72 (m, 2H), 7.48 (s, 1H), 4.30-4.25 (m, 3H), 3.23-3.17 (m, 2H), 3.16-3.10 (m, 2H), 2.66 (s, 3H), 2.36-2.26 (m, 2H)

Example 48

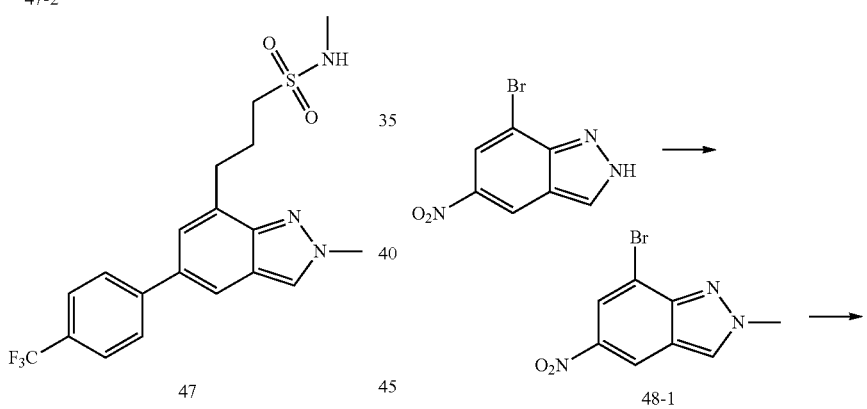

47

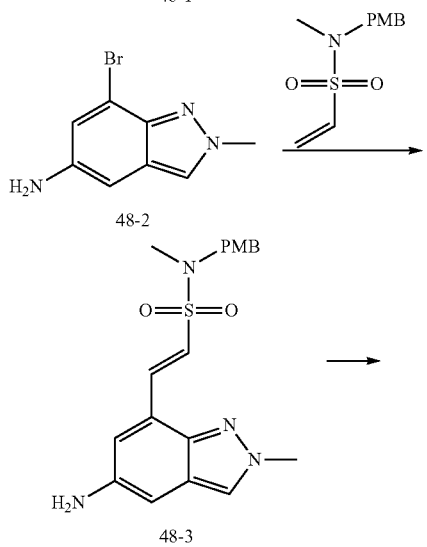

48-1

48-2

48-3

Step 1: Preparation of Compound 47-1

To a solution of 1-(4-methoxyphenyl)-N-methylmethanamine (1.00 g, 6.61 mmol) in DCM (10 mL) was added TEA (1.30 g, 13.2 mmol) and prop-2-ene-1-sulfonyl chloride (0.90 g, 6.61 mmol), the reaction was stirred at room temperature for 18 hrs. The reaction mixture was extracted with EtOAc (10 mL×3), washed with brine (10 mL×2), dried over with $Na_2SO_4$, filtered and concentrated to give crude N-(4-methoxybenzyl)-N-methylprop-2-ene-1-sulfonamide (71.9 mg, 0.28 mmol), which was further dissolved in DMF (1 mL), and added Compound 46-1 (100 mg, 0.282 mmol), TEA (0.12 mL, 0.85 mmol) and palladium (0) bis[tris (2-methylprop-2-yl) phosphane] (14.4 mg, 0.028 mmol). The mixture was degassed and purged with $N_2$ for 3 times, stirred at 130° C. for 2 hrs under $N_2$ atmosphere. The reaction was cooled to r.t., quenched by water, extracted with EtOAc (2 mL×3), dried over with $Na_2SO_4$, filtered and concentrated. The residue was purified by column chroma- -continued

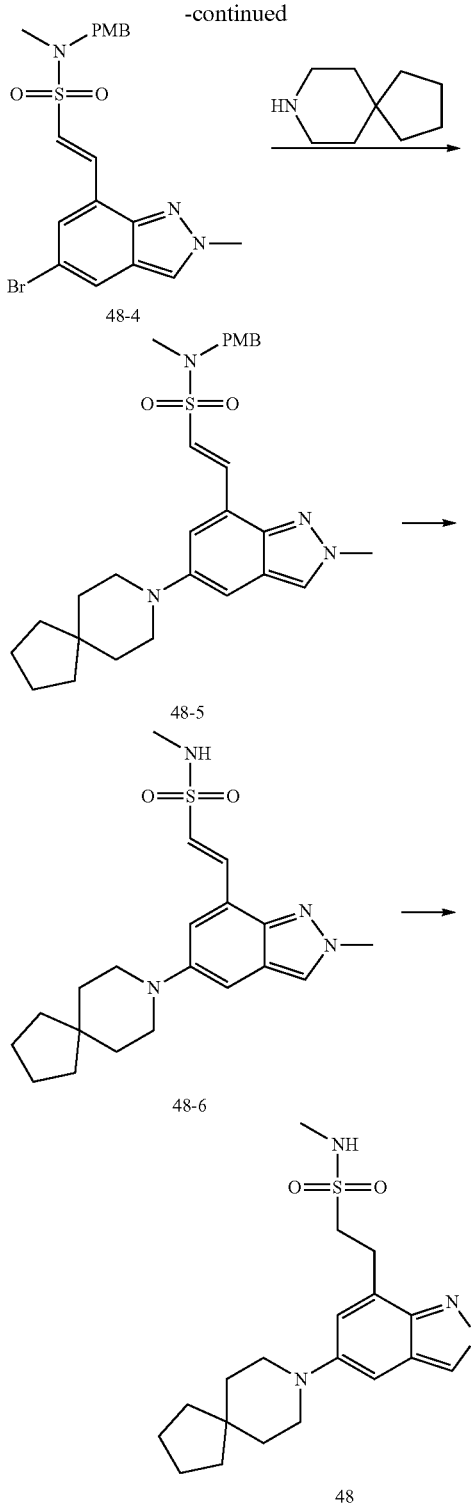

Step 1: Preparation of Compound 48-1

To a solution of 7-bromo-5-nitro-2H-indazole (5.00 g, 20.6 mmol) in EtOAc (50 mL) were added trimethyloxonium tetrafluoroborate (3.1 g, 20.6 mmol) and the reaction was stirred at 25° C. for 18 hrs. Concentrated under reduced pressure to remove EtOAc, the residue was concentrated, and pH was adjusted to around 8 with NaHCO₃ solution. After filtration, solid residue was washed with water (100 mL×3), concentrated to give Compound 48-1 (5.90 g, 19.5 mmol, crude). $^1$H NMR (400 MHz, DMSO-$d_6$) δ 8.84-8.81 (m, 1H), 8.15-8.14 (m, 1H), 4.25 (s, 3H).

Step 2: Preparation of Compound 48-2

To a solution of Compound 48-1 (5.90 g, 19.5 mmol, crude) in EtOH (60 mL) and H₂O (60 mL) were added Fe (5.10 g, 92.1 mmol) and NH₄Cl (4.90 g, 92.1 mmol) under N₂, the reaction was stirred at 80° C. for 2 hrs. The reaction was filtered and concentrated, extracted with DCM (100 mL×4). The combined organic layers were dried over anhydrous Na₂SO₄, concentrated to give Compound 48-2 (3.8 g, 16.8 mmol, 73.0% yield). LCMS: 228.3 [M+H]⁺;

Step 3: Preparation of Compound 48-3

To a solution of Compound 48-2 (300 mg, 1.17 mmol) and N-(4-methoxybenzyl)-N-methylethenesulfonamide (384 mg, 1.59 mmol) in DMF (3 mL) were added TEA (551 μL, 3.98 mmol) and Pd(P(t-Bu)₃)₂(67.8 mg, 0.133 mmol) under N₂ at 25° C., the reaction was stirred at 120° C. for 2 hrs under microwave. The reaction was extracted with EtOAc (20 mL×4) and H₂O (10 mL), washed with brine (1 mL×3), dried over with Na₂SO₄, filtered and concentrated, dried over with Na₂SO₄, filtered and concentrated. The residue was purified by prep-TLC to give Compound 48-3 (265 mg, 0.686 mmol, 51.7% yield). LCMS: 387.4 [M+H]⁺;

Step 4: Preparation of Compound 48-4

To a solution of Compound 48-3 (210 mg, 0.543 mmol) in HBr (2 mL) and H₂O (2 mL), was added NaNO₂(45.0 mg, 0.652 mmol) in H₂O (2 mL) solution under N₂ at 0° C. The reaction was stirred at 0° C. for 0.5 hr, CuBr (233 mg, 1.63 mmol) in HBr (2 mL) was added under N₂ at 0° C., the reaction was stirred at 25° C. for 8 hrs. A solution of CuBr (77.9 mg, 0.543 mmol) in HBr (1 mL) was added under N₂ at 0° C., reaction was stirred at 25° C. for 8 hr, pH was adjusted to around 6 with NaHCO₃ solution., then filter and extracted with EtOAc 60 mL (20 mL×3), dried with Na₂SO₄, filtered, concentrated and purified by prep-TLC to give Compound 48-4 (101 mg, 0.224 mmol, 41.3% yield). LCMS: 452.3 [M+H]⁺;

Step 5: Preparation of Compound 48-5

To a solution of Compound 48-4 (80 mg, 0.178 mmol) and 8-azaspiro[4.5]decane hydrochloride (46.8 mg, 0.266 mmol) in DMF (1 mL) was added t-BuONa (51.2 mg, 0.533 mmol), RuPhos (33.2 mg, 0.071 mmol), tris[(1E,4E)-1,5-diphenylpenta-1,4-dien-3-one] bis[palladium(0)] (32.5 mg, 0.036 mmol) under N₂ at 25° C., the reaction was stirred at 100° C. for 2 hrs. The reaction mixture was quenched by H₂O (5 mL), extracted with EtOAC (10 mL×3), dried over with Na₂SO₄, filtered and concentrated, purified by prep-TLC to give Compound 48-5 (51 mg, 0.100 mmol, 56.4%). LCMS: 509.5 [M+H]⁺;

Step 6: Preparation of Compound 48-6

A solution of Compound 48-5 (51 mg, 0.100 mmol) in DCM (1 mL) and TFA (0.3 mL) was stirred at 25° C. for 2 hrs under N₂ atmosphere, pH was adjusted to around 7 with NaHCO₃ solution. The reaction mixture was extracted with EtOAC (5 mL×4), dried over with Na₂SO₄, filtered, concentrated to give Compound 48-6 (42.0 mg, 0.108 mmol, crude). LCMS: 389.4 [M+H]⁺.

Step 7: Preparation of Example 48

To a solution of Compound 48-6 (42.0 mg, 0.108 mmol) in MeOH (5 mL) was added Pd/C 10% (20 mg, 0.188 mmol) under Ar atmosphere. The suspension was degassed and purged with H₂ for 3 times, stirred under H₂ (15 Psi) at 25° C. for 8 hrs. The reaction was filtered, washed with MeOH (20 mL×3), concentrated and purified by HPLC to give Example 48 (6.8 mg, 0.017 mmol, 16.1%). LCMS: 391.2 [M+H]⁺. ¹HNMR (400 MHz, METHANOL-d₄) δ 8.02 (s, 1H), 7.09-7.03 (m, 2H), 4.18 (s, 3H), 3.56-3.50 (m, 2H), 3.40-3.34 (m, 2H), 3.14-3.09 (m, 4H), 2.72 (s, 3H), 1.72-1.67 (m, 8H), 1.57-1.51 (m, 4H)

Example 49

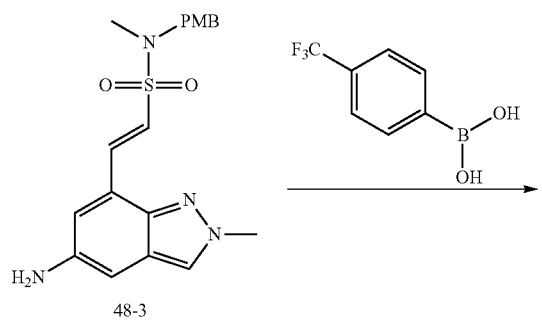

48-3

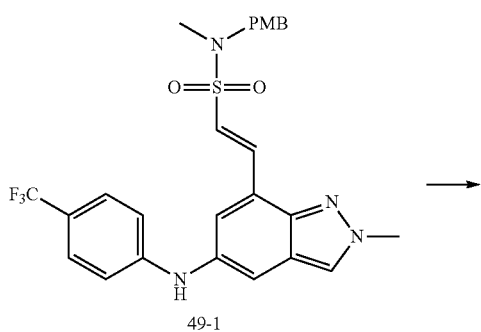

49-1

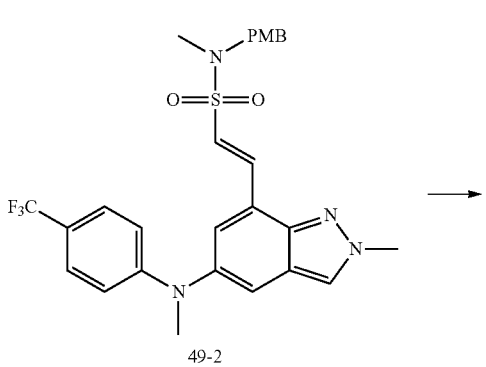

49-2

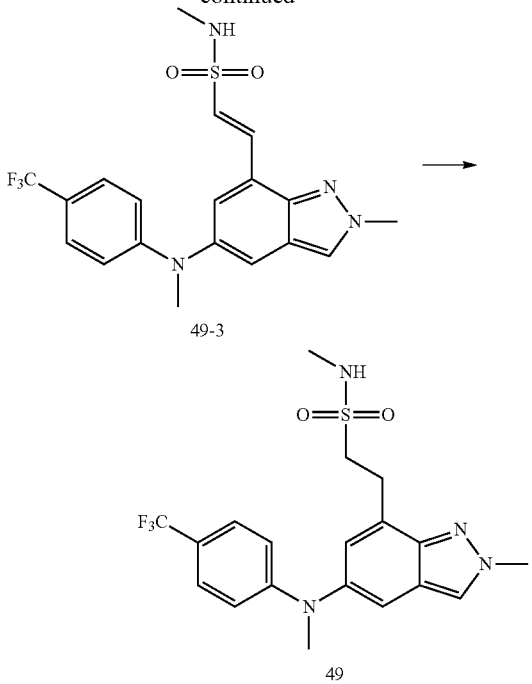

49-3

49

Step 1: Preparation of Compound 49-1

Compound 48-3 (720 mg, 1.86 mmol), [(4-(trifluoromethyl)phenyl)boronic acid (389.1 mg, 2.04 mmol), cupric bis(acetate) (507.4 mg, 2.79 mmol), TEA (1.29 mL, 9.31 mmol) in DCM (0.5 mL) was stirred at 25° C. for 2 hrs. The reaction was quenched by H₂O (5 mL), extracted with DCM (3 mL×3), dried over with Na₂SO₄, filter, concentrated and purified by prep-TLC to give Compound 49-1 (70.0 mg, 0.13 mmol). LCMS: 531.1 [M+H]⁺;

Step 2: Preparation of Compound 49-2

NaH (15.8 mg, 0.39 mmol) in DMF (0.5 mL) was added Compound 49-1 (70.0 mg, 0.13 mmol) at 0° C., stirred for 30 min, iodomethane (20.6 mg, 0.14 mmol) was added. After stirred at 25° C. for 5 hrs, the reaction was quenched by H₂O (1 mL), extracted with EtOAc (1 mL×3), washed with NaCl (1 mL×3), dried over with Na₂SO₄, filter and concentrated to give Compound 49-2 (140 mg, 0.25 mmol, crude). LCMS: 545.4 [M+H]⁺;

Step 3: Preparation of Compound 49-3

Compound 49-2 (130 mg, 0.23 mmol) in DCM (0.10 mL) was added TFA (1.50 mL, 0.03 mmol), stirred at 45° C. for 12 hrs. NaHCO₃ water solution was added to adjust the pH value to around 8, the mixture was extracted with EtOAc (2 mL×3), dried over with Na₂SO₄, filter, concentrated and purified with prep-TLC to give Compound 49-3 (25.0 mg, 0.05 mmol). LCMS: 425.2 [M+H]⁺;

Step 4: Preparation of Example 49

Compound 49-3 (30.0 mg, 0.07 mmol) and Pd/C (7.50 mg, 0.07 mmol) in MeOH (0.5 mL) was stirred at 25° C. for 2 hrs under H₂ atmosphere. The mixture was filtered, concentrated, and purified with prep-HPLC to give Example 49

(5.9 mg, 0.01 mmol, 19.5%). LCMS: 427.2 [M+H]+. ¹HNMR (400 MHz, METHANOL-d₄) δ 8.37 (s, 1H), 7.54-7.44 (m, 1H), 7.43-7.38 (m, 2H), 7.19 (s, 1H), 6.89-6.81 (m, 2H), 4.29 (s, 3H), 3.57-3.47 (m, 2H), 3.43-3.33 (m, 5H), 2.74 (s, 3H)

Example 50

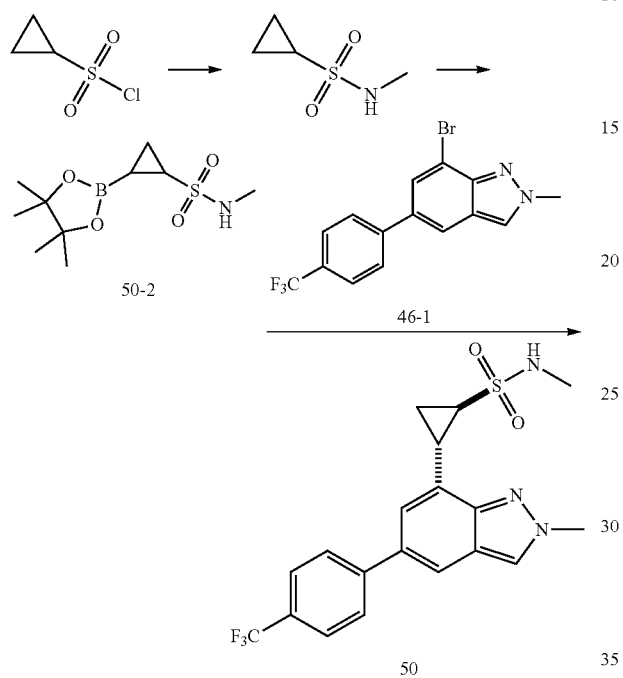

Step 1: Preparation of Compound 50-1

Cyclopropane sulfonyl chloride (2.00 g, 14.2 mmol) in DCM (20 mL) was added TEA (3.94 mL, 28.4 mmol) and DMAP (0.30 g, 2.13 mmol), the mixture was stirred at 25° C. for 3 hrs. The reaction was diluted with water (50 mL), extracted with EtOAc (50 mL×3), dried over with Na₂SO₄, filtered, concentrated and purified by column chromatography to give Compound 50-1 (1.20 g, 8.87 mmol). ¹HNMR (400 MHz, DMSO-d₆) δ 8.86-8.85 (m, 1H), 2.62-2.60 (m, 3H), 2.53-2.50 (m, 1H), 0.95-0.91 (m, 2H), 0.89-0.87 (m, 2H)

Step 2: Preparation of Compound 50-2

To a mixture of Compound 50-1 (0.90 g, 6.65 mmol) and B₂pin₂ (2.50 g, 9.99 mmol) in THF (5 mL), was added 2,9-dimethylpyrido[3,2-H]quinoline (0.10 g, 0.660 mmol) and (1,5-Cyclooctadiene) (methoxy)iridium(I) Dimer (0.20 g, 0.333 mmol). The mixture was stirred at 100° C. for 5 hrs under microwave condition. The reaction was diluted with water (50 mL), extracted with EtOAc (50 mL×3), washed with brine (100 mL), dried over with Na₂SO₄, filtered, concentrated and purified by column chromatography to give Compound 50-2 (1.60 g, 6.12 mmol). ¹HNMR (400 MHz, DMSO-d₆) δ 8.87-8.86 (m, 1H), 2.65-2.60 (m, 3H), 2.53-2.50 (m, 1H), 1.16 (s, 12H), 0.95-0.92 (m, 2H), 0.89-0.88 (m, 2H)

Step 3: Preparation of Example 50

To a solution of Compound 50-2 (441 mg, 1.68 mmol) and Compound 46-1 (150 mg, 0.422 mmol) in dioxane (5 mL) and H₂O (2 mL) was added Pd(dppf)Cl₂ (46.3 mg, 0.063 mmol) and K₂CO₃ (146 mg, 1.05 mmol). After stirred under N₂ atmosphere at 95° C. for 3 hrs, the mixture was diluted with H₂O (50 mL), extracted with EtOAc (80 mL×2), dried over with Na₂SO₄, filtered, concentrated, and purified by HPLC to give Example 50 (26.3 mg, 0.064 mmol, 15.2%). LCMS: 410.2 [M+H]+, ¹HNMR (400 MHz, METHANOL-d₄) δ 8.28 (s, 1H), 7.89-7.85 (m, 3H), 7.75 (s, 2H), 7.40 (s, 1H), 4.26 (s, 3H), 3.44-3.36 (m, 1H), 3.13-3.04 (m, 1H), 2.81 (s, 3H), 2.00-1.93 (m, 1H), 1.81-1.70 (m, 1H)

Example 51

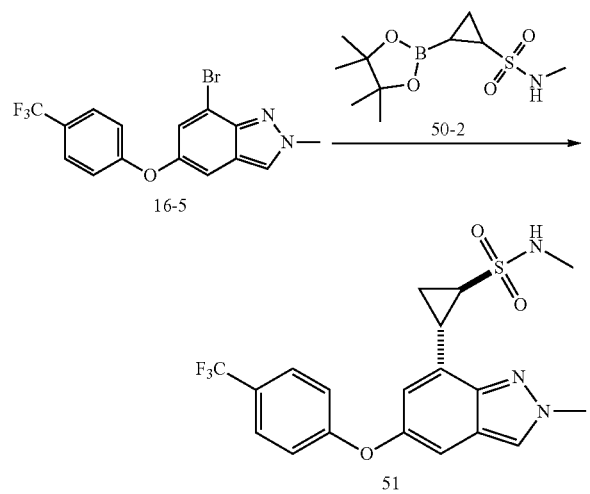

Example 51 (3 mg, 0.007 mmol, 6.4%) was prepared according to the similar procedures as Example 50 starting from Compound 16-5 (150 mg, 0.422 mmol). LCMS: 426.2 [M+H]+, ¹HNMR (400 MHz, METHANOL-d₄) δ 8.15 (s, 1H), 7.62-7.60 (m, 2H), 7.20-7.19 (m, 1H), 7.07-7.05 (m, 2H), 6.87-6.86 (m, 1H), 4.21 (s, 3H), 3.31-3.25 (m, 1H), 3.06-2.97 (m, 1H), 2.76 (s, 3H), 1.86-1.84 (m, 1H), 1.71-1.69 (m, 1H)

Example 76a & 76b

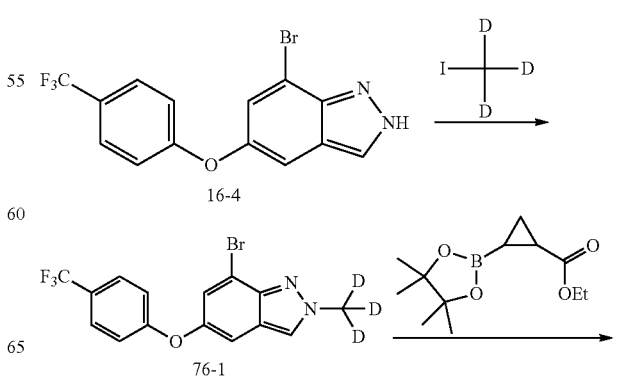

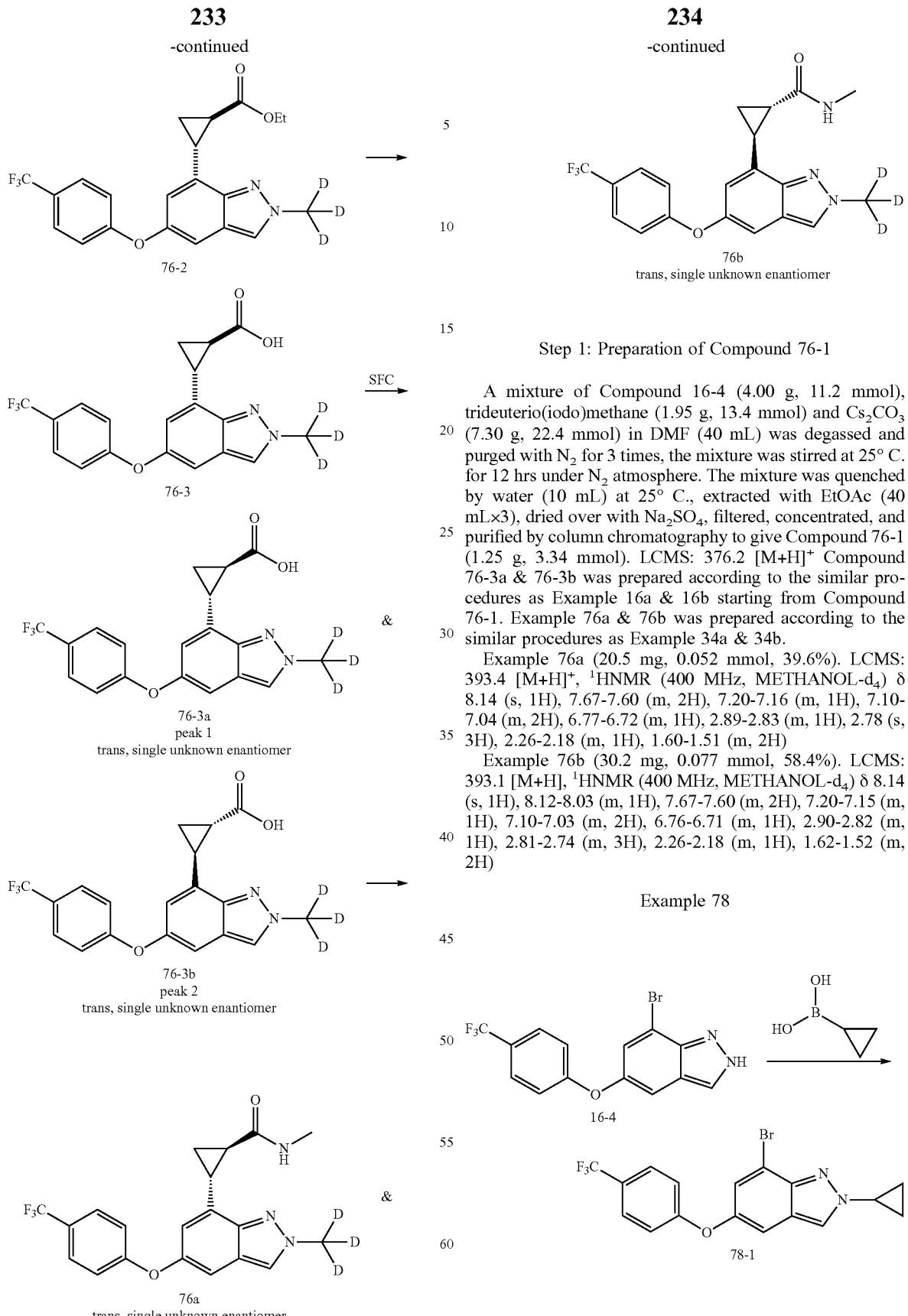

Step 1: Preparation of Compound 76-1

A mixture of Compound 16-4 (4.00 g, 11.2 mmol), trideuterio(iodo)methane (1.95 g, 13.4 mmol) and Cs$_2$CO$_3$ (7.30 g, 22.4 mmol) in DMF (40 mL) was degassed and purged with N$_2$ for 3 times, the mixture was stirred at 25° C. for 12 hrs under N$_2$ atmosphere. The mixture was quenched by water (10 mL) at 25° C., extracted with EtOAc (40 mL×3), dried over with Na$_2$SO$_4$, filtered, concentrated, and purified by column chromatography to give Compound 76-1 (1.25 g, 3.34 mmol). LCMS: 376.2 [M+H]$^+$ Compound 76-3a & 76-3b was prepared according to the similar procedures as Example 16a & 16b starting from Compound 76-1. Example 76a & 76b was prepared according to the similar procedures as Example 34a & 34b.

Example 76a (20.5 mg, 0.052 mmol, 39.6%). LCMS: 393.4 [M+H]$^+$, $^1$HNMR (400 MHz, METHANOL-d$_4$) δ 8.14 (s, 1H), 7.67-7.60 (m, 2H), 7.20-7.16 (m, 1H), 7.10-7.04 (m, 2H), 6.77-6.72 (m, 1H), 2.89-2.83 (m, 1H), 2.78 (s, 3H), 2.26-2.18 (m, 1H), 1.60-1.51 (m, 2H)

Example 76b (30.2 mg, 0.077 mmol, 58.4%). LCMS: 393.1 [M+H], $^1$HNMR (400 MHz, METHANOL-d$_4$) δ 8.14 (s, 1H), 8.12-8.03 (m, 1H), 7.67-7.60 (m, 2H), 7.20-7.15 (m, 1H), 7.10-7.03 (m, 2H), 6.76-6.71 (m, 1H), 2.90-2.82 (m, 1H), 2.81-2.74 (m, 3H), 2.26-2.18 (m, 1H), 1.62-1.52 (m, 2H)

Example 78

Step 1: Preparation of Compound 78-1

A mixture of Compound 16-4 (1.00 g, 2.80 mmol), cyclopropylboranediol (433 mg, 5.04 mmol), Na$_2$CO$_3$ (742 mg, 7.00 mmol), cupric bis(acetate) (763 mg, 4.20 mmol) and 2-(pyridin-2-yl)pyridine (875 mg, 5.60 mmol) in 1,2-dichloroethane (10 mL) was degassed and purged with $N_2$ for 3 times, the mixture was stirred at 25° C. for 12 hrs under $N_2$ atmosphere. The mixture was quenched by water (10 mL) at 25° C., diluted with brine (10 mL), extracted with EtOAc (20 mL×3), dried over with $Na_2SO_4$, filtered, concentrated, and purified by column chromatography to give Compound 78-1 (128 mg, 0.322 mmol). LCMS: 399.2 $[M+H]^+$;

Example 78 (21.21 mg, 0.051 mmol, 51.4%) was prepared according to the similar procedures as Example 16 and Example 34 starting from Compound 78-1. LCMS: 416.4 $[M+H]^+$, $^1$HNMR (400 MHz, METHANOL-$d_4$) δ 8.21 (s, 1H), 7.66-7.59 (m, 2H), 7.16-7.12 (m, 1H), 7.09-7.00 (m, 2H), 6.74-6.72 (m, 1H), 4.13-3.97 (m, 1H), 2.88-2.82 (m, 1H), 2.78 (s, 3H), 2.28-2.21 (m, 1H), 1.61-1.55 (m, 2H), 1.41-1.33 (m, 2H), 1.21-1.17 (m, 2H)

Example 79

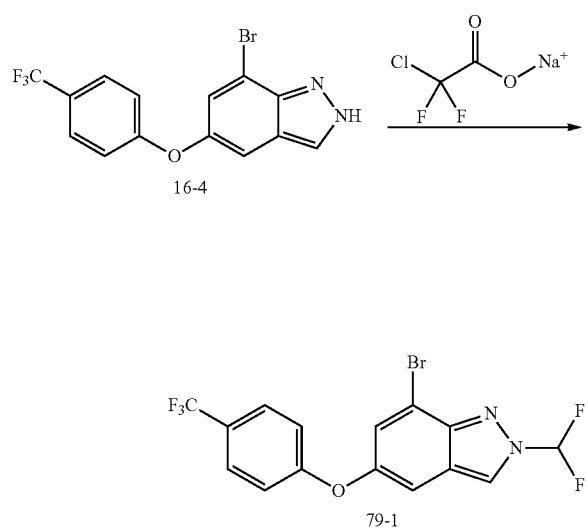

Step 1: Preparation of Compound 79-1

To a solution of Compound 16-4 (2.00 g, 5.60 mmol), sodium 2-chloro-2,2-difluoroacetate (1.71 mg, 11.2 mmol) in DMF (20 mL) was added NaH (448 mg, 11.2 mmol) at 0° C. The mixture was stirred at 80° C. for 12 hrs. The mixture was quenched by addition of $NH_4Cl$ water solution (10 mL) at 0° C., diluted and washed with water (50 mL×3), extracted with EtOAc (20 mL×3), dried over with $Na_2SO_4$, filtered, concentrated, and purified by column chromatography to give Compound 79-1 (460 mg, 1.13 mmol). LCMS: 416.4 $[M+H]^+$;

Example 79 (71.0 mg, 0.167 mmol, 55.1%) was prepared according to the similar procedures as Example 16 and Example 34 starting from Compound 79-1. LCMS: 426.3 $[M+H]^+$, $^1$HNMR (400 MHz, METHANOL-$d_4$) δ 8.58 (s, 1H), 7.97-7.76 (m, 1H), 7.70-7.64 (m, 2H), 7.20-7.17 (m, 1H), 7.17-7.06 (m, 2H), 6.93-6.88 (m, 1H), 2.89-2.82 (m, 1H), 2.78 (s, 3H), 2.39-2.27 (m, 1H), 1.72-1.65 (m, 1H), 1.61-1.55 (m, 1H)

Example 81

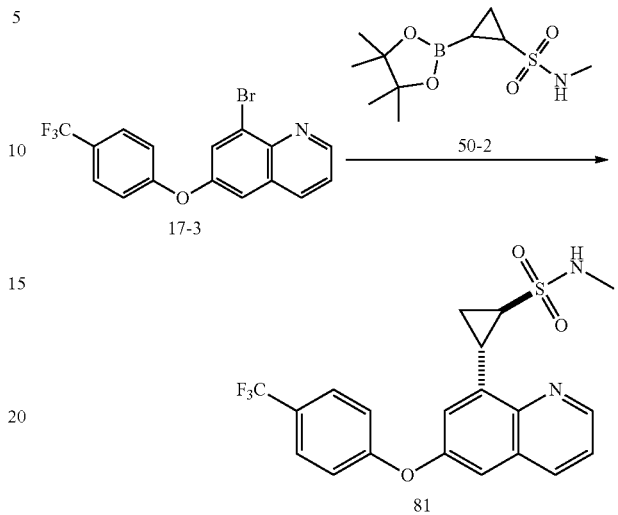

Example 81 (108 mg, 0.256 mmol, 18.8%) was prepared according to the similar procedures as Example 50 starting from Compound 17-3 (500 mg, 1.35 mmol). LCMS: 423.1 $[M+H]^+$, $^1$HNMR (400 MHz, METHANOL-$d_4$) δ 8.89-8.85 (m, 1H), 8.26-8.21 (m, 1H), 7.74-7.65 (m, 2H), 7.56-7.45 (m, 1H), 7.37-7.31 (m, 1H), 7.30-7.25 (m, 1H), 7.22-7.16 (m, 2H), 3.71-3.61 (m, 1H), 3.11-3.00 (m, 1H), 2.77 (s, 3H), 1.85-1.76 (m, 1H), 1.73-1.64 (m, 1H)

Example 82

Example 82 (1.14 mg, 0.003 mmol, 61.3%) was prepared according to the similar procedures as Example 7 starting from 6-bromo-4-nitro-1H-indazole, replacing (4-(trifluoromethyl)phenyl)boronic acid with 4-(trifluoromethyl)hexahydropyridine. LCMS: 368.0 $[M+H]^+$, $^1$HNMR (400 MHz, METHANOL-$d_4$) δ 8.46 (br s, 1H), 7.92 (s, 1H), 6.76-6.72 (m, 1H), 6.71-6.60 (m, 1H), 3.97 (s, 3H), 3.90-3.83 (m, 2H), 2.82-2.67 (m, 3H), 2.41-2.30 (m, 1H), 2.05-1.91 (m, 3H), 1.81-1.67 (m, 2H), 1.63-1.54 (m, 1H), 1.50-1.40 (m, 1H)

Example 83

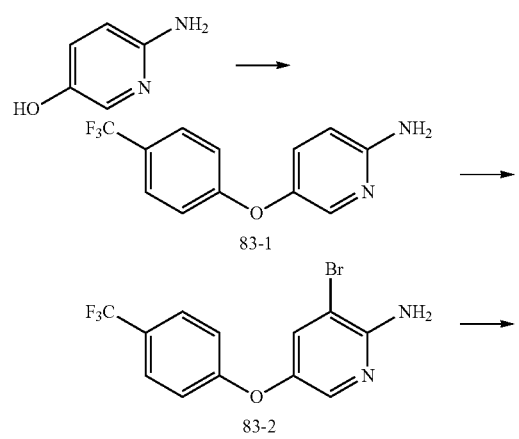

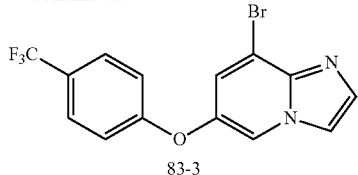

83-3

Step 1: Preparation of Compound 83-1

To a solution of 6-aminopyridin-3-ol (3.00 g, 27.2 mmol) in DMF (20 mL) were added 4-fluoro-1-(trifluoromethyl)benzene (4.90 g, 30.0 mmol), $Cs_2CO_3$ (26.6 g, 81.7 mmol), the reaction was stirred at 100° C. for 2 hrs. The reaction was diluted with water (50 mL), extracted with EtOAc (40 mL×3), dried over with $Na_2SO_4$, filtered, concentrated, and purified by column chromatography to give Compound 83-1 (6.00 g, 23.6 mmol, 86.6%). LCMS: 255.1 $[M+H]^+$;

Step 2: Preparation of Compound 83-2

To a solution of Compound 83-1 (6.00 g, 23.6 mmol) in ACN (60 mL) was added NBS (4.20 g, 23.6 mmol), the reaction was stirred at 25° C. for 1 hr. The mixture was diluted with EtOAc and water, washed with saturated NaCl water solution, concentrated, purified by column chromatography to give Compound 83-2 (5 g, 15.01 mmol, 63.6%). LCMS: 333.2 $[M+H]^+$;

Step 3: Preparation of Compound 83-3

To a solution of Compound 83-2 (2.00 g, 6.00 mmol) in EtOH (20 mL), $H_2O$ (4 mL) was added 2-chloroacetaldehyde (2.40 g, 12.0 mmol), $NaHCO_3$ (0.6 g, 7.20 mmol), the reaction was stirred at 90° C. for 3 hrs. The reaction was diluted, extracted with EtOAc (40 mL×3), dried over with $Na_2SO_4$, filtered, concentrated, and purified by column chromatography to give Compound 83-3 (1.20 g, 3.36 mmol, 56.0%). LCMS: 359.1 $[M+H]^+$;

Example 83 (4.38 mg, 0.012 mmol, 6.70%) was prepared according to the similar procedures as Example 16 by replacing Compound 16-5 with Compound 83-3. LCMS: 363.2 $[M+H]^+$, $^1$HNMR (400 MHz, METHANOL-$d_4$) δ 8.25 (s, 1H), 7.84 (s, 1H), 7.69-7.63 (m, 2H), 7.58 (s, 1H), 7.17-7.10 (m, 2H), 6.80-6.74 (m, 1H), 2.98-2.86 (m, 1H), 2.05-1.94 (m, 1H), 1.66-1.54 (m, 1H), 1.35-1.25 (m, 1H)

Example 85a & 85b

Example 85a (17.63 mg, 0.041 mmol, 51.3%) and Example 85b (9.76 mg, 0.023 mmol, 28.4) was prepared according to the similar procedures as Example 83 by replacing 2-chloroacetaldehyde with 1-chloropropan-2-one, and similar procedures as Example 58a and Example 58b.

Example 85a. LCMS: 432.4 $[M+H]^+$, $^1$HNMR (400 MHz, METHANOL-$d_4$) δ 8.30-8.19 (m, 1H), 7.72-7.62 (m, 3H), 7.20-7.14 (m, 2H), 6.98-6.92 (m, 1H), 4.64-4.54 (m, 1H), 4.53-4.45 (m, 1H), 4.32-4.20 (m, 1H), 4.11-4.01 (m, 1H), 3.90-3.74 (m, 1H), 2.89-2.77 (m, 1H), 2.50-2.43 (i, 3H), 2.10-1.99 (m, 1H), 1.67-1.60 (m, 1H), 1.53-1.46 (m, 1H)

Example 85b. LCMS: 432.3 $[M+H]^+$, $^1$HNMR (400 MHz, METHANOL-$d_4$) δ 8.28-8.24 (m, 1H), 7.71-7.64 (m, 3H), 7.20-7.14 (m, 2H), 6.98-6.94 (m, 1H), 4.66-4.56 (m, 1H), 4.54-4.46 (m, 1H), 4.31-4.19 (m, 1H), 4.11-4.04 (m, 1H), 3.90-3.76 (mi, 1H), 2.89-2.79 (m, 1H), 2.52-2.43 (m, 3H), 2.11-2.002 (m, 1H), 1.68-1.59 (m, 1H), 1.541-1.46 (m, 1H)

Compounds in Table 4 below were prepared in accordance with the synthetic sequence in Example 16/16a/16b using the corresponding starting materials to get carboxylic intermediates or final compounds. Carboxylic intermediates were further coupled with amines to yield corresponding amide according to the similar procedures as Example 22.

TABLE 4

| Example | Starting material for Carboxylic acid | Amines | MW $[M + H]^+$ & $^1$H NMR |
|---|---|---|---|
| 87a & 87b | (1R,4R)-4-(trifluoromethyl)cyclohexyl-methanesulfonate & 3-methyl-4-nitrophenol | azetidin-3-ol | Example 87a. LCMS: 438.1 $[M + H]^+$, $^1$HNMR (400 MHz, METHANOL-$d_4$) δ 8.05-8.00 (m, 1H), 6.93-6.89 (m, 1H), 6.73-6.69 (m, 1H), 4.65-4.54 (m, 2H), 4.55-4.47 (m, 1H), 4.32-4.22 (m, 1H), 4.20-4.13 (m, 3H), 4.10-4.05 (m, 1H), 3.87-3.76 (m, 1H), 2.80-2.74 (m, 1H), 2.31-2.11 (m, 3H), 2.10-2.00 (m, 1H), 1.82-1.73 (m, 4H), 1.70-1.57 (m, 4H) Example 87b. LCMS: 438.2 $[M + H]^+$, $^1$HNMR (400 MHz, METHANOL-$d_4$) δ 8.03 (s, 1H), 6.95-6.86 (m, 1H), 6.75-6.65 (m, 1H), 4.64-4.56 (m, 2H), 4.55-4.45 (m, 1H), 4.31-4.25 (m, 1H), 4.19-4.11 (m, 3H), 4.09-4.02 (m, 1H), 3.89-3.75 (m, 1H), 2.81-2.71 (m, 1H), 2.30-2.00 (m, 4H), 1.82-1.70 (m, 4H), 1.70-1.55 (m, 4H) |
| 88a & 88b | 2-fluoro-5-(trifluoromethyl)pyridine & 3-methyl-4-nitrophenol | azetidin-3-ol | Example 88a. LCMS: 433.2 $[M + H]^+$, $^1$HNMR (400 MHz, METHANOL-$d_4$) δ 8.42 (s, 1H), 8.22-8.15 (m, 1H), 8.13-8.01 (m, 1H), 7.31-7.28 (m, 1H), 7.15-7.05 (m, 1H), 6.88-6.73 (m, 1H), 4.65-4.55 (m, 1H), 4.53-4.42 (m, 1H), 4.29-4.19 (m, 4H), 4.07-4.00 (m, 1H), 3.90-3.73 (m, 1H), 2.87-2.73 (m, 1H), 2.20-2.08 (m, 1H), 1.67-1.48 (m, 2H) Example 88b. LCMS: 433.3 $[M + H]^+$, $^1$HNMR (400 MHz, METHANOL-$d_4$) δ 8.41 (s, 1H), 8.21-8.14 (m, 1H), 8.10-8.03 (m, 1H), 7.33-7.26 (m, 1H), 7.15-7.06 (m, 1H), 6.86-6.75 (m, 1H), 4.64-4.53 (m, 1H), 4.52-4.39 (m, 1H), 4.31-4.18 (m, 4H), 4.10-4.00 (m, 1H), 3.88-3.75 (m, 1H), 2.87-2.75 (m, 1H), 2.19-2.08 (m, 1H), 1.68-1.51 (m, 2H) |

TABLE 4-continued

| Example | Starting material for Carboxylic acid | Amines | MW [M + H]⁺ & ¹H NMR |
|---|---|---|---|
| 89a & 89b | 4-(difluoromethyl) phenol & 4-fluoro-2-methyl-1-nitrobenzene | azetidin-3-ol | Example 89a. LCMS: 414.3 [M + H]⁺, ¹HNMR (400 MHz, METHANOL-d₄) δ 8.15-8.10 (m, 1H), 7.56-7.48 (m, 2H), 7.15-7.10 (m, 1H), 7.07-7.01 (m, 2H), 6.90-6.58 (m, 2H), 4.64-4.57 (m, 1H), 4.54-4.46 (m, 1H), 4.31-4.19 (m, 4H), 4.10-4.02 (m, 1H), 3.89-3.76 (m, 1H), 2.86-2.76 (m, 1H), 2.18-2.10 (m, 1H), 1.66-1.56 (m, 2H)<br>Example 89b. LCMS: 414.2 [M + H]⁺, ¹HNMR (400 MHz, METHANOL-d₄) δ 8.15-8.11 (m, 1H), 7.60-7.45 (m, 2H), 7.15-7.11 (m, 1H), 7.06-7.01 (m, 2H), 6.89-6.59 (m, 2H), 4.64-4.57 (m, 1H), 4.54-4.46 (m, 1H), 4.30-4.20 (m, 4H), 4.10-4.03 (m, 1H), 3.88-3.77 (m, 1H), 2.85-2.76 (m, 1H), 2.19-2.09 (m, 1H), 1.65-1.56 (m, 2H) |
| 90a & 90b | 3,4-difluorophenol & 4-fluoro-2-methyl-1-nitrobenzene | azetidin-3-ol | Example 90a. LCMS: 400.3 [M + H]⁺, ¹HNMR (400 MHz, METHANOL-d₄) δ 8.14-8.10 (m, 1H), 7.29-7.18 (m, 1H), 7.11-7.04 (m, 1H), 6.93-6.86 (m, 1H), 6.82-6.79 (m, 1H), 6.78-6.73 (m, 1H), 4.64-4.57 (m, 1H), 4.55-4.46 (m, 1H), 4.31-4.24 (m, 1H), 4.23-4.22 (m, 3H), 4.12-4.03 (m, 1H), 3.88-3.77 (m, 1H), 2.84-2.76 (m, 1H), 2.20-2.09 (m, 1H), 1.67-1.57 (m, 2H)<br>Example 90b. LCMS: 400.3 [M + H]⁺, ¹HNMR (400 MHz, METHANOL-d₄) δ 8.15-8.09 (m, 1H), 7.28-7.19 (m, 1H), 7.09-7.05 (m, 1H), 6.94-6.85 (m, 1H), 6.81-6.79 (m, 1H), 6.78-6.73 (m, 1H), 4.64-4.57 (m, 1H), 4.54-4.46 (m, 1H), 4.31-4.24 (m, 1H), 4.24-4.20 (m, 3H), 4.11-4.03 (m, 1H), 3.89-3.77 (m, 1H), 2.85-2.75 (m, 1H), 2.21-2.09 (m, 1H), 1.67-1.56 (m, 2H) |
| 93 | 6,6-difluorospiro[3.3]heptan-2-ol & 4-fluoro-2-methyl-1-nitrobenzene | — | LCMS: 363.4 [M + H]⁺, ¹HNMR (400 MHz, METHANOL-d₄) δ 7.99 (s, 1H), 6.73-6.67 (m, 1H), 6.59-6.53 (m, 1H), 4.71-4.64 (m, 1H), 4.17 (s, 3H), 2.92-2.82 (m, 1H), 2.72-2.58 (m, 6H), 2.31-2.24 (m, 2H), 2.21-2.07 (m, 1H), 1.66-1.53 (m, 2H) |
| 126 | 6-(trifluoromethyl) pyridin-3-ol & 4-fluoro-2-methyl-1-nitrobenzene | azetidin-3-ol | LCMS: 433.1 [M + H]⁺, ¹HNMR (400 MHz, METHANOL-d₄) δ 8.42-8.38 (m, 1H), 8.25-8.12 (m, 1H), 7.84-7.69 (m, 1H), 7.51-7.40 (m, 1H), 7.31-7.22 (m, 1H), 6.86-6.76 (m, 1H), 4.62-4.55 (m, 1H), 4.53-4.41 (m, 1H), 4.29-4.18 (m, 4H), 4.08-4.01 (m, 1H), 3.86-3.74 (m, 1H), 2.84-2.75 (m, 1H), 2.22-2.11 (m, 1H), 1.69-1.52 (m, 2H) |
| 127 | 2-(trifluoromethyl) pyrimidin-5-ol & 4-fluoro-2-methyl-1-nitrobenzene | azetidin-3-ol | LCMS: 434.1 [M + H]⁺, ¹HNMR (400 MHz, METHANOL-d₄) δ 8.63-8.56 (m, 2H), 8.26-8.19 (m, 1H), 7.39-7.34 (m, 1H), 6.96-6.91 (m, 1H), 4.63-4.57 (m, 1H), 4.55-4.47 (m, 1H), 4.30-4.23 (m, 4H), 4.11-4.04 (m, 1H), 3.88-3.77 (m, 1H), 2.89-2.81 (m, 1H), 2.25-2.17 (m, 1H), 1.72-1.65 (m, 1H), 1.64-1.57 (m, 1H) |
| 129 | 3,4,5-trifluorophenol & 4-fluoro-2-methyl-1-nitrobenzene | azetidin-3-ol | LCMS: 418.2 [M + H]⁺, ¹HNMR (400 MHz, METHANOL-d₄) δ 8.19-8.13 (m, 1H), 7.20-7.14 (m, 1H), 6.82-6.78 (m, 1H), 6.77-6.68 (m, 2H), 4.66-4.57 (m, 1H), 4.55-4.45 (m, 1H), 4.30-4.22 (m, 4H), 4.11-4.03 (m, 1H), 3.89-3.76 (m, 1H), 2.86-2.77 (m, 1H), 2.22-2.12 (m, 1H), 1.70-1.63 (m, 1H), 1.62-1.56 (m, 1H) |
| 130 | 4-chlorophenol & 4-fluoro-2-methyl-1-nitrobenzene | azetidin-3-ol | LCMS: 398.0 [M + H]⁺, ¹HNMR (400 MHz, METHANOL-d₄) δ 8.08 (d, J = 2.5 Hz, 1H), 7.34-7.28 (m, 2H), 7.04-7.00 (m, 1H), 6.96-6.91 (m, 2H), 6.79-6.76 (m, 1H), 4.63-4.54 (m, 1H), 4.52-4.43 (m, 1H), 4.30-4.22 (m, 1H), 4.22-4.16 (m, 3H), 4.11-3.99 (m, 1H), 3.87-3.76 (m, 1H), 2.82-2.74 (m, 1H), 2.16-2.03 (m, 1H), 1.64-1.54 (m, 2H) |
| 131 | 4-(pentafluorosulfur) phenol & 4-fluoro-2-methyl-1-nitrobenzene | azetidin-3-ol | LCMS: 398.0 [M + H]⁺, ¹HNMR (400 MHz, METHANOL-d₄) δ 8.12-8.21 (m, 1 H), 7.73-7.82 (m, 2 H), 7.17-7.25 (m, 1 H), 6.95-7.08 (m, 2 H), 6.75-6.84 (m, 1 H), 4.42-4.61 (m, 2 H), 4.15-4.29 (m, 4 H), 4.00-4.09 (m, 1 H), 3.73-3.87 (m, 1 H), 2.75-2.83 (m, 1 H), 2.08-2.21 (m, 1 H), 1.51-1.71 (m, 2 H) |
| 132 & 133 | 2,4-difluoro-1-(trifluoromethyl) benzene & 3-methyl-4-nitrophenol | azetidin-3-ol | Example 132. LCMS: 450.1 [M + H]⁺, ¹HNMR (400 MHz, METHANOL-d₄) δ 8.15-8.19 (m, 1 H), 7.57-7.64 (m, 1 H), 7.21-7.26 (m, 1 H), 6.73-6.92 (m, 3 H), 4.43-4.63 (m, 2 H), 4.16-4.29 (m, 4 H), 4.00-4.09 (m, 1 H), 3.74-3.87 (m, 1 H), 2.76-2.86 (m, 1 H), 2.07-2.21 (m, 1 H), 1.51-1.69 (m, 2 H) |

TABLE 4-continued

| Example | Starting material for Carboxylic acid | Amines | MW [M + H]+ & 1H NMR |
|---|---|---|---|
| | | | Example 132a. LCMS: 450.1 [M + H]+, 1HNMR (400 MHz, METHANOL-d4) δ 8.15-8.21 (m, 1 H), 7.71-7.78 (m, 1 H), 7.16-7.22 (m, 1 H), 6.90-6.97 (m, 1 H), 6.76-6.83 (m, 1 H), 6.57-6.64 (m, 1 H), 4.55-4.64 (m, 1 H), 4.44-4.55 (m, 1 H), 4.17-4.30 (m, 4 H), 4.01-4.11 (m, 1 H), 3.73-3.89 (m, 1 H), 2.76-2.85 (m, 1 H), 2.11-2.23 (m, 1 H), 1.54-1.71 (m, 2 H) |
| 137 | 1-fluoro-4-(methylsulfonyl)benzene & 3-methyl-4-nitrophenol | azetidin-3-ol | LCMS: 442.1 [M + H]+, 1HNMR (400 MHz, METHANOL-d4) δ 8.20-8.15 (m, 1H), 7.92-7.88 (m, 2H), 7.24-7.21 (m, 1H), 7.08-7.13 (m, 2H), 6.80 (s, 1H), 4.55-4.62 (m, 1H), 4.44-4.53 (m, 1H), 4.20-4.30 (m, 4H), 4.19-4.28 (m, 1H), 3.75-3.86 (m, 1H), 3.10 (s, 3H), 2.76-2.83 (m, 1H), 2.08-2.21 (m, 1H), 1.54-1.67 (m, 2H) |
| 138 | 3,4,5-trifluorophenol & 4-fluoro-2-methyl-1-nitrobenzene | (1S,4S,5S)-2-azabicyclo[2.2.1]heptan-5-ol | LCMS: 458.1 [M + H]+, 1HNMR (400 MHz, METHANOL-d4) δ 8.16-8.10 (m, 1H), 7.16-7.11 (m, 1H), 6.83-6.76 (m, 1H), 6.72-6.63 (m, 2H), 4.51-4.41 (m, 1H), 4.39-4.29 (m, 1H), 4.21 (d, J = 4.1 Hz, 3H), 4.02-3.81 (m, 1H), 3.44-3.37 (m, 1H), 3.27-3.20 (m, 1H), 2.89-2.79 (m, 1H), 2.65-2.57 (m, 1H), 2.45-2.33 (m, 1H), 2.11-1.93 (m, 1H), 1.84-1.69 (m, 1H), 1.67-1.52 (m, 3H), 1.40-1.27 (m, 1H) |
| 139 | 4-chlorophenol & 4-fluoro-2-methyl-1-nitrobenzene | (1S,4S,5S)-2-azabicyclo[2.2.1]heptan-5-ol | LCMS: 438.2 [M + H]+, 1HNMR (400 MHz, METHANOL-d4) δ 8.05 (d, J = 4.3 Hz, 1H), 7.31-7.24 (m, 2H), 7.02-6.97 (m, 1H), 6.94-6.88 (m, 2H), 6.80-6.72 (m, 1H), 4.50-4.39 (m, 1H), 4.38-4.29 (m, 1H), 4.01-3.81 (m, 1H), 3.40-3.35 (m, 1H), 3.26-3.20 (m, 1H), 2.87-2.78 (m, 1H), 2.65-2.56 (m, 1H), 2.42-2.28 (m, 1H), 2.10-1.90 (m, 1H), 1.83-1.66 (m, 1H), 1.65-1.50 (m, 3H), 1.40-1.25 (m, 1H) |
| 140 | 2,4-difluoro-1-(trifluoromethyl)benzene & 3-methyl-4-nitrophenol | (1S,4S,5S)-2-azabicyclo[2.2.1]heptan-5-ol | LCMS: 490.2 [M + H]+, 1HNMR (400 MHz, METHANOL-d4) δ 8.15-8.21 (m, 1H), 7.56-7.65 (m, 1 H), 7.21-7.28 (m, 1 H), 6.79-6.88 (m, 3 H), 4.42-4.52 (m, 1 H), 4.29-4.40 (m, 1 H), 4.18-4.27 (m, 3 H), 3.96-4.03 (m, 1 H), 3.80-3.87 (m, 1 H), 3.39-3.45 (m, 1 H), 3.20-3.27 (m, 1 H), 2.80-2.93 (m, 1 H), 2.56-2.67 (m, 1 H), 2.35-2.48 (m, 1 H), 1.93-2.12 (m, 1 H), 1.70-1.86 (m, 1 H), 1.55-1.68 (m, 3 H), 1.27-1.40 (m, 1 H) |
| 141 | 2,4-difluoro-1-(trifluoromethyl)benzene & 3-methyl-4-nitrophenol | dimethylamine | LCMS: 422.2 [M + H]+, 1HNMR (400 MHz, METHANOL-d4) δ 8.14-8.20 (m, 1 H), 7.57-7.65 (m, 1 H), 7.21-7.26 (m, 1 H), 6.80-6.89 (m, 3 H), 4.19-4.27 (m, 3 H), 3.14-3.21 (m, 3 H), 2.95-3.02 (m, 3 H), 2.74-2.87 (m, 1 H), 2.53-2.64 (m, 1 H), 1.52-1.65 (m, 2 H) |

Example 106 & 107

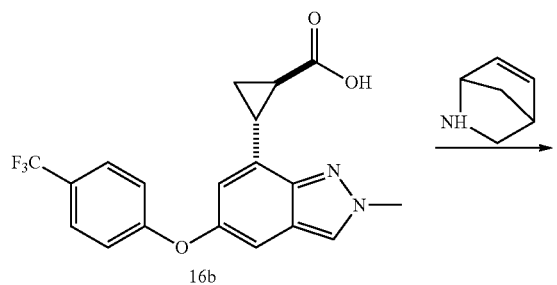

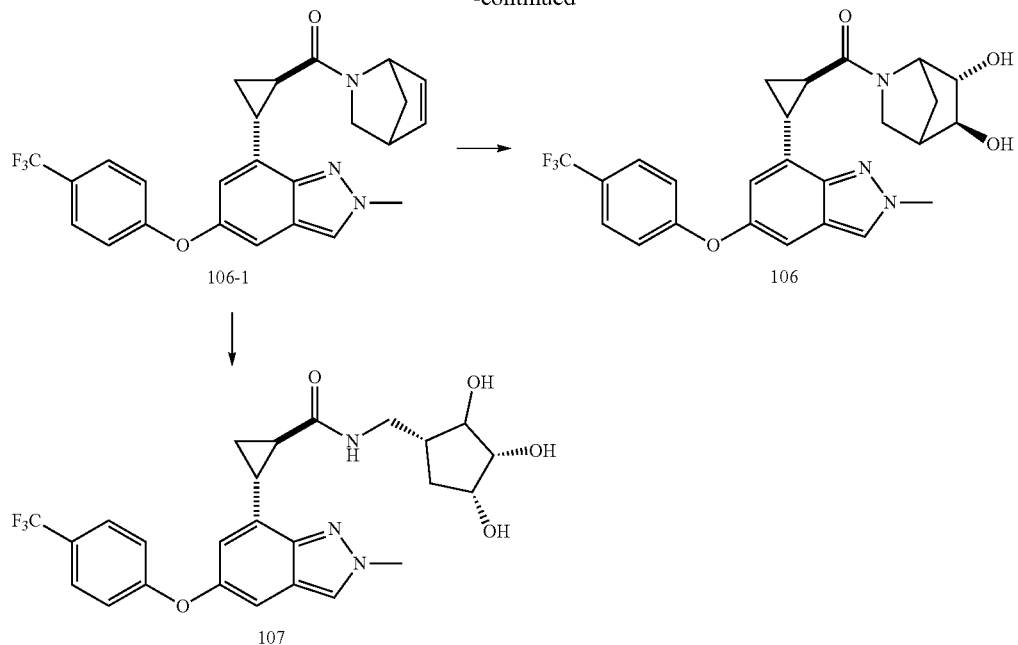

Step 1: Preparation of Compound 106-1

To a solution of Example 16b (500 mg, 1.33 mmol) in DMF (10 mL) was added HATU (757 mg, 1.99 mmol) and DIEA (2.20 mL, 13.2 mmol), the reaction was stirred at 25° C. for 10 min. 2-azabicyclo[2.2.1]hept-5-ene oxalic acid (446 mg, 1.59 mmol) was added at 25° C., the reaction was stirred at 25° C. for 2 hrs. The mixture was extracted with EtOAc (10 mL×5) and water (10 mL), dried over with $Na_2SO_4$, filtered, concentrated, and purified by prep-TLC to give Compound 106-1. (200 mg, 0.44 mmol). LCMS: 454.1 $[M+H]^+$;

Preparation of Example 106

To a solution of Compound 106-1(80 mg, 0.18 mmol) in DCM (2 mL), was added M-CPBA (72.5 mg, 0.35 mmol) under $N_2$ at 0° C. and the reaction was stirred at 25° C. for 2 hrs. Saturated aqueous $Na_2SO_3$ solution was added to the mixture, extracted with DCM (3×5 mL), dried over with $Na_2SO_4$, filtered, concentrated, and purified by HPLC to give Example 106 (11 mg, 0.02 mmol, 12.9% yield). LCMS: 488.2 $[M+H]^+$, $^1HNMR$ (400 MHz, METHANOL-$d_4$) δ 8.12 (s, 1H), 7.64-7.56 (m, 2H), 7.17-7.14 (m, 1H), 7.08-7.02 (m, 2H), 6.74-6.71 (m, 1H), 4.21 (s, 3H), 3.89-3.85 (m, 1H), 3.44-3.39 (m, 2H), 3.39-3.33 (m, 1H), 2.88-2.78 (m, 1H), 2.26-2.15 (m, 2H), 1.80-1.68 (m, 1H), 1.60-1.51 (m, 2H), 1.51-1.43 (m, 1H)

Preparation of Example 107

To a solution of Compound 106-1 (120 mg, 0.27 mmol) in acetone (2 mL) and $H_2O$ (0.4 mL) was added 4-methyl-1,4-oxazinane 4-oxide (62 mg, 0.53 mmol) and dipotassium dioxidodioxo-λ6-osmium(VI) dehydrate (19.5 mg, 0.053 mmol) in 1-propanol (0.4 mL) solution under $N_2$ at 0° C., the reaction was stirred at 25° C. for 8 hrs. Saturated aqueous $Na_2SO_3$ solution was added to the mixture, extracted with DCM (3×5 mL), dried over with $Na_2SO_4$, filtered, concentrated, and purified by HPLC to give Example 107 (32.2 mg, 0.07 mmol, 25.0% yield). LCMS: 506.2 $[M+H]^+$, $^1HNMR$ (400 MHz, METHANOL-$d_4$) δ 8.12 (s, 1H), 7.63-7.58 (m, 2H), 7.17-7.12 (m, 1H), 7.07-7.02 (m, 2H), 6.74-6.70 (m, 1H), 4.21 (s, 3H), 4.13-3.92 (m, 2H), 3.87-3.66 (m, 2H), 3.47-3.33 (m, 1H), 3.26-3.11 (m, 1H), 2.88-2.79 (m, 1H), 2.39-2.14 (m, 2H), 1.99-1.77 (m, 1H), 1.65-1.44 (m, 3H)

Example 108a & 108b

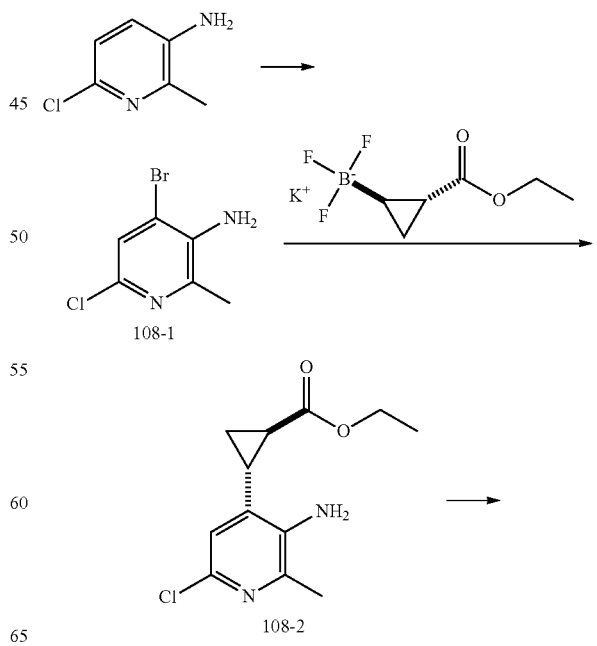

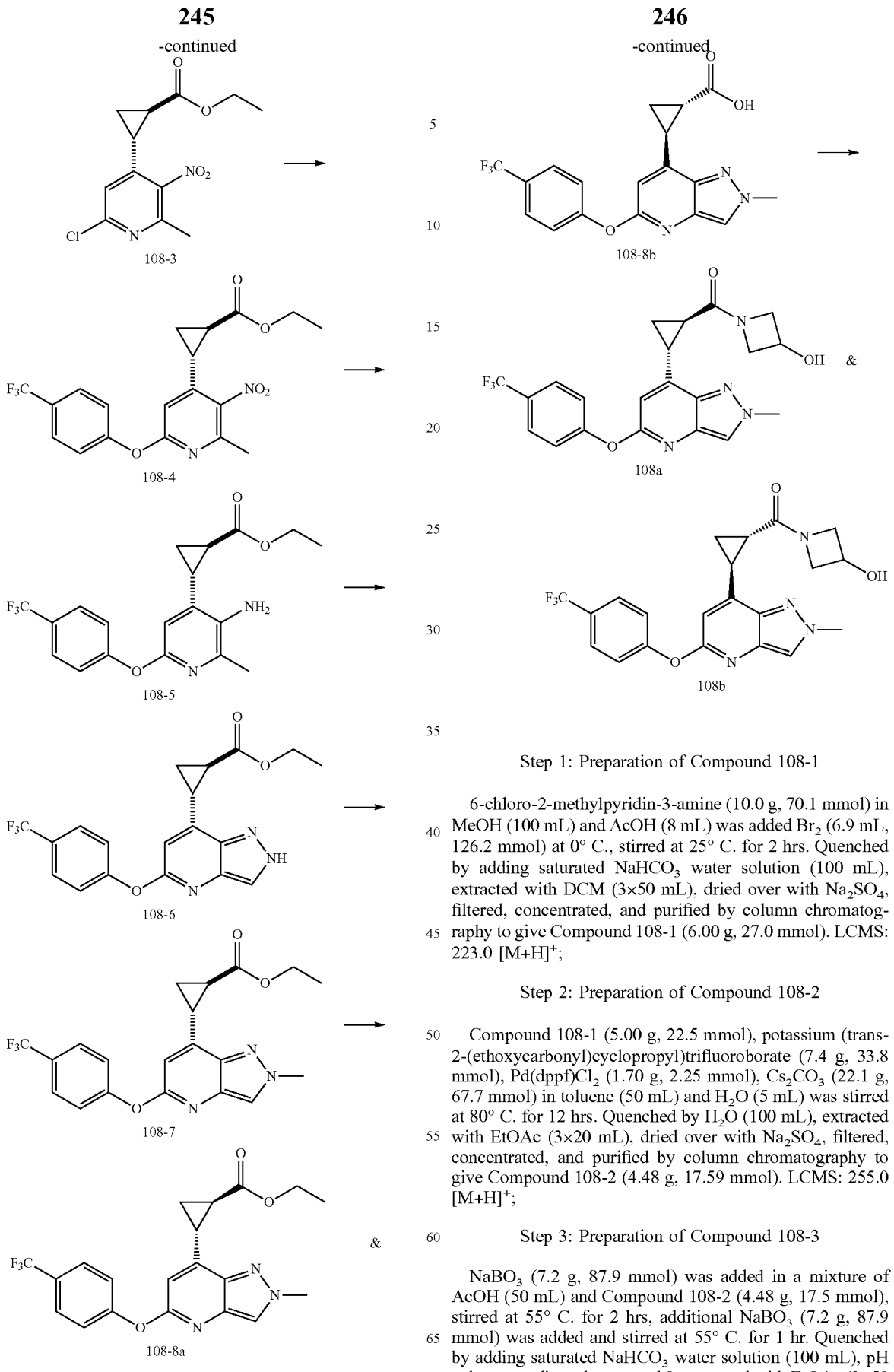

Step 1: Preparation of Compound 108-1

6-chloro-2-methylpyridin-3-amine (10.0 g, 70.1 mmol) in MeOH (100 mL) and AcOH (8 mL) was added Br$_2$ (6.9 mL, 126.2 mmol) at 0° C., stirred at 25° C. for 2 hrs. Quenched by adding saturated NaHCO$_3$ water solution (100 mL), extracted with DCM (3×50 mL), dried over with Na$_2$SO$_4$, filtered, concentrated, and purified by column chromatography to give Compound 108-1 (6.00 g, 27.0 mmol). LCMS: 223.0 [M+H]$^+$;

Step 2: Preparation of Compound 108-2

Compound 108-1 (5.00 g, 22.5 mmol), potassium (trans-2-(ethoxycarbonyl)cyclopropyl)trifluoroborate (7.4 g, 33.8 mmol), Pd(dppf)Cl$_2$ (1.70 g, 2.25 mmol), Cs$_2$CO$_3$ (22.1 g, 67.7 mmol) in toluene (50 mL) and H$_2$O (5 mL) was stirred at 80° C. for 12 hrs. Quenched by H$_2$O (100 mL), extracted with EtOAc (3×20 mL), dried over with Na$_2$SO$_4$, filtered, concentrated, and purified by column chromatography to give Compound 108-2 (4.48 g, 17.59 mmol). LCMS: 255.0 [M+H]$^+$;

Step 3: Preparation of Compound 108-3

NaBO$_3$ (7.2 g, 87.9 mmol) was added in a mixture of AcOH (50 mL) and Compound 108-2 (4.48 g, 17.5 mmol), stirred at 55° C. for 2 hrs, additional NaBO$_3$ (7.2 g, 87.9 mmol) was added and stirred at 55° C. for 1 hr. Quenched by adding saturated NaHCO$_3$ water solution (100 mL), pH value was adjusted to around 8, extracted with EtOAc (3×50 mL), dried over with Na$_2$SO$_4$, filtered, concentrated, and purified by column chromatography to give Compound 108-3 (2.14 g, 7.51 mmol). TLC (PE:EA=3:1, P1: Rf=0.6, RI: Rf=0.3);

Step 4: Preparation of Compound 108-4

Compound 108-3 (1.60 g, 5.62 mmol), 4-(trifluoromethyl)phenol (1.80 g, 11.2 mmol), K$_2$CO$_3$ (2.30 g, 16.8 mmol) in DMF (20 mL) was stirred at 80° C. for 3 hrs. The mixture was filtered, extracted with EtOAc (3×10 mL), dried with Na$_2$SO$_4$, filter and concentrated to give Compound 108-4 (3.82 g, 9.31 mmol, crude). LCMS: 411.1 [M+H]$^+$;

Step 5: Preparation of Compound 108-5

Compound 108-4 (3.30 g, 8.04 mmol), Fe (1.30 g, 24.1 mmol), NH$_4$Cl (1.30 g, 24.1 mmol) in EtOH (15 mL) and H$_2$O (15 mL) was stirred at 100° C. for 2 hrs. The mixture was extracted with EtOAc (10 mL×3), dried with Na$_2$SO$_4$, concentrated, purified by column chromatography to give Compound 108-5 (2.26 g, 5.94 mmol). LCMS: 381.1 [M+H]$^+$;

Step 6: Preparation of Compound 108-6

Compound 108-5 (2.06 g, 5.41 mmol) in toluene (20 mL) was added AcOH (9.3 mL, 162.4 mmol), isoamyl nitrite (1.00 g, 8.12 mmol), potassium acetate (1.10 g, 10.8 mmol) and stirred at 30° C. for 3 hrs. Quenched by adding saturated NaHCO$_3$ water solution (100 mL), pH value was adjusted to around 8, extracted with EtOAc (3×20 mL), dried over with Na$_2$SO$_4$, filtered, concentrated, and purified by column chromatography to give Compound 108-6 (1.78 g, 4.55 mmol). LCMS: 392.0 [M+H]$^+$;

Step 7: Preparation of Compound 108-7

Compound 108-6 (1.58 g, 4.03 mmol) in EtOAc (20 mL) was added trimethyloxonium tetrafluoroborate (0.80 g, 5.24 mmol), stirred at 25° C. for 3 hrs. Quenched by adding saturated NaHCO$_3$ water solution (20 mL), pH value was adjusted to around 8, extracted with EtOAc (3×10 mL), dried over with Na$_2$SO$_4$, filtered, concentrated, and purified by column chromatography to give Compound 108-7 (1.20 g, 2.96 mmol). LCMS: 406.1 [M+H]$^+$;

Step 8: Preparation of Compound 108-8a & 108-8b

Compound 108-7 (1.10 g, 2.71 mmol) in H$_2$O (2 mL) and ACN (10 mL) was added lithium hydroxide hydrate (0.30 g, 8.14 mmol), stirred at 50° C. for 2 hrs. The mixture was added HCl to adjusted pH to around 3, extracted with EtOAc (10 mL×3), dried with Na2SO4, filter and concentrated, purified by SFC to give Compound 108-8a (335 mg, 0.88 mmol). SFC Ret. Time: 1.197, LCMS: 378.1 [M+H]+& Compound 108-8b (417 mg, 1.11 mmol). SFC Ret. Time: 1.345, LCMS: 378.1 [M+H]$^+$ Preparation of Example 108a & 108b Compound 108-8a or 108-8b (50 mg, 0.13 mmol) in DMF (1 mL) was added azetidin-3-ol hydrochloride (21.8 mg, 0.19 mmol), DIEA (0.07 mL, 0.39 mmol), HATU (100 mg, 0.26 mmol), stirred at 25° C. for 2 hrs. The mixture was concentrated and purified by HPLC to give Example 108a (20.9 mg, 0.04 mmol, 36.6%). LCMS: 433.1 [M+H]$^+$, $^1$HNMR (400 MHz, METHANOL-d$_4$) δ 8.06-8.04 (m, 1H), 7.89-7.55 (m, 2H), 7.41-7.26 (m, 2H), 6.88-6.69 (m, 1H), 4.66-4.42 (m, 2H), 4.31-4.22 (m, 1H), 4.21-4.16 (m, 3H), 4.15-3.99 (m, 1H), 3.86-3.75 (m, 1H), 2.87-2.77 (m, 1H), 2.61-2.39 (m, 1H), 1.94-1.80 (m, 1H), 1.72-1.59 (m, 1H); & Example 108b (27.7 mg, 0.06 mmol, 48.3%). LCMS: 433.1 [M+H]$^+$, $^1$HNMR (400 MHz, METHANOL-d$_4$) δ 8.05 (s, 1H), 7.75-7.70 (m, 2H), 7.36-7.30 (m, 2H), 6.86-6.83 (m, 1H), 4.64-4.44 (m, 2H), 4.29-4.21 (m, 1H), 4.20-4.15 (m, 3H), 4.13-4.00 (m, 1H), 3.85-3.77 (m, 1H), 2.84-2.76 (m, 1H), 2.53-2.44 (m, 1H), 1.91-1.81 (m, 1H), 1.69-1.61 (m, 1H)

Example 109a & 109b

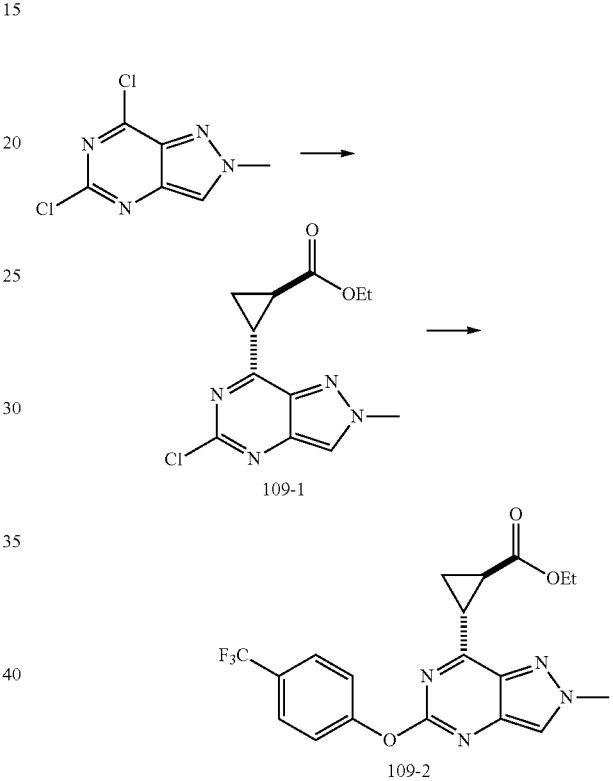

Step 1: Preparation of Compound 109-1

To a solution of 5,7-dichloro-2-methyl-2H-pyrazolo[4,3-d]pyrimidine (380 mg, 1.87 mmol) in toluene (5 mL) and H$_2$O (0.5 mL) was added potassium (trans-2-(ethoxycarbonyl)cyclopropyl)trifluoroborate (677 mg, 3.74 mmol), Pd(dppf)Cl$_2$ (68.5 mg, 0.094 mmol) and Cs$_2$CO$_3$ (1.83 g, 5.62 mmol). The mixture was stirred at 80° C. for 3 hrs. The mixture was quenched by addition water (10 mL) at 25° C., extracted with EtOAc (20 mL×3), dried over with Na$_2$SO$_4$, filtered, concentrated, and purified by column chromatography to give Compound 109-1 (177 mg, 0.631 mmol). LCMS: 281.1 [M+H]$^+$;

Step 2: Preparation of Compound 109-2

To a solution of Compound 109-1 (177 mg, 0.63 mmol) in toluene (3 mL) was added 4-(trifluoromethyl)phenol (102 mg, 0.63 mmol), Cs$_2$CO$_3$ (616 mg, 1.89 mmol), Pd$_2$(dba)$_3$ (57.7 mg, 0.06 mmol) and t-Bu XPhos (54 mg, 0.13 mmol). The mixture was stirred at 120° C. for 12 hrs, quenched by addition water (2 mL) at 25° C., diluted with brine (1 mL), extracted with EtOAc (5 mL×3), dried over with Na$_2$SO$_4$, filtered, concentrated, and purified by prep-TLC to give Compound 109-2 (90.0 mg, 0.221 mmol). LCMS: 407.1 [M+H]$^+$;

Example 109a (10.3 mg, 0.024 mmol, 29.9%) and Example 109b (11.6 mg, 0.027 mmol, 33.7%) was prepared according to the similar procedures as Example 108a & 108b by replacing Compound 108-7 with Compound 109-2.

Example 109a. LCMS: 434.1 [M+H]$^+$, $^1$HNMR (400 MHz, METHANOL-d$_4$) δ 8.19 (s, 1H), 7.80-7.75 (m, 2H), 7.42-7.36 (m, 2H), 4.66-4.45 (m, 2H), 4.30-4.28 (m, 3H), 4.27-4.20 (m, 1H), 4.13-4.00 (m, 1H), 3.86-3.77 (m, 1H), 3.22-3.14 (m, 1H), 2.55-2.47 (m, 1H), 1.88-1.79 (m, 1H), 1.78-1.69 (m, 1H)

Example 109b. LCMS: 434.1 [M+H]$^+$, $^1$HNMR (400 MHz, METHANOL-d$_4$) δ 8.19 (s, 1H), 7.80-7.73 (m, 2H), 7.44-7.35 (m, 2H), 4.63-4.45 (m, 2H), 4.31-4.28 (m, 3H), 4.27-4.21 (m, 1H), 4.12-3.99 (m, 1H), 3.85-3.78 (m, 1H), 3.22-3.15 (m, 1H), 2.54-2.48 (m, 1H), 1.85-1.79 (m, 1H), 1.78-1.72 (m, 1H)

Example 113

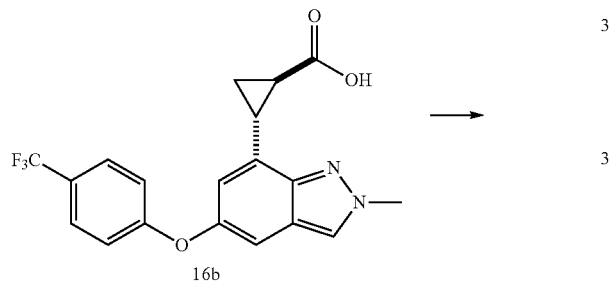

16b

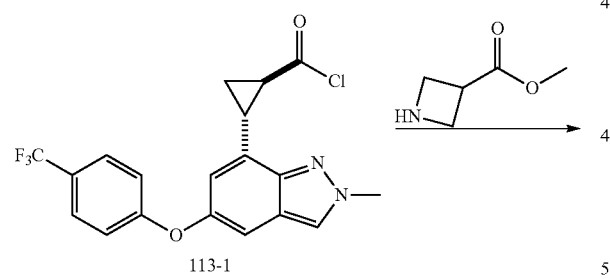

113-1

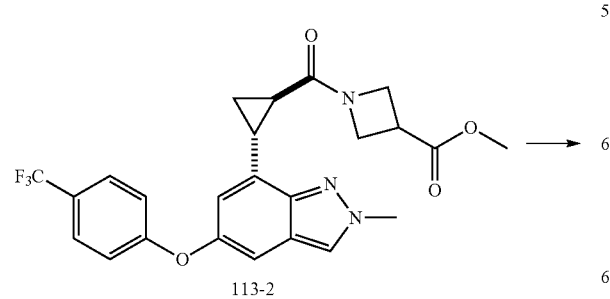

113-2

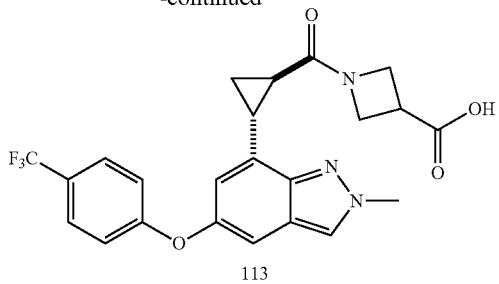

113

Step 1: Preparation of Compound 113-1

To a mixture of Compound 16b (100 mg, 0.27 mmol) in DCM (5 mL) was added oxalyl dichloride (0.15 g, 1.116 mmol, 0.4 mL), the mixture was stirred at 0° C. for 1 hr under N$_2$. The reaction was concentrated to give Compound 113-1 (56 mg, 0.14 mmol, crude).

Step 2: Preparation of Compound 113-2

Mixture of Compound 113-2 (56 mg, 0.14 mmol) and methyl azetidine-3-carboxylate (97 mg, 0.82 mmol) in DCM (5 mL) was added TEA (282 μL, 2.03 mmol) at 0° C. and stirred at 25° C. for 1 hr. The reaction was concentrated to give Compound 113-2 (45 mg, 0.10 mmol, crude). LCMS: 474.1 [M+H]$^+$;

Preparation of Example 113

Mixture of Compound 113-2 (45.2 mg, 0.10 mmol) in EtOH (8 mL) and H$_2$O (3 mL) was added LiOH (121 mg, 5 mmol), the mixture was stirred at 25° C. for 5 hrs. The reaction was concentrated and purified by HPLC to give Example 113 (18.9 mg, 0.04 mmol, 40%). LCMS: 460.1 [M+H]$^+$, $^1$HNMR (400 MHz, METHANOL-d$_4$) δ 8.18-8.14 (m, 1H), 7.66-7.61 (m, 2H), 7.19 (s, 1H), 7.10-7.06 (m, 2H), 6.82 (s, 1H), 4.50-4.43 (m, 2H), 4.29-4.09 (m, 4H), 3.55-3.43 (m, 1H), 2.87-2.78 (m, 1H), 2.68 (s, 1H), 2.18-2.08 (m, 1H), 1.67-1.56 (m, 2H)

Example 142

Example 142 (11.3 mg, 0.028 mmol, 22.6%) was prepared according to the similar procedures as Example 45. LCMS: 411.2 [M+H]$^+$, $^1$HNMR (400 MHz, METHANOL-d$_4$) δ 8.90-8.85 (m, 1H), 8.25-8.20 (m, 1H), 7.70 (d, J=8.6 Hz, 2H), 7.56-7.47 (m, 2H), 7.38 (d, J=2.6 Hz, 1H), 7.26-7.18 (m, J=8.5 Hz, 2H), 3.71-3.60 (m, 2H), 3.60-3.49 (m, 2H), 2.77 (s, 3H)

Example 142 was added to a solution of Pd/C 10% and stirred at 25° C. for 2 hrs, the reaction mixture was filtered and concentrated, purified by HPLC to give Example 143 (13.0 mg, 0.03 mmol, 32.0%). The similar preparation procedure was employed to yield Example 144, Example 145, Example 146 with corresponding stating material.

Example 143. LCMS: 415.2 [M+H]$^+$, $^1$HNMR (400 MHz, METHANOL-d$_4$) δ 7.55 (d, J=8.8 Hz, 2H), 6.99 (d, J=8.8 Hz, 2H), 6.69-6.62 (m, 1H), 6.64-6.58 (m, 1H), 3.36-3.32 (m, 2H), 3.30-3.25 (m, 2H), 2.97-2.82 (m, 2H), 2.77 (t, J=6.4 Hz, 2H), 2.69 (s, 3H), 1.97-1.84 (m, 2H)

Example 144. Stating material: Example 17 and PtO$_2$. LCMS: 377.6 [M+H]$^+$, $^1$HNMR (400 MHz, METHANOL-d$_4$) δ 7.60-7.50 (m, 2H), 7.02-6.89 (m, 2H), 6.64-6.58 (m, 1H), 6.57-6.51 (m, 1H), 3.43-3.35 (m, 2H), 2.83-2.73 (m, 2H), 2.29-2.15 (m, 1H), 1.99-1.89 (m, 2H), 1.74-1.63 (m, 1H), 1.54-1.42 (m, 1H), 1.24-1.13 (m, 1H)

Example 145. Stating material: Example 80 and PtO$_2$. LCMS: 391.0 [M+H]$^+$, $^1$HNMR (400 MHz, METHANOL-d$_4$) δ 7.59-7.51 (m, 2H), 7.02-6.90 (m, 2H), 6.61-6.57 (m, 1H), 6.57-6.53 (m, 1H), 3.41-3.34 (m, 2H), 2.78-2.74 (m, 5H), 2.17-2.07 (m, 1H), 1.98-1.88 (m, 2H), 1.76-1.68 (m, 1H), 1.47-1.38 (m, 1H), 1.04-0.97 (m, 1H)

Example 146. Stating material: Example 81 and PtO$_2$. LCMS: 427.2 [M+H]$^+$, $^1$HNMR (400 MHz, METHANOL-d$_4$) δ 7.55 (d, J=8.6 Hz, 2H), 7.05-6.89 (m, 2H), 6.70-6.54 (m, 2H), 3.47-3.35 (m, 2H), 2.82-2.70 (m, 5H), 2.68-2.51 (m, 1H), 2.39-2.23 (m, 1H), 2.01-1.81 (m, 2H), 1.68-1.55 (m, 1H), 1.51-1.33 (m, 1H)

Example A: Cell Growth Assay

Cell Culture

RPMI1640 medium (Gibco, 31800)+10% FBS (Biosera, FB-1058/500) for NCI-H226 cells (from ATCC).

Reagents

CellTiter-Glo reagent (CTG reagent, Promega, G7573).

Procedure

Cells were plated into 384-well microplate (150 cells/well, 50 mL medium/well). Also seeding an extra plate as Day 0 control measurement. The microplates were incubated at 37° C., 5% CO$_2$ overnight.

Compounds were 3-fold serial diluted in DMSO and final top-concentration was 30 mM, 10 points. 0.3% DMSO as vehicle control. In addition, 25 mL/well of CTG reagent was added into the extra plate and incubated at room temperature for 30 minutes and detected luminescence signals as Day 0 control by using EnVision (PerkinElmer, 2104 Mutilabel Reader).

Incubated other compounds treated plates at 37° C. for another 7 days and 25 mL/well of CTG reagent was added into the plates and incubated at room temperature for 30 minutes and detected luminescence signals.

Data Analysis

Day 0 luminescence signals were used as negative control or baseline.

Signal$_{day0}$=average luminescence signals of Day 0 control cells.

Signal$_{blank\ control}$=average luminescence signals of blank control.

Signal$_{DMSO\ vehicle\ control}$=average luminescence signals of Day 7 DMSO vehicle control cells.

Signal$_{cpds\ treatment}$=luminescence signals of Day 7 compounds treatment cells.

Inhibition %=1−(Signal$_{cpds\ treatment}$−Signal$_{blank\ control}$)/(Signal$_{DMSO\ vehicle\ control}$−Signal$_{blank\ control}$)*100.

(Inhibitory concentration 50% (IC$_{50}$) and maximum inhibition % were calculated using dose response curves.

TABLE 5

| Example | H226 CTG IC$_{50}$ |
|---|---|
| 1 | D |
| 2 | A |
| 3 | D |
| 4 | D |
| 5 | D |
| 6 | B |
| 7 | B |

TABLE 5-continued

| Example | H226 CTG IC$_{50}$ |
|---|---|
| 8 | D |
| 9 | B |
| 10 | B |
| 11 | C |
| 12 | A |
| 13 | A |
| 14 | D |
| 15 | B |
| 16 | B |
| 17 | B |
| 18 | B |
| 19 | D |
| 20 | B |
| 21 | A |
| 22 | A |
| 23 | B |
| 24 | B |
| 25 | A |
| 26 | B |
| 27 | B |
| 28 | B |
| 29 | C |
| 30 | B |
| 31 | B |
| 32 | B |
| 33 | A |
| 34 | A |
| 34a | B |
| 34b | A |
| 35 | A |
| 36 | A |
| 37 | D |
| 38 | B |
| 39 | D |
| 40 | B |
| 41 | A |
| 42 | A |
| 43 | D |
| 44 | A |
| 45 | B |
| 46 | D |
| 47 | D |
| 48 | D |
| 49 | NT |
| 50 | NT |
| 51 | D |
| 52 | D |
| 53 | A |
| 54 | A |
| 55 | A |
| 56 | A |
| 56a | C |
| 56b | A |
| 57 | B |
| 58a | D |
| 58b | A |
| 59a | B |
| 59b | B |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | D |
| 72 | A |
| 73 | A |
| 74 | A |
| 75a | A |
| 75b | A |
| 78 | B |
| 79 | B |

TABLE 5-continued

| Example | H226 CTG IC$_{50}$ |
|---|---|
| 80 | B |
| 81 | C |
| 82 | D |
| 85a | D |
| 85b | A |
| 86 | D |
| 88b | A |
| 89b | A |
| 90b | A |
| 93 | B |
| 94 | B |
| 95 | A |
| 96 | A |
| 97 | A |
| 98 | B |
| 102 | A |
| 103a | A |
| 103b | A |
| 103c | A |
| 103d | A |
| 103e | A |
| 103f | A |
| 104 | A |
| 105 | A |
| 108b | A |
| 112b | A |
| 117 | A |
| 121 | A |
| 123 | A |
| 124 | D |
| 125 | A |
| 126 | A |
| 128 | A |
| 129 | A |
| 130 | A |
| 131 | A |
| 132 | A |
| 134 | A |
| 135 | B |
| 139 | A |
| 140 | A |
| 141 | A |
| 142 | B |
| 143 | A |
| 144 | D |
| 145 | B |
| 146 | B |

H226 CTG IC$_{50}$: 0 < A ≤ 100 nM; 100 nM < B ≤ 500 nM; 500 nM < C ≤ 1000 nM; 1000 nM < D ≤ 30000 nM
NT: not tested Example B: Thermal Shift Assay Experiment Protocol 1) Prepare a fresh dilution of Protein Thermal Shift™ Dye (Applied Biosystems, 1000×) to 8× by using.

2) To ensure the same DMSO concentration, the compounds were diluted as follows: Prepare 10 mM stock solution of compounds;

The final DMSO concentration was 0.1%

10 μM: Diluting stock solution to 100 μM by using PBS.

1 μM: Diluting stock solution to 1 mM by using DMSO, then dilute to 10 μM by using PBS.

3) Prepare TEAD protein:

TEAD1: the stock concentration was 2.9 mg/ml; the final concentration was 0.2 mg/ml. TEAD2: the stock concentration was 1.8 mg/ml; the final concentration was 0.08 mg/ml.

TEAD3: the stock concentration was 2.4 mg/ml; the final concentration was 0.1 mg/ml.

TEAD4: the stock concentration was 2.3 mg/ml; the final concentration was 0.1 mg/ml.

4) Place the appropriate reaction plate or tubes on ice, then prepare the protein melt reactions:

| Reaction Mixture | | | |
|---|---|---|---|
| Compound (μl) | Protein + PBS (μl) | PBS (μl) | 8*Dye (μl) |
| 1 (final con. 10 μM) | 5 | 1.5 | 2.5 |

5) Pipet each reaction up and down 10 times to mix well.

6) Seal the plate with MicroAmp™ Optical Adhesive Film, spin it at 1000 rpm for 1 minute.

7) Set up and run on the qPCR instrument.

Data Analysis

Using thermal Shift™ Software v1.3 to analysis.

The data is shown in Table 6.

TABLE 6

| Example | TEAD1 ΔTm (° C.) | TEAD2 ΔTm (° C.) | TEAD3 ΔTm (° C.) | TEAD4 ΔTm (° C.) |
|---|---|---|---|---|
| 2 | 8.1 | 7 | 2.7 | 11.4 |
| 4 | 5 | 1.6 | 1.1 | 4.2 |
| 7 | 5.7 | 5.7 | 2 | 7.2 |
| 9 | 5.8 | 4.1 | 1.2 | 5.6 |
| 10 | 6 | 7.7 | 2 | 7.3 |
| 11 | 5.5 | 7.8 | 2.2 | 8.2 |
| 12 | 7.7 | 9.4 | 2.3 | 11.5 |
| 13 | 7.7 | 6.6 | 1.8 | 8.3 |
| 14 | 0.4 | 0.3 | 0 | 0.2 |
| 15 | 5 | 5.1 | 1.2 | 3.7 |
| 16 | 11.6 | 12.7 | 13.1 | 11.8 |
| 16a | 11.3 | 13.7 | 2 | 11.4 |
| 16b | 12.1 | 14.9 | 15 | 12.5 |
| 17 | 9.2 | 14.2 | 11.7 | 10.1 |
| 18 | 8.8 | 14 | 7.4 | 9.1 |
| 19 | 1.9 | 3.4 | 0.9 | 1.8 |
| 20 | 3.8 | 6.8 | 3.2 | 5.9 |
| 21 | 11 | 6.7 | 5.2 | 9.3 |
| 22 | 4.5 | 5.5 | 1.1 | 5.7 |
| 23 | 4.7 | 3.5 | 0.7 | 6.5 |
| 24 | 2.4 | 4.5 | 0.3 | 2.4 |
| 25 | 5.4 | 6.9 | 0.7 | 6.6 |
| 26 | 1.7 | 1.9 | 0.1 | 1.7 |
| 27 | 0.6 | 0.5 | 0.3 | 0.6 |
| 28 | 3.7 | 0.5 | 0.5 | 2.4 |
| 30 | 1.6 | 0.8 | 0.1 | 0.9 |
| 31 | 3 | 2.7 | 0 | 2.8 |
| 32 | 2.1 | 0.9 | 0.2 | 1.3 |
| 33 | 4 | 6.7 | 0.6 | 6.5 |
| 34 | 8.5 | 12.7 | 6.6 | 10.3 |
| 34a | 5.2 | 10.2 | 1.4 | 5.2 |
| 34b | 10.2 | 14.2 | 10.9 | 11.3 |
| 35 | 5.4 | 11.2 | 5.4 | 6.1 |
| 36 | 6.8 | 12.9 | 4.6 | 4.3 |
| 37 | 0.2 | 0.9 | 0.1 | 0.1 |
| 38 | 1.1 | 0.8 | 0.5 | 0.2 |
| 39 | 0 | 0 | 0 | 0 |
| 40 | 1.9 | 2.7 | 0.2 | 0.7 |
| 41 | 2.1 | 1.2 | 0.7 | 1.4 |
| 42 | 7.3 | 4.1 | 3.5 | 3.8 |
| 44 | 9.1 | 7.6 | 3.0 | 10 |
| 45 | 9.3 | 10.3 | 4 | 10.6 |
| 46 | 10.4 | 10.9 | 7.2 | 11.2 |
| 47 | 4.7 | 1.9 | −0.8 | 5.7 |
| 48 | 6.3 | 9.4 | 1.9 | 8.4 |
| 49 | 3.2 | 2.6 | 0.1 | 5.1 |
| 50 | 4.2 | 2.5 | 0.7 | 5.7 |
| 51 | 7.5 | 9.7 | 10.6 | 9.1 |
| 52 | 4.7 | 9.8 | −0.5 | 4.3 |
| 53 | 9.2 | 13.7 | 9.8 | 10.5 |
| 54 | 8.5 | 9.8 | 1.2 | 9.5 |
| 55 | 11.3 | 11.1 | 10.2 | 11.5 |

TABLE 6-continued

| Example | TEAD1 ΔTm (° C.) | TEAD2 ΔTm (° C.) | TEAD3 ΔTm (° C.) | TEAD4 ΔTm (° C.) |
|---|---|---|---|---|
| 56 | 8.3 | 9 | 7.2 | 8.6 |
| 56a | 5.4 | 6.5 | −0.3 | 2.6 |
| 56b | 9.1 | 10.0 | 8.1 | 12.5 |
| 57 | 7.6 | 9.4 | 12.4 | 14 |
| 58b | 9.2 | 12.9 | 10.9 | 11.3 |
| 59a | 6.9 | 4.7 | 0.4 | 7.9 |
| 59b | 9.4 | 11.3 | 13.1 | 15.6 |
| 60 | 9.5 | 12.7 | 11.2 | 12.3 |
| 61 | 9.3 | 12.2 | 0.8 | 10.4 |
| 62 | 7.4 | 10.6 | 1.2 | 7.7 |
| 63 | 10.2 | 13.2 | 9.6 | 10.8 |
| 64 | 11.0 | 12.7 | 11.7 | 11.9 |
| 65 | 9.8 | 12.0 | 11.4 | 10.9 |
| 66 | 11.1 | 14.7 | 10.6 | 11.7 |
| 67 | 8.8 | 9.9 | 1.7 | 7.9 |
| 69 | 10.9 | 13.9 | 11.6 | 12.9 |
| 70 | 8.4 | 11.7 | 7.0 | 8.6 |
| 71 | 11.2 | 13.4 | 12.2 | 12.2 |
| 72 | 3.5 | 8.6 | 1.7 | 4.7 |
| 73 | 9.5 | 15.1 | 13.9 | 12.1 |
| 74 | 10.7 | 12.9 | 11.4 | 10.2 |
| 75a | 9.0 | 12.2 | 10.0 | 11.3 |
| 75b | 9.3 | 11.9 | 10.1 | 11.6 |
| 76a | 5.4 | 10.3 | 0.6 | 4.7 |
| 76b | 11.5 | 15.4 | 10.9 | 12.6 |
| 78 | 9.2 | 11.1 | 0.4 | 6.6 |
| 79 | 8.1 | 12.3 | 1.0 | 7.7 |
| 80 | 6.0 | 10.5 | 5.1 | 6.2 |
| 81 | 5.5 | 9.6 | 8.9 | 8.2 |
| 83 | 2.7 | 8.0 | 1.4 | 3.6 |
| 84 | 1.0 | 6.5 | 1.2 | 3.1 |
| 85b | 7.4 | 7.1 | 1.8 | 4.4 |
| 86 | 2.6 | 2.7 | 0.2 | 2.6 |
| 87a | 4.9 | 10.1 | 1.0 | 6.8 |
| 87b | −0.4 | 2.6 | 0.0 | 0.3 |
| 88a | −0.3 | 1.5 | 0.1 | 0.1 |
| 88b | 7.6 | 10.9 | 2.6 | 9.7 |
| 89a | 0.0 | 3.3 | 0.2 | −0.2 |
| 89b | 8.6 | 12.4 | 8.8 | 11.4 |
| 90a | −0.2 | 2.6 | 0.2 | 0.6 |
| 90b | 7.7 | 10.5 | 2.9 | 10.3 |
| 93 | 6.7 | 9.3 | 1.3 | 6.4 |
| 94 | 3.3 | 6.5 | 0.7 | 2.6 |
| 95 | 9.4 | 10.6 | 6.4 | 9.4 |
| 96 | 10.5 | 13.1 | 12.3 | 12.6 |
| 97 | 9.9 | 9.0 | 7.6 | 10.2 |
| 98 | 7.3 | 9.2 | 0 | 8.4 |
| 102 | 7.3 | 9.1 | 2.1 | 8.7 |
| 103a | 6.4 | 9.9 | 3.0 | 9.0 |
| 103b | 9.2 | 12.0 | 10.4 | 11.8 |
| 103c | 9.2 | 11.1 | 9.4 | 10.7 |
| 103d | 9.5 | 11.6 | 10.3 | 11.2 |
| 103e | 6.9 | 9.1 | 1.8 | 8.7 |
| 103f | 8.2 | 9.8 | 9.2 | 11.1 |
| 104 | 6.5 | 9.0 | 2.0 | 8.1 |
| 105 | 6.8 | 8.2 | 2.2 | 8.1 |
| 106 | 6.4 | 9.9 | 2.2 | 8.5 |
| 107 | 5.0 | 4.9 | 1.1 | 6.1 |
| 108b | 7.9 | 9.1 | 8.8 | 8.3 |
| 109b | 1.8 | 2.2 | 0.9 | 3.4 |
| 110 | 4.1 | 5.2 | 1.0 | 4.1 |
| 111 | 3.0 | 3.7 | 0.7 | 3.2 |
| 112a | 7.2 | 9.5 | 2.0 | 8.6 |
| 112b | 8.4 | 10.2 | 1.9 | 10.1 |
| 113 | 4.1 | 5.7 | 1.5 | 4.2 |
| 114 | 4.6 | 7.1 | 1.5 | 7.1 |
| 115 | 4.2 | 3.5 | 1.3 | 3.5 |
| 116a | 4.6 | 6.1 | 1.8 | 6.1 |
| 116b | 5.5 | 5.3 | 2.2 | 7.1 |
| 117 | 7.1 | 9.4 | 2.3 | 7.7 |
| 118 | 4.6 | 6.2 | 1.6 | 6.1 |
| 119 | 4.2 | 6.1 | 1.6 | 4.7 |
| 120 | 4.1 | 6.5 | 1.2 | 4.5 |
| 121 | 7.9 | 10.6 | 2.0 | 8.9 |
| 122 | 5.9 | 6.5 | 1.8 | 4.9 |
| 123 | 7.7 | 9.1 | 1.8 | 9.2 |
| 124 | 6.0 | 9.8 | 1.0 | 7.7 |
| 125 | 9.1 | 11.9 | 9.3 | 9.6 |
| 126 | 6.8 | 9.7 | 1.9 | 7.9 |
| 127 | 3.9 | 6.1 | 1.5 | 5.7 |
| 128 | 5.9 | 10.4 | 1.9 | 7.2 |
| 129 | 8.2 | 10.3 | 9.5 | 10.3 |
| 130 | 9.1 | 12.4 | 6.4 | 11.4 |
| 131 | 9.8 | 12.9 | 13.1 | 11.7 |
| 132 | 10.9 | 15.8 | 13.9 | 13.7 |
| 133 | 1.1 | 8.5 | 0.3 | 4.9 |
| 134 | 6.8 | 6.0 | 1.5 | 5.8 |
| 135 | 25.0 | 25.0 | 18.0 | 6.9 |
| 136 | 7.1 | 12.4 | 1.7 | 10.3 |
| 138 | 4.2 | 6.8 | 2.3 | 6.4 |
| 139 | 5.5 | 9.2 | 2.8 | 7.6 |
| 140 | 7.6 | 11.1 | 8.9 | 10.6 |
| 141 | 9.3 | 16.2 | 11.4 | 12.0 |
| 142 | 8.9 | 11.4 | 10.2 | 9.7 |
| 143 | 9.6 | 13.2 | 10.3 | 8.8 |
| 144 | 10.6 | 18.2 | 13.1 | 9.9 |
| 145 | 4.8 | 9.9 | 1.0 | 2.9 |
| 146 | 5.5 | 12.0 | 1.0 | 6.7 |

Example C: Pharmacokinetic Profile Evaluation

Three CD-1 mice of SPF. (Sino-British SIPPR/BK Lab Animal Ltd, Shanghai.) were intravenously administrated with given compounds (Formulation: 5% DMSO+10% Solutol+85% Saline) or orally gavage administrated with given compounds (Formulation: 5% DMSO+10% Solutol+85% Saline). The blood samples were taken via cephalic vein at timepoints 0.083 h, 0.25 h, 0.5 h, 1 h, 2 h, 4 h, 8 h, and 24 h after intravenous (iv) administration or at timepoints 0.25 h, 0.5 h, 1 h, 2 h, 4 h, 6 h, 8 h, and 24 h after oral gavage administration, 30 μL/time point. Blood samples were placed in tubes containing K2-EDTA and stored on ice until centrifuged. The blood samples were centrifuged at 6800 g for 6 minutes at 2-8° C. within 1 h after collected and stored frozen at approximately −80° C. An aliquot of 20 μL plasma samples were protein precipitated with 400 μL MeOH in which contains 100 ng/mL Verapamil (IS). The mixture was vortexed for 1 min and centrifuged at 18000 g for 10 min. Transfer 400 μL supernatant to 96 well plates. An aliquot of 5 μL supernatant was injected for LC-MS/MS analysis by LC-MS/MS-27 (TQ6500+) instrument. The analytical results were confirmed using quality control samples for intra-assay variation. The accuracy of >66.7% of the quality control samples should be between 80-120% of the known value(s). Standard set of parameters including Area Under the Curve ($AUC_{(0-t)}$), maximum plasma concentration ($C_{max}$), elimination half-life ($T_{1/2}$) will be calculated using noncompartmental analysis modules in FDA certified pharmacokinetic program Phoenix WinNonlin 7.0 (Pharsight, USA).

The data for Example C is shown in Table 7.

TABLE 7

Mouse PK profile after oral administration at 10 mg/kg

| Example | $C_{max}$ (ng/mL) | $T_{1/2}$ (h) | $AUC_{0-t}$ (ng*h/mL) |
|---|---|---|---|
| 2 | 9746 | 5.4 | 104258 |
| 16 | 40127 | 26.4 | 675700 |
| 17 | 33732 | 26 | 496545 |
| 18 | 41168 | 11.2 | 616612 |
| 24 | 5532 | 5.2 | 70031 |

TABLE 7-continued

Mouse PK profile after oral administration at 10 mg/kg

| Example | $C_{max}$ (ng/mL) | $T_{1/2}$ (h) | $AUC_{0-t}$ (ng*h/mL) |
|---|---|---|---|
| 34b | 3182 | 2.2 | 31847 |
| 44 | 2466 | 2.6 | 16140 |
| 45 | 3100 | 2.2 | 11527 |
| 58b | 1706 | 3.6 | 17180 |
| 63 | 2167 | 4.1 | 11518 |
| 64 | 1338 | 3.2 | 9395 |
| 65 | 1216 | 3.2 | 7403 |
| 75a | 1647 | 2.3 | 10707 |
| 103f | 4123 | 4.8 | 51551 |

Example D: In Vivo Pharmacodynamic and Efficacy Study

The objective of the research is to evaluate the in vivo anti-tumor efficacy of Example 58b, 64, 75a in human lung cancer NCI-H226 xenograft model in BALB/c Nude mice. (Jiangsu GemPharmatech Co., Ltd, female, 6-9 weeks)
Method:

The NCI-H226 cancer cells was maintained in vitro with RPMI1640 medium supplemented with 10% fetal bovine serum at 37° C. in an atmosphere of 5% $CO_2$ in the air. The cells in exponential growth phase will be harvested and quantitated by cell counter before tumor inoculation. Each mouse was inoculated subcutaneously it the right front flank region with NCI-H226 tumor cells (lx 107) in 0.2 ml of PBS mixed with Matrigel (1:1) for tumor development. Animals were randomized when the average tumor volume reached 150-200 mm³. The test article was administered to the mice orally once a day from the day of grouping, total 21 days (QD×21 Days). Body weight change of animals was monitored regularly as an indicator of drug safety. The major endpoint was to see if the tumor growth could be delayed or mice could be cured. Tumor sizes were measured two times per week in two dimensions using a caliper, and the volume were expressed in mm³ using the formula: $V=0.5a \times b^2$ where a and b are the long and short diameters of the tumor, respectively.

The tumor volume were then used for the calculations of TGI. TGI is calculated for each group using the formula: TGI (%)=$[1-(T_i-T_0)/(C_i-C_0)] \times 100$; $T_i$ is the average tumor volume of a treatment group on a given day, $T_0$ is the average tumor volume of the treatment group on the first day of treatment, $C_i$ is the average tumor volume of the vehicle control group on the same day with $T_i$, and $C_0$ is the average tumor volume of the vehicle group on the first day of treatment. To compare tumor volumes of different groups at a pre-specified day, Bartlett's test was used to check the assumption of homogeneity of variance across all groups. The results are shown in table 8.

TABLE 8

Tumor growth inhibition calculation in the NCI-H226 xenograft model based on tumor volume at day 21 and body weight change of day 21 compared to day 1.

| Group | Dose (mg/kg) | TGI (%) | P Value | Body weight change(%) |
|---|---|---|---|---|
| Vehicle | — | — | — | +2.7 |
| 58b | 1 mg/kg, QD | 95 | <0.05 | +8.2 |
| 58b | 3 mg/kg, QD | 103 | <0.05 | +4.0 |
| 58b | 10 mg/kg, QD | 128 | <0.01 | +1.6 |
| 58b | 30 mg/kg, QD | 145 | <0.01 | +2.9 |
| 64 | 3 mg/kg, QD | 104 | <0.01 | −1.1 |
| 64 | 10 mg/kg, QD | 116 | <0.01 | +0.8 |
| 64 | 30 mg/kg, QD | 119 | <0.01 | −1.4 |
| 64 | 60 mg/kg, QD | 122 | <0.01 | +0.4 |
| 75a | 3 mg/kg, QD | 90 | <0.05 | +6.7 |
| 75a | 10 mg/kg, QD | 119 | <0.01 | +3.0 |
| 75a | 30 mg/kg, QD | 150 | <0.01 | +4.0 |
| 75a | 60 mg/kg, QD | 149 | <0.01 | +1.5 |

After 21 days treatment, selected examples of this application produced significant anti-tumor activities compared with the vehicle group in tumor volume.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A compound of Formula (Ic), or a pharmaceutically acceptable salt, or stereoisomer thereof:

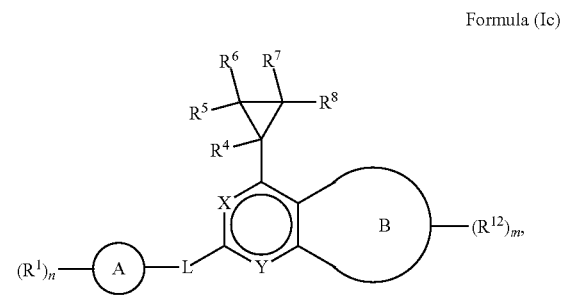

Formula (Ic)

wherein:
X is —$CR^X$—;
$R^X$ is hydrogen;
Y is —$CR^Y$—;
$R^Y$ is hydrogen;
Ring A is phenyl;
each $R^1$ is independently halogen, —CN, —OH, —$OR^a$, —$NR^cR^d$, $C_1$-$C_6$alkyl, or $C_1$-$C_6$haloalkyl;
n is 0, 1, or 2;
L is —O—;
$R^4$, $R^5$, $R^6$, and $R^7$ are each hydrogen;
$R^8$ is —C(=O)$OR^9$ or —C(=O)$NR^{10}R^{11}$;
$R^9$ is hydrogen;
$R^{10}$ and $R^{11}$ are each independently hydrogen, $C_1$-$C_6$alkyl, or $C_1$-$C_6$hydroxyalkyl; wherein each alkyl is independently optionally substituted with one or more $R^{10a}$;
or $R^{10}$ and $R^{11}$ are taken together with the atom to which they are attached to form a heterocycloalkyl optionally substituted with one or more $R^{10b}$;
each $R^{10a}$ is independently halogen or —CN;

each $R^{10b}$ is independently halogen, —CN, —OH, —OR, —NR$^c$R$^d$, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

or two $R^{10b}$ on the same atom are taken together to form an oxo;

Ring B is a 5-membered heteroaryl;
each $R^{12}$ is independently C$_1$-C$_6$alkyl;
m is 0 or 1;
each $R^a$ is independently C$_1$-C$_6$alkyl or C$_1$-C$_6$haloalkyl; and
$R^c$ and $R^d$ are each independently hydrogen, C$_1$-C$_6$alkyl, or C$_1$-C$_6$haloalkyl.

2. The compound of claim 1, or a pharmaceutically acceptable salt, or stereoisomer thereof, wherein $R^8$ is —C(=O)OR$^9$.

3. The compound of claim 1, or a pharmaceutically acceptable salt, or stereoisomer thereof, wherein $R^8$ is —C(=O)NR$^{10}$R$^{11}$.

4. The compound of claim 1, or a pharmaceutically acceptable salt, or stereoisomer thereof, wherein $R^{10}$ and $R^{11}$ are taken together with the atom to which they are attached to form a monocyclic heterocycloalkyl optionally substituted with one or more $R^{10b}$.

5. The compound of claim 1, or a pharmaceutically acceptable salt, or stereoisomer thereof, wherein $R^{10}$ and $R^{11}$ are taken together with the atom to which they are attached to form a bicyclic heterocycloalkyl optionally substituted with one or more $R^{10b}$.

6. The compound of claim 1, or a pharmaceutically acceptable salt, or stereoisomer thereof, wherein each $R^{10b}$ is independently —OH.

7. The compound of claim 1, or a pharmaceutically acceptable salt, or stereoisomer thereof, wherein $R^8$ is

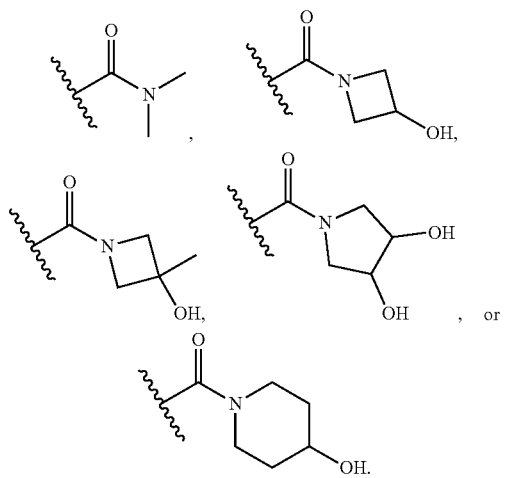

8. The compound of claim 1, or a pharmaceutically acceptable salt, or stereoisomer thereof, wherein

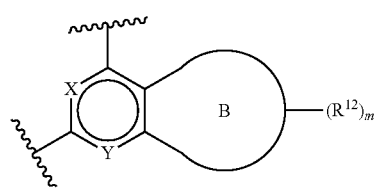

is

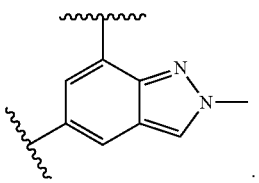 [SMILES: *c1cc(*)c2nn(C)cc2c1]

9. The compound of claim 1, wherein

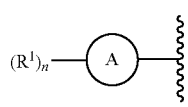

is

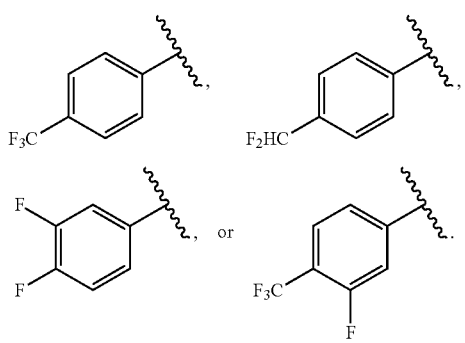

10. The compound of claim 1 selected from the group consisting of:

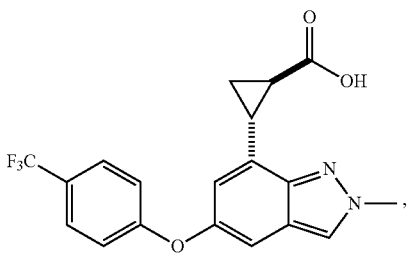

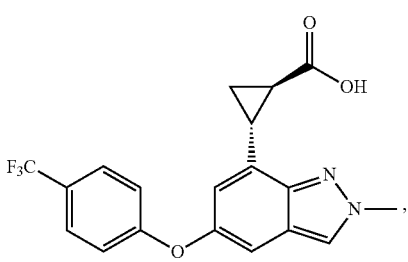

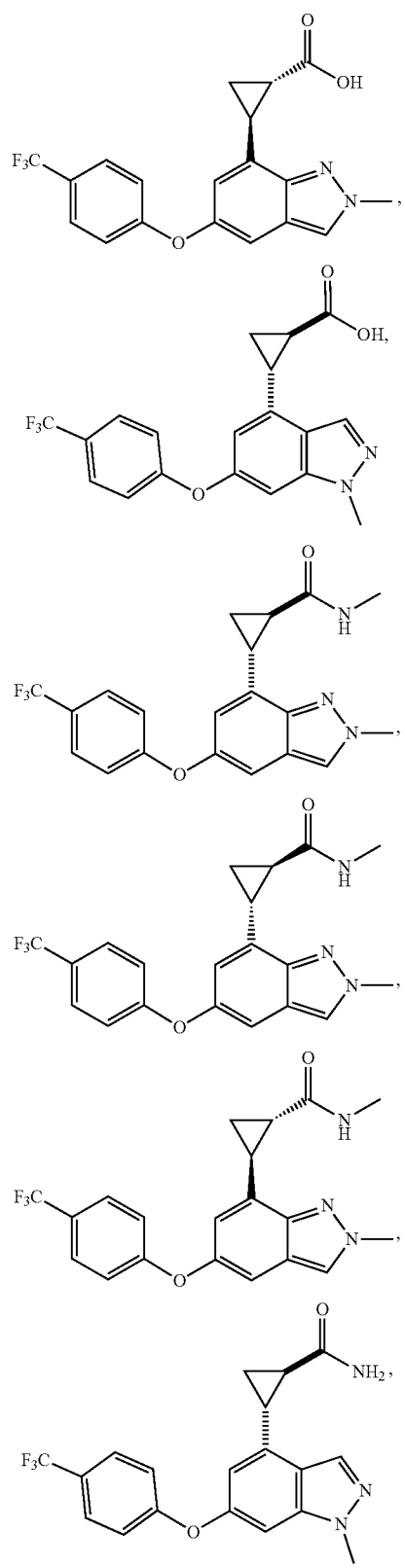
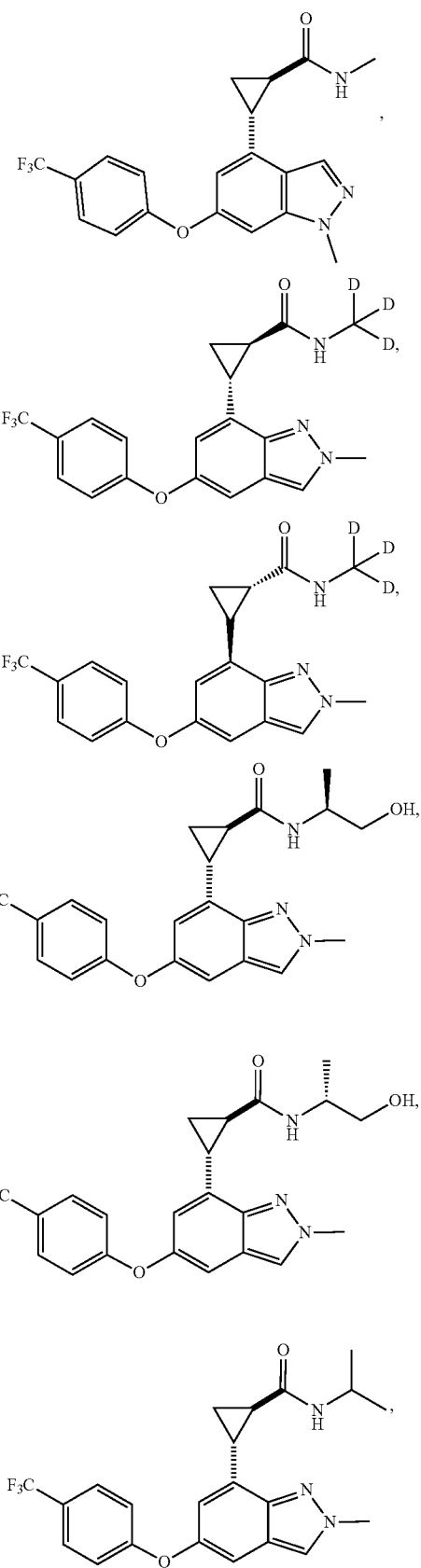

263
-continued
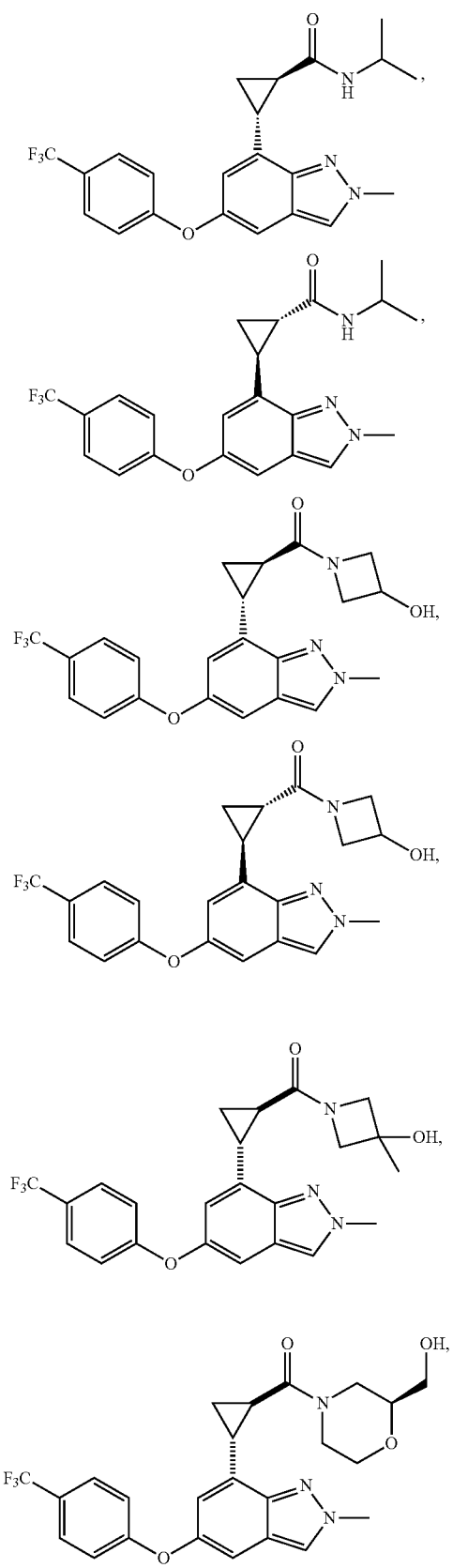
264
-continued
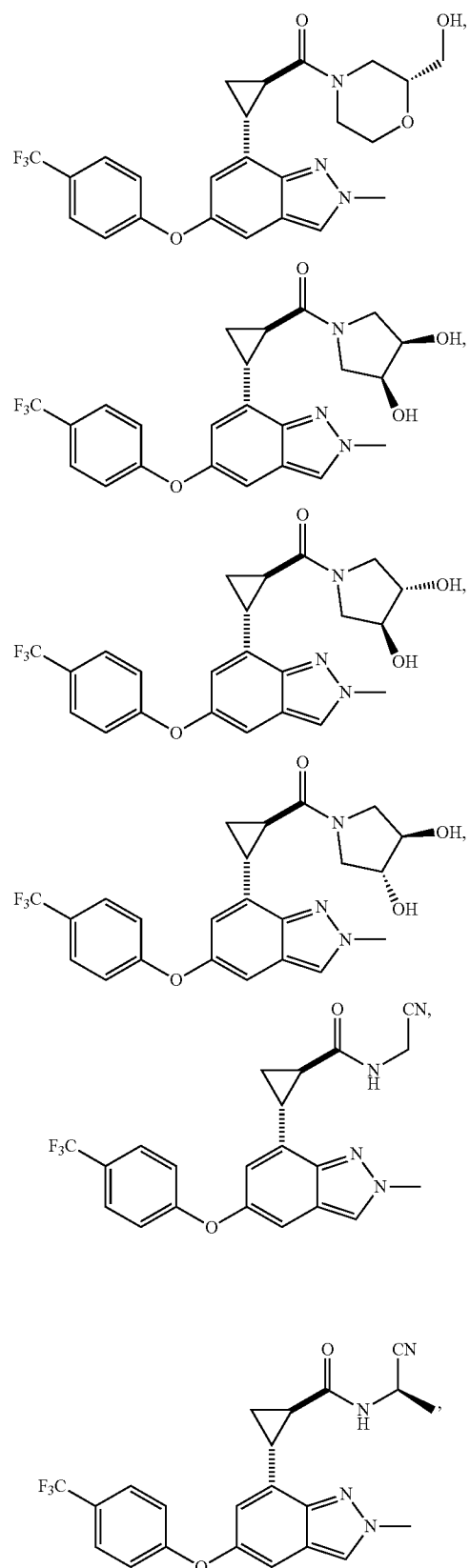

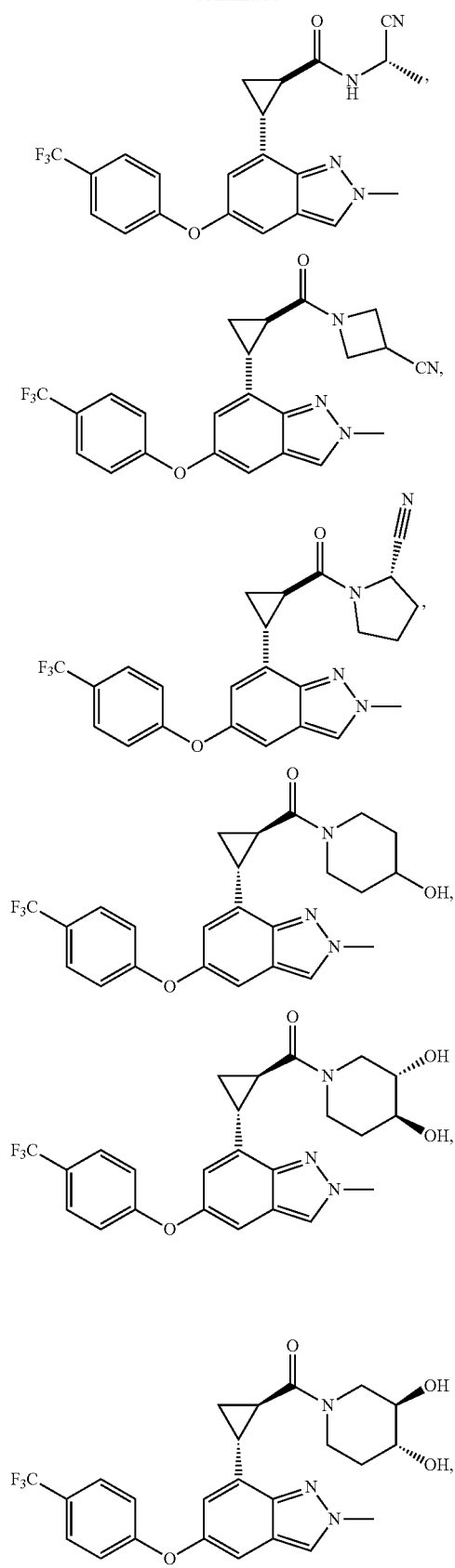
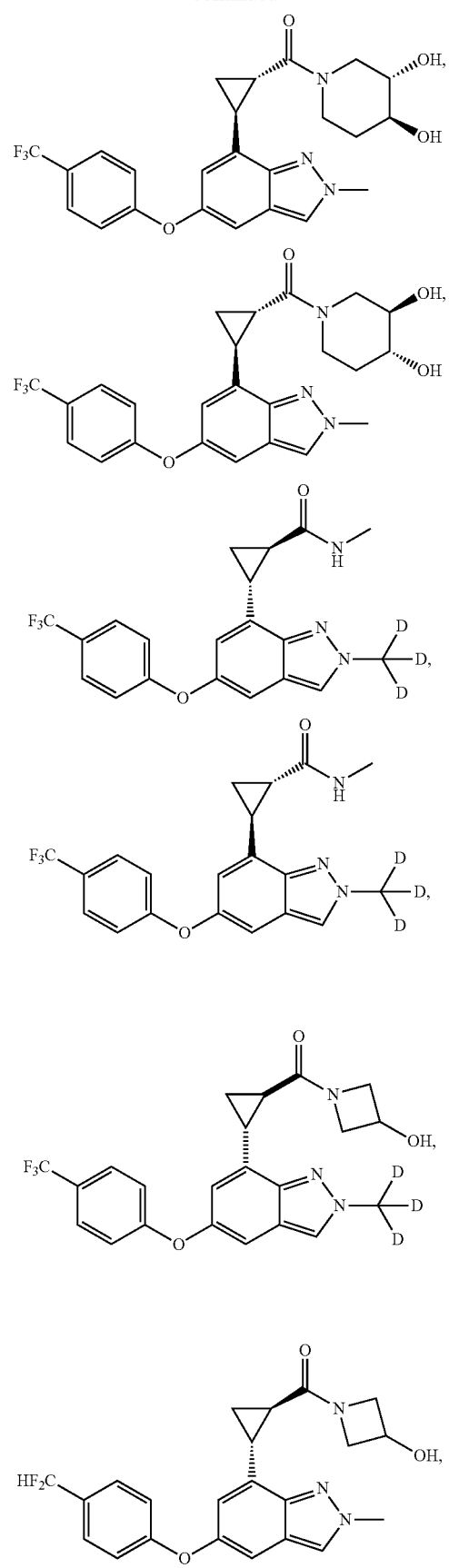

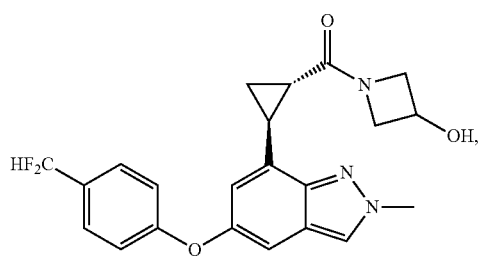
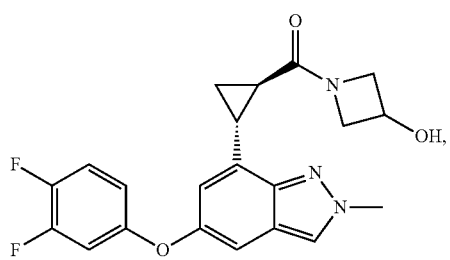
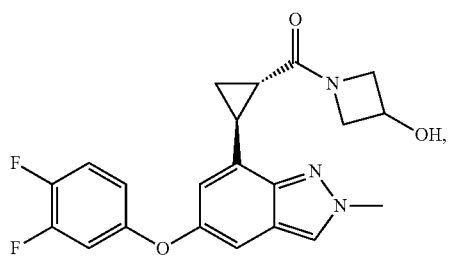
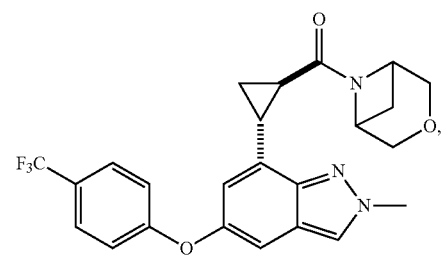
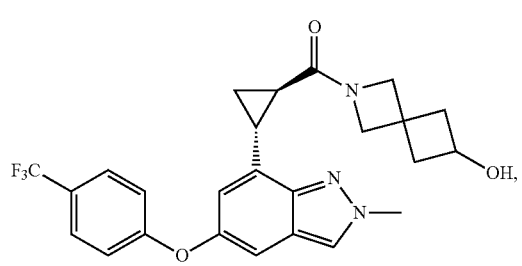
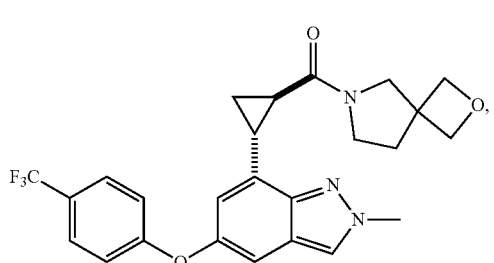
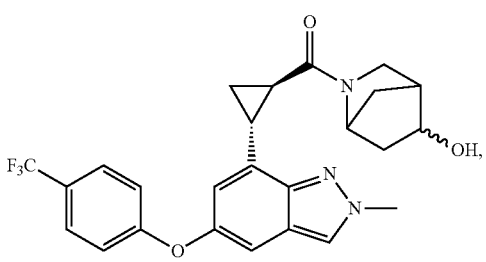
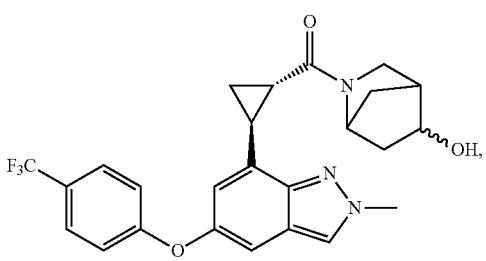
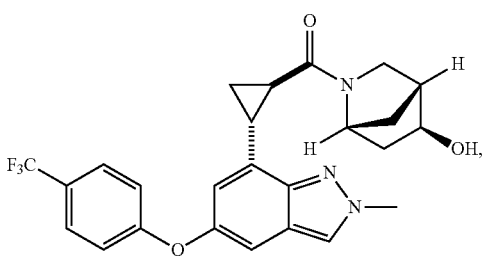
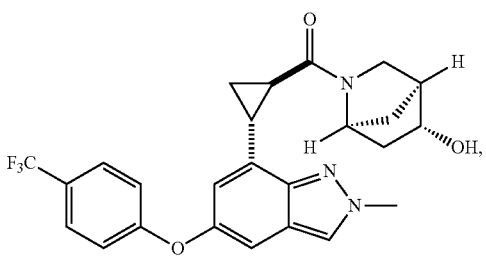
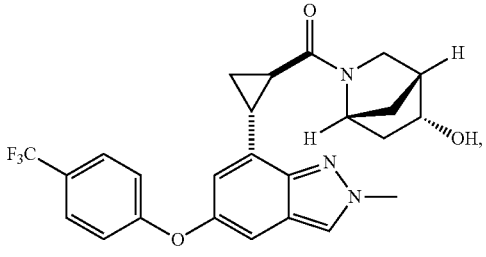
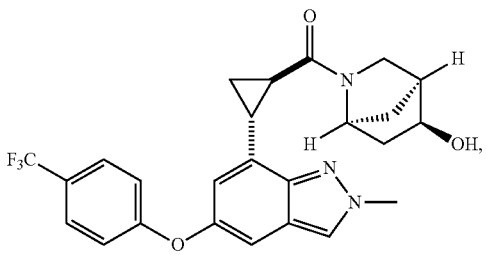

269
-continued
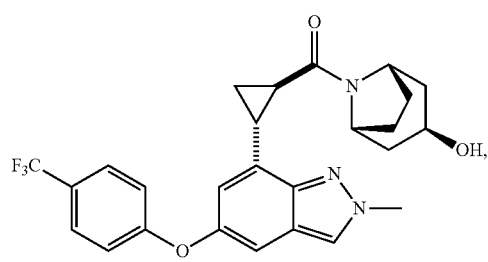
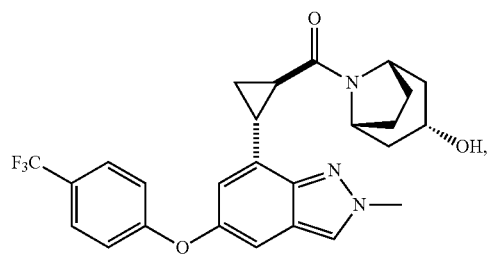
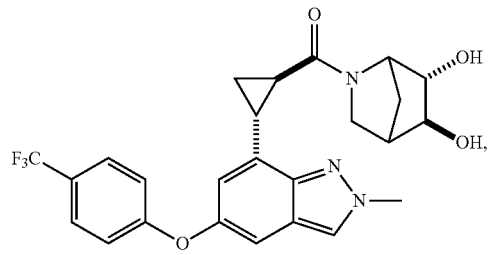
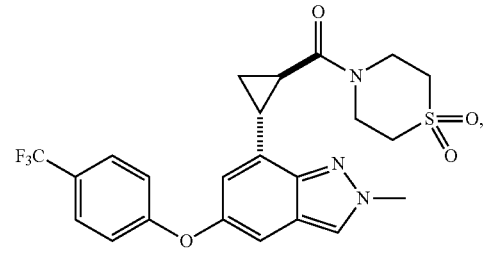
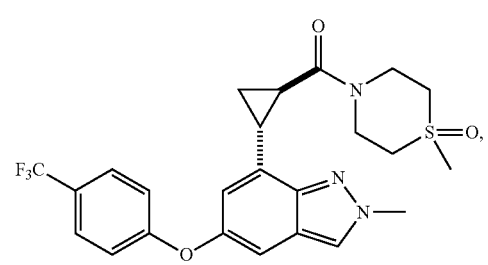
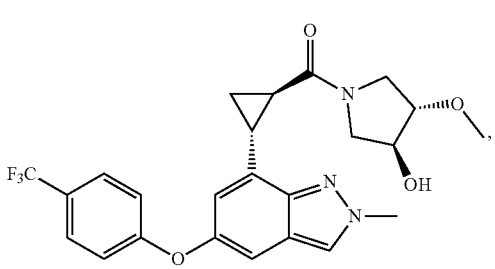
270
-continued
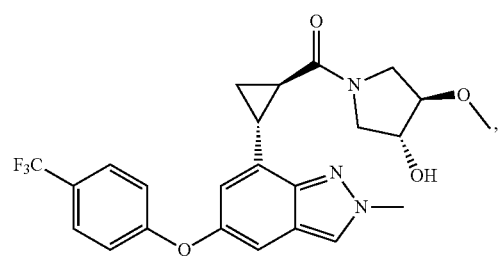
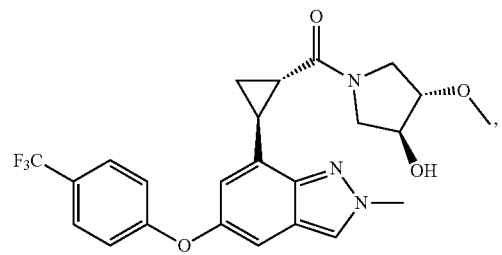
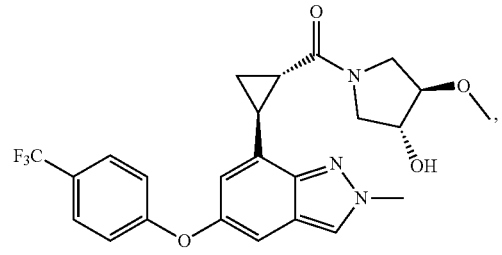
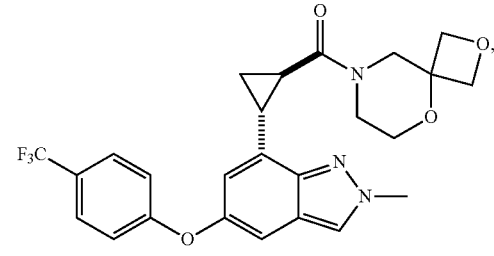
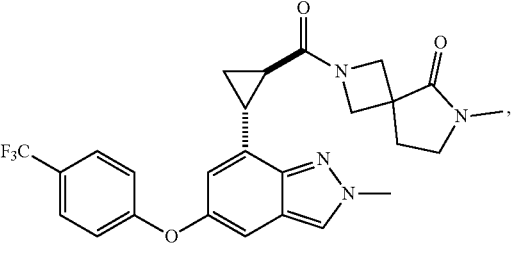
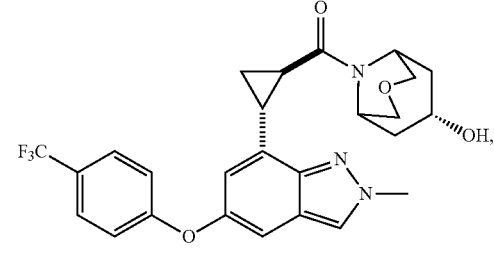

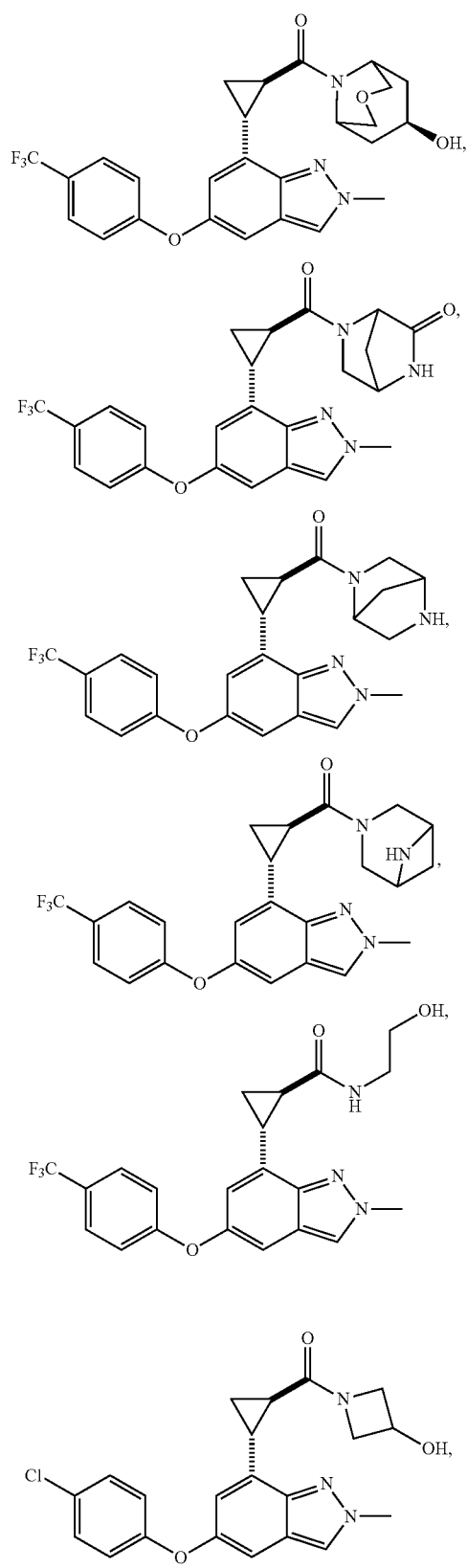
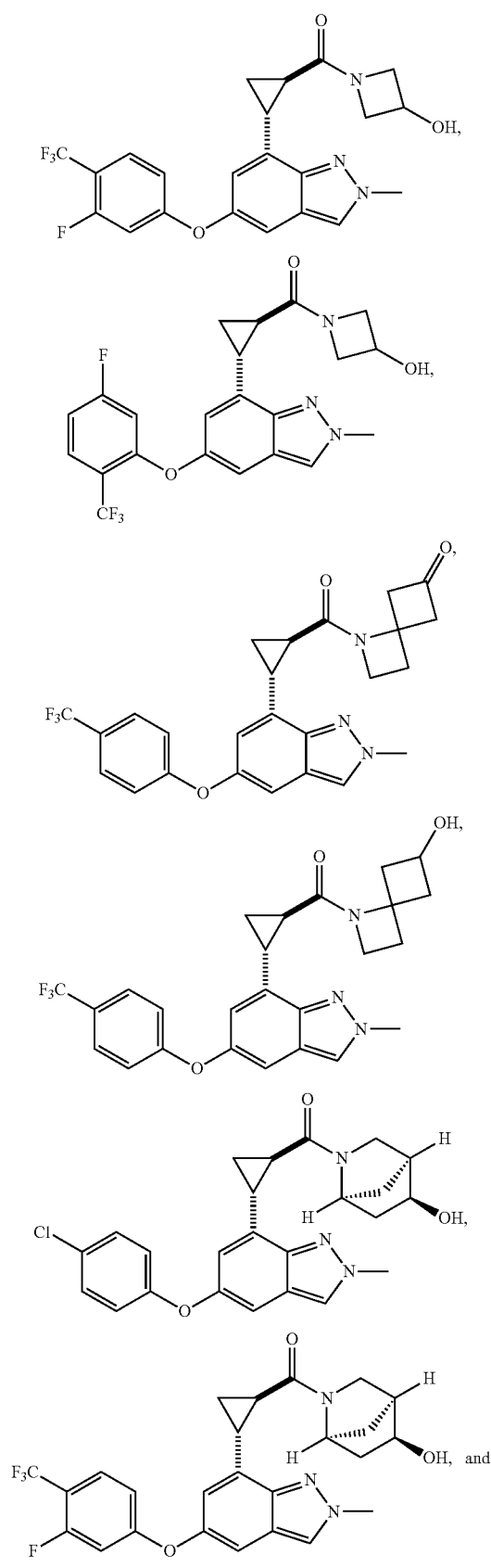

-continued

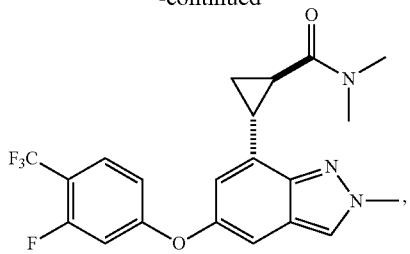

or a pharmaceutically acceptable salt or stereoisomer thereof.

11. The compound of claim 1 that is

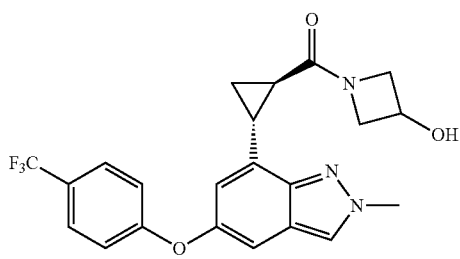 [SMILES: Cn1cc2cc(Oc3ccc(C(F)(F)F)cc3)cc([C@@H]3C[C@H]3C(=O)N3CC(O)C3)c2n1]

or a pharmaceutically acceptable salt or stereoisomer thereof.

12. The compound of claim 1 that is

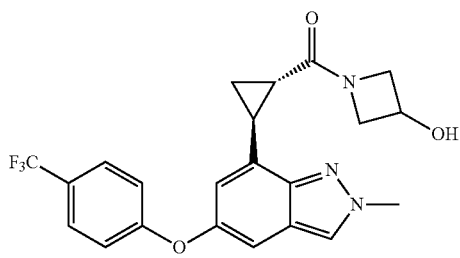 [SMILES: Cn1cc2cc(Oc3ccc(C(F)(F)F)cc3)cc([C@H]3C[C@@H]3C(=O)N3CC(O)C3)c2n1]

or a pharmaceutically acceptable salt or stereoisomer thereof.

13. The compound of claim 1 that is

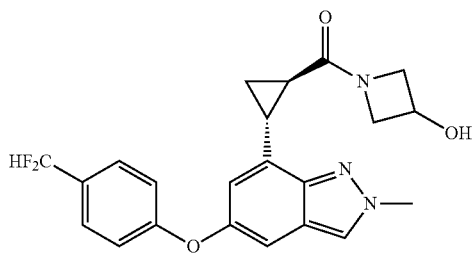

or a pharmaceutically acceptable salt or stereoisomer thereof.

14. The compound of claim 1 that is

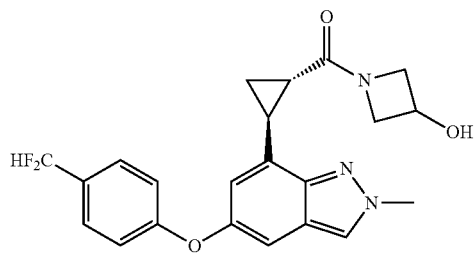

or a pharmaceutically acceptable salt or stereoisomer thereof.

15. The compound of claim 1 that is

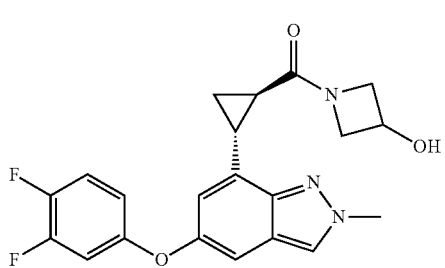 [SMILES: Cn1cc2cc(Oc3ccc(F)c(F)c3)cc([C@@H]3C[C@H]3C(=O)N3CC(O)C3)c2n1]

or a pharmaceutically acceptable salt or stereoisomer thereof.

16. The compound of claim 1 that is

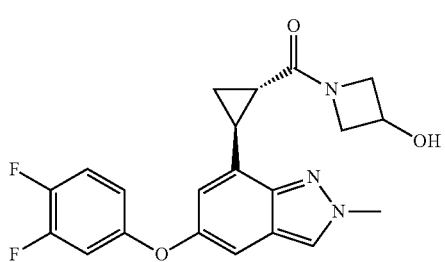 [SMILES: Cn1cc2cc(Oc3ccc(F)c(F)c3)cc([C@H]3C[C@@H]3C(=O)N3CC(O)C3)c2n1]

or a pharmaceutically acceptable salt or stereoisomer thereof.

17. The compound of claim 1 that is

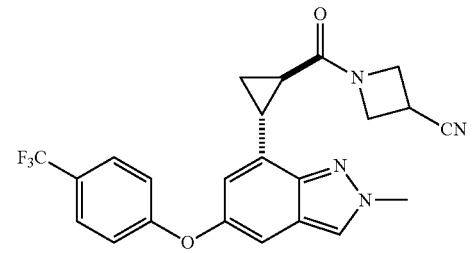

or a pharmaceutically acceptable salt or stereoisomer thereof.

18. The compound of claim 1 that is

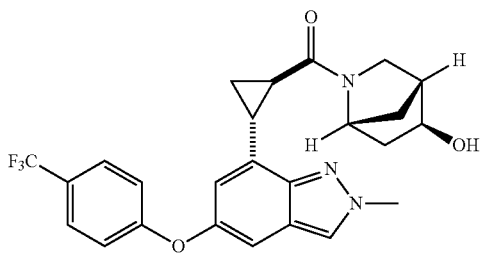

or a pharmaceutically acceptable salt or stereoisomer thereof.

19. The compound of claim 1 that is

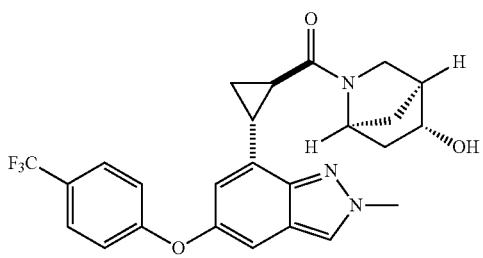

or a pharmaceutically acceptable salt or stereoisomer thereof.

20. The compound of claim 1 that is

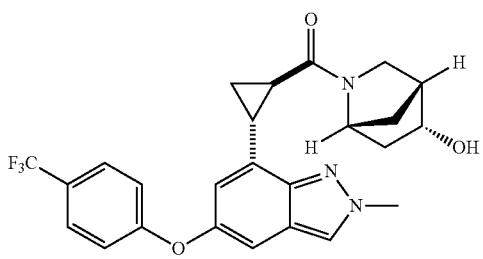

or a pharmaceutically acceptable salt or stereoisomer thereof.

21. The compound of claim 1 that is

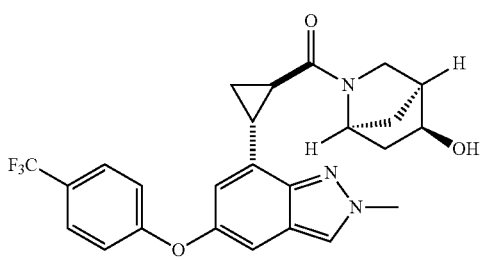

or a pharmaceutically acceptable salt or stereoisomer thereof.

22. The compound of claim 1 that is

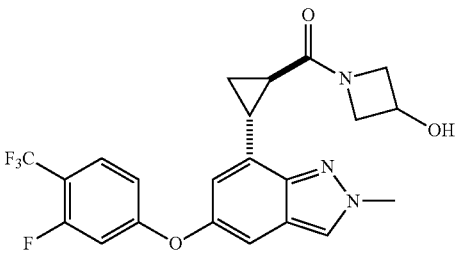

or a pharmaceutically acceptable salt or stereoisomer thereof.

23. The compound of claim 1 that is

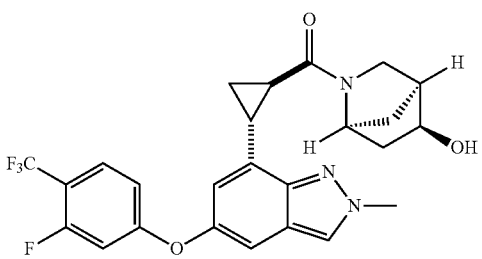

or a pharmaceutically acceptable salt or stereoisomer thereof.

24. The compound of claim 1 that is

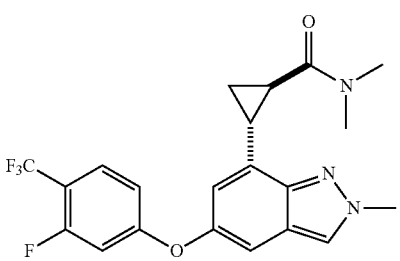

or a pharmaceutically acceptable salt or stereoisomer thereof.

25. A pharmaceutical composition comprising a compound of claim 1, or a pharmaceutically acceptable salt or stereoisomer thereof, and a pharmaceutically acceptable excipient.

26. A method of treating a cancer by inhibiting TEAD in a subject in need thereof, the method comprising administering an effective amount of a compound of claim 1, or a pharmaceutically acceptable salt or stereoisomer thereof, to the subject in need thereof.

* * * * *

UNITED STATES PATENT AND TRADEMARK OFFICE
CERTIFICATE OF CORRECTION

PATENT NO. : 12,103,915 B2  
APPLICATION NO. : 18/529689  
DATED : October 1, 2024  
INVENTOR(S) : Xiao Ding et al.

Page 1 of 1

It is certified that error appears in the above-identified patent and that said Letters Patent is hereby corrected as shown below:

In the Claims

Column 259, Line 1:
In Claim 1, replace: "—OR" with -- —OR$^a$ --

Column 269, Lines 43-53:

In Claim 10, replace: " 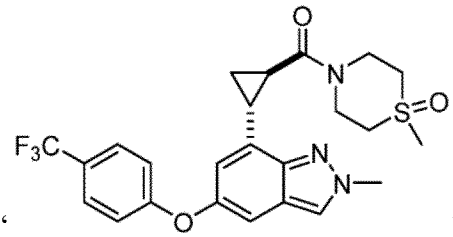 " with

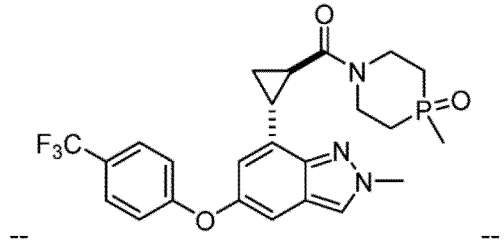

-- --

Signed and Sealed this  
Twelfth Day of November, 2024

Katherine Kelly Vidal  
*Director of the United States Patent and Trademark Office*